US011793864B2

(12) United States Patent
Deperthes et al.

(10) Patent No.: US 11,793,864 B2
(45) Date of Patent: Oct. 24, 2023

(54) USE OF SERINE PROTEASE INHIBITORS IN THE TREATMENT OF SKIN DISEASES

(71) Applicants: DERMADIS SA, Archamps (FR); INSTITUT NATIONAL DE LA SANTE ET DE LA RECHERCHE MEDICALE (INSERM), Paris (FR)

(72) Inventors: David Deperthes, Etoy (CH); Christoph Kundig, Lausanne (CH); Alain Hovnanian, Paris (FR); Celine Deraison, Toulouse (FR)

(73) Assignees: DERMADIS SA, Archamps (FR); INSTITUT NATIONAL DE LA SANTE ET DE LA RECHERCHE MEDICALE, Paris (FR)

(*) Notice: Subject to any disclaimer, the term of this patent is extended or adjusted under 35 U.S.C. 154(b) by 0 days.

(21) Appl. No.: 16/217,957

(22) Filed: Dec. 12, 2018

(65) Prior Publication Data

US 2019/0183989 A1  Jun. 20, 2019

Related U.S. Application Data

(63) Continuation of application No. 14/447,317, filed on Jul. 30, 2014, now abandoned, which is a continuation of application No. 12/863,651, filed as application No. PCT/IB2009/000089 on Jan. 21, 2009, now abandoned.

(60) Provisional application No. 61/006,576, filed on Jan. 22, 2008, provisional application No. 61/022,386, filed on Jan. 21, 2008.

(51) Int. Cl.
*A61K 38/49* (2006.01)
*A61K 8/64* (2006.01)
*A61Q 19/00* (2006.01)
*A61K 38/57* (2006.01)
*A61K 38/48* (2006.01)
*C12Q 1/37* (2006.01)
*G01N 33/50* (2006.01)

(52) U.S. Cl.
CPC .......... *A61K 38/49* (2013.01); *A61K 8/64* (2013.01); *A61K 38/482* (2013.01); *A61K 38/484* (2013.01); *A61K 38/486* (2013.01); *A61K 38/4826* (2013.01); *A61K 38/4853* (2013.01); *A61K 38/57* (2013.01); *A61Q 19/00* (2013.01); *C12Q 1/37* (2013.01); *G01N 33/502* (2013.01); *A61K 2800/782* (2013.01); *G01N 2333/96455* (2013.01); *G01N 2500/04* (2013.01)

(58) Field of Classification Search
CPC .................................. A61K 38/49; A61K 8/64
See application file for complete search history.

(56) References Cited

U.S. PATENT DOCUMENTS

| 7,105,172 B1* | 9/2006 | Bolla | A61K 31/74 424/400 |
| 8,309,596 B2* | 11/2012 | Flohr | A61K 31/401 514/423 |
| 2003/0054445 A1 | 3/2003 | Chen et al. | |
| 2006/0269536 A1* | 11/2006 | Deperthes | C12N 15/62 424/94.2 |
| 2014/0341881 A1 | 11/2014 | Deperthes et al. | |

FOREIGN PATENT DOCUMENTS

| WO | WO-00/07620 A1 | 2/2000 | |
| WO | WO-2004/045634 A1 | 6/2004 | |
| WO | WO 2004/087912 | * 10/2004 | ............ C12N 15/09 |
| WO | WO-2005/117955 A1 | 12/2005 | |
| WO | WO-2006/037606 A2 | 4/2006 | |
| WO | WO-2006/090282 A2 | 8/2006 | |
| WO | WO-2007/072012 A1 | 6/2007 | |
| WO | WO-2009/024528 A1 | 2/2009 | |

OTHER PUBLICATIONS

Shaw et al, Distribution of 15 Human Kallikreins in Tissues and Biological Fluids, Clinical Chemistry, 2007, 53, pp. 1423-1432.*
Kalinska et al, Kallikreins—The melting pot of activity and function, Biochimie, 2016, 122, pp. 270-282.*
Avgeris et al, Kallikrein-related peptidases (KLKs) as emerging therapeutic targets: focus on prostate cancer and skin pathologies, Expert Opinion on Therapeutic Targets, 2016, 20, pp. 801-818.*
Affidavit under 37 CFR 1.132 filed with SN 14447317, May 1, 2017, pp. 1-13.*
Declaration of Christoph Kundig submitted in the parent U.S. Appl. No. 14/447,317 on Jul. 30, 2014, 13 pages.*
Egelrud et al., 2005, hK5 and hK7, two serine proteinases abundant in human skin, are inhibited by LEKTI domain 6, British Journal of Dermatology, 153: 1200-1203.*
Parsanejad et al., 2008, The Time Course of Expression of Genes Involved in Specific Pathways in Normal Human Bronchial Epithelial Cells Following Exposure to Cigarette Smoke, Experimental Lung Research, 34: 513-530.*
Komatsu et al., 2006, Elevated Human Tissue Kallikrein Levels in the Stratum Corneum and Serum of Peeling Skin Syndrome-Type B Patients Suggests an Over-desquamation of Corneocytes, Journal of Investigative Dermatology, 126: 2338-2342.*
Komatsu et al., 2005, Multiple tissue kallikrein mRNA and protein expression in normal skin and skin diseases, British Journal of Dermatology, 153: 274-281.*

(Continued)

*Primary Examiner* — Amber D Steele
(74) *Attorney, Agent, or Firm* — Foley & Lardner LLP

(57) ABSTRACT

This invention relates to therapeutic compounds which are inhibitors of serine proteases, to pharmaceutical compositions thereof and to their use in the treatment of the human or animal body. More specifically, the present invention relates to a method for the treatment, diagnosis or prognosis of skin diseases comprising the administration to a subject in need thereof of a therapeutically effective amount of a Serine protease inhibitor.

18 Claims, 31 Drawing Sheets

Specification includes a Sequence Listing.

(56) References Cited

OTHER PUBLICATIONS

Deraison et al., 2007, LEKTI Fragments Specifically Inhibit KLK5, KLK7, and KLK14 and Control Desquamation through a pH-dependent Interaction, Molecular Biology of the Cell, 18: 3607-3619.*

Komatsu et al., 2007, Human tissue kallikrein expression in the stratum corneum and serum of atopic dermatitis patients, Experimental Dermatology, 16: 513-519.*

Harvey et al., 2000, Tissue-specific Expression Patterns and Fine Mapping of the Human Kallikrein (KLK) Locus on Proximal 19q13.4, The Journal of Biological Chemistry, 275(48): 37397-37406.*

Clements et al., 2001, The Expanded Human Kallikrein (KLK) Gene Family: Genomic Organization, Tissue-Specific Expression and Potential Functions, Biol. Chem., 382: 5-14.*

Izaki et al., 1989, Modulation of Plasma and Tissue Kallikreins in Psoriasis vulgaris and Psoriasis pustulosa, Dermatologica, 179: 116-117.*

Hibino et al., 1988, Partial Purification of Plasma and Tissue Kallikreins in Psoriatic Epidermis, J Invest Dermatol, 90: 505-510.*

Shaw et al., 2007, Distribution of 15 Human Kallikreins in Tissues and Biological Fluids, Clinical Chemistry, 53(8): 1423-1432.*

Yousef et al., 2001, The New Human Tissue Kallikrein Gene Family: Structure, Function, and Association to Disease, Endocrine Reviews, 22(2): 184-204.*

Assis et al., 2013, Novel Inhibitory Activity for Serine Protease Inhibitor Kazal Type-3 (Spink3) on Human Recombinant Kallikreins, Protein & Peptide Letters, 20: 1098-1107.*

Fischer et al., 2014, Characterization of Spink6 in Mouse Skin: The Conserved Inhibitor of Kallikrein-Related peptidases is Reduced by Barrier Injury, Journal of Investigative Dermatology, 134: 1305-1312.*

Hachem et al., 2006, Serine protease Activity and Residual LEKTI Expression Determine Phenotype in Netherton Syndrome, Journal of Investigative Dermatology, 126: 1609-1621.*

Komatsu et al., published online Nov. 8, 2007, Correlation between SPINK5 Gene Mutations and Clinical Manifestations in Netherton Syndrome Patients, Journal of Investigative Dermatology, 128: 1148-1159.*

A to Z of skin diseases, from http://www.britishskinfoundation.org.uk/SkinInformation/AtoZofSkinDisease.aspx, pp. 1-2, accessed Sep. 3, 2015.

Beren Osen, "A Glimpse of the Holy Grail?", Science, 1998, 282, pp. 642-643.

Borgono et al, "Potential Role for Multiple Tissue Kallikrein Serine Proteases in Epidermal Desquamation," The journal of Biological Chemistry, 2007, 282, pp. 3640-3652.

Bradley et al., "Limits of cooperativity in a Structurally Modular Protein: Response of the Notch Ankyrin Domain to Analogous Alanine Substitutions in Each Repeat," J. Mol. Biol (2002) 324, 373-386.

C. Ong, et al., "LEKTI demonstrable by immunohistochemistry of the skin: a potential diagnostic skin test for Netherton syndrome," British Journal of Dermatology 2004: 151: 1253-1257.

Caliendo et al., "Kallikrein Protease Activated Receptor (PAR) Axis: An Attractive Target for Drug Development, Journal of Medicinal Chemistry," 2012, 55, pp. 6669-6686.

Chavanas et al., "Mutations in SPINKS, encoding a serine protease inhibitor," cause Netherton syndrome, 2000 Nature Genetics, Nature Publishing Group, pp. 141-142.

Cloutier, S., et al., "Development of recombinant inhibitors specific to human kallikrein 2 using phage-display selected substrates", Feb. 2004, Eur. J. Biochem, 271, (607-613).

Common Skin Problems, from http://www.dermweb.com/common_skin_problems, pp. 1-5, accessed Sep. 3, 2015.

Dickinson, Joanne L. et al., "The C-D interhelical domain of the serpin plasminogen activator inhibitor-type 2 is reguired for protection from TNF-a induced apoptosis," 1998 Cell Death & Differentiation, vol. 5, No. 2 (pp. 163-171).

Goettig, Peter et al., "Natural and synthetic inhibitors of kallikrein-related peptidases (KLKs)," 2010 Biochimie, vol. 92 (pp. 1546-1567).

Harrop, Stephen J. et al., "The crystal structure of plasminogen activator inhibitor 2 at 2.0 A resolution: implications for serpin function," 1999 Structure, vol. 7 (pp. 43-54).

Jensen, Poul H. et al., "A Unigue Interhelical Insertion in Plasminogen Activator Inhibitor-2 Contains Three Glutamines, Gln83, Gln84, Gln86, Essential for Transglutaminase-mediated Cross-LinkinQ," 1994 The Journal of BioloQical Chemistry, vol. 269, No. 21 (pp. 15394-15398).

Lundwall et al, Kallikrein-related peptidases, Cellular and Molecular Life Sciences, 2008, 65, pp. 2019-2038.

Mazereeuw-Hautier, Juliette et al., "Topical Recombinant Alpha1-Antitrypsin: A Potential Treatment for Netherton Syndrome?," 2006 Arch Dermatol., vol. 142, No. 3 (pp. 393-403).

Ngo et al., "Computational Complexity, Protein Structure Protection, and the Levinthal Paradox," 1994, pp. 491-494.

Ovaere et al., "The emerging roles of serine protease cascades in the epidermis," Trends in Biochemical Sciences, 2009, 34, pp. 453-463.

Patent Cooperation Treaty Office, International Search Report and Written Opinion, dated Oct. 13, 2009, 13 pgs.

Patent Cooperation Treaty Office, Notification of Transmittal of The International Preliminary Report on Patentability and the International Preliminary Report on Patentability, dated May 3, 2010, 12 pgs.

Patent Cooperation Treaty Office, Notification of Transmittal of the International Search Report and The Written Opinion of the International Searching Authority, or the Declaration, dated Oct. 13, 2009, 3 pgs.

Prassas et al, "Unleashing the therapeutic potential or human Kallikrein-related serine proteases," Nature Reviews/Drug Discovery, 2015, 14, pp. 183-202.

Rudinger, Peptide Hormones, JA Parsons, Ed., 1976, pp. 1-7.

Schecter, N.M. et al., "Inhibition of human kallikrein-5 (SCTE) and -7 (SCEE) by lymphoepithelial Kazal-type inhibitor (LEKTI) supports a role for proteolysis in Netherton disease and desquamation," 2009 Journal of Investigative Dermatology, vol. 124, No. 4, Suppl. S. (2 pages).

Simonovic, Miljan et al., "Crystal structure of viral serpin crmA provides insights into its mechanism of cysteine proteinase inhibition," 2000 Protein Science, vol. 9 (pp. 1423-1427).

Sprecher, Eli et al., "The Spectrum of Pathogenic Mutations in SPINKS in 19 Families with Netherton Syndrome: Implications for Mutation Detection and First Case of Prenatal Diagnosis," 2001 J Invest Dermatol 117 (pp. 179-187).

Stoop, A. Allart et al., "Different Structural Requirements for Plasminogen Activator Inhibitor 1 (PAI-1) during Latency Transition and Proteinase Inhibition as Evidenced by Phage-displayed Hypermutated PAI-1 Libraries," 2001 J. Mol. Biol., vol. 305 (pp. 773-783).

Tian, W., et al., "How Well is Enzyme Function Conserved as a Function of Pairwise Sequence Identity?", 2003, J. Mol. Biol., 333 (pp. 863-882).

Voet et al., Biochemistry, John Wiley & Sons Inc., 1995, pp. 235-241.

Yampolsky et al., "The Exchangeability of Amino Acids in Proteins," Genetics, 2005, 170, pp. 1459-1472.

Felber et al., "Mutant recombinant serpins as highly specific inhibitors of human kallikrein 14," FEBS Journal 273, pp. 2505-2514 (2006).

* cited by examiner

FIG. 1

Italic : start codon ATG
Bold : His-tag
Underlined : DNA mutation
Underlined and grey : DNA sequence encoding RSL mutation.

DNA Sequence ACT variants : MD 820

SEQ ID N°1

*ATG*AGAGGATCCCATCACCATCACCATCACTCTAGACACCCTAACAGCCCACTTGACGAGGAGA
ATCTGACCCAGGAGAACCAAGACCGAGGGACACACGTGGACCTCGGATTAGCCTCCGCCAACGT
GGACTTCGCTTTCAGCCTGTACAAGCAGTTAGTCCTGAAGGCCCCTGATAAGAATGTCATCTTC
TCCCCACTGAGCATCTCCACCGCCTTGGCCTTCCTGTCTCTGGGGGCCCATAATACCACCCTGA
CAGAGATTCTCAAAGGCCTCAAGTTCAACCTCACGGAGACTTCTGAGGCAGAAATTCACCAGAG
CTTCCAGCACCTCCTGCGCACCCTCAATCAGTCCAGCGATGAGCTGCAGCTGAGTATGGGAAAT
GCCATGTTTGTCAAAGAGCAACTCAGTCTGCTGGACAGGTTCACGGAGGATGCCAAGAGGCTGT
ATGGCTCCGAGGCCTTTGCCACTGACTTTCAGGACTCAGCTGCAGCTAAGAAGCTCATCAACGA
CTACGTGAAGAATGGAACTAGGGGGAAAATCACAGATCTGATCAAGGACCTTGACTCGCAGACA
ATGATGGTCCTGGTGAATTACATCTTCTTTAAAGCAAATGGGAGATGCCCTTTGACCCCCAAG
ATACTCATCAGTCAAGGTTCTACTTGAGCAAGAAAAAGTGGGTAATGGTGCCCATGATGAGTTT
GCATCACCTGACTATACCTTACTTCCGGGACGAGGAGCTGTCCTGCACCGTGGTGGAGCTGAAG
TACACAGGCAATGCCAGCGCACTCTTCATCCTCCCTGATCAAGACAAGATGGAGGAAGTGGAAG
CCATGCTGCTCCCAGAGACCCTGAAGCGGTGGAGAGACTCTCTGGAGTTCAGAGAGATAGGTGA
GCTCTACCTGCCAAAGTTTTCCATCTCGAGGGACTATAACCTGAACGACATACTTCTCCAGCTG
GGCATTGAGGAAGCCTTCACCAGCAAGGCTGACCTGTCAGGGATCACAGGGGCCAGGAACCTAG
CAGTCTCCCAGGTGGTCCATAAGGCTGTGCTTGATGTATTTGAGGAGGGCACAGAAGCATCTGC
TGCCACCGCGGTCAAAATCACCCTCCGTTCTCGAGCAGTGGAGACGCGTACCATTGTGCGTTTC
AACAGGCCCTTCCTGATGATCATTGTCCCTACAGACACCCAGAACATCTTCTTCATGAGCAAAG
TCACCAATCCCAAGCAAGCCTAA

Protein Sequence ACT variants : MD 820

SEQ ID N°2

*M*RGSHHHHHHSRHPNSPLDEENLTQENQDRGTHVDLGLASANVDFAFSLYKQLVLKAPDKNVIF
SPLSISTALAFLSLGAHNTTLTEILKGLKFNLTETSEAEIHQSFQHLLRTLNQSSDELQLSMGN
AMFVKEQLSLLDRFTEDAKRLYGSEAFATDFQDSAAAKKLINDYVKNGTRGKITDLIKDLDSQT
MMVLVNYIFFKAKWEMPFDPQDTHQSRFYLSKKKWVMVPMMSLHHLTIPYFRDEELSCTVVELK
YTGNASALFILPDQDKMEEVEAMLLPETLKRWRDSLEFREIGELYLPKFSISRDYNLNDILLQL
GIEEAFTSKADLSGITGARNLAVSQVVHKAVLDVFEEGTEASAATAVKITLRSRAVETRTIVRF
NRPFLMIIVPTDTQNIFFMSKVTNPKQA*

FIG. 2

Italic : start codon ATG
Bold : His-tag
Underlined : DNA mutation
Underlined and grey : DNA sequence encoding RSL mutation.

DNA Sequence ACT variant : MD 62

SEQ ID N°3

*ATG*AGAGGATCCCATCACCATCACCATCACTCTAGACACCCTAACAGCCCACTTGACGAGGAGA
ATCTGACCCAGGAGAACCAAGACCGAGGGACACACGTGGACCTCGGATTAGCCTCCGCCAACGT
GGACTTCGCTTTCAGCCTGTACAAGCAGTTAGTCCTGAAGGCCCCTGATAAGAATGTCATCTTC
TCCCCACTGAGCATCTCCACCGCCTTGGCCTTCCTGTCTCTGGGGGCCCATAATACCACCCTGA
CAGAGATTCTCAAAGGCCTCAAGTTCAACCTCACGGAGACTTCTGAGGCAGAAATTCACCAGAG
CTTCCAGCACCTCCTGCGCACCCTCAATCAGTCCAGCGATGAGCTGCAGCTGAGTATGGGAAAT
GCCATGTTTGTCAAAGAGCAACTCAGTCTGCTGGACAGGTTCACGGAGGATGCCAAGAGGCTGT
ATGGCTCCGAGGCCTTTGCCACTGACTTTCAGGACTCAGCTGCAGCTAAGAAGCTCATCAACGA
CTACGTGAAGAATGGAACTAGGGGGAAAATCACAGATCTGATCAAGGACCTTGACTCGCAGACA
ATGATGGTCCTGGTGAATTACATCTTCTTTAAAGCCAAATGGGAGATGCCCTTTGACCCCCAAG
ATACTCATCAGTCAAGGTTCTACTTGAGCAAGAAAAAGTGGGTAATGGTGCCCATGATGAGTTT
GCATCACCTGACTATACCTTACTTCCGGGACGAGGAGCTGTCCTGCACCGTGGTGGAGCTGAAG
TACACAGGCAATGCCAGCGCACTCTTCATCCTCCCTGATCAAGACAAGATGGAGGAAGTGGAAG
CCATGCTGCTCCCAGAGACCCTGAAGCGGTGGAGAGACTCTCTGGAGTTCAGAGAGATAGGTGA
GCTCTACCTGCCAAAGTTTTCCATCTCGAGGGACTATAACCTGAACGACATACTTCTCCAGCTG
GGCATTGAGGAAGCCTTCACCAGCAAGGCTGACCTGTCAGGGATCACAGGGGCCAGGAACCTAG
CAGTCTCCCAGGTGGTCCATAAGGCTGTGCTTGATGTATTTGAGGAGGGCACAGAAGCATCTGC
TGCCACCGCGGTCAAAATCACC<u>AGGAGG</u>TC<u>TATCGAT</u>GTGGAGAC<u>G</u>CGTACCATTGTGCGTTTC
AACAGGCCCTTCCTGATGATCATTGTCCCTACAGACACCCAGAACATCTTCTTCATGAGCAAAG
TCACCAATCCCAAGCAAGCCTAA

Protein Sequence ACT variant : MD 62

SEQ ID N°4

*M*RGSHHHHHHSRHPNSPLDEENLTQENQDRGTHVDLGLASANVDFAFSLYKQLVLKAPDKNVIF
SPLSISTALAFLSLGAHNTTLTEILKGLKFNLTETSEAEIHQSFQHLLRTLNQSSDELQLSMGN
AMFVKEQLSLLDRFTEDAKRLYGSEAFATDFQDSAAAKKLINDYVKNGTRGKITDLIKDLDSQT
MMVLVNYIFFKAKWEMPFDPQDTHQSRFYLSKKKWVMVPMMSLHHLTIPYFRDEELSCTVVELK
YTGNASALFILPDQDKMEEVEAMLLPETLKRWRDSLEFREIGELYLPKFSISRDYNLNDILLQL
GIEEAFTSKADLSGITGARNLAVSQVVHKAVLDVFEEGTEASAATAVKIT<u>RRSID</u>VETRTIVRF
NRPFLMIIVPTDTQNIFFMSKVTNPKQA*

FIG. 3

Italic : start codon ATG
Bold : His-tag
Underlined : DNA mutation
Underlined and grey : DNA sequence encoding RSL mutation.

DNA Sequence ACT variant : MD 83

SEQ ID N°5

*ATG*AGAGGATCCCATCACCATCACCATCACTCTAGACACCCTAACAGCCCACTTGACGAGGAGA
ATCTGACCCAGGAGAACCAAGACCGAGGGACACACGTGGACCTCGGATTAGCCTCCGCCAACGT
GGACTTCGCTTTCAGCCTGTACAAGCAGTTAGTCCTGAAGGCCCCTGATAAGAATGTCATCTTC
TCCCCACTGAGCATCTCCACCGCCTTGGCCTTCCTGTCTCTGGGGGCCCATAATACCACCCTGA
CAGAGATTCTCAAAGGCCTCAAGTTCAACCTCACGGAGACTTCTGAGGCAGAAATTCACCAGAG
CTTCCAGCACCTCCTGCGCACCCTCAATCAGTCCAGCGATGAGCTGCAGCTGAGTATGGGAAAT
GCCATGTTTGTCAAAGAGCAACTCAGTCTGCTGGACAGGTTCACGGAGGATGCCAAGAGGCTGT
ATGGCTCCGAGGCCTTTGCCACTGACTTTCAGGACTCAGCTGCAGCTAAGAAGCTCATCAACGA
CTACGTGAAGAATGGAACTAGGGGGAAAATCACAGATCTGATCAAGGACCTTGACTCGCAGACA
ATGATGGTCCTGGTGAATTACATCTTCTTTAAAGCCAAATGGGAGATGCCCTTTGACCCCCAAG
ATACTCATCAGTCAAGGTTCTACTTGAGCAAGAAAAAGTGGGTAATGGTGCCCATGATGAGTTT
GCATCACCTGACTATACCTTACTTCCGGGACGAGGAGCTGTCCTGCACCGTGGTGGAGCTGAAG
TACACAGGCAATGCCAGCGCACTCTTCATCCTCCCTGATCAAGACAAGATGGAGGAAGTGGAAG
CCATGCTGCTCCCAGAGACCCTGAAGCGGTGGAGAGACTCTCTGGAGTTCAGAGAGATAGGTGA
GCTCTACCTGCCAAAGTTTTCCATCTCGAGGGACTATAACCTGAACGACATACTTCTCCAGCTG
GGCATTGAGGAAGCCTTCACCAGCAAGGCTGACCTGTCAGGGATCACAGGGGCCAGGAACCTAG
CAGTCTCCCAGGTGGTCCATAAGGCTGTGCTTGATGTATTTGAGGAGGGCACAGAAGCATCTGC
TGCCACCGCGGTCAAAATCAGGGGGAGATCTGAGTTAGTGGAGACGCGTACCATTGTGCGTTTC
AACAGGCCCTTCCTGATGATCATTGTCCCTACAGACACCCAGAACATCTTCTTCATGAGCAAAG
TCACCAATCCCAAGCAAGCCTAA

Protein Sequence ACT variant : MD 83

SEQ ID N°6

MRGSHHHHHHSRHPNSPLDEENLTQENQDRGTHVDLGLASANVDFAFSLYKQLVLKAPDKNVIF
SPLSISTALAFLSLGAHNTTLTEILKGLKFNLTETSEAEIHQSFQHLLRTLNQSSDELQLSMGN
AMFVKEQLSLLDRFTEDAKRLYGSEAFATDFQDSAAAKKLINDYVKNGTRGKITDLIKDLDSQT
MMVLVNYIFFKAKWEMPFDPQDTHQSRFYLSKKKWVMVPMMSLHHLTIPYFRDEELSCTVVELK
YTGNASALFILPDQDKMEEVEAMLLPETLKRWRDSLEFREIGELYLPKFSISRDYNLNDILLQL
GIEEAFTSKADLSGITGARNLAVSQVVHKAVLDVFEEGTEASAATAVKIRGRSELVETRTIVRF
NRPFLMIIVPTDTQNIFFMSKVTNPKQA*

FIG. 4

Italic : start codon ATG
Bold : His-tag
Underlined : DNA mutation
Underlined and grey : DNA sequence encoding RSL mutation.

DNA Sequence ACT variant : MD 67

SEQ ID N°7

*ATG*AGAGGATCCCATCACCATCACCATCACTCTAGACACCCTAACAGCCCACTTGACGAGGAGA
ATCTGACCCAGGAGAACCAAGACCGAGGGACACACGTGGACCTCGGATTAGCCTCCGCCAACGT
GGACTTCGCTTTCAGCCTGTACAAGCAGTTAGTCCTGAAGGCCCCTGATAAGAATGTCATCTTC
TCCCCACTGAGCATCTCCACCGCCTTGGCCTTCCTGTCTCTGGGGGCCCATAATACCACCCTGA
CAGAGATTCTCAAAGGCCTCAAGTTCAACCTCACGGAGACTTCTGAGGCAGAAATTCACCAGAG
CTTCCAGCACCTCCTGCGCACCCTCAATCAGTCCAGCGATGAGCTGCAGCTGAGTATGGGAAAT
GCCATGTTTGTCAAAGAGCAACTCAGTCTGCTGGACAGGTTCACGGAGGATGCCAAGAGGCTGT
ATGGCTCCGAGGCCTTTGCCACTGACTTTCAGGACTCAGCTGCAGCTAAGAAGCTCATCAACGA
CTACGTGAAGAATGGAACTAGGGGGAAAATCACAGATCTGATCAAGGACCTTGACTCGCAGACA
ATGATGGTCCTGGTGAATTACATCTTCTTTAAAGCCAAATGGGAGATGCCCTTTGACCCCCAAG
ATACTCATCAGTCAAGGTTCTACTTGAGCAAGAAAAAGTGGGTAATGGTGCCCATGATGAGTTT
GCATCACCTGACTATACCTTACTTCCGGGACGAGGAGCTGTCCTGCACCGTGGTGGAGCTGAAG
TACACAGGCAATGCCAGCGCACTCTTCATCCTCCCTGATCAAGACAAGATGGAGGAAGTGGAAG
CCATGCTGCTCCCAGAGACCCTGAAGCGGTGGAGAGACTCTCTGGAGTTCAGAGAGATAGGTGA
GCTCTACCTGCCAAAGTTTTCCATCTCGAGGGACTATAACCTGAACGACATACTTCTCCAGCTG
GGCATTGAGGAAGCCTTCACCAGCAAGGCTGACCTGTCAGGGATCACAGGGGCCAGGAACCTAG
CAGTCTCCCAGGTGGTCCATAAGGCTGTGCTTGATGTATTTGAGGAGGGCACAGAAGCATCTGC
TGCCACCGCGGTCAAAATCA<u>AGCTTAGAACAA</u>CATTAGTGGAGACG<u>CG</u>TACCATTGTGCGTTTC
AACAGGCCCTTCCTGATGATCATTGTCCCTACAGACACCCAGAACATCTTCTTCATGAGCAAAG
TCACCAATCCCAAGCAAGCCTAA

Protein Sequence ACT variant: MD 67

SEQ ID N°8

MRGSHHHHHHSRHPNSPLDEENLTQENQDRGTHVDLGLASANVDFAFSLYKQLVLKAPDKNVIF
SPLSISTALAFLSLGAHNTTLTEILKGLKFNLTETSEAEIHQSFQHLLRTLNQSSDELQLSMGN
AMFVKEQLSLLDRFTEDAKRLYGSEAFATDFQDSAAAKKLINDYVKNGTRGKITDLIKDLDSQT
MMVLVNYIFFKAKWEMPFDPQDTHQSRFYLSKKKWVMVPMMSLHHLTIPYFRDEELSCTVVELK
YTGNASALFILPDQDKMEEVEAMLLPETLKRWRDSLEFREIGELYLPKFSISRDYNLNDILLQL
GIEEAFTSKADLSGITGARNLAVSQVVHKAVLDVFEEGTEASAATAVKI<u>KLRTT</u>LVETRTIVRF
NRPFLMIIVPTDTQNIFFMSKVTNPKQA*

FIG. 5

Italic : start codon ATG
Bold : His-tag
Underlined : DNA mutation
Underlined and grey : DNA sequence encoding RSL mutation.

DNA Sequence ACT variant : MD 61

SEQ ID N°9

*ATG*AGAGGATCCCATCACCATCACCATCACTCTAGACACCCTAACAGCCCACTTGACGAGGAGA
ATCTGACCCAGGAGAACCAAGACCGAGGGACACACGTGGACCTCGGATTAGCCTCCGCCAACGT
GGACTTCGCTTTCAGCCTGTACAAGCAGTTAGTCCTGAAGGCCCCTGATAAGAATGTCATCTTC
TCCCCACTGAGCATCTCCACCGCCTTGGCCTTCCTGTCTCTGGGGGCCCATAATACCACCCTGA
CAGAGATTCTCAAAGGCCTCAAGTTCAACCTCACGGAGACTTCTGAGGCAGAAATTCACCAGAG
CTTCCAGCACCTCCTGCGCACCCTCAATCAGTCCAGCGATGAGCTGCAGCTGAGTATGGGAAAT
GCCATGTTTGTCAAAGAGCAACTCAGTCTGCTGGACAGGTTCACGGAGGATGCCAAGAGGCTGT
ATGGCTCCGAGGCCTTTGCCACTGACTTTCAGGACTCAGCTGCAGCTAAGAAGCTCATCAACGA
CTACGTGAAGAATGGAACTAGGGGGAAAATCACAGATCTGATCAAGGACCTTGACTCGCAGACA
ATGATGGTCCTGGTGAATTACATCTTCTTTAAAGCCAAATGGGAGATGCCCTTTGACCCCCAAG
ATACTCATCAGTCAAGGTTCTACTTGAGCAAGAAAAGTGGGTAATGGTGCCCATGATGAGTTT
GCATCACCTGACTATACCTTACTTCCGGGACGAGGAGCTGTCCTGCACCGTGGTGGAGCTGAAG
TACACAGGCAATGCCAGCGCACTCTTCATCCTCCCTGATCAAGACAAGATGGAGGAAGTGGAAG
CCATGCTGCTCCCAGAGACCCTGAAGCGGTGGAGAGACTCTCTGGAGTTCAGAGAGATAGGTGA
GCTCTACCTGCCAAAGTTTTCCATCTCGAGGGACTATAACCTGAACGACATACTTCTCCAGCTG
GGCATTGAGGAAGCCTTCACCAGCAAGGCTGACCTGTCAGGGATCACAGGGGCCAGGAACCTAG
CAGTCTCCCAGGTGGTCCATAAGGCTGTGCTTGATGTATTTGAGGAGGGCACAGAAGCATCTGC
TGCCACCGCGGTCAAAATCATGACAAGATCTAACGCAGTGGAGACGCGTACCATTGTGCGTTTC
AACAGGCCCTTCCTGATGATCATTGTCCCTACAGACACCCAGAACATCTTCTTCATGAGCAAAG
TCACCAATCCCAAGCAAGCCTAA

Protein Sequence ACT variant : MD 61

SEQ ID N°10

MRGSHHHHHHSRHPNSPLDEENLTQENQDRGTHVDLGLASANVDFAFSLYKQLVLKAPDKNVIF
SPLSISTALAFLSLGAHNTTLTEILKGLKFNLTETSEAEIHQSFQHLLRTLNQSSDELQLSMGN
AMFVKEQLSLLDRFTEDAKRLYGSEAFATDFQDSAAAKKLINDYVKNGTRGKITDLIKDLDSQT
MMVLVNYIFFKAKWEMPFDPQDTHQSRFYLSKKKWVMVPMMSLHHLTIPYFRDEELSCTVVELK
YTGNASALFILPDQDKMEEVEAMLLPETLKRWRDSLEFREIGELYLPKFSISRDYNLNDILLQL
GIEEAFTSKADLSGITGARNLAVSQVVHKAVLDVFEEGTEASAATAVKIMTRSNAVETRTIVRF
NRPFLMIIVPTDTQNIFFMSKVTNPKQA*

FIG. 6

Italic : start codon ATG
Bold : His-tag
Underlined : DNA mutation
Underlined and grey : DNA sequence encoding RSL mutation.

DNA Sequence ACT variants : MD 518

SEQ ID N°11

*ATG*AGAGGATCCCATCACCATCACCATCACTCTAGACACCCTAACAGCCCACTTGACGAGGAGA
ATCTGACCCAGGAGAACCAAGACCGAGGGACACACGTGGACCTCGGATTAGCCTCCGCCAACGT
GGACTTCGCTTTCAGCCTGTACAAGCAGTTAGTCCTGAAGGCCCCTGATAAGAATGTCATCTTC
TCCCCACTGAGCATCTCCACCGCCTTGGCCTTCCTGTCTCTGGGGGCCCATAATACCACCCTGA
CAGAGATTCTCAAAGGCCTCAAGTTCAACCTCACGGAGACTTCTGAGGCAGAAATTCACCAGAG
CTTCCAGCACCTCCTGCGCACCCTCAATCAGTCCAGCGATGAGCTGCAGCTGAGTATGGGAAAT
GCCATGTTTGTCAAAGAGCAACTCAGTCTGCTGGACAGGTTCACGGAGGATGCCAAGAGGCTGT
ATGGCTCCGAGGCCTTTGCCACTGACTTTCAGGACTCAGCTGCAGCTAAGAAGCTCATCAACGA
CTACGTGAAGAATGGAACTAGGGGGAAAATCACAGATCTGATCAAGGACCTTGACTCGCAGACA
ATGATGGTCCTGGTGAATTACATCTTCTTTAAAGCCAATGGGAGATGCCCTTTGACCCCCAAG
ATACTCATCAGTCAAGGTTCTACTTGAGCAAGAAAAGTGGGTAATGGTGCCCATGATGAGTTT
GCATCACCTGACTATACCTTACTTCCGGGACGAGGAGCTGTCCTGCACCGTGGTGGAGCTGAAG
TACACAGGCAATGCCAGCGCACTCTTCATCCTCCCTGATCAAGACAAGATGGAGGAAGTGGAAG
CCATGCTGCTCCCAGAGACCCTGAAGCGGTGGAGAGACTCTCTGGAGTTCAGAGAGATAGGTGA
GCTCTACCTGCCAAAGTTTTCCATCTCGAGGGACTATAACCTGAACGACATACTTCTCCAGCTG
GGCATTGAGGAAGCCTTCACCAGCAAGGCTGACCTGTCAGGGATCACAGGGGCCAGGAACCTAG
CAGTCTCCCAGGTGGTCCATAAGGCTGTGCTTGATGTATTTGAGGAGGGCACAGAAGCATCTGC
TGCCAC<u>C</u>GCGGTCAAAATCACC<u>GAGCGTGTCTCGCCC</u>GTGGAGAC<u>G</u>CGTACCATTGTGCGTTTC
AACAGGCCCTTCCTGATGATCATTGTCCCTACAGACACCCAGAACATCTTCTTCATGAGCAAAG
TCACCAATCCCAAGCAAGCCTAA

Protein Sequence ACT variants: MD 518

SEQ ID N°12

*M*RGSHHHHHHSRHPNSPLDEENLTQENQDRGTHVDLGLASANVDFAFSLYKQLVLKAPDKNVIF
SPLSISTALAFLSLGAHNTTLTEILKGLKFNLTETSEAEIHQSFQHLLRTLNQSSDELQLSMGN
AMFVKEQLSLLDRFTEDAKRLYGSEAFATDFQDSAAAKKLINDYVKNGTRGKITDLIKDLDSQT
MMVLVNYIFFKAKWEMPFDPQDTHQSRFYLSKKKWVMVPMMSLHHLTIPYFRDEELSCTVVELK
YTGNASALFILPDQDKMEEVEAMLLPETKRWRDSLEFREIGELYLPKFSISRDYNLNDILLQL
GIEEAFTSKADLSGITGARNLAVSQVVHKAVLDVFEEGTEASAATAVKIT<u>ERVSP</u>VETRTIVRF
NRPFLMIIVPTDTQNIFFMSKVTNPKQA*

FIG. 7

Italic : start codon ATG
Bold : His-tag
Underlined : DNA mutation
Underlined and grey : DNA sequence encoding RSL mutation.

DNA Sequence ACT variants : MDCl

SEQ ID N°13

*ATG*AGAGGATCCCATCACCATCACCATCACTCTAGACACCCTAACAGCCCACTTGACGAGGAGA
ATCTGACCCAGGAGAACCAAGACCGAGGGACACACGTGGACCTCGGATTAGCCTCCGCCAACGT
GGACTTCGCTTTCAGCCTGTACAAGCAGTTAGTCCTGAAGGCCCCTGATAAGAATGTCATCTTC
TCCCCACTGAGCATCTCCACCGCCTTGGCCTTCCTGTCTCTGGGGGCCCATAATACCACCCTGA
CAGAGATTCTCAAAGGCCTCAAGTTCAACCTCACGGAGACTTCTGAGGCAGAAATTCACCAGAG
CTTCCAGCACCTCCTGCGCACCCTCAATCAGTCCAGCGATGAGCTGCAGCTGAGTATGGGAAAT
GCCATGTTTGTCAAAGAGCAACTCAGTCTGCTGGACAGGTTCACGGAGGATGCCAAGAGGCTGT
ATGGCTCCGAGGCCTTTGCCACTGACTTTCAGGACTCAGCTGCAGCTAAGAAGCTCATCAACGA
CTACGTGAAGAATGGAACTAGGGGGAAAATCACAGATCTGATCAAGGACCTTGACTCGCAGACA
ATGATGGTCCTGGTGAATTACATCTTCTTTAAAGCCAAATGGGAGATGCCCTTTGACCCCCAAG
ATACTCATCAGTCAAGGTTCTACTTGAGCAAGAAAAGTGGGTAATGGTGCCCATGATGAGTTT
GCATCACCTGACTATACCTTACTTCCGGGACGAGGAGCTGTCCTGCACCGTGGTGGAGCTGAAG
TACACAGGCAATGCCAGCGCACTCTTCATCCTCCCTGATCAAGACAAGATGGAGGAAGTGGAAG
CCATGCTGCTCCCAGAGACCCTGAAGCGGTGGAGAGACTCTCTGGAGTTCAGAGAGATAGGTGA
GCTCTACCTGCCAAAGTTTTCCATCTCGAGGGACTATAACCTGAACGACATACTTCTCCAGCTG
GGCATTGAGGAAGCCTTCACCAGCAAGGCTGACCTGTCAGGGATCACAGGGGCCAGGAACCTAG
CAGTCTCCCAGGTGGTCCATAAGGCTGTGCTTGATGTATTTGAGGAGGGCACAGAAGCATCTGC
TGCCACCGCGGTCAAAATCACC<u>TTTAGA</u>TCTGCATTAGTGGAGAC<u>G</u>CGTACCATTGTGCGTTTC
AACAGGCCCTTCCTGATGATCATTGTCCCTACAGACACCCAGAACATCTTCTTCATGAGCAAAG
TCACCAATCCCAAGCAAGCCTAA

Protein Sequence ACT variants: MD Cl

SEQ ID N°14

MRGSHHHHHHSRHPNSPLDEENLTQENQDRGTHVDLGLASANVDFAFSLYKQLVLKAPDKNVIF
SPLSISTALAFLSLGAHNTTLTEILKGLKFNLTETSEAEIHQSFQHLLRTLNQSSDELQLSMGN
AMFVKEQLSLLDRFTEDAKRLYGSEAFATDFQDSAAAKKLINDYVKNGTRGKITDLIKDLDSQT
MMVLVNYIFFKAKWEMPFDPQDTHQSRFYLSKKKWVMVPMMSLHHLTIPYFRDEELSCTVVELK
YTGNASALFILPDQDKMEEVEAMLLPETLKRWRDSLEFREIGELYLPKFSISRDYNLNDILLQL
GIEEAFTSKADLSGITGARNLAVSQVVHKAVLDVFEEGTEASAATAVKITF̲RSALVETRTIVRF
NRPFLMIIVPTDTQNIFFMSKVTNPKQA*

FIG. 8

Legend

```
Italic and bold : start codon ATG
Bold and underlined: His-tag
Underlined : DNA mutation (added codon)
Underlined and grey : DNA sequence encoding RSL mutation.
```

SEQ ID N° 16 :   DNA SEQUENCE ACT-MS : ACT-WILD TYPE(WT)

ATGAGAGGATCCCATCACCATCACCATCACTCTAGACACCCTAACAGCCCACTTGACGAGGAGA
ATCTGACCCAGGAGAACCAAGACCGAGGGACACACGTGGACCTCGGATTAGCCTCCGCCAACGT
GGACTTCGCTTTCAGCCTGTACAAGCAGTTAGTCCTGAAGGCCCCTGATAAGAATGTCATCTTC
TCCCCACTGAGCATCTCCACCGCCTTGGCCTTCCTGTCTCTGGGGGCCCATAATACCACCCTGA
CAGAGATTCTCAAAGGCCTCAAGTTCAACCTCACGGAGACTTCTGAGGCAGAAATTCACCAGAG
CTTCCAGCACCTCCTGCGCACCCTCAATCAGTCCAGCGATGAGCTGCAGCTGAGTATGGGAAAT
GCCATGTTTGTCAAAGAGCAACTCAGTCTGCTGGACAGGTTCACGGAGGATGCCAAGAGGCTGT
ATGGCTCCGAGGCCTTTGCCACTGACTTTCAGGACTCAGCTGCAGCTAAGAAGCTCATCAACGA
CTACGTGAAGAATGGAACTAGGGGAAAATCACAGATCTGATCAAGGACCTTGACTCGCAGACA
ATGATGGTCCTGGTGAATTACATCTTCTTTAAAGCCAAATGGGAGATGCCCTTTGACCCCCAAG
ATACTCATCAGTCAAGGTTCTACTTGAGCAAGAAAAGTGGGTAATGGTGCCCATGATGAGTTT
GCATCACCTGACTATACCTTACTTCCGGGACGAGGAGCTGTCCTGCACCGTGGTGGAGCTGAAG
TACACAGGCAATGCCAGCGCACTCTTCATCCTCCCTGATCAAGACAAGATGGAGGAAGTGGAAG
CCATGCTGCTCCCAGAGACCCTGAAGCGGTGGAGAGACTCTCTGGAGTTCAGAGAGATAGGTGA
GCTCTACCTGCCAAAGTTTTCCATCTCGAGGGACTATAACCTGAACGACATACTTCTCCAGCTG
GGCATTGAGGAAGCCTTCACCAGCAAGGCTGACCTGTCAGGGATCACAGGGGCCAGGAACCTAG
CAGTCTCCCAGGTGGTCCATAAGGCTGTGCTTGATGTATTTGAGGAGGGCACAGAAGCATCTGC
TGCCACCGCGGTCAAAATCACCCTCCTTTCTGCATTAGTGGAGACGCTACCATTGTGCGTTTC
AACAGGCCCTTCCTGATGATCATTGTCCCTACAGACACCCAGAACATCTTCTTCATGAGCAAAG
TCACCAATCCCAAGCAAGCCTAA

Legend

```
Italic and bold: start Methionin
Bold and underlined: His-tag
Underlined : amino acid mutation (added)
Underlined and grey : RSL mutation
```

SEQ ID N° 38:   PROTEIN SEQUENCE ACT-MS : ACT-WT

MRGSHHHHHHSRHPNSPLDEENLTQENQDRGTHVDLGLASANVDFAFSLYKQLVLKAPDKNVIF
SPLSISTALAFLSLGAHNTTLTEILKGLKFNLTETSEAEIHQSFQHLLRTLNQSSDELQLSMGN
AMFVKEQLSLLDRFTEDAKRLYGSEAFATDFQDSAAAKKLINDYVKNGTRGKITDLIKDLDSQT
MMVLVNYIFFKAKWEMPFDPQDTHQSRFYLSKKKWVMVPMMSLHHLTIPYFRDEELSCTVVELK
YTGNASALFILPDQDKMEEVEAMLLPETLKRWRDSLEFREIGELYLPKFSISRDYNLNDILLQL
GIEEAFTSKADLSGITGARNLAVSQVVHKAVLDVFEEGTEASAATAVKITLLSALVETRTIVRF
NRPFLMIIVPTDTQNIFFMSKVTNPKQA*

FIG. 9

Legend

```
Italic and bold : start codon ATG
Bold and underlined: His-tag
Underlined : DNA mutation (added codon)
Underlined and grey : DNA sequence encoding RSL mutation.
```

SEQ ID N° 17 :   DNA SEQUENCE: ACT-G1

*ATG*AGAGGATCCCATCACCATCACCATCACTCTAGACACCCTAACAGCCCACTTGACGAGGAGA
ATCTGACCCAGGAGAACCAAGACCGAGGGACACACGTGGACCTCGGATTAGCCTCCGCCAACGT
GGACTTCGCTTTCAGCCTGTACAAGCAGTTAGTCCTGAAGGCCCCTGATAAGAATGTCATCTTC
TCCCCACTGAGCATCTCCACCGCCTTGGCCTTCCTGTCTCTGGGGGCCCATAATACCACCCTGA
CAGAGATTCTCAAAGGCCTCAAGTTCAACCTCACGGAGACTTCTGAGGCAGAAATTCACCAGAG
CTTCCAGCACCTCCTGCGCACCCTCAATCAGTCCAGCGATGAGCTGCAGCTGAGTATGGGAAAT
GCCATGTTTGTCAAAGAGCAACTCAGTCTGCTGGACAGGTTCACGGAGGATGCCAAGAGGCTGT
ATGGCTCCGAGGCCTTTGCCACTGACTTTCAGGACTCAGCTGCAGCTAAGAAGCTCATCAACGA
CTACGTGAAGAATGGAACTAGGGGGAAAATCACAGATCTGATCAAGGACCTTGACTCGCAGACA
ATGATGGTCCTGGTGAATTACATCTTCTTTAAAGCCAAATGGGAGATGCCCTTTGACCCCCAAG
ATACTCATCAGTCAAGGTTCTACTTGAGCAAGAAAAGTGGGTAATGGTGCCCATGATGAGTTT
GCATCACCTGACTATACCTTACTTCCGGGACGAGGAGCTGTCCTGCACCGTGGTGGAGCTGAAG
TACACAGGCAATGCCAGCGCACTCTTCATCCTCCCTGATCAAGACAAGATGGAGGAAGTGGAAG
CCATGCTGCTCCCAGAGACCCTGAAGCGGTGGAGAGACTCTCTGGAGTTCAGAGAGATAGGTGA
GCTCTACCTGCCAAAGTTTTCCATCTCGAGGGACTATAACCTGAACGACATACTTCTCCAGCTG
GGCATTGAGGAAGCCTTCACCAGCAAGGCTGACCTGTCAGGGATCACAGGGGCCAGGAACCTAG
CAGTCTCCCAGGTGGTCCATAAGGCTGTGCTTGATGTATTTGAGGAGGGCACAGAAGCATCTGC
TGCCAC<u>C</u>GC<u>G</u>GTCAAA<u>GGTTC</u>T<u>C</u>TG<u>C</u>GTTCTGC<u>TCT</u>GGTGGAGAC<u>GCG</u>TACCATTGTGCGTTTC
AACAGGCCCTTCCTGATGATCATTGTCCCTACAGACACCCAGAACATCTTCTTCATGAGCAAAG
TCACCAATCCCAAGCAAGCCTAA

SEQ ID N° 39:   PROTEIN SEQUENCE: ACT-G1

Legend

```
Italic and bold: start Methionin
Bold and underlined: His-tag
Underlined : amino acid mutation(added)
Underlined and grey : RSL mutation
```

*M*RGSHHHHHHSRHPNSPLDEENLTQENQDRGTHVDLGLASANVDFAFSLYKQLVLKAPDKNVIF
SPLSISTALAFLSLGAHNTTLTEILKGLKFNLTETSEAEIHQSFQHLLRTLNQSSDELQLSMGN
AMFVKEQLSLLDRFTEDAKRLYGSEAFATDFQDSAAAKKLINDYVKNGTRGKITDLIKDLDSQT
MMVLVNYIFFKAKWEMPFDPQDTHQSRFYLSKKKWVMVPMMSLHHLTIPYFRDEELSCTVVELK
YTGNASALFILPDQDKMEEVEAMLLPETLKRWRDSLEFREIGELYLPKFSISRDYNLNDILLQL
GIEEAFTSKADLSGITGARNLAVSQVVHKAVLDVFEEGTEASAATAVK<u>GS</u>L<u>R</u>SALVETRTIVRF
NRPFLMIIVPTDTQNIFFMSKVTNPKQA*

FIG. 10

Legend

```
Italic and bold : start codon ATG
Bold and underlined: His-tag
Underlined : DNA mutation (added codon)
Underlined and grey : DNA sequence encoding RSL mutation.
```

SEQ ID N° 18 :   DNA Sequence: ACT-G1G

*ATG*AGAGGATCCCATCACCATCACCATCACTCTAGACACCCTAACAGCCCACTTGACGAGGAGA
ATCTGACCCAGGAGAACCAAGACCGAGGGACACACGTGGACCTCGGATTAGCCTCCGCCAACGT
GGACTTCGCTTTCAGCCTGTACAAGCAGTTAGTCCTGAAGGCCCCTGATAAGAATGTCATCTTC
TCCCCACTGAGCATCTCCACCGCCTTGGCCTTCCTGTCTCTGGGGGCCCATAATACCACCCTGA
CAGAGATTCTCAAAGGCCTCAAGTTCAACCTCACGGAGACTTCTGAGGCAGAAATTCACCAGAG
CTTCCAGCACCTCCTGCGCACCCTCAATCAGTCCAGCGATGAGCTGCAGCTGAGTATGGGAAAT
GCCATGTTTGTCAAAGAGCAACTCAGTCTGCTGGACAGGTTCACGGAGGATGCCAAGAGGCTGT
ATGGCTCCGAGGCCTTTGCCACTGACTTTCAGGACTCAGCTGCAGCTAAGAAGCTCATCAACGA
CTACGTGAAGAATGGAACTAGGGGGAAAATCACAGATCTGATCAAGGACCTTGACTCGCAGACA
ATGATGGTCCTGGTGAATTACATCTTCTTTAAAGCCAAATGGGAGATGCCCTTTGACCCCCAAG
ATACTCATCAGTCAAGGTTCTACTTGAGCAAGAAAAGTGGGTAATGGTGCCCATGATGAGTTT
GCATCACCTGACTATACCTTACTTCCGGGACGAGGAGCTGTCCTGCACCGTGGTGGAGCTGAAG
TACACAGGCAATGCCAGCGCACTCTTCATCCTCCCTGATCAAGACAAGATGGAGGAAGTGGAAG
CCATGCTGCTCCCAGAGACCCTGAAGCGGTGGAGAGACTCTCTGGAGTTCAGAGAGATAGGTGA
GCTCTACCTGCCAAAGTTTTCCATCTCGAGGGACTATAACCTGAACGACATACTTCTCCAGCTG
GGCATTGAGGAAGCCTTCACCAGCAAGGCTGACCTGTCAGGGATCACAGGGGCCAGGAACCTAG
CAGTCTCCCAGGTGGTCCATAAGGCTGTGCTTGATGTATTTGAGGAGGGCACAGAAGCATCTGC
TGCCAC<u>CGCG</u>GTCAAA<u>GGTTCT</u>CT<u>GCGTGG</u>TGC<u>TCT</u>GGTGGAGAC<u>GCG</u>TACCATTGTGCGTTTC
AACAGGCCCTTCCTGATGATCATTGTCCCTACAGACACCCAGAACATCTTCTTCATGAGCAAAG
TCACCAATCCCAAGCAAGCCTAA

SEQ ID N° 40:   Protein Sequence: ACT-G1G

Legend

```
Italic and bold: start Methionin
Bold and underlined: His-tag
Underlined : amino acid mutation(added)
Underlined and grey : RSL mutation
```

*M*RGSHHHHHHSRHPNSPLDEENLTQENQDRGTHVDLGLASANVDFAFSLYKQLVLKAPDKNVIF
SPLSISTALAFLSLGAHNTTLTEILKGLKFNLTETSEAEIHQSFQHLLRTLNQSSDELQLSMGN
AMFVKEQLSLLDRFTEDAKRLYGSEAFATDFQDSAAAKKLINDYVKNGTRGKITDLIKDLDSQT
MMVLVNYIFFKAKWEMPFDPQDTHQSRFYLSKKKWVMVPMMSLHHLTIPYFRDEELSCTVVELK
YTGNASALFILPDQDKMEEVEAMLLPETLKRWRDSLEFREIGELYLPKFSISRDYNLNDILLQL
GIEEAFTSKADLSGITGARNLAVSQVVHKAVLDVFEEGTEASAATAVK<u>GSL</u><u>RG</u>ALVETRTIVRF
NRPFLMIIVPTDTQNIFFMSKVTNPKQA*

FIG. 11

Legend

```
Italic and bold: start codon ATG
Bold and underlined: His-tag
Underlined : DNA mutation (added codon)
Underlined and grey : DNA sequence encoding RSL mutation.
```

SEQ ID N° 19 :     DNA SEQUENCE: ACT-C11

*ATGAGAGGATCCCATCACCATCACCATCACTCTAGACACCCTAACAGCCCACTTGACGAGGAGA
ATCTGACCCAGGAGAACCAAGACCGAGGGACACACGTGGACCTCGGATTAGCCTCCGCCAACGT
GGACTTCGCTTTCAGCCTGTACAAGCAGTTAGTCCTGAAGGCCCCTGATAAGAATGTCATCTTC
TCCCCACTGAGCATCTCCACCGCCTTGGCCTTCCTGTCTCTGGGGGCCCATAATACCACCCTGA
CAGAGATTCTCAAAGGCCTCAAGTTCAACCTCACGGAGACTTCTGAGGCAGAAATTCACCAGAG
CTTCCAGCACCTCCTGCGCACCCTCAATCAGTCCAGCGATGAGCTGCAGCTGAGTATGGGAAAT
GCCATGTTTGTCAAAGAGCAACTCAGTCTGCTGGACAGGTTCACGGAGGATGCCAAGAGGCTGT
ATGGCTCCGAGGCCTTTGCCACTGACTTTCAGGACTCAGCTGCAGCTAAGAAGCTCATCAACGA
CTACGTGAAGAATGGAACTAGGGGGAAAATCACAGATCTGATCAAGGACCTTGACTCGCAGACA
ATGATGGTCCTGGTGAATTACATCTTCTTTAAAGCCAAATGGGAGATGCCCTTTGACCCCCAAG
ATACTCATCAGTCAAGGTTCTACTTGAGCAAGAAAAGTGGGTAATGGTGCCCATGATGAGTTT
GCATCACCTGACTATACCTTACTTCCGGGACGAGGAGCTGTCCTGCACCGTGGTGGAGCTGAAG
TACACAGGCAATGCCAGCGCACTCTTCATCCTCCCTGATCAAGACAAGATGGAGGAAGTGGAAG
CCATGCTGCTCCCAGAGACCCTGAAGCGGTGGAGAGACTCTCTGGAGTTCAGAGAGATAGGTGA
GCTCTACCTGCCAAAGTTTTCCATCTCGAGGGACTATAACCTGAACGACATACTTCTCCAGCTG
GGCATTGAGGAAGCCTTCACCAGCAAGGCTGACCTGTCAGGGATCACAGGGGCCAGGAACCTAG
CAGTCTCCCAGGTGGTCCATAAGGCTGTGCTTGATGTATTTGAGGAGGGCACAGAAGCATCTGC
TGCCAC<u>CGC</u>GGTCAAAATCACCCTG<u>CGTCAGACCAAC</u>GTGGAGAC<u>GCG</u>TACCATTGTGCGTTTC
AACAGGCCCTTCCTGATGATCATTGTCCCTACAGACACCCAGAACATCTTCTTCATGAGCAAAG
TCACCAATCCCAAGCAAGCCTAA

SEQ ID N° 41:     PROTEIN SEQUENCE: ACT-C11

Legend

```
Italic and bold: start Methionin
Bold and underlined: His-tag
Underlined : amino acid mutation(added)
Underlined and grey : RSL mutation
```

<u>*M*</u>RGSHHHHHHSRHPNSPLDEENLTQENQDRGTHVDLGLASANVDFAFSLYKQLVLKAPDKNVIF
SPLSISTALAFLSLGAHNTTLTEILKGLKFNLTETSEAEIHQSFQHLLRTLNQSSDELQLSMGN
AMFVKEQLSLLDRFTEDAKRLYGSEAFATDFQDSAAAKKLINDYVKNGTRGKITDLIKDLDSQT
MMVLVNYIFFKAKWEMPFDPQDTHQSRFYLSKKKWVMVPMMSLHHLTIPYFRDEELSCTVVELK
YTGNASALFILPDQDKMEEVEAMLLPETLKRWRDSLEFREIGELYLPKFSISRDYNLNDILLQL
GIEEAFTSKADLSGITGARNLAVSQVVHKAVLDVFEEGTEASAATAVKITL<u>RQTN</u>VETRTIVRF
NRPFLMIIVPTDTQNIFFMSKVTNPKQA*

FIG. 12

Legend

```
Italic and bold : start codon ATG
Bold and underlined: His-tag
Underlined : DNA mutation (added codon)
Underlined and grey : DNA sequence encoding RSL mutation.
```

SEQ ID N° 20 :    DNA SEQUENCE: ACT-C11G

*ATG*AGAGGATCCCATCACCATCACCATCACTCTAGACACCCTAACAGCCCACTTGACGAGGAGA
ATCTGACCCAGGAGAACCAAGACCGAGGGACACACGTGGACCTCGGATTAGCCTCCGCCAACGT
GGACTTCGCTTTCAGCCTGTACAAGCAGTTAGTCCTGAAGGCCCCTGATAAGAATGTCATCTTC
TCCCCACTGAGCATCTCCACCGCCTTGGCCTTCCTGTCTCTGGGGGCCCATAATACCACCCTGA
CAGAGATTCTCAAAGGCCTCAAGTTCAACCTCACGGAGACTTCTGAGGCAGAAATTCACCAGAG
CTTCCAGCACCTCCTGCGCACCCTCAATCAGTCCAGCGATGAGCTGCAGCTGAGTATGGGAAAT
GCCATGTTTGTCAAAGAGCAACTCAGTCTGCTGGACAGGTTCACGGAGGATGCCAAGAGGCTGT
ATGGCTCCGAGGCCTTTGCCACTGACTTTCAGGACTCAGCTGCAGCTAAGAAGCTCATCAACGA
CTACGTGAAGAATGGAACTAGGGGGAAAATCACAGATCTGATCAAGGACCTTGACTCGCAGACA
ATGATGGTCCTGGTGAATTACATCTTCTTTAAAGCCAAATGGGAGATGCCCTTTGACCCCCAAG
ATACTCATCAGTCAAGGTTCTACTTGAGCAAGAAAAGTGGGTAATGGTGCCCATGATGAGTTT
GCATCACCTGACTATACCTTACTTCCGGGACGAGGAGCTGTCCTGCACCGTGGTGGAGCTGAAG
TACACAGGCAATGCCAGCGCACTCTTCATCCTCCCTGATCAAGACAAGATGGAGGAAGTGGAAG
CCATGCTGCTCCCAGAGACCCTGAAGCGGTGGAGAGACTCTCTGGAGTTCAGAGAGATAGGTGA
GCTCTACCTGCCAAAGTTTTCCATCTCGAGGGACTATAACCTGAACGACATACTTCTCCAGCTG
GGCATTGAGGAAGCCTTCACCAGCAAGGCTGACCTGTCAGGGATCACAGGGGCCAGGAACCTAG
CAGTCTCCCAGGTGGTCCATAAGGCTGTGCTTGATGTATTTGAGGAGGGCACAGAAGCATCTGC
TGCCAC<u>C</u>GC<u>G</u>GTCAAAATCACC<u>GGT</u>C<u>G</u>T<u>CAGA</u>C<u>CAAC</u>GTGGAGAC<u>GC</u>G<u>T</u>ACCATTGTGCGTTTC
AACAGGCCCTTCCTGATGATCATTGTCCCTACAGACACCCAGAACATCTTCTTCATGAGCAAAG
TCACCAATCCCAAGCAAGCCTAA

SEQ ID N° 42:    PROTEIN SEQUENCE: ACT-C11G

Legend

```
Italic and bold: start Methionin
Bold and underlined: His-tag
Underlined : amino acid mutation(added)
Underlined and grey : RSL mutation
```

*M*RGSHHHHHHSRHPNSPLDEENLTQENQDRGTHVDLGLASANVDFAFSLYKQLVLKAPDKNVIF
SPLSISTALAFLSLGAHNTTLTEILKGLKFNLTETSEAEIHQSFQHLLRTLNQSSDELQLSMGN
AMFVKEQLSLLDRFTEDAKRLYGSEAFATDFQDSAAAKKLINDYVKNGTRGKITDLIKDLDSQT
MMVLVNYIFFKAKWEMPFDPQDTHQSRFYLSKKKWVMVPMMSLHHLTIPYFRDEELSCTVVELK
YTGNASALFILPDQDKMEEVEAMLLPETLKRWRDSLEFREIGELYLPKFSISRDYNLNDILLQL
GIEEAFTSKADLSGITGARNLAVSQVVHKAVLDVFEEGTEASAATAVKIT<u>GRQTN</u>VETRTIVRF
NRPFLMIIVPTDTQNIFFMSKVTNPKQA*

FIG. 13

Legend

Italic and bold: start codon ATG
Bold and underlined: His-tag
Underlined : DNA mutation (added codon)
Underlined and grey : DNA sequence encoding RSL mutation.

SEQ ID N° 21 :   DNA Sequence: ACT-E5

*ATGAGAGGATCCCATCACCATCACCATCACTCTAGACACCCTAACAGCCCACTTGACGAGGAGA
ATCTGACCCAGGAGAACCAAGACCGAGGGACACACGTGGACCTCGGATTAGCCTCCGCCAACGT
GGACTTCGCTTTCAGCCTGTACAAGCAGTTAGTCCTGAAGGCCCCTGATAAGAATGTCATCTTC
TCCCCACTGAGCATCTCCACCGCCTTGGCCTTCCTGTCTCTGGGGGCCCATAATACCACCCTGA
CAGAGATTCTCAAAGGCCTCAAGTTCAACCTCACGGAGACTTCTGAGGCAGAAATTCACCAGAG
CTTCCAGCACCTCCTGCGCACCCTCAATCAGTCCAGCGATGAGCTGCAGCTGAGTATGGGAAAT
GCCATGTTTGTCAAAGAGCAACTCAGTCTGCTGGACAGGTTCACGGAGGATGCCAAGAGGCTGT
ATGGCTCCGAGGCCTTTGCCACTGACTTTCAGGACTCAGCTGCAGCTAAGAAGCTCATCAACGA
CTACGTGAAGAATGGAACTAGGGGGAAAATCACAGATCTGATCAAGGACCTTGACTCGCAGACA
ATGATGGTCCTGGTGAATTACATCTTCTTTAAAGCCAAATGGGAGATGCCCTTTGACCCCCAAG
ATACTCATCAGTCAAGGTTCTACTTGAGCAAGAAAAGTGGGTAATGGTGCCCATGATGAGTTT
GCATCACCTGACTATACCTTACTTCCGGGACGAGGAGCTGTCCTGCACCGTGGTGGAGCTGAAG
TACACAGGCAATGCCAGCGCACTCTTCATCCTCCCTGATCAAGACAAGATGGAGGAAGTGGAAG
CCATGCTGCTCCCAGAGACCCTGAAGCGGTGGAGAGACTCTCTGGAGTTCAGAGAGATAGGTGA
GCTCTACCTGCCAAAGTTTTCCATCTCGAGGGACTATAACCTGAACGACATACTTCTCCAGCTG
GGCATTGAGGAAGCCTTCACCAGCAAGGCTGACCTGTCAGGGATCACAGGGGCCAGGAACCTAG
CAGTCTCCCAGGTGGTCCATAAGGCTGTGCTTGATGTATTTGAGGAGGGCACAGAAGCATCTGC
TGCCACCGCGGTCAAAATCAACCAGCGTTCTTCCCTGGTGGAGACGCGTACCATTGTGCGTTTC
AACAGGCCCTTCCTGATGATCATTGTCCCTACAGACACCCAGAACATCTTCTTCATGAGCAAAG
TCACCAATCCCAAGCAAGCCTAA

SEQ ID N° 43:   Protein Sequence: ACT-E5

Legend

Italic and bold: start Methionin
Bold and underlined: His-tag
Underlined : amino acid mutation (added)
Underlined and grey : RSL mutation

*M*RGSHHHHHHSRHPNSPLDEENLTQENQDRGTHVDLGLASANVDFAFSLYKQLVLKAPDKNVIF
SPLSISTALAFLSLGAHNTTLTEILKGLKFNLTETSEAEIHQSFQHLLRTLNQSSDELQLSMGN
AMFVKEQLSLLDRFTEDAKRLYGSEAFATDFQDSAAAKKLINDYVKNGTRGKITDLIKDLDSQT
MMVLVNYIFFKAKWEMPFDPQDTHQSRFYLSKKKWVMVPMMSLHHLTIPYFRDEELSCTVVELK
YTGNASALFILPDQDKMEEVEAMLLPETLKRWRDSLEFREIGELYLPKFSISRDYNLNDILLQL
GIEEAFTSKADLSGITGARNLAVSQVVHKAVLDVFEEGTEASAATAVKINQRSSLVETRTIVRF
NRPFLMIIVPTDTQNIFFMSKVTNPKQA*

FIG. 14

Legend

```
Italic and bold: start codon ATG
Bold and underlined: His-tag
Underlined : DNA mutation (added codon)
Underlined and grey : DNA sequence encoding RSL mutation.
```

SEQ ID N° 22 :      DNA SEQUENCE: ACT-E8

*ATG*AGAGGATCCCATCACCATCACCATCACTCTAGACACCCTAACAGCCCACTTGACGAGGAGA
ATCTGACCCAGGAGAACCAAGACCGAGGGACACACGTGGACCTCGGATTAGCCTCCGCCAACGT
GGACTTCGCTTTCAGCCTGTACAAGCAGTTAGTCCTGAAGGCCCCTGATAAGAATGTCATCTTC
TCCCCACTGAGCATCTCCACCGCCTTGGCCTTCCTGTCTCTGGGGGCCCATAATACCACCCTGA
CAGAGATTCTCAAAGGCCTCAAGTTCAACCTCACGGAGACTTCTGAGGCAGAAATTCACCAGAG
CTTCCAGCACCTCCTGCGCACCCTCAATCAGTCCAGCGATGAGCTGCAGCTGAGTATGGGAAAT
GCCATGTTTGTCAAAGAGCAACTCAGTCTGCTGGACAGGTTCACGGAGGATGCCAAGAGGCTGT
ATGGCTCCGAGGCCTTTGCCACTGACTTTCAGGACTCAGCTGCAGCTAAGAAGCTCATCAACGA
CTACGTGAAGAATGGAACTAGGGGGAAAATCACAGATCTGATCAAGGACCTTGACTCGCAGACA
ATGATGGTCCTGGTGAATTACATCTTCTTTAAAGCCAAATGGGAGATGCCCTTTGACCCCCAAG
ATACTCATCAGTCAAGGTTCTACTTGAGCAAGAAAAGTGGGTAATGGTGCCCATGATGAGTTT
GCATCACCTGACTATACCTTACTTCCGGGACGAGGAGCTGTCCTGCACCGTGGTGGAGCTGAAG
TACACAGGCAATGCCAGCGCACTCTTCATCCTCCCTGATCAAGACAAGATGGAGGAAGTGGAAG
CCATGCTGCTCCCAGAGACCCTGAAGCGGTGGAGAGACTCTCTGGAGTTCAGAGAGATAGGTGA
GCTCTACCTGCCAAAGTTTTCCATCTCGAGGGACTATAACCTGAACGACATACTTCTCCAGCTG
GGCATTGAGGAAGCCTTCACCAGCAAGGCTGACCTGTCAGGGATCACAGGGGCCAGGAACCTAG
CAGTCTCCCAGGTGGTCCATAAGGCTGTGCTTGATGTATTTGAGGAGGGCACAGAAGCATCTGC
TGCCACCGCGGTCAAAATCCTGCAGCGTGCTATCCTGGTGGAGACGCGTACCATTGTGCGTTTC
AACAGGCCCTTCCTGATGATCATTGTCCCTACAGACACCCAGAACATCTTCTTCATGAGCAAAG
TCACCAATCCCAAGCAAGCCTAA

SEQ ID N° 44:      PROTEIN SEQUENCE: ACT-E8

Legend

```
Italic and bold: start Methionin
Bold and underlined: His-tag
Underlined : amino acid mutation (added)
Underlined and grey : RSL mutation
```

*M*RGSHHHHHHSRHPNSPLDEENLTQENQDRGTHVDLGLASANVDFAFSLYKQLVLKAPDKNVIF
SPLSISTALAFLSLGAHNTTLTEILKGLKFNLTETSEAEIHQSFQHLLRTLNQSSDELQLSMGN
AMFVKEQLSLLDRFTEDAKRLYGSEAFATDFQDSAAAKKLINDYVKNGTRGKITDLIKDLDSQT
MMVLVNYIFFKAKWEMPFDPQDTHQSRFYLSKKKWVMVPMMSLHHLTIPYFRDEELSCTVVELK
YTGNASALFILPDQDKMEEVEAMLLPETLKRWRDSLEFREIGELYLPKFSISRDYNLNDILLQL
GIEEAFTSKADLSGITGARNLAVSQVVHKAVLDVFEEGTEASAATAVKILQRAILVETRTIVRF
NRPFLMIIVPTDTQNIFFMSKVTNPKQA*

FIG. 15

Legend

```
Italic and bold: start codon ATG
Bold and underlined: His-tag
Underlined : DNA mutation (added codon)
Underlined and grey : DNA sequence encoding RSL mutation.
```

SEQ ID N° 23 :    DNA SEQUENCE: ACT-F11

*ATG*AGAGGATCCCATCACCATCACCATCACTCTAGACACCCTAACAGCCCACTTGACGAGGAGA
ATCTGACCCAGGAGAACCAAGACCGAGGGACACACGTGGACCTCGGATTAGCCTCCGCCAACGT
GGACTTCGCTTTCAGCCTGTACAAGCAGTTAGTCCTGAAGGCCCCTGATAAGAATGTCATCTTC
TCCCCACTGAGCATCTCCACCGCCTTGGCCTTCCTGTCTCTGGGGGCCCATAATACCACCCTGA
CAGAGATTCTCAAAGGCCTCAAGTTCAACCTCACGGAGACTTCTGAGGCAGAAATTCACCAGAG
CTTCCAGCACCTCCTGCGCACCCTCAATCAGTCCAGCGATGAGCTGCAGCTGAGTATGGGAAAT
GCCATGTTTGTCAAAGAGCAACTCAGTCTGCTGGACAGGTTCACGGAGGATGCCAAGAGGCTGT
ATGGCTCCGAGGCCTTTGCCACTGACTTTCAGGACTCAGCTGCAGCTAAGAAGCTCATCAACGA
CTACGTGAAGAATGGAACTAGGGGGAAAATCACAGATCTGATCAAGGACCTTGACTCGCAGACA
ATGATGGTCCTGGTGAATTACATCTTCTTTAAAGCCAAATGGGAGATGCCCTTTGACCCCCAAG
ATACTCATCAGTCAAGGTTCTACTTGAGCAAGAAAAGTGGGTAATGGTGCCCATGATGAGTTT
GCATCACCTGACTATACCTTACTTCCGGGACGAGGAGCTGTCCTGCACCGTGGTGGAGCTGAAG
TACACAGGCAATGCCAGCGCACTCTTCATCCTCCCTGATCAAGACAAGATGGAGGAAGTGGAAG
CCATGCTGCTCCCAGAGACCCTGAAGCGGTGGAGAGACTCTCTGGAGTTCAGAGAGATAGGTGA
GCTCTACCTGCCAAAGTTTTCCATCTCGAGGGACTATAACCTGAACGACATACTTCTCCAGCTG
GGCATTGAGGAAGCCTTCACCAGCAAGGCTGACCTGTCAGGGATCACAGGGGCCAGGAACCTAG
CAGTCTCCCAGGTGGTCCATAAGGCTGTGCTTGATGTATTTGAGGAGGGCACAGAAGCATCTGC
TGCCAC<u>C</u>GC<u>G</u>GTCAAA<u>CAGCGT</u>CT<u>G</u>C<u>GT</u>GA<u>C</u>GC<u>TC</u>T<u>G</u>GTGGAGAC<u>GC</u>G<u>T</u>ACCATTGTGCGTTTC
AACAGGCCCTTCCTGATGATCATTGTCCCTACAGACACCCAGAACATCTTCTTCATGAGCAAAG
TCACCAATCCCAAGCAAGCCTAA

SEQ ID N° 45:    PROTEIN SEQUENCE: ACT-F11

Legend

```
Italic and bold: start Methionin
Bold and underlined: His-tag
Underlined : amino acid mutation (added)
Underlined and grey : RSL mutation
```

<u>M</u>RGSHHHHHHSRHPNSPLDEENLTQENQDRGTHVDLGLASANVDFAFSLYKQLVLKAPDKNVIF
SPLSISTALAFLSLGAHNTTLTEILKGLKFNLTETSEAEIHQSFQHLLRTLNQSSDELQLSMGN
AMFVKEQLSLLDRFTEDAKRLYGSEAFATDFQDSAAAKKLINDYVKNGTRGKITDLIKDLDSQT
MMVLVNYIFFKAKWEMPFDPQDTHQSRFYLSKKKWVMVPMMSLHHLTIPYFRDEELSCTVVELK
YTGNASALFILPDQDKMEEVEAMLLPETLKRWRDSLEFREIGELYLPKFSISRDYNLNDILLQL
GIEEAFTSKADLSGITGARNLAVSQVVHKAVLDVFEEGTEASAATAVK<u>QRL</u>R<u>D</u>ALVETRTIVRF
NRPFLMIIVPTDTQNIFFMSKVTNPKQA*

FIG. 16

Legend

```
Italic and bold: start codon ATG
Bold and underlined: His-tag
Underlined : DNA mutation (added codon)
Underlined and grey : DNA sequence encoding RSL mutation.
```

SEQ ID N° 24 :     DNA SEQUENCE: ACT-F3

*ATGAGAGGATCCCATCACCATCACCATCACTCTAGACACCCTAACAGCCCACTTGACGAGGAGA
ATCTGACCCAGGAGAACCAAGACCGAGGGACACACGTGGACCTCGGATTAGCCTCCGCCAACGT
GGACTTCGCTTTCAGCCTGTACAAGCAGTTAGTCCTGAAGGCCCCTGATAAGAATGTCATCTTC
TCCCCACTGAGCATCTCCACCGCCTTGGCCTTCCTGTCTCTGGGGGCCCATAATACCACCCTGA
CAGAGATTCTCAAAGGCCTCAAGTTCAACCTCACGGAGACTTCTGAGGCAGAAATTCACCAGAG
CTTCCAGCACCTCCTGCGCACCCTCAATCAGTCCAGCGATGAGCTGCAGCTGAGTATGGGAAAT
GCCATGTTTGTCAAAGAGCAACTCAGTCTGCTGGACAGGTTCACGGAGGATGCCAAGAGGCTGT
ATGGCTCCGAGGCCTTTGCCACTGACTTTCAGGACTCAGCTGCAGCTAAGAAGCTCATCAACGA
CTACGTGAAGAATGGAACTAGGGGGAAAATCACAGATCTGATCAAGGACCTTGACTCGCAGACA
ATGATGGTCCTGGTGAATTACATCTTCTTTAAAGCCAAATGGGAGATGCCCTTTGACCCCCAAG
ATACTCATCAGTCAAGGTTCTACTTGAGCAAGAAAAGTGGGTAATGGTGCCCATGATGAGTTT
GCATCACCTGACTATACCTTACTTCCGGGACGAGGAGCTGTCCTGCACCGTGGTGGAGCTGAAG
TACACAGGCAATGCCAGCGCACTCTTCATCCTCCCTGATCAAGACAAGATGGAGGAAGTGGAAG
CCATGCTGCTCCCAGAGACCCTGAAGCGGTGGAGAGACTCTCTGGAGTTCAGAGAGATAGGTGA
GCTCTACCTGCCAAAGTTTTCCATCTCGAGGGACTATAACCTGAACGACATACTTCTCCAGCTG
GGCATTGAGGAAGCCTTCACCAGCAAGGCTGACCTGTCAGGGATCACAGGGGCCAGGAACCTAG
CAGTCTCCCAGGTGGTCCATAAGGCTGTGCTTGATGTATTTGAGGAGGGCACAGAAGCATCTGC
TGCCACCGCGGTCAAAATCCCGGACCGTCACATGCTGGTGGAGACGCGTACCATTGTGCGTTTC
AACAGGCCCTTCCTGATGATCATTGTCCCTACAGACACCCAGAACATCTTCTTCATGAGCAAAG
TCACCAATCCCAAGCAAGCCTAA*

SEQ ID N° 46:     PROTEIN SEQUENCE: ACT-F3

Legend

```
Italic and bold: start Methionin
Bold and underlined: His-tag
Underlined : amino acid mutation(added)
Underlined and grey : RSL mutation
```

*M*RGSHHHHHHSRHPNSPLDEENLTQENQDRGTHVDLGLASANVDFAFSLYKQLVLKAPDKNVIF
SPLSISTALAFLSLGAHNTTLTEILKGLKFNLTETSEAEIHQSFQHLLRTLNQSSDELQLSMGN
AMFVKEQLSLLDRFTEDAKRLYGSEAFATDFQDSAAAKKLINDYVKNGTRGKITDLIKDLDSQT
MMVLVNYIFFKAKWEMPFDPQDTHQSRFYLSKKKWVMVPMMSLHHLTIPYFRDEELSCTVVELK
YTGNASALFILPDQDKMEEVEAMLLPETLKRWRDSLEFREIGELYLPKFSISRDYNLNDILLQL
GIEEAFTSKADLSGITGARNLAVSQVVHKAVLDVFEEGTEASAATAVKIPDRHMLVETRTIVRF
NRPFLMIIVPTDTQNIFFMSKVTNPKQA*

FIG. 17

Legend

```
Italic and bold: start codon ATG
Bold and underlined: His-tag
Underlined : DNA mutation (added codon)
Underlined and grey : DNA sequence encoding RSL mutation.
```

SEQ ID N° 25 :   DNA Sequence: ACT-G9

*ATG*AGAGGATCCCATCACCATCACCATCACTCTAGACACCCTAACAGCCCACTTGACGAGGAGA
ATCTGACCCAGGAGAACCAAGACCGAGGGACACACGTGGACCTCGGATTAGCCTCCGCCAACGT
GGACTTCGCTTTCAGCCTGTACAAGCAGTTAGTCCTGAAGGCCCCTGATAAGAATGTCATCTTC
TCCCCACTGAGCATCTCCACCGCCTTGGCCTTCCTGTCTCTGGGGGCCCATAATACCACCCTGA
CAGAGATTCTCAAAGGCCTCAAGTTCAACCTCACGGAGACTTCTGAGGCAGAAATTCACCAGAG
CTTCCAGCACCTCCTGCGCACCCTCAATCAGTCCAGCGATGAGCTGCAGCTGAGTATGGGAAAT
GCCATGTTTGTCAAAGAGCAACTCAGTCTGCTGGACAGGTTCACGGAGGATGCCAAGAGGCTGT
ATGGCTCCGAGGCCTTTGCCACTGACTTTCAGGACTCAGCTGCAGCTAAGAAGCTCATCAACGA
CTACGTGAAGAATGGAACTAGGGGGAAAATCACAGATCTGATCAAGGACCTTGACTCGCAGACA
ATGATGGTCCTGGTGAATTACATCTTCTTTAAAGCCAAATGGGAGATGCCCTTTGACCCCCAAG
ATACTCATCAGTCAAGGTTCTACTTGAGCAAGAAAAGTGGGTAATGGTGCCCATGATGAGTTT
GCATCACCTGACTATACCTTACTTCCGGGACGAGGAGCTGTCCTGCACCGTGGTGGAGCTGAAG
TACACAGGCAATGCCAGCGCACTCTTCATCCTCCCTGATCAAGACAAGATGGAGGAAGTGGAAG
CCATGCTGCTCCCAGAGACCCTGAAGCGGTGGAGAGACTCTCTGGAGTTCAGAGAGATAGGTGA
GCTCTACCTGCCAAAGTTTTCCATCTCGAGGGACTATAACCTGAACGACATACTTCTCCAGCTG
GGCATTGAGGAAGCCTTCACCAGCAAGGCTGACCTGTCAGGGATCACAGGGGCCAGGAACCTAG
CAGTCTCCCAGGTGGTCCATAAGGCTGTGCTTGATGTATTTGAGGAGGGCACAGAAGCATCTGC
TGCCAC<u>C</u>GC<u>G</u>GTCAAAA<u>C</u>C<u>GTTGA</u>C<u>TACG</u>CTGC<u>TC</u>T<u>G</u>GTGGAGAC<u>GC</u>G<u>T</u>ACCATTGTGCGTTTC
AACAGGCCCTTCCTGATGATCATTGTCCCTACAGACACCCAGAACATCTTCTTCATGAGCAAAG
TCACCAATCCCAAGCAAGCCTAA

SEQ ID N° 47:   Protein Sequence: ACT-G9

Legend

```
Italic and bold: start Methionin
Bold and underlined: His-tag
Underlined : amino acid mutation(added)
Underlined and grey : RSL mutation
```

<u>*M*</u>RGSHHHHHHSRHPNSPLDEENLTQENQDRGTHVDLGLASANVDFAFSLYKQLVLKAPDKNVIF
SPLSISTALAFLSLGAHNTTLTEILKGLKFNLTETSEAEIHQSFQHLLRTLNQSSDELQLSMGN
AMFVKEQLSLLDRFTEDAKRLYGSEAFATDFQDSAAAKKLINDYVKNGTRGKITDLIKDLDSQT
MMVLVNYIFFKAKWEMPFDPQDTHQSRFYLSKKKWVMVPMMSLHHLTIPYFRDEELSCTVVELK
YTGNASALFILPDQDKMEEVEAMLLPETLKRWRDSLEFREIGELYLPKFSISRDYNLNDILLQL
GIEEAFTSKADLSGITGARNLAVSQVVHKAVLDVFEEGTEASAATAVK<u>TVDYA</u>ALVETRTIVRF
NRPFLMIIVPTDTQNIFFMSKVTNPKQA*

FIG. 18

Legend

```
Italic and bold: start codon ATG
Bold and underlined: His-tag
Underlined : DNA mutation (added codon)
```

<u>SEQ ID N°26 :</u>    DNA Sequence: AAT-WT

*ATG*AGAGGATCGCATCACCATCACCATCACGGATCCGATGATCCCCAGGGAGATGCTGCCCAGA
AGACAGATACATCCCACCATGATCAGGATCACCCAACCTTCAACAAGATCACCCCCAACCTGGC
TGAGTTCGCCTTCAGCCTATACCGCCAGCTGGCACACCAGTCCAACAGCACCAATATCTTCTTC
TCCCCAGTGAGCATCGCTACAGCCTTTGCAATGCTCTCCCTGGGGACCAAGGCTGACACTCACG
ATGAAATCCTGGAGGGCCTGAATTTCAACCTCACGGAGATTCCGGAGGCTCAGATCCATGAAGG
CTTCCAGGAACTCCTCCGTACCCTCAACCAGCCAGACAGCCAGCTCCAGCTGACCACCGGCAAT
GGCCTGTTCCTCAGCGAGGGCCTGAAGCTAGTGGATAAGTTTTTGGAGGATGTTAAAAAGTTGT
ACCACTCAGAAGCCTTCACTGTCAACTTCGGGGACACCGAAGAGGCCAAGAAACAGATCAACGA
TTACGTGGAGAAGGGTACTCAAGGGAAAATTGTGGATTTGGTCAAGGAGCTTGACAGAGACACA
GTTTTTGCTCTGGTGAATTACATCTTCTTTAAAGGCAAATGGGAGAGACCCTTTGAAGTCAAGG
ACACCGAGGAAGAGGACTTCCACGTGGACCAGGCGACCACCGTGAAGGTGCCTATGATGAAGCG
TTTAGGCATGTTTAACATCCAGCACTGTAAGAAGCTGTCCAGCTGGGTGCTGCTGATGAAATAC
CTGGGCAATGCCACCGCCATCTTCTTCCTGCCTGATGAGGGGAAACTACAGCACCTGGAAAATG
AACTCACCCACGATATCATCACCAAGTTCCTGGAAAATGAAGACAGAAGGTCTGCCAGCTTACA
TTTACCCAAACTGTCCATTACTGGAACCTATGATCTGAAGAGCGTCCTGGGTCAACTGGGCATC
ACTAAGGTCTTCAGCAATGGGGCTGACCTCTCCGGGGTCACAGAGGAGGCACCCCTGAAGCTCT
CCAAGGCCGTGCATAAGGCTGTGCTGACCATCGACGAGAAAGGGACTGAAGCTGCTGGGGCCAT
GTTTTTAGAGGCCATACCCATGTCTATCCCCCCGAGGTCAAGTTCAACAAACCCTTTGTCTTC
TTAATGATTGAACAAAATACCAAGTCTCCCCTCTTCATGGGAAAAGTGGTGAATCCCACCCAAA
AATAA

<u>SEQ ID N° 48:</u>    Protein Sequence: AAT-WT

Legend

```
Italic and bold: start Methionin
Bold and underlined: His-tag
Underlined : amino acid mutation(added)
```

*M*<u>RGSHHHHHHG</u>SDDPQGDAAQKTDTSHHDQDHPTFNKITPNLAEFAFSLYRQLAHQSNSTNIFF
SPVSIATAFAMLSLGTKADTHDEILEGLNFNLTEIPEAQIHEGFQELLRTLNQPDSQLQLTTGN
GLFLSEGLKLVDKFLEDVKKLYHSEAFTVNFGDTEEAKKQINDYVEKGTQGKIVDLVKELDRDT
VFALVNYIFFKGKWERPFEVKDTEEEDFHVDQATTVKVPMMKRLGMFNIQHCKKLSSWVLLMKY
LGNATAIFFLPDEGKLQHLENELTHDIITKFLENEDRRSASLHLPKLSITGTYDLKSVLGQLGI
TKVFSNGADLSGVTEEAPLKLSKAVHKAVLTIDEKGTEAAGAMFLEAIPMSIPPEVKFNKPFVF
LMIEQNTKSPLFMGKVVNPTQK*

FIG. 19

Legend

```
Italic and bold: start codon ATG
Bold and underlined: His-tag
Underlined : DNA mutation (added codon)
Underlined and grey : DNA sequence encoding RSL mutation.
```

SEQ ID N°27 :     DNA SEQUENCE: AAT-G1

*ATG*AGAGGATCGCATCACCATCACCATCACGGATCCGATGATCCCCAGGGAGATGCTGCCCAGA
AGACAGATACATCCCACCATGATCAGGATCACCCAACCTTCAACAAGATCACCCCCAACCTGGC
TGAGTTCGCCTTCAGCCTATACCGCCAGCTGGCACACCAGTCCAACAGCACCAATATCTTCTTC
TCCCCAGTGAGCATCGCTACAGCCTTTGCAATGCTCTCCCTGGGGACCAAGGCTGACACTCACG
ATGAAATCCTGGAGGGCCTGAATTTCAACCTCACGGAGATTCCGGAGGCTCAGATCCATGAAGG
CTTCCAGGAACTCCTCCGTACCCTCAACCAGCCAGACAGCCAGCTCCAGCTGACCACCGGCAAT
GGCCTGTTCCTCAGCGAGGGCCTGAAGCTAGTGGATAAGTTTTTGGAGGATGTTAAAAAGTTGT
ACCACTCAGAAGCCTTCACTGTCAACTTCGGGGACACCGAAGAGGCCAAGAAACAGATCAACGA
TTACGTGGAGAAGGGTACTCAAGGGAAAATTGTGGATTTGGTCAAGGAGCTTGACAGAGACACA
GTTTTTGCTCTGGTGAATTACATCTTCTTTAAAGGCAAATGGGAGAGACCCTTTGAAGTCAAGG
ACACCGAGGAAGAGGACTTCCACGTGGACCAGGCGACCACCGTGAAGGTGCCTATGATGAAGCG
TTTAGGCATGTTTAACATCCAGCACTGTAAGAAGCTGTCCAGCTGGGTGCTGCTGATGAAATAC
CTGGGCAATGCCACCGCCATCTTCTTCCTGCCTGATGAGGGGAAACTACAGCACCTGGAAAATG
AACTCACCCACGATATCATCACCAAGTTCCTGGAAAATGAAGACAGAAGGTCTGCCAGCTTACA
TTTACCCAAACTGTCCATTACTGGAACCTATGATCTGAAGAGCGTCCTGGGTCAACTGGGCATC
ACTAAGGTCTTCAGCAATGGGGCTGACCTCTCCGGGGTCACAGAGGAGGCACCCCTGAAGCTCT
CCAAGGCCGTGCATAAGGCTGTGCTGACCATCGACGAGAAGGGACTGAAGCTGCTGG<u>C</u>GCCAT
GTTT<u>C</u>TAGAGG<u>GTTCT</u>C<u>TGCGT</u>TCTATCCC<u>G</u>CC<u>T</u>GAGGTCAAGTTCAACAAACCCTTTGTCTTC
TTAATGATTGAACAAAATACCAAGTCTCCCCTCTTCATGGGAAAAGTGGTGAATCCCACCCAAA
AATAA

SEQ ID N° 49:     PROTEIN SEQUENCE: AAT-G1

Legend

```
Italic and bold: start Methionin
Bold and underlined: His-tag
Underlined : amino acid mutation(added)
Underlined and grey : RSL mutation.
```

*M*RGSHHHHHHGSDDPQGDAAQKTDTSHHDQDHPTFNKITPNLAEFAFSLYRQLAHQSNSTNIFF
SPVSIATAFAMLSLGTKADTHDEILEGLNFNLTEIPEAQIHEGFQELLRTLNQPDSQLQLTTGN
GLFLSEGLKLVDKFLEDVKKLYHSEAFTVNFGDTEEAKKQINDYVEKGTQGKIVDLVKELDRDT
VFALVNYIFFKGKWERPFEVKDTEEEDFHVDQATTVKVPMMKRLGMFNIQHCKKLSSWVLLMKY
LGNATAIFFLPDEGKLQHLENELTHDIITKFLENEDRRSASLHLPKLSITGTYDLKSVLGQLGI
TKVFSNGADLSGVTEEAPLKLSKAVHKAVLTIDEKGTEAAGAMFLE<u>GSLR</u>SIPPEVKFNKPFVF
LMIEQNTKSPLFMGKVVNPTQK*

FIG. 20

Legend

```
Italic and bold: start codon ATG
Bold and underlined: His-tag
Underlined : DNA mutation (added codon)
Underlined and grey : DNA sequence encoding RSL mutation.
```

SEQ ID N°28 :   DNA S<small>EQUENCE</small>: AAT-G1G

*ATG*AGAGGATCGCATCACCATCACCATCACGGATCCGATGATCCCCAGGGAGATGCTGCCCAGA
AGACAGATACATCCCACCATGATCAGGATCACCCAACCTTCAACAAGATCACCCCCAACCTGGC
TGAGTTCGCCTTCAGCCTATACCGCCAGCTGGCACACCAGTCCAACAGCACCAATATCTTCTTC
TCCCCAGTGAGCATCGCTACAGCCTTTGCAATGCTCTCCCTGGGGACCAAGGCTGACACTCACG
ATGAAATCCTGGAGGGCCTGAATTTCAACCTCACGGAGATTCCGGAGGCTCAGATCCATGAAGG
CTTCCAGGAACTCCTCCGTACCCTCAACCAGCCAGACAGCCAGCTCCAGCTGACCACCGGCAAT
GGCCTGTTCCTCAGCGAGGGCCTGAAGCTAGTGGATAAGTTTTTGGAGGATGTTAAAAAGTTGT
ACCACTCAGAAGCCTTCACTGTCAACTTCGGGGACACCGAAGAGGCCAAGAAACAGATCAACGA
TTACGTGGAGAAGGGTACTCAAGGGAAAATTGTGGATTTGGTCAAGGAGCTTGACAGAGACACA
GTTTTTGCTCTGGTGAATTACATCTTCTTTAAAGGCAAATGGGAGAGACCCTTTGAAGTCAAGG
ACACCGAGGAAGAGGACTTCCACGTGGACCAGGCGACCACCGTGAAGGTGCCTATGATGAAGCG
TTTAGGCATGTTTAACATCCAGCACTGTAAGAAGCTGTCCAGCTGGGTGCTGCTGATGAAATAC
CTGGGCAATGCCACCGCCATCTTCTTCCTGCCTGATGAGGGGAAACTACAGCACCTGGAAAATG
AACTCACCCACGATATCATCACCAAGTTCCTGGAAAATGAAGACAGAAGGTCTGCCAGCTTACA
TTTACCCAAACTGTCCATTACTGGAACCTATGATCTGAAGAGCGTCCTGGGTCAACTGGGCATC
ACTAAGGTCTTCAGCAATGGGGCTGACCTCTCCGGGGTCACAGAGGAGGCACCCCTGAAGCTCT
CCAAGGCCGTGCATAAGGCTGTGCTGACCATCGACGAGAAGGGACTGAAGCTGCTGG<u>C</u>GCCAT
GTTT<u>C</u>TAGAGG<u>GTTCT</u>C<u>TGCGTGG</u>TATCCC<u>G</u>CC<u>T</u>GAGGTCAAGTTCAACAAACCCTTTGTCTTC
TTAATGATTGAACAAAATACCAAGTCTCCCCTCTTCATGGGAAAAGTGGTGAATCCCACCCAAA
AATAA

SEQ ID N° 50:   P<small>ROTEIN</small> S<small>EQUENCE</small>: AAT-G1G

Legend

```
Italic and bold: start Methionin
Bold and underlined: His-tag
Underlined : amino acid mutation(added)
Underlined and grey : RSL mutation.
```

*M*RGSHHHHHHGSDDPQGDAAQKTDTSHHDQDHPTFNKITPNLAEFAFSLYRQLAHQSNSTNIFF
SPVSIATAFAMLSLGTKADTHDEILEGLNFNLTEIPEAQIHEGFQELLRTLNQPDSQLQLTTGN
GLFLSEGLKLVDKFLEDVKKLYHSEAFTVNFGDTEEAKKQINDYVEKGTQGKIVDLVKELDRDT
VFALVNYIFFKGKWERPFEVKDTEEEDFHVDQATTVKVPMMKRLGMFNIQHCKKLSSWVLLMKY
LGNATAIFFLPDEGKLQHLENELTHDIITKFLENEDRRSASLHLPKLSITGTYDLKSVLGQLGI
TKVFSNGADLSGVTEEAPLKLSKAVHKAVLTIDEKGTEAAGAMFLE<u>GSLRG</u>IPPEVKFNKPFVF
LMIEQNTKSPLFMGKVVNPTQK*

FIG. 21

Legend

```
Italic and bold : start codon ATG
Bold and underlined: His-tag
Underlined : DNA mutation (added codon)
Underlined and grey : DNA sequence encoding RSL mutation.
```

SEQ ID N°29 :   DNA SEQUENCE: AAT-C11

*ATGAGAGGATCGCATCACCATCACCATCACGGATCCGATGATCCCCAGGGAGATGCTGCCCAGA
AGACAGATACATCCCACCATGATCAGGATCACCCAACCTTCAACAAGATCACCCCCAACCTGGC
TGAGTTCGCCTTCAGCCTATACCGCCAGCTGGCACACCAGTCCAACAGCACCAATATCTTCTTC
TCCCCAGTGAGCATCGCTACAGCCTTTGCAATGCTCTCCCTGGGGACCAAGGCTGACACTCACG
ATGAAATCCTGGAGGGCCTGAATTTCAACCTCACGGAGATTCCGGAGGCTCAGATCCATGAAGG
CTTCCAGGAACTCCTCCGTACCCTCAACCAGCCAGACAGCCAGCTCCAGCTGACCACCGGCAAT
GGCCTGTTCCTCAGCGAGGGCCTGAAGCTAGTGGATAAGTTTTTGGAGGATGTTAAAAAGTTGT
ACCACTCAGAAGCCTTCACTGTCAACTTCGGGGACACCGAAGAGGCCAAGAAACAGATCAACGA
TTACGTGGAGAAGGGTACTCAAGGGAAAATTGTGGATTTGGTCAAGGAGCTTGACAGAGACACA
GTTTTTGCTCTGGTGAATTACATCTTCTTTAAAGGCAAATGGGAGAGACCCTTTGAAGTCAAGG
ACACCGAGGAAGAGGACTTCCACGTGGACCAGGCGACCACCGTGAAGGTGCCTATGATGAAGCG
TTTAGGCATGTTTAACATCCAGCACTGTAAGAAGCTGTCCAGCTGGGTGCTGCTGATGAAATAC
CTGGGCAATGCCACCGCCATCTTCTTCCTGCCTGATGAGGGGAAACTACAGCACCTGGAAAATG
AACTCACCCACGATATCATCACCAAGTTCCTGGAAAATGAAGACAGAAGGTCTGCCAGCTTACA
TTTACCCAAACTGTCCATTACTGGAACCTATGATCTGAAGAGCGTCCTGGGTCAACTGGGCATC
ACTAAGGTCTTCAGCAATGGGGCTGACCTCTCCGGGGTCACAGAGGAGGCACCCCTGAAGCTCT
CCAAGGCCGTGCATAAGGCTGTGCTGACCATCGACGAGAAAGGGACTGAAGCTGCTGG͟CGCCAT
GTTT͟CTAGAGGC͟TAT͟CC͟GCGTCAGA͟C͟CAA͟CCC͟TGAGGTCAAGTTCAACAAACCCTTTGTCTTC
TTAATGATTGAACAAAATACCAAGTCTCCCCTCTTCATGGGAAAGTGGTGAATCCCACCCAAA
AATAA

SEQ ID N° 51:   PROTEIN SEQUENCE: AAT-C11

Legend

```
Italic and bold: start Methionin
Bold and underlined: His-tag
Underlined : amino acid mutation(added)
Underlined and grey : RSL mutation.
```

*M*RGSHHHHHHGSDDPQGDAAQKTDTSHHDQDHPTFNKITPNLAEFAFSLYRQLAHQSNSTNIFF
SPVSIATAFAMLSLGTKADTHDEILEGLNFNLTEIPEAQIHEGFQELLRTLNQPDSQLQLTTGN
GLFLSEGLKLVDKFLEDVKKLYHSEAFTVNFGDTEEAKKQINDYVEKGTQGKIVDLVKELDRDT
VFALVNYIFFKGKWERPFEVKDTEEEDFHVDQATTVKVPMMKRLGMFNIQHCKKLSSWVLLMKY
LGNATAIFFLPDEGKLQHLENELTHDIITKFLENEDRRSASLHLPKLSITGTYDLKSVLGQLGI
TKVFSNGADLSGVTEEAPLKLSKAVHKAVLTIDEKGTEAAGAMFLEAIP͟RQTN͟PEVKFNKPFVF
LMIEQNTKSPLFMGKVVNPTQK*

FIG. 22

Legend

```
Italic and bold: start codon ATG
Bold and underlined: His-tag
Underlined : DNA mutation (added codon)
Underlined and grey : DNA sequence encoding RSL mutation.
```

SEQ ID N°30 :   DNA SEQUENCE: AAT-C11G

*ATG*AGAGGATCGCATCACCATCACCATCACGGATCCGATGATCCCCAGGGAGATGCTGCCCAGA
AGACAGATACATCCCACCATGATCAGGATCACCCAACCTTCAACAAGATCACCCCCAACCTGGC
TGAGTTCGCCTTCAGCCTATACCGCCAGCTGGCACACCAGTCCAACAGCACCAATATCTTCTTC
TCCCCAGTGAGCATCGCTACAGCCTTTGCAATGCTCTCCCTGGGGACCAAGGCTGACACTCACG
ATGAAATCCTGGAGGGCCTGAATTTCAACCTCACGGAGATTCCGGAGGCTCAGATCCATGAAGG
CTTCCAGGAACTCCTCCGTACCCTCAACCAGCCAGACAGCCAGCTCCAGCTGACCACCGGCAAT
GGCCTGTTCCTCAGCGAGGGCCTGAAGCTAGTGGATAAGTTTTTGGAGGATGTTAAAAAGTTGT
ACCACTCAGAAGCCTTCACTGTCAACTTCGGGGACACCGAAGAGGCCAAGAAACAGATCAACGA
TTACGTGGAGAAGGGTACTCAAGGGAAAATTGTGGATTTGGTCAAGGAGCTTGACAGAGACACA
GTTTTTGCTCTGGTGAATTACATCTTCTTTAAAGGCAAATGGGAGAGACCCTTTGAAGTCAAGG
ACACCGAGGAAGAGGACTTCCACGTGGACCAGGCGACCACCGTGAAGGTGCCTATGATGAAGCG
TTTAGGCATGTTTAACATCCAGCACTGTAAGAAGCTGTCCAGCTGGGTGCTGCTGATGAAATAC
CTGGGCAATGCCACCGCCATCTTCTTCCTGCCTGATGAGGGGAAACTACAGCACCTGGAAAATG
AACTCACCCACGATATCATCACCAAGTTCCTGGAAAATGAAGACAGAAGGTCTGCCAGCTTACA
TTTACCCAAACTGTCCATTACTGGAACCTATGATCTGAAGAGCGTCCTGGGTCAACTGGGCATC
ACTAAGGTCTTCAGCAATGGGGCTGACCTCTCCGGGGTCACAGAGGAGGCACCCCTGAAGCTCT
CCAAGGCCGTGCATAAGGCTGTGCTGACCATCGACGAGAAAGGGACTGAAGCTGCTGG<u>C</u>GCCAT
GTTT<u>C</u>TAGAGGC<u>T</u>AT<u>CGGTCGTCAGAC</u>C<u>AA</u>CCC<u>T</u>GAGGTCAAGTTCAACAAACCCTTTGTCTTC
TTAATGATTGAACAAAATACCAAGTCTCCCCTCTTCATGGGAAAGTGGTGAATCCCACCCAAA
AATAA

SEQ ID N° 52:   PROTEIN SEQUENCE: AAT-C11G

Legend

```
Italic and bold: start Methionin
Bold and underlined: His-tag
Underlined : amino acid mutation(added)
Underlined and grey : RSL mutation.
```

*M*RGSHHHHHHGSDDPQGDAAQKTDTSHHDQDHPTFNKITPNLAEFAFSLYRQLAHQSNSTNIFF
SPVSIATAFAMLSLGTKADTHDEILEGLNFNLTEIPEAQIHEGFQELLRTLNQPDSQLQLTTGN
GLFLSEGLKLVDKFLEDVKKLYHSEAFTVNFGDTEEAKKQINDYVEKGTQGKIVDLVKELDRDT
VFALVNYIFFKGKWERPFEVKDTEEEDFHVDQATTVKVPMMKRLGMFNIQHCKKLSSWVLLMKY
LGNATAIFFLPDEGKLQHLENELTHDIITKFLENEDRRSASLHLPKLSITGTYDLKSVLGQLGI
TKVFSNGADLSGVTEEAPLKLSKAVHKAVLTIDEKGTEAAGAMFLEAI<u>GRQTN</u>PEVKFNKPFVF
LMIEQNTKSPLFMGKVVNPTQK*

FIG. 23

Legend

```
Italic and bold : start codon ATG
Bold and underlined: His-tag
Underlined : DNA mutation (added codon)
Underlined and grey : DNA sequence encoding RSL mutation.
```

SEQ ID N°31 :       DNA SEQUENCE: AAT-E5

*ATG*AGAGGATCGCATCACCATCACCATCACGGATCCGATGATCCCCAGGGAGATGCTGCCCAGA
AGACAGATACATCCCACCATGATCAGGATCACCCAACCTTCAACAAGATCACCCCCAACCTGGC
TGAGTTCGCCTTCAGCCTATACCGCCAGCTGGCACACCAGTCCAACAGCACCAATATCTTCTTC
TCCCCAGTGAGCATCGCTACAGCCTTTGCAATGCTCTCCCTGGGGACCAAGGCTGACACTCACG
ATGAAATCCTGGAGGGCCTGAATTTCAACCTCACGGAGATTCCGGAGGCTCAGATCCATGAAGG
CTTCCAGGAACTCCTCCGTACCCTCAACCAGCCAGACAGCCAGCTCCAGCTGACCACCGGCAAT
GGCCTGTTCCTCAGCGAGGGCCTGAAGCTAGTGGATAAGTTTTTGGAGGATGTTAAAAAGTTGT
ACCACTCAGAAGCCTTCACTGTCAACTTCGGGGACACCGAAGAGGCCAAGAAACAGATCAACGA
TTACGTGGAGAAGGGTACTCAAGGGAAAATTGTGGATTTGGTCAAGGAGCTTGACAGAGACACA
GTTTTTGCTCTGGTGAATTACATCTTCTTTAAAGGCAAATGGGAGAGACCCTTTGAAGTCAAGG
ACACCGAGGAAGAGGACTTCCACGTGGACCAGGCGACCACCGTGAAGGTGCCTATGATGAAGCG
TTTAGGCATGTTTAACATCCAGCACTGTAAGAAGCTGTCCAGCTGGGTGCTGCTGATGAAATAC
CTGGGCAATGCCACCGCCATCTTCTTCCTGCCTGATGAGGGGAAACTACAGCACCTGGAAAATG
AACTCACCCACGATATCATCACCAAGTTCCTGGAAAATGAAGACAGAAGGTCTGCCAGCTTACA
TTTACCCAAACTGTCCATTACTGGAACCTATGATCTGAAGAGCGTCCTGGGTCAACTGGGCATC
ACTAAGGTCTTCAGCAATGGGGCTGACCTCTCCGGGGTCACAGAGGAGGCACCCCTGAAGCTCT
CCAAGGCCGTGCATAAGGCTGTGCTGACCATCGACGAGAAAGGGACTGAAGCTGCTGGCGCCAT
GTTTCTAGAGGCTAACCAGCGTTCTTCCCCGCCTGAGGTCAAGTTCAACAAACCCTTTGTCTTC
TTAATGATTGAACAAAATACCAAGTCTCCCCTCTTCATGGGAAAAGTGGTGAATCCCACCCAAA
AATAA

SEQ ID N° 53:       PROTEIN SEQUENCE: AAT-E5

Legend

```
Italic and bold : start Methionin
Bold and underlined: His-tag
Underlined : amino acid mutation(added)
Underlined and grey : RSL mutation.
```

*M*RGSHHHHHHGSDDPQGDAAQKTDTSHHDQDHPTFNKITPNLAEFAFSLYRQLAHQSNSTNIFF
SPVSIATAFAMLSLGTKADTHDEILEGLNFNLTEIPEAQIHEGFQELLRTLNQPDSQLQLTTGN
GLFLSEGLKLVDKFLEDVKKLYHSEAFTVNFGDTEEAKKQINDYVEKGTQGKIVDLVKELDRDT
VFALVNYIFFKGKWERPFEVKDTEEEDFHVDQATTVKVPMMKRLGMFNIQHCKKLSSWVLLMKY
LGNATAIFFLPDEGKLQHLENELTHDIITKFLENEDRRSASLHLPKLSITGTYDLKSVLGQLGI
TKVFSNGADLSGVTEEAPLKLSKAVHKAVLTIDEKGTEAAGAMFLEANQRSSPPEVKFNKPFVF
LMIEQNTKSPLFMGKVVNPTQK*

FIG. 24

Legend

```
Italic and bold : start codon ATG
Bold and underlined: His-tag
Underlined : DNA mutation (added codon)
Underlined and grey : DNA sequence encoding RSL mutation.
```

SEQ ID N°32 :     DNA SEQUENCE: AAT-E8

*ATG*AGAGGATCGCATCACCATCACCATCACGGATCCGATGATCCCCAGGGAGATGCTGCCCAGA
AGACAGATACATCCCACCATGATCAGGATCACCCAACCTTCAACAAGATCACCCCCAACCTGGC
TGAGTTCGCCTTCAGCCTATACCGCCAGCTGGCACACCAGTCCAACAGCACCAATATCTTCTTC
TCCCCAGTGAGCATCGCTACAGCCTTTGCAATGCTCTCCCTGGGGACCAAGGCTGACACTCACG
ATGAAATCCTGGAGGGCCTGAATTTCAACCTCACGGAGATTCCGGAGGCTCAGATCCATGAAGG
CTTCCAGGAACTCCTCCGTACCCTCAACCAGCCAGACAGCCAGCTCCAGCTGACCACCGGCAAT
GGCCTGTTCCTCAGCGAGGGCCTGAAGCTAGTGGATAAGTTTTTGGAGGATGTTAAAAAGTTGT
ACCACTCAGAAGCCTTCACTGTCAACTTCGGGGACACCGAAGAGGCCAAGAAACAGATCAACGA
TTACGTGGAGAAGGGTACTCAAGGGAAAATTGTGGATTTGGTCAAGGAGCTTGACAGAGACACA
GTTTTTGCTCTGGTGAATTACATCTTCTTTAAAGGCAAATGGGAGAGACCCTTTGAAGTCAAGG
ACACCGAGGAAGAGGACTTCCACGTGGACCAGGCGACCACCGTGAAGGTGCCTATGATGAAGCG
TTTAGGCATGTTTAACATCCAGCACTGTAAGAAGCTGTCCAGCTGGGTGCTGCTGATGAAATAC
CTGGGCAATGCCACCGCCATCTTCTTCCTGCCTGATGAGGGGAAACTACAGCACCTGGAAAATG
AACTCACCCACGATATCATCACCAAGTTCCTGGAAAATGAAGACAGAAGGTCTGCCAGCTTACA
TTTACCCAAACTGTCCATTACTGGAACCTATGATCTGAAGAGCGTCCTGGGTCAACTGGGCATC
ACTAAGGTCTTCAGCAATGGGGCTGACCTCTCCGGGGTCACAGAGGAGGCACCCCTGAAGCTCT
CCAAGGCCGTGCATAAGGCTGTGCTGACCATCGACGAGAAGGGACTGAAGCTGCTGGC̱GCCAT
GTTTC̱TAGAGGCṮC̱ṮGC̱AGC̱GṮGCTATCCCG̱CCṮGAGGTCAAGTTCAACAAACCCTTTGTCTTC
TTAATGATTGAACAAAATACCAAGTCTCCCCTCTTCATGGGAAAAGTGGTGAATCCCACCCAAA
AATAA

SEQ ID N° 54:     PROTEIN SEQUENCE: AAT-E8

Legend

```
Italic and bold: start Methionin
Bold and underlined: His-tag
Underlined : amino acid mutation(added)
Underlined and grey : RSL mutation.
```

*M*RGSHHHHHHGSDDPQGDAAQKTDTSHHDQDHPTFNKITPNLAEFAFSLYRQLAHQSNSTNIFF
SPVSIATAFAMLSLGTKADTHDEILEGLNFNLTEIPEAQIHEGFQELLRTLNQPDSQLQLTTGN
GLFLSEGLKLVDKFLEDVKKLYHSEAFTVNFGDTEEAKKQINDYVEKGTQGKIVDLVKELDRDT
VFALVNYIFFKGKWERPFEVKDTEEEDFHVDQATTVKVPMMKRLGMFNIQHCKKLSSWVLLMKY
LGNATAIFFLPDEGKLQHLENELTHDIITKFLENEDRRSASLHLPKLSITGTYDLKSVLGQLGI
TKVFSNGADLSGVTEEAPLKLSKAVHKAVLTIDEKGTEAAGAMFLEAḺQ̱ṞA̱IPPEVKFNKPFVF
LMIEQNTKSPLFMGKVVNPTQK*

FIG. 25

Legend

```
Italic and bold : start codon ATG
Bold and underlined: His-tag
Underlined : DNA mutation (added codon)
Underlined and grey : DNA sequence encoding RSL mutation.
```

SEQ ID N°33 :   DNA SEQUENCE: AAT-F11

*ATG*AGAGGATCGCATCACCATCACCATCACGGATCCGATGATCCCCAGGGAGATGCTGCCCAGA
AGACAGATACATCCCACCATGATCAGGATCACCCAACCTTCAACAAGATCACCCCCAACCTGGC
TGAGTTCGCCTTCAGCCTATACCGCCAGCTGGCACACCAGTCCAACAGCACCAATATCTTCTTC
TCCCCAGTGAGCATCGCTACAGCCTTTGCAATGCTCTCCCTGGGGACCAAGGCTGACACTCACG
ATGAAATCCTGGAGGGCCTGAATTTCAACCTCACGGAGATTCCGGAGGCTCAGATCCATGAAGG
CTTCCAGGAACTCCTCCGTACCCTCAACCAGCCAGACAGCCAGCTCCAGCTGACCACCGGCAAT
GGCCTGTTCCTCAGCGAGGGCCTGAAGCTAGTGGATAAGTTTTTGGAGGATGTTAAAAAGTTGT
ACCACTCAGAAGCCTTCACTGTCAACTTCGGGGACACCGAAGAGGCCAAGAAACAGATCAACGA
TTACGTGGAGAAGGGTACTCAAGGGAAAATTGTGGATTTGGTCAAGGAGCTTGACAGAGACACA
GTTTTTGCTCTGGTGAATTACATCTTCTTTAAAGGCAAATGGGAGAGACCCTTTGAAGTCAAGG
ACACCGAGGAAGAGGACTTCCACGTGGACCAGGCGACCACCGTGAAGGTGCCTATGATGAAGCG
TTTAGGCATGTTTAACATCCAGCACTGTAAGAAGCTGTCCAGCTGGGTGCTGCTGATGAAATAC
CTGGGCAATGCCACCGCCATCTTCTTCCTGCCTGATGAGGGGAAACTACAGCACCTGGAAAATG
AACTCACCCACGATATCATCACCAAGTTCCTGGAAAATGAAGACAGAAGGTCTGCCAGCTTACA
TTTACCCAAACTGTCCATTACTGGAACCTATGATCTGAAGAGCGTCCTGGGTCAACTGGGCATC
ACTAAGGTCTTCAGCAATGGGGCTGACCTCTCCGGGGTCACAGAGGAGGCACCCCTGAAGCTCT
CCAAGGCCGTGCATAAGGCTGTGCTGACCATCGACGAGAAAGGGACTGAAGCTGCTGG<u>C</u>GCCAT
GTTT<u>C</u>TAGAG<u>CAGCGTCTGCGTGAC</u>ATCCC<u>G</u>CC<u>T</u>GAGGTCAAGTTCAACAAACCCTTTGTCTTC
TTAATGATTGAACAAAATACCAAGTCTCCCCTCTTCATGGGAAAAGTGGTGAATCCCACCCAAA
AATAA

SEQ ID N° 55:   PROTEIN SEQUENCE: AAT-F11

Legend

```
Italic and bold: start Methionin
Bold and underlined: His-tag
Underlined : amino acid mutation(added)
Underlined and grey : RSL mutation.
```

*M*RGSHHHHHHGSDDPQGDAAQKTDTSHHDQDHPTFNKITPNLAEFAFSLYRQLAHQSNSTNIFF
SPVSIATAFAMLSLGTKADTHDEILEGLNFNLTEIPEAQIHEGFQELLRTLNQPDSQLQLTTGN
GLFLSEGLKLVDKFLEDVKKLYHSEAFTVNFGDTEEAKKQINDYVEKGTQGKIVDLVKELDRDT
VFALVNYIFFKGKWERPFEVKDTEEEDFHVDQATTVKVPMMKRLGMFNIQHCKKLSSWVLLMKY
LGNATAIFFLPDEGKLQHLENELTHDIITKFLENEDRRSASLHLPKLSITGTYDLKSVLGQLGI
TKVFSNGADLSGVTEEAPLKLSKAVHKAVLTIDEKGTEAAGAMFLE<u>QRLRD</u>IPPEVKFNKPFVF
LMIEQNTKSPLFMGKVVNPTQK*

FIG. 26

Legend

```
Italic and bold : start codon ATG
Bold and underlined: His-tag
Underlined : DNA mutation (added codon)
Underlined and grey : DNA sequence encoding RSL mutation.
```

SEQ ID N°34 :  DNA SEQUENCE: AAT-F3

*ATG*AGAGGATCGCATCACCATCACCATCACGGATCCGATGATCCCCAGGGAGATGCTGCCCAGA
AGACAGATACATCCCACCATGATCAGGATCACCCAACCTTCAACAAGATCACCCCCAACCTGGC
TGAGTTCGCCTTCAGCCTATACCGCCAGCTGGCACACCAGTCCAACAGCACCAATATCTTCTTC
TCCCCAGTGAGCATCGCTACAGCCTTTGCAATGCTCTCCCTGGGGACCAAGGCTGACACTCACG
ATGAAATCCTGGAGGGCCTGAATTTCAACCTCACGGAGATTCCGGAGGCTCAGATCCATGAAGG
CTTCCAGGAACTCCTCCGTACCCTCAACCAGCCAGACAGCCAGCTCCAGCTGACCACCGGCAAT
GGCCTGTTCCTCAGCGAGGGCCTGAAGCTAGTGGATAAGTTTTTGGAGGATGTTAAAAAGTTGT
ACCACTCAGAAGCCTTCACTGTCAACTTCGGGGACACCGAAGAGGCCAAGAAACAGATCAACGA
TTACGTGGAGAAGGGTACTCAAGGGAAAATTGTGGATTTGGTCAAGGAGCTTGACAGAGACACA
GTTTTTGCTCTGGTGAATTACATCTTCTTTAAAGGCAAATGGGAGAGACCCTTTGAAGTCAAGG
ACACCGAGGAAGAGGACTTCCACGTGGACCAGGCGACCACCGTGAAGGTGCCTATGATGAAGCG
TTTAGGCATGTTTAACATCCAGCACTGTAAGAAGCTGTCCAGCTGGGTGCTGCTGATGAAATAC
CTGGGCAATGCCACCGCCATCTTCTTCCTGCCTGATGAGGGGAAACTACAGCACCTGGAAAATG
AACTCACCCACGATATCATCACCAAGTTCCTGGAAAATGAAGACAGAAGGTCTGCCAGCTTACA
TTTACCCAAACTGTCCATTACTGGAACCTATGATCTGAAGAGCGTCCTGGGTCAACTGGGCATC
ACTAAGGTCTTCAGCAATGGGGCTGACCTCTCCGGGGTCACAGAGGAGGCACCCCTGAAGCTCT
CCAAGGCCGTGCATAAGGCTGTGCTGACCATCGACGAGAAAGGGACTGAAGCTGCTGGCGCCAT
GTTTCTAGAGGCTCCGGACCGTCACATGCCGCCTGAGGTCAAGTTCAACAAACCCTTTGTCTTC
TTAATGATTGAACAAAATACCAAGTCTCCCCTCTTCATGGGAAAAGTGGTGAATCCCACCCAAA
AATAA

SEQ ID N° 56:  PROTEIN SEQUENCE: AAT-F3

Legend

```
Italic and bold : start Methionin
Bold and underlined: His-tag
Underlined : amino acid mutation(added)
Underlined and grey : RSL mutation.
```

*M*RGSHHHHHHGSDDPQGDAAQKTDTSHHDQDHPTFNKITPNLAEFAFSLYRQLAHQSNSTNIFF
SPVSIATAFAMLSLGTKADTHDEILEGLNFNLTEIPEAQIHEGFQELLRTLNQPDSQLQLTTGN
GLFLSEGLKLVDKFLEDVKKLYHSEAFTVNFGDTEEAKKQINDYVEKGTQGKIVDLVKELDRDT
VFALVNYIFFKGKWERPFEVKDTEEEDFHVDQATTVKVPMMKRLGMFNIQHCKKLSSWVLLMKY
LGNATAIFFLPDEGKLQHLENELTHDIITKFLENEDRRSASLHLPKLSITGTYDLKSVLGQLGI
TKVFSNGADLSGVTEEAPLKLSKAVHKAVLTIDEKGTEAAGAMFLEAPDRHMPPEVKFNKPFVF
LMIEQNTKSPLFMGKVVNPTQK*

FIG. 27

Legend

```
Italic and bold : start codon ATG
Bold and underlined: His-tag
Underlined : DNA mutation (added codon)
Underlined and grey : DNA sequence encoding RSL mutation.
```

SEQ ID N°35 :   DNA SEQUENCE: AAT-G9

*ATG*AGAGGATCGCATCACCATCACCATCACGGATCCGATGATCCCCAGGGAGATGCTGCCCAGA
AGACAGATACATCCCACCATGATCAGGATCACCCAACCTTCAACAAGATCACCCCCAACCTGGC
TGAGTTCGCCTTCAGCCTATACCGCCAGCTGGCACACCAGTCCAACAGCACCAATATCTTCTTC
TCCCCAGTGAGCATCGCTACAGCCTTTGCAATGCTCTCCCTGGGGACCAAGGCTGACACTCACG
ATGAAATCCTGGAGGGCCTGAATTTCAACCTCACGGAGATTCCGGAGGCTCAGATCCATGAAGG
CTTCCAGGAACTCCTCCGTACCCTCAACCAGCCAGACAGCCAGCTCCAGCTGACCACCGGCAAT
GGCCTGTTCCTCAGCGAGGGCCTGAAGCTAGTGGATAAGTTTTTGGAGGATGTTAAAAAGTTGT
ACCACTCAGAAGCCTTCACTGTCAACTTCGGGGACACCGAAGAGGCCAAGAAACAGATCAACGA
TTACGTGGAGAAGGGTACTCAAGGGAAAATTGTGGATTTGGTCAAGGAGCTTGACAGAGACACA
GTTTTTGCTCTGGTGAATTACATCTTCTTTAAAGGCAAATGGGAGAGACCCTTTGAAGTCAAGG
ACACCGAGGAAGAGGACTTCCACGTGGACCAGGCGACCACCGTGAAGGTGCCTATGATGAAGCG
TTTAGGCATGTTTAACATCCAGCACTGTAAGAAGCTGTCCAGCTGGGTGCTGCTGATGAAATAC
CTGGGCAATGCCACCGCCATCTTCTTCCTGCCTGATGAGGGGAAACTACAGCACCTGGAAAATG
AACTCACCCACGATATCATCACCAAGTTCCTGGAAAATGAAGACAGAAGGTCTGCCAGCTTACA
TTTACCCAAACTGTCCATTACTGGAACCTATGATCTGAAGAGCGTCCTGGGTCAACTGGGCATC
ACTAAGGTCTTCAGCAATGGGGCTGACCTCTCCGGGGTCACAGAGGAGGCACCCCTGAAGCTCT
CCAAGGCCGTGCATAAGGCTGTGCTGACCATCGACGAGAAAGGGACTGAAGCTGCTGG<u>C</u>GCCAT
GTTT<u>C</u>TAGAG<u>A</u>CC<u>GT</u><u>TGAC</u><u>TACG</u>CTATCCC<u>G</u>CC<u>T</u>GAGGTCAAGTTCAACAAACCCTTT<u>G</u>TCTTC
TTAATGATTGAACAAAATACCAAGTCTCCCCTCTTCATGGGAAAAGTGGTGAATCCCACCCAAA
AATAA

SEQ ID N° 57:   PROTEIN SEQUENCE: AAT-G9

Legend

```
Italic and bold: start Methionin
Bold and underlined: His-tag
Underlined : amino acid mutation(added)
Underlined and grey : RSL mutation.
```

*M*RGSHHHHHHGSDDPQGDAAQKTDTSHHDQDHPTFNKITPNLAEFAFSLYRQLAHQSNSTNIFF
SPVSIATAFAMLSLGTKADTHDEILEGLNFNLTEIPEAQIHEGFQELLRTLNQPDSQLQLTTGN
GLFLSEGLKLVDKFLEDVKKLYHSEAFTVNFGDTEEAKKQINDYVEKGTQGKIVDLVKELDRDT
VFALVNYIFFKGKWERPFEVKDTEEEDFHVDQATTVKVPMMKRLGMFNIQHCKKLSSWVLLMKY
LGNATAIFFLPDEGKLQHLENELTHDIITKFLENEDRRSASLHLPKLSITGTYDLKSVLGQLGI
TKVFSNGADLSGVTEEAPLKLSKAVHKAVLTIDEKGTEAAGAMFLE<u>IVDYA</u>IPPEVKFNKPFVF
LMIEQNTKSPLFMGKVVNPTQK*

FIG. 28

Legend

```
Italic and bold : start codon ATG
Bold and underlined: His-tag
Underlined : DNA mutation (added codon)
Underlined and grey : DNA sequence encoding RSL mutation.
```

SEQ ID N° 36 :    DNA SEQUENCE: ACT-G1V

*ATG*AGAGGATCCCATCACCATCACCATCACTCTAGACACCCTAACAGCCCACTTGACGAGGAGA
ATCTGACCCAGGAGAACCAAGACCGAGGGACACACGTGGACCTCGGATTAGCCTCCGCCAACGT
GGACTTCGCTTTCAGCCTGTACAAGCAGTTAGTCCTGAAGGCCCCTGATAAGAATGTCATCTTC
TCCCCACTGAGCATCTCCACCGCCTTGGCCTTCCTGTCTCTGGGGGCCCATAATACCACCCTGA
CAGAGATTCTCAAAGGCCTCAAGTTCAACCTCACGGAGACTTCTGAGGCAGAAATTCACCAGAG
CTTCCAGCACCTCCTGCGCACCCTCAATCAGTCCAGCGATGAGCTGCAGCTGAGTATGGGAAAT
GCCATGTTTGTCAAAGAGCAACTCAGTCTGCTGGACAGGTTCACGGAGGATGCCAAGAGGCTGT
ATGGCTCCGAGGCCTTTGCCACTGACTTTCAGGACTCAGCTGCAGCTAAGAAGCTCATCAACGA
CTACGTGAAGAATGGAACTAGGGGGAAAATCACAGATCTGATCAAGGACCTTGACTCGCAGACA
ATGATGGTCCTGGTGAATTACATCTTCTTTAAAGCCAAATGGGAGATGCCCTTTGACCCCCAAG
ATACTCATCAGTCAAGGTTCTACTTGAGCAAGAAAAGTGGGTAATGGTGCCCATGATGAGTTT
GCATCACCTGACTATACCTTACTTCCGGGACGAGGAGCTGTCCTGCACCGTGGTGGAGCTGAAG
TACACAGGCAATGCCAGCGCACTCTTCATCCTCCCTGATCAAGACAAGATGGAGGAAGTGGAAG
CCATGCTGCTCCCAGAGACCCTGAAGCGGTGGAGAGACTCTCTGGAGTTCAGAGAGATAGGTGA
GCTCTACCTGCCAAAGTTTTCCATCTCGAGGGACTATAACCTGAACGACATACTTCTCCAGCTG
GGCATTGAGGAAGCCTTCACCAGCAAGGCTGACCTGTCAGGGATCACAGGGGCCAGGAACCTAG
CAGTCTCCCAGGTGGTCCATAAGGCTGTGCTTGATGTATTTGAGGAGGGCACAGAAGCATCTGC
TGCCAC<u>CGC</u>GGTC<u>GTTGGTTCT</u>CTG<u>C</u>GTTCTGCATTAGTGGAGAC<u>GCG</u>TACCATTGTGCGTTTC
AACAGGCCCTTCCTGATGATCATTGTCCCTACAGACACCCAGAACATCTTCTTCATGAGCAAAG
TCACCAATCCCAAGCAAGCCTAA

SEQ ID N° 58 :    PROTEIN SEQUENCE: ACT-G1V

Legend

```
Italic and bold: start Methionin
Bold and underlined: His-tag
Underlined : amino acid mutation(added)
Underlined and grey : RSL mutation
```

*M*RGSHHHHHHSRHPNSPLDEENLTQENQDRGTHVDLGLASANVDFAFSLYKQLVLKAPDKNVIF
SPLSISTALAFLSLGAHNTTLTEILKGLKFNLTETSEAEIHQSFQHLLRTLNQSSDELQLSMGN
AMFVKEQLSLLDRFTEDAKRLYGSEAFATDFQDSAAAKKLINDYVKNGTRGKITDLIKDLDSQT
MMVLVNYIFFKAKWEMPFDPQDTHQSRFYLSKKKWVMVPMMSLHHLTIPYFRDEELSCTVVELK
YTGNASALFILPDQDKMEEVEAMLLPETLKRWRDSLEFREIGELYLPKFSISRDYNLNDILLQL
GIEEAFTSKADLSGITGARNLAVSQVVHKAVLDVFEEGTEASAATA<u>VGSLR</u>SALVETRTIVRF
NRPFLMIIVPTDTQNIFFMSKVTNPKQA*

FIG. 29

Legend

```
Italic and bold : start codon ATG
Bold and underlined: His-tag
Underlined : DNA mutation (added codon)
Underlined and grey : DNA sequence encoding RSL mutation.
```

SEQ ID N° 37 :   DNA SEQUENCE: ACT-C11D

*ATG*AGAGGATCCCATCACCATCACCATCACTCTAGACACCCTAACAGCCCACTTGACGAGGAGA
ATCTGACCCAGGAGAACCAAGACCGAGGGACACACGTGGACCTCGGATTAGCCTCCGCCAACGT
GGACTTCGCTTTCAGCCTGTACAAGCAGTTAGTCCTGAAGGCCCCTGATAAGAATGTCATCTTC
TCCCCACTGAGCATCTCCACCGCCTTGGCCTTCCTGTCTCTGGGGGCCCATAATACCACCCTGA
CAGAGATTCTCAAAGGCCTCAAGTTCAACCTCACGGAGACTTCTGAGGCAGAAATTCACCAGAG
CTTCCAGCACCTCCTGCGCACCCTCAATCAGTCCAGCGATGAGCTGCAGCTGAGTATGGGAAAT
GCCATGTTTGTCAAAGAGCAACTCAGTCTGCTGGACAGGTTCACGGAGGATGCCAAGAGGCTGT
ATGGCTCCGAGGCCTTTGCCACTGACTTTCAGGACTCAGCTGCAGCTAAGAAGCTCATCAACGA
CTACGTGAAGAATGGAACTAGGGGGAAAATCACAGATCTGATCAAGGACCTTGACTCGCAGACA
ATGATGGTCCTGGTGAATTACATCTTCTTTAAAGCCAAATGGGAGATGCCCTTTGACCCCCAAG
ATACTCATCAGTCAAGGTTCTACTTGAGCAAGAAAAGTGGGTAATGGTGCCCATGATGAGTTT
GCATCACCTGACTATACCTTACTTCCGGGACGAGGAGCTGTCCTGCACCGTGGTGGAGCTGAAG
TACACAGGCAATGCCAGCGCACTCTTCATCCTCCCTGATCAAGACAAGATGGAGGAAGTGGAAG
CCATGCTGCTCCCAGAGACCCTGAAGCGGTGGAGAGACTCTCTGGAGTTCAGAGAGATAGGTGA
GCTCTACCTGCCAAAGTTTTCCATCTCGAGGGACTATAACCTGAACGACATACTTCTCCAGCTG
GGCATTGAGGAAGCCTTCACCAGCAAGGCTGACCTGTCAGGGATCACAGGGGCCAGGAACCTAG
CAGTCTCCCAGGTGGTCCATAAGGCTGTGCTTGATGTATTTGAGGAGGGCACAGAAGCATCTGC
TGCCAC<u>C</u>GC<u>G</u>GTCAAAATCACCCTCC<u>GTCAGACCAACGAC</u>GAGAC<u>GC</u>G<u>T</u>ACCATTGTGCGTTTC
AACAGGCCCTTCCTGATGATCATTGTCCCTACAGACACCCAGAACATCTTCTTCATGAGCAAAG
TCACCAATCCCAAGCAAGCCTAA

SEQ ID N° 59:   PROTEIN SEQUENCE: ACT-C11D

Legend

```
Italic and bold: start Methionin
Bold and underlined: His-tag
Underlined : amino acid mutation(added)
Underlined and grey : RSL mutation
```

*M*<u>RGS</u>HHHHHHSRHPNSPLDEENLTQENQDRGTHVDLGLASANVDFAFSLYKQLVLKAPDKNVIF
SPLSISTALAFLSLGAHNTTLTEILKGLKFNLTETSEAEIHQSFQHLLRTLNQSSDELQLSMGN
AMFVKEQLSLLDRFTEDAKRLYGSEAFATDFQDSAAAKKLINDYVKNGTRGKITDLIKDLDSQT
MMVLVNYIFFKAKWEMPFDPQDTHQSRFYLSKKKWVMVPMMSLHHLTIPYFRDEELSCTVVELK
YTGNASALFILPDQDKMEEVEAMLLPETLKRWRDSLEFREIGELYLPKFSISRDYNLNDILLQL
GIEEAFTSKADLSGITGARNLAVSQVVHKAVLDVFEEGTEASAATAVKITL<u>RQTNDE</u>TRTIVRF
NRPFLMIIVPTDTQNIFFMSKVTNPKQA*

Grade 1: low severity – value = 1

Grade 2: low to mid-severity – value = 2

Grade 3: mid high severity – value = 3

Grade 4: high severity – value = 4

SEQUENCE LISTING

```
<160> NUMBER OF SEQ ID NOS: 203

<210> SEQ ID NO 1
<211> LENGTH: 1239
<212> TYPE: DNA
<213> ORGANISM: Artificial Sequence
<220> FEATURE:
<223> OTHER INFORMATION: Synthetic

<400> SEQUENCE: 1
atgagaggat cccatcacca tcaccatcac tctagacacc ctaacagccc acttgacgag      60
gagaatctga cccaggagaa ccaagaccga gggacacacg tggacctcgg attagcctcc     120
gccaacgtgg acttcgcttt cagcctgtac aagcagttag tcctgaaggc ccctgataag     180
aatgtcatct tctccccact gagcatctcc accgccttgg ccttcctgtc tctggggggcc    240 cataatacca ccctgacaga gattctcaaa ggcctcaagt tcaacctcac ggagacttct     300
gaggcagaaa ttcaccagag cttccagcac ctcctgcgca ccctcaatca gtccagcgat     360
gagctgcagc tgagtatggg aaatgccatg tttgtcaaag agcaactcag tctgctggac     420
aggttcacgg aggatgccaa gaggctgtat ggctccgagg cctttgccac tgactttcag     480
gactcagctg cagctaagaa gctcatcaac gactacgtga agaatggaac taggggggaaa    540 atcacagatc tgatcaagga ccttgactcg cagacaatga tggtcctggt gaattacatc     600
ttctttaaag ccaaatggga gatgcccttt gacccccaag atactcatca gtcaaggttc     660
tacttgagca agaaaaagtg ggtaatggtg cccatgatga gtttgcatca cctgactata     720
ccttacttcc gggacgagga gctgtcctgc accgtggtgg agctgaagta cacaggcaat     780
gccagcgcac tcttcatcct ccctgatcaa gacaagatgg aggaagtgga agccatgctg     840
ctcccagaga ccctgaagcg gtggagagac tctctggagt tcagagagat aggtgagctc     900
tacctgccaa agttttccat ctcgagggac tataacctga cgacatact tctccagctg     960 ggcattgagg aagccttcac cagcaaggct gacctgtcag ggatcacagg ggccaggaac    1020
ctagcagtct cccaggtggt ccataaggct gtgcttgatg tatttgagga gggcacagaa    1080
gcatctgctg ccaccgcggt caaaatcacc ctccgttctc gagcagtgga gacgcgtacc    1140
```

-continued

```
attgtgcgtt tcaacaggcc cttcctgatg atcattgtcc ctacagacac ccagaacatc    1200
ttcttcatga gcaaagtcac caatcccaag caagcctaa                           1239
```

<210> SEQ ID NO 2
<211> LENGTH: 412
<212> TYPE: PRT
<213> ORGANISM: Artificial Sequence
<220> FEATURE:
<223> OTHER INFORMATION: Synthetic

<400> SEQUENCE: 2

```
Met Arg Gly Ser His His His His His His Ser Arg His Pro Asn Ser
1               5                   10                  15

Pro Leu Asp Glu Glu Asn Leu Thr Gln Glu Asn Gln Asp Arg Gly Thr
            20                  25                  30

His Val Asp Leu Gly Leu Ala Ser Ala Asn Val Asp Phe Ala Phe Ser
        35                  40                  45

Leu Tyr Lys Gln Leu Val Leu Lys Ala Pro Asp Lys Asn Val Ile Phe
    50                  55                  60

Ser Pro Leu Ser Ile Ser Thr Ala Leu Ala Phe Leu Ser Leu Gly Ala
65                  70                  75                  80

His Asn Thr Thr Leu Thr Glu Ile Leu Lys Gly Leu Lys Phe Asn Leu
                85                  90                  95

Thr Glu Thr Ser Glu Ala Glu Ile His Gln Ser Phe Gln His Leu Leu
            100                 105                 110

Arg Thr Leu Asn Gln Ser Ser Asp Glu Leu Gln Leu Ser Met Gly Asn
        115                 120                 125

Ala Met Phe Val Lys Glu Gln Leu Ser Leu Leu Asp Arg Phe Thr Glu
    130                 135                 140

Asp Ala Lys Arg Leu Tyr Gly Ser Glu Ala Phe Ala Thr Asp Phe Gln
145                 150                 155                 160

Asp Ser Ala Ala Ala Lys Lys Leu Ile Asn Asp Tyr Val Lys Asn Gly
                165                 170                 175

Thr Arg Gly Lys Ile Thr Asp Leu Ile Lys Asp Leu Asp Ser Gln Thr
            180                 185                 190

Met Met Val Leu Val Asn Tyr Ile Phe Phe Lys Ala Lys Trp Glu Met
        195                 200                 205

Pro Phe Asp Pro Gln Asp Thr His Gln Ser Arg Phe Tyr Leu Ser Lys
    210                 215                 220

Lys Lys Trp Val Met Val Pro Met Met Ser Leu His His Leu Thr Ile
225                 230                 235                 240

Pro Tyr Phe Arg Asp Glu Glu Leu Ser Cys Thr Val Val Glu Leu Lys
                245                 250                 255

Tyr Thr Gly Asn Ala Ser Ala Leu Phe Ile Leu Pro Asp Gln Asp Lys
            260                 265                 270

Met Glu Glu Val Glu Ala Met Leu Leu Pro Glu Thr Leu Lys Arg Trp
        275                 280                 285

Arg Asp Ser Leu Glu Phe Arg Glu Ile Gly Glu Leu Tyr Leu Pro Lys
    290                 295                 300

Phe Ser Ile Ser Arg Asp Tyr Asn Leu Asn Asp Ile Leu Leu Gln Leu
305                 310                 315                 320

Gly Ile Glu Glu Ala Phe Thr Ser Lys Ala Asp Leu Ser Gly Ile Thr
                325                 330                 335

Gly Ala Arg Asn Leu Ala Val Ser Gln Val Val His Lys Ala Val Leu
            340                 345                 350
```

```
Asp Val Phe Glu Glu Gly Thr Glu Ala Ser Ala Ala Thr Ala Val Lys
        355                 360                 365

Ile Thr Leu Arg Ser Arg Ala Val Glu Thr Arg Thr Ile Val Arg Phe
    370                 375                 380

Asn Arg Pro Phe Leu Met Ile Ile Val Pro Thr Asp Thr Gln Asn Ile
385                 390                 395                 400

Phe Phe Met Ser Lys Val Thr Asn Pro Lys Gln Ala
                405                 410
```

<210> SEQ ID NO 3
<211> LENGTH: 1239
<212> TYPE: DNA
<213> ORGANISM: Artificial Sequence
<220> FEATURE:
<223> OTHER INFORMATION: Synthetic

<400> SEQUENCE: 3

```
atgagaggat cccatcacca tcaccatcac tctagacacc ctaacagccc acttgacgag      60
gagaatctga cccaggagaa ccaagaccga gggacacacg tggacctcgg attagcctcc    120
gccaacgtgg acttcgcttt cagcctgtac aagcagttag tcctgaaggc ccctgataag    180
aatgtcatct ctctccccac tgagcatctc caccgccttg ccttcctgtc tctgggggcc    240
cataatacca ccctgacaga gattctcaaa ggcctcaagt tcaacctcac ggagacttct    300
gaggcagaaa ttcaccagag cttccagcac ctcctgcgca ccctcaatca gtccagcgat    360
gagctgcagc tgagtatggg aaatgccatg tttgtcaaag agcaactcag tctgctggac    420
aggttcacgg aggatgccaa gaggctgtat ggctccgagg cctttgccac tgactttcag    480
gactcagctg cagctaagaa gctcatcaac gactacgtga agaatggaac tagggggaaa    540
atcacagatc tgatcaagga ccttgactcg cagacaatga tggtcctggt gaattacatc    600
ttctttaaag ccaaatggga gatgcccttt gaccccaagg atactcatca gtcaaggttc    660
tacttgagca gaaaaagtg ggtaatggtg cccatgatga gtttgcatca cctgactata    720
ccttacttcc gggacgagga gctgtcctgc accgtggtgg agctgaagta cacaggcaat    780
gccagcgcac tcttcatcct ccctgatcaa gacaagatgg aggaagtgga agccatgctg    840
ctcccagaga ccctgaagcg gtggagagac tctctggagt tcagagagat aggtgagctc    900
tacctgccaa agttttccat ctcgagggac tataacctga cgacatact ctctccagctg    960
ggcattgagg aagccttcac cagcaaggct gacctgtcag ggatcacagg ggccaggaac   1020
ctagcagtct cccaggtggt ccataaggct gtgcttgatg tatttgagga gggcacagaa   1080
gcatctgctg ccaccgcggt caaaatcacc aggaggtcta tcgatgtgga gacgcgtacc   1140
attgtgcgtt tcaacaggcc cttcctgatg atcattgtcc ctacagacac ccagaacatc   1200
ttcttcatga gcaaagtcac caatcccaag caagcctaa                          1239
```

<210> SEQ ID NO 4
<211> LENGTH: 412
<212> TYPE: PRT
<213> ORGANISM: Artificial Sequence
<220> FEATURE:
<223> OTHER INFORMATION: Synthetic

<400> SEQUENCE: 4

```
Met Arg Gly Ser His His His His His His Ser Arg His Pro Asn Ser
1               5                   10                  15

Pro Leu Asp Glu Glu Asn Leu Thr Gln Glu Asn Gln Asp Arg Gly Thr
            20                  25                  30
```

His Val Asp Leu Gly Leu Ala Ser Ala Asn Val Asp Phe Ala Phe Ser
            35                  40                  45

Leu Tyr Lys Gln Leu Val Leu Lys Ala Pro Asp Lys Asn Val Ile Phe
 50                  55                  60

Ser Pro Leu Ser Ile Ser Thr Ala Leu Ala Phe Leu Ser Leu Gly Ala
 65                  70                  75                  80

His Asn Thr Thr Leu Thr Glu Ile Leu Lys Gly Leu Lys Phe Asn Leu
                 85                  90                  95

Thr Glu Thr Ser Glu Ala Glu Ile His Gln Ser Phe Gln His Leu Leu
            100                 105                 110

Arg Thr Leu Asn Gln Ser Ser Asp Glu Leu Gln Leu Ser Met Gly Asn
        115                 120                 125

Ala Met Phe Val Lys Glu Gln Leu Ser Leu Leu Asp Arg Phe Thr Glu
130                 135                 140

Asp Ala Lys Arg Leu Tyr Gly Ser Glu Ala Phe Ala Thr Asp Phe Gln
145                 150                 155                 160

Asp Ser Ala Ala Ala Lys Lys Leu Ile Asn Asp Tyr Val Lys Asn Gly
                165                 170                 175

Thr Arg Gly Lys Ile Thr Asp Leu Ile Lys Asp Leu Asp Ser Gln Thr
            180                 185                 190

Met Met Val Leu Val Asn Tyr Ile Phe Phe Lys Ala Lys Trp Glu Met
        195                 200                 205

Pro Phe Asp Pro Gln Asp Thr His Gln Ser Arg Phe Tyr Leu Ser Lys
210                 215                 220

Lys Lys Trp Val Met Val Pro Met Met Ser Leu His His Leu Thr Ile
225                 230                 235                 240

Pro Tyr Phe Arg Asp Glu Glu Leu Ser Cys Thr Val Val Glu Leu Lys
                245                 250                 255

Tyr Thr Gly Asn Ala Ser Ala Leu Phe Ile Leu Pro Asp Gln Asp Lys
            260                 265                 270

Met Glu Glu Val Glu Ala Met Leu Leu Pro Glu Thr Leu Lys Arg Trp
        275                 280                 285

Arg Asp Ser Leu Glu Phe Arg Glu Ile Gly Glu Leu Tyr Leu Pro Lys
290                 295                 300

Phe Ser Ile Ser Arg Asp Tyr Asn Leu Asn Asp Ile Leu Leu Gln Leu
305                 310                 315                 320

Gly Ile Glu Glu Ala Phe Thr Ser Lys Ala Asp Leu Ser Gly Ile Thr
                325                 330                 335

Gly Ala Arg Asn Leu Ala Val Ser Gln Val Val His Lys Ala Val Leu
            340                 345                 350

Asp Val Phe Glu Glu Gly Thr Glu Ala Ser Ala Ala Thr Ala Val Lys
        355                 360                 365

Ile Thr Arg Arg Ser Ile Asp Val Glu Thr Arg Thr Ile Val Arg Phe
370                 375                 380

Asn Arg Pro Phe Leu Met Ile Ile Val Pro Thr Asp Thr Gln Asn Ile
385                 390                 395                 400

Phe Phe Met Ser Lys Val Thr Asn Pro Lys Gln Ala
                405                 410

<210> SEQ ID NO 5
<211> LENGTH: 1239
<212> TYPE: DNA
<213> ORGANISM: Artificial Sequence
<220> FEATURE:
<223> OTHER INFORMATION: Synthetic

<400> SEQUENCE: 5

```
atgagaggat cccatcacca tcaccatcac tctagacacc ctaacagccc acttgacgag      60
gagaatctga cccaggagaa ccaagaccga gggacacacg tggacctcgg attagcctcc     120
gccaacgtgg acttcgcttt cagcctgtac aagcagttag tcctgaaggc ccctgataag     180
aatgtcatct tctccccact gagcatctcc accgccttgg ccttcctgtc tctgggggcc     240
cataatacca ccctgacaga gattctcaaa ggcctcaagt tcaacctcac ggagacttct     300
gaggcagaaa ttcaccagag cttccagcac ctcctgcgca ccctcaatca gtccagcgat     360
gagctgcagc tgagtatggg aaatgccatg tttgtcaaag agcaactcag tctgctggac     420
aggttcacgg aggatgccaa gaggctgtat ggctccgagg cctttgccac tgactttcag     480
gactcagctg cagctaagaa gctcatcaac gactacgtga agaatggaac taggggggaaa     540
atcacagatc tgatcaagga ccttgactcg cagacaatga tggtcctggt gaattacatc     600
ttctttaaag ccaaatggga gatgcccttt gaccccccaag atactcatca gtcaaggttc     660
tacttgagca agaaaaagtg ggtaatggtg cccatgatga gtttgcatca cctgactata     720
ccttacttcc gggacgagga gctgtcctgc accgtggtgg agctgaagta cacaggcaat     780
gccagcgcac tcttcatcct ccctgatcaa gacaagatgg aggaagtgga agccatgctg     840
ctcccagaga ccctgaagcg gtggagagac tctctggagt tcagagagat aggtgagctc     900
tacctgccaa gttttccat ctcgagggac ataacctga acgacatact ctccagctg     960
ggcattgagg aagccttcac cagcaaggct gacctgtcag ggatcacagg ggccaggaac    1020
ctagcagtct cccaggtggt ccataaggct gtgcttgatg tatttgagga gggcacagaa    1080
gcatctgctg ccaccgcggt caaaatcagg gggagatctg agttagtgga gacgcgtacc    1140
attgtgcgtt tcaacaggcc cttcctgatg atcattgtcc ctacagacac ccagaacatc    1200
ttcttcatga gcaaagtcac caatcccaag caagcctaa                          1239
```

<210> SEQ ID NO 6
<211> LENGTH: 412
<212> TYPE: PRT
<213> ORGANISM: Artificial Sequence
<220> FEATURE:
<223> OTHER INFORMATION: Synthetic

<400> SEQUENCE: 6

```
Met Arg Gly Ser His His His His His Ser Arg His Pro Asn Ser
1               5                   10                  15

Pro Leu Asp Glu Glu Asn Leu Thr Gln Glu Asn Gln Asp Arg Gly Thr
            20                  25                  30

His Val Asp Leu Gly Leu Ala Ser Ala Asn Val Asp Phe Ala Phe Ser
        35                  40                  45

Leu Tyr Lys Gln Leu Val Leu Lys Ala Pro Asp Lys Asn Val Ile Phe
    50                  55                  60

Ser Pro Leu Ser Ile Ser Thr Ala Leu Ala Phe Leu Ser Leu Gly Ala
65                  70                  75                  80

His Asn Thr Thr Leu Thr Glu Ile Leu Lys Gly Leu Lys Phe Asn Leu
                85                  90                  95

Thr Glu Thr Ser Glu Ala Glu Ile His Gln Ser Phe Gln His Leu Leu
            100                 105                 110

Arg Thr Leu Asn Gln Ser Ser Asp Glu Leu Gln Leu Ser Met Gly Asn
        115                 120                 125
```

```
Ala Met Phe Val Lys Glu Gln Leu Ser Leu Leu Asp Arg Phe Thr Glu
    130                 135                 140

Asp Ala Lys Arg Leu Tyr Gly Ser Glu Ala Phe Ala Thr Asp Phe Gln
145                 150                 155                 160

Asp Ser Ala Ala Lys Lys Leu Ile Asn Asp Tyr Val Lys Asn Gly
                165                 170                 175

Thr Arg Gly Lys Ile Thr Asp Leu Ile Lys Asp Leu Asp Ser Gln Thr
                180                 185                 190

Met Met Val Leu Val Asn Tyr Ile Phe Phe Lys Ala Lys Trp Glu Met
        195                 200                 205

Pro Phe Asp Pro Gln Asp Thr His Gln Ser Arg Phe Tyr Leu Ser Lys
210                 215                 220

Lys Lys Trp Val Met Val Pro Met Met Ser Leu His His Leu Thr Ile
225                 230                 235                 240

Pro Tyr Phe Arg Asp Glu Glu Leu Ser Cys Thr Val Val Glu Leu Lys
                245                 250                 255

Tyr Thr Gly Asn Ala Ser Ala Leu Phe Ile Leu Pro Asp Gln Asp Lys
            260                 265                 270

Met Glu Glu Val Glu Ala Met Leu Leu Pro Glu Thr Leu Lys Arg Trp
        275                 280                 285

Arg Asp Ser Leu Glu Phe Arg Glu Ile Gly Glu Leu Tyr Leu Pro Lys
290                 295                 300

Phe Ser Ile Ser Arg Asp Tyr Asn Leu Asn Asp Ile Leu Leu Gln Leu
305                 310                 315                 320

Gly Ile Glu Glu Ala Phe Thr Ser Lys Ala Asp Leu Ser Gly Ile Thr
                325                 330                 335

Gly Ala Arg Asn Leu Ala Val Ser Gln Val Val His Lys Ala Val Leu
            340                 345                 350

Asp Val Phe Glu Glu Gly Thr Glu Ala Ser Ala Ala Thr Ala Val Lys
        355                 360                 365

Ile Arg Gly Arg Ser Glu Leu Val Glu Thr Arg Thr Ile Val Arg Phe
            370                 375                 380

Asn Arg Pro Phe Leu Met Ile Ile Val Pro Thr Asp Thr Gln Asn Ile
385                 390                 395                 400

Phe Phe Met Ser Lys Val Thr Asn Pro Lys Gln Ala
                405                 410

<210> SEQ ID NO 7
<211> LENGTH: 1239
<212> TYPE: DNA
<213> ORGANISM: Artificial Sequence
<220> FEATURE:
<223> OTHER INFORMATION: Synthetic

<400> SEQUENCE: 7
atgagaggat cccatcacca tcaccatcac tctagacacc ctaacagccc acttgacgag    60
gagaatctga cccaggagaa ccaagaccga gggacacacg tggacctcgg attagcctcc   120
gccaacgtgg acttcgcttt cagcctgtac aagcagttag tcctgaaggc ccctgataag   180
aatgtcatct ctctccccac tgagcatctc ccaccgcttg gccttcctgt ctgggggcc    240 cataatacca ccctgacaga gattctcaaa ggcctcaagt tcaacctcac ggagacttct   300
gaggcagaaa ttcaccagag cttccagcac ctcctgcgca ccctcaatca gtccagcgat   360
gagctgcagc tgagtatggg aaatgccatg tttgtcaaag agcaactcag tctgctggac   420
aggttcacgg aggatgccaa gaggctgtat ggctccgagg cctttgccac tgactttcag   480
```

-continued

```
gactcagctg cagctaagaa gctcatcaac gactacgtga agaatggaac tagggggaaa    540
atcacagatc tgatcaagga ccttgactcg cagacaatga tggtcctggt gaattacatc    600
ttctttaaag ccaaatggga gatgcccttt gaccccaag atactcatca gtcaaggttc     660
tacttgagca agaaaaagtg ggtaatggtg cccatgatga gtttgcatca cctgactata    720
ccttacttcc gggacgagga gctgtcctgc accgtggtgg agctgaagta cacaggcaat    780
gccagcgcac tcttcatcct ccctgatcaa gacaagatgg aggaagtgga agccatgctg    840
ctcccagaga ccctgaagcg gtggagagac tctctggagt tcagagagat aggtgagctc    900
tacctgccaa agttttccat ctcgagggac tataacctga cgacatact ctctccagctg     960 ggcattgagg aagccttcac cagcaaggct gacctgtcag ggatcacagg ggccaggaac   1020
ctagcagtct cccaggtggt ccataaggct gtgcttgatg tatttgagga gggcacagaa   1080
gcatctgctg ccaccgcggt caaaatcaag cttagaacaa cattagtgga gacgcgtacc   1140
attgtgcgtt tcaacaggcc cttcctgatg atcattgtcc ctacagacac ccagaacatc   1200
ttcttcatga gcaaagtcac caatcccaag caagcctaa                          1239
```

<210> SEQ ID NO 8
<211> LENGTH: 412
<212> TYPE: PRT
<213> ORGANISM: Artificial Sequence
<220> FEATURE:
<223> OTHER INFORMATION: Synthetic

<400> SEQUENCE: 8

```
Met Arg Gly Ser His His His His His Ser Arg His Pro Asn Ser
1               5                   10                  15

Pro Leu Asp Glu Glu Asn Leu Thr Gln Glu Asn Gln Asp Arg Gly Thr
            20                  25                  30

His Val Asp Leu Gly Leu Ala Ser Ala Asn Val Asp Phe Ala Phe Ser
        35                  40                  45

Leu Tyr Lys Gln Leu Val Leu Lys Ala Pro Asp Lys Asn Val Ile Phe
    50                  55                  60

Ser Pro Leu Ser Ile Ser Thr Ala Leu Ala Phe Leu Ser Leu Gly Ala
65                  70                  75                  80

His Asn Thr Thr Leu Thr Glu Ile Leu Lys Gly Leu Lys Phe Asn Leu
                85                  90                  95

Thr Glu Thr Ser Glu Ala Glu Ile His Gln Ser Phe Gln His Leu Leu
            100                 105                 110

Arg Thr Leu Asn Gln Ser Ser Asp Glu Leu Gln Leu Ser Met Gly Asn
        115                 120                 125

Ala Met Phe Val Lys Glu Gln Leu Ser Leu Leu Asp Arg Phe Thr Glu
    130                 135                 140

Asp Ala Lys Arg Leu Tyr Gly Ser Glu Ala Phe Ala Thr Asp Phe Gln
145                 150                 155                 160

Asp Ser Ala Ala Ala Lys Lys Leu Ile Asn Asp Tyr Val Lys Asn Gly
                165                 170                 175

Thr Arg Gly Lys Ile Thr Asp Leu Ile Lys Asp Leu Asp Ser Gln Thr
            180                 185                 190

Met Met Val Leu Val Asn Tyr Ile Phe Phe Lys Ala Lys Trp Glu Met
        195                 200                 205

Pro Phe Asp Pro Gln Asp Thr His Gln Ser Arg Phe Tyr Leu Ser Lys
    210                 215                 220
```

```
Lys Lys Trp Val Met Val Pro Met Met Ser Leu His His Leu Thr Ile
225                 230                 235                 240

Pro Tyr Phe Arg Asp Glu Glu Leu Ser Cys Thr Val Val Glu Leu Lys
            245                 250                 255

Tyr Thr Gly Asn Ala Ser Ala Leu Phe Ile Leu Pro Asp Gln Asp Lys
        260                 265                 270

Met Glu Glu Val Glu Ala Met Leu Leu Pro Glu Thr Leu Lys Arg Trp
    275                 280                 285

Arg Asp Ser Leu Glu Phe Arg Glu Ile Gly Glu Leu Tyr Leu Pro Lys
290                 295                 300

Phe Ser Ile Ser Arg Asp Tyr Asn Leu Asn Asp Ile Leu Leu Gln Leu
305                 310                 315                 320

Gly Ile Glu Glu Ala Phe Thr Ser Lys Ala Asp Leu Ser Gly Ile Thr
                325                 330                 335

Gly Ala Arg Asn Leu Ala Val Ser Gln Val Val His Lys Ala Val Leu
            340                 345                 350

Asp Val Phe Glu Glu Gly Thr Glu Ala Ser Ala Ala Thr Ala Val Lys
        355                 360                 365

Ile Lys Leu Arg Thr Thr Leu Val Glu Thr Arg Thr Ile Val Arg Phe
370                 375                 380

Asn Arg Pro Phe Leu Met Ile Ile Val Pro Thr Asp Thr Gln Asn Ile
385                 390                 395                 400

Phe Phe Met Ser Lys Val Thr Asn Pro Lys Gln Ala
                405                 410
```

```
<210> SEQ ID NO 9
<211> LENGTH: 1239
<212> TYPE: DNA
<213> ORGANISM: Artificial Sequence
<220> FEATURE:
<223> OTHER INFORMATION: Synthetic

<400> SEQUENCE: 9
atgagaggat cccatcacca tcaccatcac tctagacacc taacagccca cttgacgag      60 gagaatctga cccaggagaa ccaagaccga gggacacacg tggacctcgg attagcctcc    120
gccaacgtgg acttcgcttt cagcctgtac aagcagttag tcctgaaggc ccctgataag    180
aatgtcatct ctccccact gagcatctcc accgccttgg ccttcctgtc tctgggggcc    240
cataatacca ccctgacaga gattctcaaa ggcctcaagt tcaacctcac ggagacttct    300
gaggcagaaa ttcaccagag cttccagcac tcctgcgca ccctcaatca gtccagcgat    360
gagctgcagc tgagtatggg aaatgccatg tttgtcaaag agcaactcag tctgctggac    420
aggttcacgg aggatgccaa gaggctgtat ggctccgagg cctttgccac tgactttcag    480
gactcagctg cagctaagaa gctcatcaac gactacgtga agaatggaac tagggggaaa    540
atcacagatc tgatcaagga ccttgactcg cagacaatga tggtcctggt gaattacatc    600
ttctttaaag ccaaatggga gatgcccttt gaccccaag atactcatca gtcaaggttc      660
tacttgagca agaaaaagtg ggtaatggtg cccatgatga gtttgcatca cctgactata    720
ccttacttcc gggacgagga gctgtcctgc accgtggtgg agctgaagta cacaggcaat    780
gccagcgcac tcttcatcct ccctgatcaa gacaagatgg aggaagtgga agccatgctg    840
ctcccagaga ccctgaagcg gtggagagac tctctggagt tcagagagat aggtgagctc    900
tacctgccaa agttttccat ctcgagggac tataacctga cgacatact ctctcagctg    960 ggcattgagg aagccttcac cagcaaggct gacctgtcag gatcacagg ggccaggaac    1020
```

```
ctagcagtct cccaggtggt ccataaggct gtgcttgatg tatttgagga gggcacagaa    1080
gcatctgctg ccaccgcggt caaaatcatg acaagatcta acgcagtgga gacgcgtacc    1140
attgtgcgtt tcaacaggcc cttcctgatg atcattgtcc ctacagacac ccagaacatc    1200
ttcttcatga gcaaagtcac caatcccaag caagcctaa                           1239
```

<210> SEQ ID NO 10
<211> LENGTH: 412
<212> TYPE: PRT
<213> ORGANISM: Artificial Sequence
<220> FEATURE:
<223> OTHER INFORMATION: Synthetic

<400> SEQUENCE: 10

```
Met Arg Gly Ser His His His His His Ser Arg His Pro Asn Ser
1               5                   10                  15

Pro Leu Asp Glu Glu Asn Leu Thr Gln Glu Asn Gln Asp Arg Gly Thr
                20                  25                  30

His Val Asp Leu Gly Leu Ala Ser Ala Asn Val Asp Phe Ala Phe Ser
            35                  40                  45

Leu Tyr Lys Gln Leu Val Leu Lys Ala Pro Asp Lys Asn Val Ile Phe
50                  55                  60

Ser Pro Leu Ser Ile Ser Thr Ala Leu Ala Phe Leu Ser Leu Gly Ala
65                  70                  75                  80

His Asn Thr Thr Leu Thr Glu Ile Leu Lys Gly Leu Lys Phe Asn Leu
                85                  90                  95

Thr Glu Thr Ser Glu Ala Glu Ile His Gln Ser Phe Gln His Leu Leu
            100                 105                 110

Arg Thr Leu Asn Gln Ser Ser Asp Glu Leu Gln Leu Ser Met Gly Asn
        115                 120                 125

Ala Met Phe Val Lys Glu Gln Leu Ser Leu Leu Asp Arg Phe Thr Glu
130                 135                 140

Asp Ala Lys Arg Leu Tyr Gly Ser Glu Ala Phe Ala Thr Asp Phe Gln
145                 150                 155                 160

Asp Ser Ala Ala Ala Lys Lys Leu Ile Asn Asp Tyr Val Lys Asn Gly
                165                 170                 175

Thr Arg Gly Lys Ile Thr Asp Leu Ile Lys Asp Leu Asp Ser Gln Thr
            180                 185                 190

Met Met Val Leu Val Asn Tyr Ile Phe Phe Lys Ala Lys Trp Glu Met
        195                 200                 205

Pro Phe Asp Pro Gln Asp Thr His Gln Ser Arg Phe Tyr Leu Ser Lys
210                 215                 220

Lys Lys Trp Val Met Val Pro Met Met Ser Leu His His Leu Thr Ile
225                 230                 235                 240

Pro Tyr Phe Arg Asp Glu Glu Leu Ser Cys Thr Val Val Glu Leu Lys
                245                 250                 255

Tyr Thr Gly Asn Ala Ser Ala Leu Phe Ile Leu Pro Asp Gln Asp Lys
            260                 265                 270

Met Glu Glu Val Glu Ala Met Leu Leu Pro Thr Leu Lys Arg Trp
        275                 280                 285

Arg Asp Ser Leu Glu Phe Arg Glu Ile Gly Glu Leu Tyr Leu Pro Lys
290                 295                 300

Phe Ser Ile Ser Arg Asp Tyr Asn Leu Asn Asp Ile Leu Leu Gln Leu
305                 310                 315                 320
```

Gly Ile Glu Glu Ala Phe Thr Ser Lys Ala Asp Leu Ser Gly Ile Thr
                325                 330                 335

Gly Ala Arg Asn Leu Ala Val Ser Gln Val Val His Lys Ala Val Leu
            340                 345                 350

Asp Val Phe Glu Glu Gly Thr Glu Ala Ser Ala Ala Thr Ala Val Lys
        355                 360                 365

Ile Met Thr Arg Ser Asn Ala Val Glu Thr Arg Thr Ile Val Arg Phe
    370                 375                 380

Asn Arg Pro Phe Leu Met Ile Ile Val Pro Thr Asp Thr Gln Asn Ile
385                 390                 395                 400

Phe Phe Met Ser Lys Val Thr Asn Pro Lys Gln Ala
                405                 410

<210> SEQ ID NO 11
<211> LENGTH: 1239
<212> TYPE: DNA
<213> ORGANISM: Artificial Sequence
<220> FEATURE:
<223> OTHER INFORMATION: Synthetic

<400> SEQUENCE: 11
atgagaggat cccatcacca tcaccatcac tctagacacc taacagccc acttgacgag      60 gagaatctga cccaggagaa ccaagaccga gggacacacg tggacctcgg attagcctcc     120
gccaacgtgg acttcgcttt cagcctgtac aagcagttag tcctgaaggc ccctgataag     180
aatgtcatct tctccccact gagcatctcc accgccttgg ccttcctgtc tctgggggcc     240
cataatacca ccctgacaga gattctcaaa ggcctcaagt tcaacctcac ggagacttct     300
gaggcagaaa ttcaccagag cttccagcac ctcctgcgca ccctcaatca gtccagcgat     360
gagctgcagc tgagtatggg aaatgccatg tttgtcaaag agcaactcag tctgctggac     420
aggttcacgg aggatgccaa gaggctgtat ggctccgagg cctttgccac tgactttcag     480
gactcagctg cagctaagaa gctcatcaac gactacgtga agaatggaac taggggaaa      540 atcacagatc tgatcaagga ccttgactcg cagacaatga tggtcctggt gaattacatc     600
ttctttaaag ccaaatggga gatgcccttt gacccccaag atactcatca gtcaaggttc     660
tacttgagca agaaaaagtg ggtaatggtg cccatgatga gtttgcatca cctgactata     720
ccttacttcc gggacgagga gctgtcctgc accgtggtgg agctgaagta cacaggcaat     780
gccagcgcac tcttcatcct ccctgatcaa gacaagatgg aggaagtgga agccatgctg     840
ctcccagaga ccctgaagcg gtggagagac tctctggagt tcagagagat aggtgagctc     900
tacctgccaa agttttccat ctcgagggac tataacctga cgacatact tctccagctg      960 ggcattgagg aagccttcac cagcaaggct gacctgtcag ggatcacagg ggccaggaac    1020
ctagcagtct cccaggtggt ccataaggct gtgcttgatg tatttgagga gggcacagaa    1080
gcatctgctg ccaccgcggt caaaatcacc gagcgtgtct cgcccgtgga gacgcgtacc    1140
attgtgcgtt tcaacaggcc cttcctgatg atcattgtcc ctacagacac ccagaacatc    1200
ttcttcatga gcaaagtcac caatcccaag caagcctaa                           1239

<210> SEQ ID NO 12
<211> LENGTH: 412
<212> TYPE: PRT
<213> ORGANISM: Artificial Sequence
<220> FEATURE:
<223> OTHER INFORMATION: Synthetic

```
<400> SEQUENCE: 12

Met Arg Gly Ser His His His His His His Ser Arg His Pro Asn Ser
1               5                   10                  15

Pro Leu Asp Glu Glu Asn Leu Thr Gln Glu Asn Gln Asp Arg Gly Thr
            20                  25                  30

His Val Asp Leu Gly Leu Ala Ser Ala Asn Val Asp Phe Ala Phe Ser
        35                  40                  45

Leu Tyr Lys Gln Leu Val Leu Lys Ala Pro Asp Lys Asn Val Ile Phe
    50                  55                  60

Ser Pro Leu Ser Ile Ser Thr Ala Leu Ala Phe Leu Ser Leu Gly Ala
65                  70                  75                  80

His Asn Thr Thr Leu Thr Glu Ile Leu Lys Gly Leu Lys Phe Asn Leu
                85                  90                  95

Thr Glu Thr Ser Glu Ala Glu Ile His Gln Ser Phe Gln His Leu Leu
            100                 105                 110

Arg Thr Leu Asn Gln Ser Ser Asp Glu Leu Gln Leu Ser Met Gly Asn
        115                 120                 125

Ala Met Phe Val Lys Glu Gln Leu Ser Leu Leu Asp Arg Phe Thr Glu
130                 135                 140

Asp Ala Lys Arg Leu Tyr Gly Ser Glu Ala Phe Ala Thr Asp Phe Gln
145                 150                 155                 160

Asp Ser Ala Ala Ala Lys Lys Leu Ile Asn Asp Tyr Val Lys Asn Gly
                165                 170                 175

Thr Arg Gly Lys Ile Thr Asp Leu Ile Lys Asp Leu Asp Ser Gln Thr
            180                 185                 190

Met Met Val Leu Val Asn Tyr Ile Phe Phe Lys Ala Lys Trp Glu Met
        195                 200                 205

Pro Phe Asp Pro Gln Asp Thr His Gln Ser Arg Phe Tyr Leu Ser Lys
    210                 215                 220

Lys Lys Trp Val Met Val Pro Met Met Ser Leu His His Leu Thr Ile
225                 230                 235                 240

Pro Tyr Phe Arg Asp Glu Glu Leu Ser Cys Thr Val Val Glu Leu Lys
                245                 250                 255

Tyr Thr Gly Asn Ala Ser Ala Leu Phe Ile Leu Pro Asp Gln Asp Lys
            260                 265                 270

Met Glu Glu Val Glu Ala Met Leu Leu Pro Glu Thr Leu Lys Arg Trp
        275                 280                 285

Arg Asp Ser Leu Glu Phe Arg Glu Ile Gly Glu Leu Tyr Leu Pro Lys
    290                 295                 300

Phe Ser Ile Ser Arg Asp Tyr Asn Leu Asn Asp Ile Leu Leu Gln Leu
305                 310                 315                 320

Gly Ile Glu Glu Ala Phe Thr Ser Lys Ala Asp Leu Ser Gly Ile Thr
                325                 330                 335

Gly Ala Arg Asn Leu Ala Val Ser Gln Val Val His Lys Ala Val Leu
            340                 345                 350

Asp Val Phe Glu Glu Gly Thr Glu Ala Ser Ala Ala Thr Ala Val Lys
        355                 360                 365

Ile Thr Glu Arg Val Ser Pro Val Glu Thr Arg Thr Ile Val Arg Phe
    370                 375                 380

Asn Arg Pro Phe Leu Met Ile Ile Val Pro Thr Asp Thr Gln Asn Ile
385                 390                 395                 400

Phe Phe Met Ser Lys Val Thr Asn Pro Lys Gln Ala
            405                 410
```

<210> SEQ ID NO 13
<211> LENGTH: 1239
<212> TYPE: DNA
<213> ORGANISM: Artificial Sequence
<220> FEATURE:
<223> OTHER INFORMATION: Synthetic

<400> SEQUENCE: 13

```
atgagaggat cccatcacca tcaccatcac tctagacacc ctaacagccc acttgacgag      60
gagaatctga cccaggagaa ccaagaccga gggacacacg tggacctcgg attagcctcc     120
gccaacgtgg acttcgcttt cagcctgtac aagcagttag tcctgaaggc ccctgataag     180
aatgtcatct ctccccact gagcatctcc accgccttgg ccttcctgtc tctgggggcc      240
cataatacca ccctgacaga gattctcaaa ggcctcaagt tcaacctcac ggagacttct     300
gaggcagaaa ttcaccagag cttccagcac ctcctgcgca ccctcaatca gtccagcgat     360
gagctgcagc tgagtatggg aaatgccatg tttgtcaaag agcaactcag tctgctggac     420
aggttcacgg aggatgccaa gaggctgtat ggctccgagg cctttgccac tgactttcag     480
gactcagctg cagctaagaa gctcatcaac gactacgtga agaatggaac tagggggaaa     540
atcacagatc tgatcaagga ccttgactcg cagacaatga tggtcctggt gaattacatc     600
ttctttaaag ccaaatggga gatgcccttt gaccccaag atactcatca gtcaaggttc       660
tacttgagca agaaaaagtg ggtaatggtg cccatgatga gtttgcatca cctgactata     720
ccttacttcc gggacgagga gctgtcctgc accgtggtgg agctgaagta cacaggcaat     780
gccagcgcac tcttcatcct ccctgatcaa gacaagatgg aggaagtgga agccatgctg     840
ctcccagaga ccctgaagcg gtggagagac tctctggagt tcagagagat aggtgagctc     900
tacctgccaa agttttccat ctcgagggac tataacctga cgacatact ctctccagctg      960
ggcattgagg aagccttcac cagcaaggct gacctgtcag ggatcacagg ggccaggaac    1020
ctagcagtct cccaggtggt ccataaggct gtgcttgatg tatttgagga gggcacagaa    1080
gcatctgctg ccaccgcggt caaaatcacc tttagatctg cattagtgga gacgcgtacc    1140
attgtgcgtt tcaacaggcc cttcctgatg atcattgtcc ctacagacac ccagaacatc    1200
ttcttcatga gcaaagtcac caatcccaag caagcctaa                           1239
```

<210> SEQ ID NO 14
<211> LENGTH: 412
<212> TYPE: PRT
<213> ORGANISM: Artificial Sequence
<220> FEATURE:
<223> OTHER INFORMATION: Synthetic

<400> SEQUENCE: 14

```
Met Arg Gly Ser His His His His His His Ser Arg His Pro Asn Ser
1               5                   10                  15

Pro Leu Asp Glu Glu Asn Leu Thr Gln Glu Asn Gln Asp Arg Gly Thr
            20                  25                  30

His Val Asp Leu Gly Leu Ala Ser Ala Asn Val Asp Phe Ala Phe Ser
        35                  40                  45

Leu Tyr Lys Gln Leu Val Leu Lys Ala Pro Asp Lys Asn Val Ile Phe
    50                  55                  60

Ser Pro Leu Ser Ile Ser Thr Ala Leu Ala Phe Leu Ser Leu Gly Ala
65                  70                  75                  80

His Asn Thr Thr Leu Thr Glu Ile Leu Lys Gly Leu Lys Phe Asn Leu
                85                  90                  95
```

```
Thr Glu Thr Ser Glu Ala Glu Ile His Gln Ser Phe Gln His Leu Leu
            100                 105                 110
Arg Thr Leu Asn Gln Ser Ser Asp Glu Leu Gln Leu Ser Met Gly Asn
        115                 120                 125
Ala Met Phe Val Lys Glu Gln Leu Ser Leu Leu Asp Arg Phe Thr Glu
    130                 135                 140
Asp Ala Lys Arg Leu Tyr Gly Ser Glu Ala Phe Ala Thr Asp Phe Gln
145                 150                 155                 160
Asp Ser Ala Ala Ala Lys Lys Leu Ile Asn Asp Tyr Val Lys Asn Gly
                165                 170                 175
Thr Arg Gly Lys Ile Thr Asp Leu Ile Lys Asp Leu Asp Ser Gln Thr
            180                 185                 190
Met Met Val Leu Val Asn Tyr Ile Phe Phe Lys Ala Lys Trp Glu Met
        195                 200                 205
Pro Phe Asp Pro Gln Asp Thr His Gln Ser Arg Phe Tyr Leu Ser Lys
    210                 215                 220
Lys Lys Trp Val Met Val Pro Met Met Ser Leu His His Leu Thr Ile
225                 230                 235                 240
Pro Tyr Phe Arg Asp Glu Glu Leu Ser Cys Thr Val Val Glu Leu Lys
                245                 250                 255
Tyr Thr Gly Asn Ala Ser Ala Leu Phe Ile Leu Pro Asp Gln Asp Lys
            260                 265                 270
Met Glu Glu Val Glu Ala Met Leu Leu Pro Glu Thr Leu Lys Arg Trp
        275                 280                 285
Arg Asp Ser Leu Glu Phe Arg Glu Ile Gly Glu Leu Tyr Leu Pro Lys
    290                 295                 300
Phe Ser Ile Ser Arg Asp Tyr Asn Leu Asn Asp Ile Leu Leu Gln Leu
305                 310                 315                 320
Gly Ile Glu Glu Ala Phe Thr Ser Lys Ala Asp Leu Ser Gly Ile Thr
                325                 330                 335
Gly Ala Arg Asn Leu Ala Val Ser Gln Val Val His Lys Ala Val Leu
            340                 345                 350
Asp Val Phe Glu Glu Gly Thr Glu Ala Ser Ala Ala Thr Ala Val Lys
        355                 360                 365
Ile Thr Phe Arg Ser Ala Leu Val Glu Thr Arg Thr Ile Val Arg Phe
    370                 375                 380
Asn Arg Pro Phe Leu Met Ile Ile Val Pro Thr Asp Thr Gln Asn Ile
385                 390                 395                 400
Phe Phe Met Ser Lys Val Thr Asn Pro Lys Gln Ala
                405                 410

<210> SEQ ID NO 15
<211> LENGTH: 25
<212> TYPE: DNA
<213> ORGANISM: Artificial Sequence
<220> FEATURE:
<223> OTHER INFORMATION: Synthetic

<400> SEQUENCE: 15
gtgattttga ccgcggtggc agcag                                         25

<210> SEQ ID NO 16
<211> LENGTH: 1239
<212> TYPE: DNA
<213> ORGANISM: Artificial Sequence
<220> FEATURE:
<223> OTHER INFORMATION: Synthetic
```

<400> SEQUENCE: 16

```
atgagaggat cccatcacca tcaccatcac tctagacacc ctaacagccc acttgacgag      60
gagaatctga cccaggagaa ccaagaccga gggacacacg tggacctcgg attagcctcc     120
gccaacgtgg acttcgcttt cagcctgtac aagcagttag tcctgaaggc ccctgataag     180
aatgtcatct tctccccact gagcatctcc accgccttgg ccttcctgtc tctggggggcc    240
cataatacca ccctgacaga gattctcaaa ggcctcaagt tcaacctcac ggagacttct     300
gaggcagaaa ttcaccagag cttccagcac ctcctgcgca ccctcaatca gtccagcgat     360
gagctgcagc tgagtatggg aaatgccatg tttgtcaaag agcaactcag tctgctggac     420
aggttcacgg aggatgccaa gaggctgtat ggctccgagg cctttgccac tgactttcag     480
gactcagctg cagctaagaa gctcatcaac gactacgtga agaatggaac taggggggaaa    540
atcacagatc tgatcaagga ccttgactcg cagacaatga tggtcctggt gaattacatc     600
ttctttaaag ccaaatggga gatgcccttt gaccccaag atactcatca gtcaaggttc      660
tacttgagca agaaaaagtg ggtaatggtg cccatgatga gtttgcatca cctgactata     720
ccttacttcc gggacgagga gctgtcctgc accgtggtgg agctgaagta cacaggcaat     780
gccagcgcac tcttcatcct ccctgatcaa gacaagatga ggaagtgga agccatgctg      840
ctcccagaga ccctgaagcg gtggagagac tctctggagt tcagagagat aggtgagctc     900
tacctgccaa agttttccat ctcgaggac tataacctga cgacatact ctccagctg        960
ggcattgagg aagccttcac cagcaaggct gacctgtcag ggatcacagg ggccaggaac    1020
ctagcagtct cccaggtggt ccataaggct gtgcttgatg tatttgagga gggcacagaa    1080
gcatctgctg ccaccgcggt caaaatcacc ctcctttctg cattagtgga gacgcgtacc    1140
attgtgcgtt tcaacaggcc cttcctgatg atcattgtcc ctacagacac ccagaacatc    1200
ttcttcatga gcaaagtcac caatcccaag caagcctaa                           1239
```

<210> SEQ ID NO 17
<211> LENGTH: 1239
<212> TYPE: DNA
<213> ORGANISM: Artificial Sequence
<220> FEATURE:
<223> OTHER INFORMATION: Synthetic

<400> SEQUENCE: 17

```
atgagaggat cccatcacca tcaccatcac tctagacacc ctaacagccc acttgacgag      60
gagaatctga cccaggagaa ccaagaccga gggacacacg tggacctcgg attagcctcc     120
gccaacgtgg acttcgcttt cagcctgtac aagcagttag tcctgaaggc ccctgataag     180
aatgtcatct tctccccact gagcatctcc accgccttgg ccttcctgtc tctggggggcc    240
cataatacca ccctgacaga gattctcaaa ggcctcaagt tcaacctcac ggagacttct     300
gaggcagaaa ttcaccagag cttccagcac ctcctgcgca ccctcaatca gtccagcgat     360
gagctgcagc tgagtatggg aaatgccatg tttgtcaaag agcaactcag tctgctggac     420
aggttcacgg aggatgccaa gaggctgtat ggctccgagg cctttgccac tgactttcag     480
gactcagctg cagctaagaa gctcatcaac gactacgtga agaatggaac taggggggaaa    540
atcacagatc tgatcaagga ccttgactcg cagacaatga tggtcctggt gaattacatc     600
ttctttaaag ccaaatggga gatgcccttt gaccccaag atactcatca gtcaaggttc      660
tacttgagca agaaaaagtg ggtaatggtg cccatgatga gtttgcatca cctgactata     720
ccttacttcc gggacgagga gctgtcctgc accgtggtgg agctgaagta cacaggcaat     780
```

| | |
|---|---|
| gccagcgcac tcttcatcct ccctgatcaa gacaagatgg aggaagtgga agccatgctg | 840 |
| ctcccagaga ccctgaagcg gtggagagac tctctggagt tcagagagat aggtgagctc | 900 |
| tacctgccaa agttttccat ctcgagggac tataacctga acgacatact tctccagctg | 960 |
| ggcattgagg aagccttcac cagcaaggct gacctgtcag ggatcacagg ggccaggaac | 1020 |
| ctagcagtct cccaggtggt ccataaggct gtgcttgatg tatttgagga gggcacagaa | 1080 |
| gcatctgctg ccaccgcggt caaaggttct ctgcgttctg ctctggtgga gacgcgtacc | 1140 |
| attgtgcgtt tcaacaggcc cttcctgatg atcattgtcc ctacagacac ccagaacatc | 1200 |
| ttcttcatga gcaaagtcac caatcccaag caagcctaa | 1239 |

<210> SEQ ID NO 18
<211> LENGTH: 1239
<212> TYPE: DNA
<213> ORGANISM: Artificial Sequence
<220> FEATURE:
<223> OTHER INFORMATION: Synthetic

<400> SEQUENCE: 18

| | |
|---|---|
| atgagaggat cccatcacca tcaccatcac tctagacacc ctaacagccc acttgacgag | 60 |
| gagaatctga cccaggagaa ccaagaccga gggacacacg tggacctcgg attagcctcc | 120 |
| gccaacgtgg acttcgcttt cagcctgtac aagcagttag tcctgaaggc ccctgataag | 180 |
| aatgtcatct ctcccccact gagcatctcc accgccttgg ccttcctgtc tctggggggcc | 240 |
| cataatacca ccctgacaga gattctcaaa ggcctcaagt tcaacctcac ggagacttct | 300 |
| gaggcagaaa ttcaccagag cttccagcac ctcctgcgca ccctcaatca gtccagcgat | 360 |
| gagctgcagc tgagtatggg aaatgccatg tttgtcaaag agcaactcag tctgctggac | 420 |
| aggttcacgg aggatgccaa gaggctgtat ggctccgagg cctttgccac tgactttcag | 480 |
| gactcagctg cagctaagaa gctcatcaac gactacgtga agaatggaac tagggggaaa | 540 |
| atcacagatc tgatcaagga ccttgactcg cagacaatga tggtcctggt gaattacatc | 600 |
| ttctttaaag ccaaatggga gatgcccttt gacccccaag atactcatca gtcaaggttc | 660 |
| tacttgagca agaaaaagtg ggtaatggtg cccatgatga gtttgcatca cctgactata | 720 |
| ccttacttcc gggacgagga gctgtcctgc accgtggtgg agctgaagta cacaggcaat | 780 |
| gccagcgcac tcttcatcct ccctgatcaa gacaagatgg aggaagtgga agccatgctg | 840 |
| ctcccagaga ccctgaagcg gtggagagac tctctggagt tcagagagat aggtgagctc | 900 |
| tacctgccaa agttttccat ctcgagggac tataacctga acgacatact tctccagctg | 960 |
| ggcattgagg aagccttcac cagcaaggct gacctgtcag ggatcacagg ggccaggaac | 1020 |
| ctagcagtct cccaggtggt ccataaggct gtgcttgatg tatttgagga gggcacagaa | 1080 |
| gcatctgctg ccaccgcggt caaaggttct ctgcgtggtg ctctggtgga gacgcgtacc | 1140 |
| attgtgcgtt tcaacaggcc cttcctgatg atcattgtcc ctacagacac ccagaacatc | 1200 |
| ttcttcatga gcaaagtcac caatcccaag caagcctaa | 1239 |

<210> SEQ ID NO 19
<211> LENGTH: 1239
<212> TYPE: DNA
<213> ORGANISM: Artificial Sequence
<220> FEATURE:
<223> OTHER INFORMATION: Synthetic

<400> SEQUENCE: 19

```
atgagaggat cccatcacca tcaccatcac tctagacacc ctaacagccc acttgacgag      60
gagaatctga cccaggagaa ccaagaccga gggacacacg tggacctcgg attagcctcc     120
gccaacgtgg acttcgcttt cagcctgtac aagcagttag tcctgaaggc ccctgataag     180
aatgtcatct tctccccact gagcatctcc accgccttgg ccttcctgtc tctgggggcc     240
cataatacca ccctgacaga gattctcaaa ggcctcaagt tcaacctcac ggagacttct     300
gaggcagaaa ttcaccagag cttccagcac ctcctgcgca ccctcaatca gtccagcgat     360
gagctgcagc tgagtatggg aaatgccatg tttgtcaaag agcaactcag tctgctggac     420
aggttcacgg aggatgccaa gaggctgtat ggctccgagg cctttgccac tgactttcag     480
gactcagctg cagctaagaa gctcatcaac gactacgtga agaatggaac taggggggaaa    540
atcacagatc tgatcaagga cctgactcg cagacaatga tggtcctggt gaattacatc     600
ttctttaaag ccaaatggga gatgcccttt gaccccaag atactcatca gtcaaggttc      660
tacttgagca agaaaaagtg ggtaatggtg cccatgatga gtttgcatca cctgactata     720
ccttacttcc gggacgagga gctgtcctgc accgtggtgg agctgaagta cacaggcaat     780
gccagcgcac tcttcatcct ccctgatcaa gacaagatga ggaagtgga agccatgctg      840
ctcccagaga ccctgaagcg gtggagagac tctctggagt tcagagagat aggtgagctc     900
tacctgccaa agttttccat ctcgaggag tataacctga cgacatact tctccagctg       960
ggcattgagg aagccttcac cagcaaggct gacctgtcag ggatcacagg ggccaggaac    1020
ctagcagtct cccaggtggt ccataaggct gtgcttgatg tatttgagga gggcacagaa    1080
gcatctgctg ccaccgcggt caaaatcacc ctgcgtcaga ccaacgtgga gacgcgtacc    1140
attgtgcgtt tcaacaggcc cttcctgatg atcattgtcc ctacagacac ccagaacatc    1200
ttcttcatga gcaaagtcac caatcccaag caagcctaa                           1239
```

<210> SEQ ID NO 20
<211> LENGTH: 1239
<212> TYPE: DNA
<213> ORGANISM: Artificial Sequence
<220> FEATURE:
<223> OTHER INFORMATION: Synthetic

<400> SEQUENCE: 20

```
atgagaggat cccatcacca tcaccatcac tctagacacc ctaacagccc acttgacgag      60
gagaatctga cccaggagaa ccaagaccga gggacacacg tggacctcgg attagcctcc     120
gccaacgtgg acttcgcttt cagcctgtac aagcagttag tcctgaaggc ccctgataag     180
aatgtcatct tctccccact gagcatctcc accgccttgg ccttcctgtc tctgggggcc     240
cataatacca ccctgacaga gattctcaaa ggcctcaagt tcaacctcac ggagacttct     300
gaggcagaaa ttcaccagag cttccagcac ctcctgcgca ccctcaatca gtccagcgat     360
gagctgcagc tgagtatggg aaatgccatg tttgtcaaag agcaactcag tctgctggac     420
aggttcacgg aggatgccaa gaggctgtat ggctccgagg cctttgccac tgactttcag     480
gactcagctg cagctaagaa gctcatcaac gactacgtga agaatggaac taggggggaaa    540
atcacagatc tgatcaagga cctgactcg cagacaatga tggtcctggt gaattacatc     600
ttctttaaag ccaaatggga gatgcccttt gaccccaag atactcatca gtcaaggttc      660
tacttgagca agaaaaagtg ggtaatggtg cccatgatga gtttgcatca cctgactata     720
ccttacttcc gggacgagga gctgtcctgc accgtggtgg agctgaagta cacaggcaat     780
```

```
gccagcgcac tcttcatcct ccctgatcaa gacaagatgg aggaagtgga agccatgctg    840
ctcccagaga ccctgaagcg gtggagagac tctctggagt tcagagagat aggtgagctc    900
tacctgccaa agttttccat ctcgagggac tataacctga acgacatact tctccagctg    960
ggcattgagg aagccttcac cagcaaggct gacctgtcag ggatcacagg ggccaggaac   1020
ctagcagtct cccaggtggt ccataaggct gtgcttgatg tatttgagga gggcacagaa   1080
gcatctgctg ccaccgcggt caaaatcacc ggtcgtcaga ccaacgtgga gacgcgtacc   1140
attgtgcgtt tcaacaggcc cttcctgatg atcattgtcc ctacagacac ccagaacatc   1200
ttcttcatga gcaaagtcac caatcccaag caagcctaa                         1239
```

<210> SEQ ID NO 21
<211> LENGTH: 1239
<212> TYPE: DNA
<213> ORGANISM: Artificial Sequence
<220> FEATURE:
<223> OTHER INFORMATION: Synthetic

<400> SEQUENCE: 21

```
atgagaggat cccatcacca tcaccatcac tctagacacc ctaacagccc acttgacgag     60
gagaatctga cccaggagaa ccaagaccga gggacacacg tggacctcgg attagcctcc    120
gccaacgtgg acttcgcttt cagcctgtac aagcagttag tcctgaaggc ccctgataag    180
aatgtcatct tctccccact gagcatctcc accgccttgg ccttcctgtc tctggggggcc   240 cataatacca ccctgacaga gattctcaaa ggcctcaagt tcaacctcac ggagacttct    300
gaggcagaaa ttcaccagag cttccagcac ctcctgcgca ccctcaatca gtccagcgat    360
gagctgcagc tgagtatggg aaatgccatg tttgtcaaag agcaactcag tctgctggac    420
aggttcacgg aggatgccaa gaggctgtat ggctccgagg cctttgccac tgactttcag    480
gactcagctg cagctaagaa gctcatcaac gactacgtga agaatggaac taggggggaaa   540 atcacagatc tgatcaagga ccttgactcg cagacaatga tggtcctggt gaattacatc    600
ttctttaaag ccaaatggga gatgcccttt gaccccaag atactcatca gtcaaggttc     660
tacttgagca agaaaaagtg ggtaatggtg cccatgatga gtttgcatca cctgactata    720
ccttacttcc gggacgagga gctgtcctgc accgtggtgg agctgaagta cacaggcaat    780
gccagcgcac tcttcatcct ccctgatcaa gacaagatgg aggaagtgga agccatgctg    840
ctcccagaga ccctgaagcg gtggagagac tctctggagt tcagagagat aggtgagctc    900
tacctgccaa agttttccat ctcgagggac tataacctga acgacatact tctccagctg    960
ggcattgagg aagccttcac cagcaaggct gacctgtcag ggatcacagg ggccaggaac   1020
ctagcagtct cccaggtggt ccataaggct gtgcttgatg tatttgagga gggcacagaa   1080
gcatctgctg ccaccgcggt caaaatcaac cagcgttctt ccctggtgga gacgcgtacc   1140
attgtgcgtt tcaacaggcc cttcctgatg atcattgtcc ctacagacac ccagaacatc   1200
ttcttcatga gcaaagtcac caatcccaag caagcctaa                         1239
```

<210> SEQ ID NO 22
<211> LENGTH: 1239
<212> TYPE: DNA
<213> ORGANISM: Artificial Sequence
<220> FEATURE:
<223> OTHER INFORMATION: Synthetic

<400> SEQUENCE: 22

```
atgagaggat cccatcacca tcaccatcac tctagacacc ctaacagccc acttgacgag      60
gagaatctga cccaggagaa ccaagaccga gggacacacg tggacctcgg attagcctcc     120
gccaacgtgg acttcgcttt cagcctgtac aagcagttag tcctgaaggc ccctgataag     180
aatgtcatct tctccccact gagcatctcc accgccttgg ccttcctgtc tctggggcc      240
cataatacca ccctgacaga gattctcaaa ggcctcaagt tcaacctcac ggagacttct     300
gaggcagaaa ttcaccagag cttccagcac ctcctgcgca ccctcaatca gtccagcgat     360
gagctgcagc tgagtatggg aaatgccatg tttgtcaaag agcaactcag tctgctggac     420
aggttcacgg aggatgccaa gaggctgtat ggctccgagg cctttgccac tgactttcag     480
gactcagctg cagctaagaa gctcatcaac gactacgtga agaatggaac taggggggaaa    540
atcacagatc tgatcaagga cctgactcg cagacaatga tggtcctggt gaattacatc      600
ttctttaaag ccaaatggga gatgcccttt gacccccaag atactcatca gtcaaggttc     660
tacttgagca agaaaaagtg ggtaatggtg cccatgatga gtttgcatca cctgactata     720
ccttacttcc gggacgagga gctgtcctgc accgtggtgg agctgaagta cacaggcaat     780
gccagcgcac tcttcatcct ccctgatcaa gacaagatga aggaagtgga agccatgctg     840
ctcccagaga ccctgaagcg gtggagagac tctctggagt tcagagagat aggtgagctc     900
tacctgccaa agttttccat ctcgaggac tataacctga acgacatact tctccagctg      960
ggcattgagg aagccttcac cagcaaggct gacctgtcag ggatcacagg ggccaggaac    1020
ctagcagtct cccaggtggt ccataaggct gtgcttgatg tatttgagga gggcacagaa    1080
gcatctgctg ccaccgcggt caaaatcctg cagcgtgcta tcctggtgga gacgcgtacc    1140
attgtgcgtt tcaacaggcc cttcctgatg atcattgtcc ctacagacac ccagaacatc    1200
ttcttcatga gcaaagtcac caatcccaag caagcctaa                           1239
```

<210> SEQ ID NO 23
<211> LENGTH: 1239
<212> TYPE: DNA
<213> ORGANISM: Artificial Sequence
<220> FEATURE:
<223> OTHER INFORMATION: Synthetic

<400> SEQUENCE: 23

```
atgagaggat cccatcacca tcaccatcac tctagacacc ctaacagccc acttgacgag      60
gagaatctga cccaggagaa ccaagaccga gggacacacg tggacctcgg attagcctcc     120
gccaacgtgg acttcgcttt cagcctgtac aagcagttag tcctgaaggc ccctgataag     180
aatgtcatct tctccccact gagcatctcc accgccttgg ccttcctgtc tctggggcc      240
cataatacca ccctgacaga gattctcaaa ggcctcaagt tcaacctcac ggagacttct     300
gaggcagaaa ttcaccagag cttccagcac ctcctgcgca ccctcaatca gtccagcgat     360
gagctgcagc tgagtatggg aaatgccatg tttgtcaaag agcaactcag tctgctggac     420
aggttcacgg aggatgccaa gaggctgtat ggctccgagg cctttgccac tgactttcag     480
gactcagctg cagctaagaa gctcatcaac gactacgtga agaatggaac taggggggaaa    540
atcacagatc tgatcaagga cctgactcg cagacaatga tggtcctggt gaattacatc      600
ttctttaaag ccaaatggga gatgcccttt gacccccaag atactcatca gtcaaggttc     660
tacttgagca agaaaaagtg ggtaatggtg cccatgatga gtttgcatca cctgactata     720
ccttacttcc gggacgagga gctgtcctgc accgtggtgg agctgaagta cacaggcaat     780
```

| | |
|---|---:|
| gccagcgcac tcttcatcct ccctgatcaa gacaagatgg aggaagtgga agccatgctg | 840 |
| ctcccagaga ccctgaagcg gtggagagac tctctggagt tcagagagat aggtgagctc | 900 |
| tacctgccaa agttttccat ctcgagggac tataacctga acgacatact tctccagctg | 960 |
| ggcattgagg aagccttcac cagcaaggct gacctgtcag ggatcacagg ggccaggaac | 1020 |
| ctagcagtct cccaggtggt ccataaggct gtgcttgatg tatttgagga gggcacagaa | 1080 |
| gcatctgctg ccaccgcggt caaacagcgt ctgcgtgacg ctctggtgga gacgcgtacc | 1140 |
| attgtgcgtt tcaacaggcc cttcctgatg atcattgtcc ctacagacac ccagaacatc | 1200 |
| ttcttcatga gcaaagtcac caatcccaag caagcctaa | 1239 |

<210> SEQ ID NO 24
<211> LENGTH: 1239
<212> TYPE: DNA
<213> ORGANISM: Artificial Sequence
<220> FEATURE:
<223> OTHER INFORMATION: Synthetic

<400> SEQUENCE: 24

| | |
|---|---:|
| atgagaggat cccatcacca tcaccatcac tctagacacc ctaacagccc acttgacgag | 60 |
| gagaatctga cccaggagaa ccaagaccga gggacacacg tggacctcgg attagcctcc | 120 |
| gccaacgtgg acttcgcttt cagcctgtac aagcagttag tcctgaaggc ccctgataag | 180 |
| aatgtcatct ctctccccact gagcatctcc accgccttgg ccttcctgtc tctgggggcc | 240 |
| cataatacca ccctgacaga gattctcaaa ggcctcaagt tcaacctcac ggagacttct | 300 |
| gaggcagaaa ttcaccagag cttccagcac ctcctgcgca ccctcaatca gtccagcgat | 360 |
| gagctgcagc tgagtatggg aaatgccatg tttgtcaaag agcaactcag tctgctggac | 420 |
| aggttcacgg aggatgccaa gaggctgtat ggctccgagg cctttgccac tgactttcag | 480 |
| gactcagctg cagctaagaa gctcatcaac gactacgtga agaatggaac tagggggaaa | 540 |
| atcacagatc tgatcaagga ccttgactcg cagacaatga tggtcctggt gaattacatc | 600 |
| ttctttaaag ccaaatggga gatgcccttt gaccccaag atactcatca gtcaaggttc | 660 |
| tacttgagca agaaaaagtg ggtaatggtg cccatgatga gtttgcatca cctgactata | 720 |
| ccttacttcc gggacgagga gctgtcctgc accgtggtgg agctgaagta cacaggcaat | 780 |
| gccagcgcac tcttcatcct ccctgatcaa gacaagatgg aggaagtgga agccatgctg | 840 |
| ctcccagaga ccctgaagcg gtggagagac tctctggagt tcagagagat aggtgagctc | 900 |
| tacctgccaa agttttccat ctcgagggac tataacctga acgacatact tctccagctg | 960 |
| ggcattgagg aagccttcac cagcaaggct gacctgtcag ggatcacagg ggccaggaac | 1020 |
| ctagcagtct cccaggtggt ccataaggct gtgcttgatg tatttgagga gggcacagaa | 1080 |
| gcatctgctg ccaccgcggt caaaatcccg gaccgtcaca tgctggtgga gacgcgtacc | 1140 |
| attgtgcgtt tcaacaggcc cttcctgatg atcattgtcc ctacagacac ccagaacatc | 1200 |
| ttcttcatga gcaaagtcac caatcccaag caagcctaa | 1239 |

<210> SEQ ID NO 25
<211> LENGTH: 1239
<212> TYPE: DNA
<213> ORGANISM: Artificial Sequence
<220> FEATURE:
<223> OTHER INFORMATION: Synthetic

<400> SEQUENCE: 25

```
atgagaggat cccatcacca tcaccatcac tctagacacc ctaacagccc acttgacgag    60
gagaatctga cccaggagaa ccaagaccga gggacacacg tggacctcgg attagcctcc   120
gccaacgtgg acttcgcttt cagcctgtac aagcagttag tcctgaaggc ccctgataag   180
aatgtcatct tctccccact gagcatctcc accgccttgg ccttcctgtc tctggggggcc   240
cataatacca ccctgacaga gattctcaaa ggcctcaagt tcaacctcac ggagacttct   300
gaggcagaaa ttcaccagag cttccagcac ctcctgcgca ccctcaatca gtccagcgat   360
gagctgcagc tgagtatggg aaatgccatg tttgtcaaag agcaactcag tctgctggac   420
aggttcacgg aggatgccaa gaggctgtat ggctccgagg cctttgccac tgactttcag   480
gactcagctg cagctaagaa gctcatcaac gactacgtga agaatggaac taggggggaaa   540
atcacagatc tgatcaagga ccttgactcg cagacaatga tggtcctggt gaattacatc   600
ttctttaaag ccaaatggga gatgcccttt gacccccaag atactcatca gtcaaggttc   660
tacttgagca agaaaaagtg ggtaatggtg cccatgatga gtttgcatca cctgactata   720
ccttacttcc gggacgagga gctgtcctgc accgtggtgg agctgaagta cacaggcaat   780
gccagcgcac tcttcatcct ccctgatcaa gacaagatga aggaagtgga agccatgctg   840
ctcccagaga ccctgaagcg gtggagagac tctctggagt tcagagagat aggtgagctc   900
tacctgccaa agttttccat ctcgagggac tataacctga cgacatact ctctccagctg   960
ggcattgagg aagccttcac cagcaaggct gacctgtcag ggatcacagg gccaggaac   1020
ctagcagtct cccaggtggt ccataaggct gtgcttgatg tatttgagga gggcacagaa   1080
gcatctgctg ccaccgcggt caaaaccgtt gactacgctg ctctggtgga gacgcgtacc   1140
attgtgcgtt tcaacaggcc cttcctgatg atcattgtcc ctacagacac ccagaacatc   1200
ttcttcatga gcaaagtcac caatcccaag caagcctaa                         1239
```

<210> SEQ ID NO 26
<211> LENGTH: 1221
<212> TYPE: DNA
<213> ORGANISM: Artificial Sequence
<220> FEATURE:
<223> OTHER INFORMATION: Synthetic

<400> SEQUENCE: 26

```
atgagaggat cgcatcacca tcaccatcac ggatccgatg atccccaggg agatgctgcc    60
cagaagacag atacatccca ccatgatcag gatcacccaa ccttcaacaa gatcacccc   120
aacctggctg agttcgcctt cagcctatac cgccagctgg cacaccagtc caacagcacc   180
aatatcttct ctccccagt gagcatcgct acagcctttg caatgctctc cctggggacc   240
aaggctgaca ctcacgatga atcctggag ggcctgaatt tcaacctcac ggagattccg   300
gaggctcaga tccatgaagg cttccaggaa ctcctccgta ccctcaacca gccagacagc   360
cagctccagc tgaccaccgg caatggcctg ttcctcagcg agggcctgaa gctagtggat   420
aagttttttgg aggatgttaa aaagttgtac cactcagaag ccttcactgt caacttcggg   480
gacaccgaag aggccaagaa acagatcaac gattacgtgg agaagggtac tcaagggaaa   540
attgtggatt tggtcaagga gcttgacaga gacacagttt ttgctctggt gaattacatc   600
ttctttaaag gcaaatggga gagacccttt gaagtcaagg acaccgagga agaggacttc   660
cacgtggacc aggcgaccac cgtgaaggtg cctatgatga gcgtttaggg catgtttaac   720
atccagcact gtaagaagct gtccagctgg gtgctgctga tgaaatacct gggcaatgcc   780
```

```
accgccatct tcttcctgcc tgatgagggg aaactacagc acctggaaaa tgaactcacc       840
cacgatatca tcaccaagtt cctggaaaat gaagacagaa ggtctgccag cttacattta       900
cccaaactgt ccattactgg aacctatgat ctgaagagcg tcctgggtca actgggcatc       960
actaaggtct tcagcaatgg ggctgacctc tccggggtca cagaggaggc accctgaag       1020 ctctccaagg ccgtgcataa ggctgtgctg accatcgacg agaaagggac tgaagctgct       1080
ggggccatgt ttttagaggc catacccatg tctatccccc ccgaggtcaa gttcaacaaa       1140 cccttttgtct tcttaatgat tgaacaaaat accaagtctc ccctcttcat gggaaaagtg       1200
gtgaatccca cccaaaaata a                                                  1221
```

<210> SEQ ID NO 27
<211> LENGTH: 1221
<212> TYPE: DNA
<213> ORGANISM: Artificial Sequence
<220> FEATURE:
<223> OTHER INFORMATION: Synthetic

<400> SEQUENCE: 27

```
atgagaggat cgcatcacca tcaccatcac ggatccgatg atccccaggg agatgctgcc        60
cagaagacag atatcccca ccatgatcag gatcacccaa ccttcaacaa gatcaccccc        120
aacctggctg agttcgcctt cagcctatac cgccagctgg cacaccagtc caacagcacc       180
aatatcttct ctccccagt gagcatcgct acagcctttg caatgctctc cctggggacc        240
aaggctgaca ctcacgatga atcctggag gcctgaatt caacctcac ggagattccg        300 gaggctcaga tccatgaagg cttccaggaa ctcctccgta ccctcaacca gccagacagc       360
cagctccagc tgaccaccgg caatggcctg ttcctcagcg agggcctgaa gctagtggat       420 aagttttttgg aggatgttaa aaagttgtac cactcagaag ccttcactgt caacttcggg       480
gacaccgaag aggccaagaa acagatcaac gattacgtgg agaagggtac tcaagggaaa       540
attgtggatt tggtcaagga gcttgacaga gacacagttt ttgctctggt gaattacatc       600
ttctttaaag gcaaatggga gagacccttt gaagtcaagg acaccgagga agaggacttc       660
cacgtggacc aggcgaccac cgtgaaggtg cctatgatga agcgtttagg catgtttaac       720
atccagcact gtaagaagct gtccagctgg gtgctgctga tgaaatacct gggcaatgcc       780
accgccatct tcttcctgcc tgatgagggg aaactacagc acctggaaaa tgaactcacc       840
cacgatatca tcaccaagtt cctggaaaat gaagacagaa ggtctgccag cttacattta       900
cccaaactgt ccattactgg aacctatgat ctgaagagcg tcctgggtca actgggcatc       960
actaaggtct tcagcaatgg ggctgacctc tccggggtca cagaggaggc acccctgaag      1020
ctctccaagg ccgtgcataa ggctgtgctg accatcgacg agaaagggac tgaagctgct      1080
ggcgccatgt ttctagaggg ttctctgcgt tctatcccgc tgaggtcaa gttcaacaaa       1140 cccttttgtct tcttaatgat tgaacaaaat accaagtctc ccctcttcat gggaaaagtg      1200
gtgaatccca cccaaaaata a                                                 1221
```

<210> SEQ ID NO 28
<211> LENGTH: 1221
<212> TYPE: DNA
<213> ORGANISM: Artificial Sequence
<220> FEATURE:
<223> OTHER INFORMATION: Synthetic

<400> SEQUENCE: 28

```
atgagaggat cgcatcacca tcaccatcac ggatccgatg atccccaggg agatgctgcc      60
cagaagacag atacatccca ccatgatcag gatcacccaa ccttcaacaa gatcaccccc     120
aacctggctg agttcgcctt cagcctatac cgccagctgg cacaccagtc caacagcacc     180
aatatcttct tctccccagt gagcatcgct acagcctttg caatgctctc cctggggacc     240
aaggctgaca ctcacgatga atcctggag ggcctgaatt tcaacctcac ggagattccg      300
gaggctcaga tccatgaagg cttccaggaa ctcctccgta ccctcaacca gccagacagc     360
cagctccagc tgaccaccgg caatggcctg ttcctcagcg agggcctgaa gctagtggat     420
aagttttttgg aggatgttaa aaagttgtac cactcagaag ccttcactgt caacttcggg    480
gacaccgaag aggccaagaa acagatcaac gattacgtgg agaagggtac tcaagggaaa     540
attgtggatt tggtcaagga gcttgacaga gacacagttt ttgctctggt gaattacatc     600
ttctttaaag gcaaatggga gagacccttt gaagtcaagg acaccgagga agaggacttc     660
cacgtggacc aggcgaccac cgtgaaggtg cctatgatga agcgtttagg catgtttaac     720
atccagcact gtaagaagct gtccagctgg gtgctgctga tgaaatacct gggcaatgcc     780
accgccatct tcttcctgcc tgatgagggg aaactacagc acctggaaaa tgaactcacc     840
cacgatatca tcaccaagtt cctggaaaat aagacagaa ggtctgccag cttacattta      900
cccaaactgt ccattactgg aacctatgat ctgaagagcg tcctgggtca actgggcatc     960
actaaggtct tcagcaatgg ggctgacctc tccggggtca cagaggaggc acccctgaag    1020
ctctccaagg ccgtgcataa ggctgtgctg accatcgacg agaaagggac tgaagctgct    1080
ggcgccatgt ttctagaggg ttctctgcgt ggtatcccgc ctgaggtcaa gttcaacaaa    1140
ccctttgtct tcttaatgat tgaacaaaat accaagtctc ccctcttcat gggaaaagtg    1200
gtgaatccca cccaaaaata a                                              1221
```

<210> SEQ ID NO 29
<211> LENGTH: 1221
<212> TYPE: DNA
<213> ORGANISM: Artificial Sequence
<220> FEATURE:
<223> OTHER INFORMATION: Synthetic

<400> SEQUENCE: 29

```
atgagaggat cgcatcacca tcaccatcac ggatccgatg atccccaggg agatgctgcc      60
cagaagacag atacatccca ccatgatcag gatcacccaa ccttcaacaa gatcaccccc     120
aacctggctg agttcgcctt cagcctatac cgccagctgg cacaccagtc caacagcacc     180
aatatcttct tctccccagt gagcatcgct acagcctttg caatgctctc cctggggacc     240
aaggctgaca ctcacgatga atcctggag ggcctgaatt tcaacctcac ggagattccg      300
gaggctcaga tccatgaagg cttccaggaa ctcctccgta ccctcaacca gccagacagc     360
cagctccagc tgaccaccgg caatggcctg ttcctcagcg agggcctgaa gctagtggat     420
aagttttttgg aggatgttaa aaagttgtac cactcagaag ccttcactgt caacttcggg    480
gacaccgaag aggccaagaa acagatcaac gattacgtgg agaagggtac tcaagggaaa     540
attgtggatt tggtcaagga gcttgacaga gacacagttt ttgctctggt gaattacatc     600
ttctttaaag gcaaatggga gagacccttt gaagtcaagg acaccgagga agaggacttc     660
cacgtggacc aggcgaccac cgtgaaggtg cctatgatga agcgtttagg catgtttaac     720
atccagcact gtaagaagct gtccagctgg gtgctgctga tgaaatacct gggcaatgcc     780
```

```
accgccatct tcttcctgcc tgatgagggg aaactacagc acctggaaaa tgaactcacc    840
cacgatatca tcaccaagtt cctggaaaat gaagacagaa ggtctgccag cttacattta    900
cccaaactgt ccattactgg aacctatgat ctgaagagcg tcctgggtca actgggcatc    960
actaaggtct tcagcaatgg ggctgacctc tccggggtca cagaggaggc acccctgaag   1020
ctctccaagg ccgtgcataa ggctgtgctg accatcgacg agaagggac tgaagctgct    1080 ggcgccatgt ttctagaggc tatcccgcgt cagaccaacc ctgaggtcaa gttcaacaaa   1140
ccctttgtct tcttaatgat tgaacaaaat accaagtctc ccctcttcat gggaaaagtg   1200
gtgaatccca cccaaaaata a                                             1221
```

```
<210> SEQ ID NO 30
<211> LENGTH: 1221
<212> TYPE: DNA
<213> ORGANISM: Artificial Sequence
<220> FEATURE:
<223> OTHER INFORMATION: Synthetic

<400> SEQUENCE: 30
atgagaggat cgcatcacca tcaccatcac ggatccgatg atccccaggg agatgctgcc     60
cagaagacag atacatccca ccatgatcag atcacccaa ccttcaacaa gatcaccccc    120
aacctggctg agttcgcctt cagcctatac cgccagctgg cacaccagtc caacagcacc    180
aatatcttct ctccccagt gagcatcgct acagcctttg caatgctctc cctggggacc    240
aaggctgaca ctcacgatga atcctggag ggcctgaatt tcaacctcac ggagattccg    300
gaggctcaga tccatgaagg cttccaggaa ctcctccgta ccctcaacca gccagacagc    360
cagctccagc tgaccaccgg caatggcctg ttcctcagcg agggcctgaa gctagtggat    420
aagtttttgg aggatgttaa aaagttgtac cactcagaag ccttcactgt caacttcggg    480
gacaccgaag aggccaagaa acagatcaac gattacgtgg agaagggtac tcaagggaaa    540
attgtggatt tggtcaagga gcttgacaga gacacagttt ttgctctggt gaattacatc    600
ttctttaaag gcaaatggga gagacccttt gaagtcaagg acaccgagga agaggacttc    660
cacgtggacc aggcgaccac cgtgaaggtg cctatgatga agcgtttagg catgtttaac    720
atccagcact gtaagaagct gtccagctgg gtgctgctga tgaaataacct gggcaatgcc    780 accgccatct tcttcctgcc tgatgagggg aaactacagc acctggaaaa tgaactcacc    840
cacgatatca tcaccaagtt cctggaaaat gaagacagaa ggtctgccag cttacattta    900
cccaaactgt ccattactgg aacctatgat ctgaagagcg tcctgggtca actgggcatc    960
actaaggtct tcagcaatgg ggctgacctc tccggggtca cagaggaggc acccctgaag   1020
ctctccaagg ccgtgcataa ggctgtgctg accatcgacg agaagggac tgaagctgct    1080 ggcgccatgt ttctagaggc tatcggtcgt cagaccaacc ctgaggtcaa gttcaacaaa   1140
ccctttgtct tcttaatgat tgaacaaaat accaagtctc ccctcttcat gggaaaagtg   1200
gtgaatccca cccaaaaata a                                             1221
```

```
<210> SEQ ID NO 31
<211> LENGTH: 1221
<212> TYPE: DNA
<213> ORGANISM: Artificial Sequence
<220> FEATURE:
<223> OTHER INFORMATION: Synthetic
```

<400> SEQUENCE: 31

```
atgagaggat cgcatcacca tcaccatcac ggatccgatg atccccaggg agatgctgcc      60
cagaagacag atacatccca ccatgatcag gatcacccaa ccttcaacaa gatcaccccc     120
aacctggctg agttcgcctt cagcctatac cgccagctgg cacaccagtc caacagcacc     180
aatatcttct tctccccagt gagcatcgct acagcctttg caatgctctc cctggggacc     240
aaggctgaca ctcacgatga atcctggag gcctgaatt tcaacctcac ggagattccg       300
gaggctcaga tccatgaagg cttccaggaa ctcctccgta ccctcaacca gccagacagc     360
cagctccagc tgaccaccgg caatggcctg ttcctcagcg agggcctgaa gctagtggat     420
aagttttttgg aggatgttaa aaagttgtac cactcagaag ccttcactgt caacttcggg    480
gacaccgaag aggccaagaa acagatcaac gattacgtgg agaagggtac tcaagggaaa    540
attgtggatt tggtcaagga gcttgacaga gacacagttt ttgctctggt gaattacatc    600
ttctttaaag gcaaatggga gagaccctt gaagtcaagg acaccgagga agaggacttc     660
cacgtggacc aggcgaccac cgtgaaggtg cctatgatga agcgtttagg catgtttaac    720
atccagcact gtaagaagct gtccagctgg gtgctgctga tgaaatacct gggcaatgcc    780
accgccatct tcttcctgcc tgatgagggg aaactacagc acctggaaaa tgaactcacc   840
cacgatatca tcaccaagtt cctgaaaaat aagacagaa ggtctgccag cttacattta    900
cccaaactgt ccattactgg aacctatgat ctgaagagcg tcctgggtca actgggcatc   960
actaaggtct tcagcaatgg ggctgacctc tccggggtca cagaggaggc acccctgaag  1020
ctctccaagg ccgtgcataa ggctgtgctg accatcgacg agaaagggac tgaagctgct  1080
ggcgccatgt ttctagaggc taaccagcgt tcttccccgc ctgaggtcaa gttcaacaaa  1140
cccttttgtct tcttaatgat tgaacaaaat accaagtctc ccctcttcat gggaaaagtg  1200
gtgaatccca cccaaaaata a                                             1221
```

<210> SEQ ID NO 32
<211> LENGTH: 1221
<212> TYPE: DNA
<213> ORGANISM: Artificial Sequence
<220> FEATURE:
<223> OTHER INFORMATION: Synthetic

<400> SEQUENCE: 32

```
atgagaggat cgcatcacca tcaccatcac ggatccgatg atccccaggg agatgctgcc      60
cagaagacag atacatccca ccatgatcag gatcacccaa ccttcaacaa gatcaccccc     120
aacctggctg agttcgcctt cagcctatac cgccagctgg cacaccagtc caacagcacc     180
aatatcttct tctccccagt gagcatcgct acagcctttg caatgctctc cctggggacc     240
aaggctgaca ctcacgatga atcctggag gcctgaatt tcaacctcac ggagattccg       300
gaggctcaga tccatgaagg cttccaggaa ctcctccgta ccctcaacca gccagacagc     360
cagctccagc tgaccaccgg caatggcctg ttcctcagcg agggcctgaa gctagtggat     420
aagttttttgg aggatgttaa aaagttgtac cactcagaag ccttcactgt caacttcggg    480
gacaccgaag aggccaagaa acagatcaac gattacgtgg agaagggtac tcaagggaaa    540
attgtggatt tggtcaagga gcttgacaga gacacagttt ttgctctggt gaattacatc    600
ttctttaaag gcaaatggga gagaccctt gaagtcaagg acaccgagga agaggacttc     660
cacgtggacc aggcgaccac cgtgaaggtg cctatgatga agcgtttagg catgtttaac    720
atccagcact gtaagaagct gtccagctgg gtgctgctga tgaaatacct gggcaatgcc    780
```

| | |
|---|---|
| accgccatct tcttcctgcc tgatgagggg aaactacagc acctggaaaa tgaactcacc | 840 |
| cacgatatca tcaccaagtt cctggaaaat gaagacagaa ggtctgccag cttacattta | 900 |
| cccaaactgt ccattactgg aacctatgat ctgaagagcg tcctgggtca actgggcatc | 960 |
| actaaggtct tcagcaatgg ggctgacctc tccggggtca cagaggaggc acccctgaag | 1020 |
| ctctccaagg ccgtgcataa ggctgtgctg accatcgacg agaaagggac tgaagctgct | 1080 |
| ggcgccatgt ttctagaggc tctgcagcgt gctatcccgc ctgaggtcaa gttcaacaaa | 1140 |
| cccttttgtct tcttaatgat tgaacaaaat accaagtctc ccctcttcat gggaaaagtg | 1200 |
| gtgaatccca cccaaaaata a | 1221 |

<210> SEQ ID NO 33
<211> LENGTH: 1221
<212> TYPE: DNA
<213> ORGANISM: Artificial Sequence
<220> FEATURE:
<223> OTHER INFORMATION: Synthetic

<400> SEQUENCE: 33

| | |
|---|---|
| atgagaggat cgcatcacca tcaccatcac ggatccgatg atccccaggg agatgctgcc | 60 |
| cagaagacag atacatccca ccatgatcag gatcacccaa ccttcaacaa gatcaccccc | 120 |
| aacctggctg agttcgcctt cagcctatac cgccagctgg cacaccagtc caacagcacc | 180 |
| aatatcttct ctccccagt gagcatcgct acagcctttg caatgctctc cctggggacc | 240 |
| aaggctgaca ctcacgatga atcctggag gcctgaatt tcaacctcac ggagattccg | 300 |
| gaggctcaga tccatgaagg cttccaggaa ctcctccgta ccctcaacca gccagacagc | 360 |
| cagctccagc tgaccaccgg caatggcctg ttcctcagcg agggcctgaa gctagtggat | 420 |
| aagttttttgg aggatgttaa aaagttgtac cactcagaag ccttcactgt caacttcggg | 480 |
| gacaccgaag aggccaagaa acagatcaac gattacgtgg agaagggtac tcaagggaaa | 540 |
| attgtggatt tggtcaagga gcttgacaga gacacagttt ttgctctggt gaattacatc | 600 |
| ttctttaaag gcaaatggga gagacccttt gaagtcaagg acaccgagga agaggacttc | 660 |
| cacgtggacc aggcgaccac cgtgaaggtg cctatgatga agcgtttagg catgtttaac | 720 |
| atccagcact gtaagaagct gtccagctgg gtgctgctga tgaaatacct gggcaatgcc | 780 |
| accgccatct tcttcctgcc tgatgagggg aaactacagc acctggaaaa tgaactcacc | 840 |
| cacgatatca tcaccaagtt cctggaaaat gaagacagaa ggtctgccag cttacattta | 900 |
| cccaaactgt ccattactgg aacctatgat ctgaagagcg tcctgggtca actgggcatc | 960 |
| actaaggtct tcagcaatgg ggctgacctc tccggggtca cagaggaggc acccctgaag | 1020 |
| ctctccaagg ccgtgcataa ggctgtgctg accatcgacg agaaagggac tgaagctgct | 1080 |
| ggcgccatgt ttctagagca gcgtctgcgt gacatcccgc ctgaggtcaa gttcaacaaa | 1140 |
| cccttttgtct tcttaatgat tgaacaaaat accaagtctc ccctcttcat gggaaaagtg | 1200 |
| gtgaatccca cccaaaaata a | 1221 |

<210> SEQ ID NO 34
<211> LENGTH: 1221
<212> TYPE: DNA
<213> ORGANISM: Artificial Sequence
<220> FEATURE:
<223> OTHER INFORMATION: Synthetic

<400> SEQUENCE: 34

```
atgagaggat cgcatcacca tcaccatcac ggatccgatg atccccaggg agatgctgcc      60
cagaagacag atacatccca ccatgatcag gatcacccaa ccttcaacaa gatcaccccc     120
aacctggctg agttcgcctt cagcctatac cgccagctgg cacaccagtc caacagcacc     180
aatatcttct tctccccagt gagcatcgct acagcctttg caatgctctc cctggggacc     240
aaggctgaca ctcacgatga atcctggag ggcctgaatt tcaacctcac ggagattccg      300
gaggctcaga tccatgaagg cttccaggaa ctcctccgta ccctcaacca gccagacagc     360
cagctccagc tgaccaccgg caatggcctg ttcctcagcg agggcctgaa gctagtggat     420
aagttttttgg aggatgttaa aagttgtac cactcagaag ccttcactgt caacttcggg     480
gacaccgaag aggccaagaa acagatcaac gattacgtgg agaagggtac tcaagggaaa     540
attgtggatt tggtcaagga gcttgacaga gacacagttt ttgctctggt gaattacatc     600
ttctttaaag gcaaatggga gagacccttt gaagtcaagg acaccgagga agaggacttc     660
cacgtggacc aggcgaccac cgtgaaggtg cctatgatga agcgtttagg catgtttaac     720
atccagcact gtaagaagct gtccagctgg gtgctgctga tgaaatacct gggcaatgcc     780
accgccatct tcttcctgcc tgatgagggg aaactacagc acctggaaaa tgaactcacc     840
cacgatatca tcaccaagtt cctggaaaat aagacagaa ggtctgccag cttacattta      900
cccaaactgt ccattactgg aacctatgat ctgaagagcg tcctgggtca actgggcatc     960
actaaggtct tcagcaatgg ggctgacctc tccggggtca cagaggaggc acccctgaag    1020
ctctccaagg ccgtgcataa ggctgtgctg accatcgacg agaaagggac tgaagctgct    1080
ggcgccatgt ttctagaggc tccggaccgt cacatgccgc tgaggtcaa gttcaacaaa     1140
cccttttgtct tcttaatgat tgaacaaaat accaagtctc ccctcttcat gggaaaagtg    1200
gtgaatccca cccaaaaata a                                              1221
```

<210> SEQ ID NO 35
<211> LENGTH: 1221
<212> TYPE: DNA
<213> ORGANISM: Artificial Sequence
<220> FEATURE:
<223> OTHER INFORMATION: Synthetic

<400> SEQUENCE: 35

```
atgagaggat cgcatcacca tcaccatcac ggatccgatg atccccaggg agatgctgcc      60
cagaagacag atacatccca ccatgatcag gatcacccaa ccttcaacaa gatcaccccc     120
aacctggctg agttcgcctt cagcctatac cgccagctgg cacaccagtc caacagcacc     180
aatatcttct tctccccagt gagcatcgct acagcctttg caatgctctc cctggggacc     240
aaggctgaca ctcacgatga atcctggag ggcctgaatt tcaacctcac ggagattccg      300
gaggctcaga tccatgaagg cttccaggaa ctcctccgta ccctcaacca gccagacagc     360
cagctccagc tgaccaccgg caatggcctg ttcctcagcg agggcctgaa gctagtggat     420
aagttttttgg aggatgttaa aagttgtac cactcagaag ccttcactgt caacttcggg     480
gacaccgaag aggccaagaa acagatcaac gattacgtgg agaagggtac tcaagggaaa     540
attgtggatt tggtcaagga gcttgacaga gacacagttt ttgctctggt gaattacatc     600
ttctttaaag gcaaatggga gagacccttt gaagtcaagg acaccgagga agaggacttc     660
cacgtggacc aggcgaccac cgtgaaggtg cctatgatga agcgtttagg catgtttaac     720
atccagcact gtaagaagct gtccagctgg gtgctgctga tgaaatacct gggcaatgcc     780
```

| | |
|---|---|
| accgccatct tcttcctgcc tgatgagggg aaactacagc acctggaaaa tgaactcacc | 840 |
| cacgatatca tcaccaagtt cctggaaaat gaagacagaa ggtctgccag cttacattta | 900 |
| cccaaactgt ccattactgg aacctatgat ctgaagagcg tcctgggtca actgggcatc | 960 |
| actaaggtct tcagcaatgg ggctgacctc tccggggtca cagaggaggc acccctgaag | 1020 |
| ctctccaagg ccgtgcataa ggctgtgctg accatcgacg agaaagggac tgaagctgct | 1080 |
| ggcgccatgt ttctagagac cgttgactac gctatcccgc ctgaggtcaa gttcaacaaa | 1140 |
| cccttttgtct tcttaatgat tgaacaaaat accaagtctc ccctcttcat gggaaaagtg | 1200 |
| gtgaatccca cccaaaaata a | 1221 |

<210> SEQ ID NO 36
<211> LENGTH: 1239
<212> TYPE: DNA
<213> ORGANISM: Artificial Sequence
<220> FEATURE:
<223> OTHER INFORMATION: Synthetic

<400> SEQUENCE: 36

| | |
|---|---|
| atgagaggat cccatcacca tcaccatcac tctagacacc ctaacagccc acttgacgag | 60 |
| gagaatctga cccaggagaa ccaagaccga gggacacacg tggacctcgg attagcctcc | 120 |
| gccaacgtgg acttcgcttt cagcctgtac aagcagttag tcctgaaggc ccctgataag | 180 |
| aatgtcatct ctctccccact gagcatctcc accgccttgg ccttcctgtc tctgggggcc | 240 |
| cataatacca ccctgacaga gattctcaaa ggcctcaagt tcaacctcac ggagacttct | 300 |
| gaggcagaaa ttcaccagag cttccagcac ctcctgcgca ccctcaatca gtccagcgat | 360 |
| gagctgcagc tgagtatggg aaatgccatg tttgtcaaag agcaactcag tctgctggac | 420 |
| aggttcacgg aggatgccaa gaggctgtat ggctccgagg cctttgccac tgactttcag | 480 |
| gactcagctg cagctaagaa gctcatcaac gactacgtga agaatggaac tagggggaaa | 540 |
| atcacagatc tgatcaagga ccttgactcg cagacaatga tggtcctggt gaattacatc | 600 |
| ttctttaaag ccaaatggga gatgcccttt gaccccaag atactcatca gtcaaggttc | 660 |
| tacttgagca agaaaaagtg ggtaatggtg cccatgatga gtttgcatca cctgactata | 720 |
| ccttacttcc gggacgagga gctgtcctgc acgtggtgg agctgaagta cacaggcaat | 780 |
| gccagcgcac tcttcatcct ccctgatcaa gacaagatgg aggaagtgga agccatgctg | 840 |
| ctcccagaga ccctgaagcg gtggagagac tctctggagt tcagagagat aggtgagctc | 900 |
| tacctgccaa gtttttccat ctcgagggac tataacctga cgacatact tctccagctg | 960 |
| ggcattgagg aagccttcac cagcaaggct gacctgtcag ggatcacagg gccaggaac | 1020 |
| ctagcagtct cccaggtggt ccataaggct gtgcttgatg tatttgagga gggcacagaa | 1080 |
| gcatctgctg ccaccgcggt cgttggttct ctgcgttctg cattagtgga gacgcgtacc | 1140 |
| attgtgcgtt tcaacaggcc cttcctgatg atcattgtcc ctacagacac ccagaacatc | 1200 |
| ttcttcatga gcaaagtcac caatcccaag caagcctaa | 1239 |

<210> SEQ ID NO 37
<211> LENGTH: 1239
<212> TYPE: DNA
<213> ORGANISM: Artificial Sequence
<220> FEATURE:
<223> OTHER INFORMATION: Synthetic

<400> SEQUENCE: 37

```
atgagaggat cccatcacca tcaccatcac tctagacacc ctaacagccc acttgacgag     60
gagaatctga cccaggagaa ccaagaccga gggacacacg tggacctcgg attagcctcc    120
gccaacgtgg acttcgcttt cagcctgtac aagcagttag tcctgaaggc ccctgataag    180
aatgtcatct tctccccact gagcatctcc accgccttgg ccttcctgtc tctgggggcc    240
cataatacca ccctgacaga gattctcaaa ggcctcaagt tcaacctcac ggagacttct    300
gaggcagaaa ttcaccagag cttccagcac ctcctgcgca ccctcaatca gtccagcgat    360
gagctgcagc tgagtatggg aaatgccatg tttgtcaaag agcaactcag tctgctggac    420
aggttcacgg aggatgccaa gaggctgtat ggctccgagg cctttgccac tgactttcag    480
gactcagctg cagctaagaa gctcatcaac gactacgtga agaatggaac taggggaaa     540
atcacagatc tgatcaagga ccttgactcg cagacaatga tggtcctggt gaattacatc    600
ttctttaaag ccaaatggga gatgccctt gaccccaag atactcatca gtcaaggttc     660
tacttgagca agaaaaagtg ggtaatggtg cccatgatga gtttgcatca cctgactata    720
ccttacttcc gggacgagga gctgtcctgc accgtggtgg agctgaagta cacaggcaat    780
gccagcgcac tcttcatcct ccctgatcaa gacaagatgg aggaagtgga agccatgctg    840
ctcccagaga ccctgaagcg gtggagagac tctctggagt tcagagagat aggtgagctc    900
tacctgccaa agttttccat ctcgagggac ataaacctga cgacatact tctccagctg     960
ggcattgagg aagccttcac cagcaaggct gacctgtcag ggatcacagg ggccaggaac   1020
ctagcagtct cccaggtggt ccataaggct gtgcttgatg tatttgagga gggcacagaa   1080
gcatctgctg ccaccgcggt caaaatcacc ctccgtcaga ccaacgacga gacgcgtacc   1140
attgtgcgtt tcaacaggcc cttcctgatg atcattgtcc ctacagacac ccagaacatc   1200
ttcttcatga gcaaagtcac caatcccaag caagcctaa                          1239
```

<210> SEQ ID NO 38
<211> LENGTH: 412
<212> TYPE: PRT
<213> ORGANISM: Artificial Sequence
<220> FEATURE:
<223> OTHER INFORMATION: Synthetic

<400> SEQUENCE: 38

```
Met Arg Gly Ser His His His His His His Ser Arg His Pro Asn Ser
1               5                   10                  15
Pro Leu Asp Glu Glu Asn Leu Thr Gln Glu Asn Gln Asp Arg Gly Thr
            20                  25                  30
His Val Asp Leu Gly Leu Ala Ser Ala Asn Val Asp Phe Ala Phe Ser
        35                  40                  45
Leu Tyr Lys Gln Leu Val Leu Lys Ala Pro Asp Lys Asn Val Ile Phe
    50                  55                  60
Ser Pro Leu Ser Ile Ser Thr Ala Leu Ala Phe Leu Ser Leu Gly Ala
65                  70                  75                  80
His Asn Thr Thr Leu Thr Glu Ile Leu Lys Gly Leu Lys Phe Asn Leu
                85                  90                  95
Thr Glu Thr Ser Glu Ala Glu Ile His Gln Ser Phe Gln His Leu Leu
            100                 105                 110
Arg Thr Leu Asn Gln Ser Ser Asp Glu Leu Gln Leu Ser Met Gly Asn
        115                 120                 125
```

```
Ala Met Phe Val Lys Glu Gln Leu Ser Leu Leu Asp Arg Phe Thr Glu
    130                 135                 140

Asp Ala Lys Arg Leu Tyr Gly Ser Glu Ala Phe Ala Thr Asp Phe Gln
145                 150                 155                 160

Asp Ser Ala Ala Lys Lys Leu Ile Asn Asp Tyr Val Lys Asn Gly
            165                 170                 175

Thr Arg Gly Lys Ile Thr Asp Leu Ile Lys Asp Leu Asp Ser Gln Thr
            180                 185                 190

Met Met Val Leu Val Asn Tyr Ile Phe Phe Lys Ala Lys Trp Glu Met
        195                 200                 205

Pro Phe Asp Pro Gln Asp Thr His Gln Ser Arg Phe Tyr Leu Ser Lys
210                 215                 220

Lys Lys Trp Val Met Val Pro Met Met Ser Leu His Leu Thr Ile
225                 230                 235                 240

Pro Tyr Phe Arg Asp Glu Leu Ser Cys Thr Val Val Glu Leu Lys
            245                 250                 255

Tyr Thr Gly Asn Ala Ser Ala Leu Phe Ile Leu Pro Asp Gln Asp Lys
            260                 265                 270

Met Glu Glu Val Glu Ala Met Leu Leu Pro Glu Thr Leu Lys Arg Trp
        275                 280                 285

Arg Asp Ser Leu Glu Phe Arg Glu Ile Gly Glu Leu Tyr Leu Pro Lys
290                 295                 300

Phe Ser Ile Ser Arg Asp Tyr Asn Leu Asn Asp Ile Leu Leu Gln Leu
305                 310                 315                 320

Gly Ile Glu Glu Ala Phe Thr Ser Lys Ala Asp Leu Ser Gly Ile Thr
            325                 330                 335

Gly Ala Arg Asn Leu Ala Val Ser Gln Val Val His Lys Ala Val Leu
            340                 345                 350

Asp Val Phe Glu Glu Gly Thr Glu Ala Ser Ala Ala Thr Ala Val Lys
        355                 360                 365

Ile Thr Leu Leu Ser Ala Leu Val Glu Thr Arg Thr Ile Val Arg Phe
370                 375                 380

Asn Arg Pro Phe Leu Met Ile Ile Val Pro Thr Asp Thr Gln Asn Ile
385                 390                 395                 400

Phe Phe Met Ser Lys Val Thr Asn Pro Lys Gln Ala
            405                 410

<210> SEQ ID NO 39
<211> LENGTH: 412
<212> TYPE: PRT
<213> ORGANISM: Artificial Sequence
<220> FEATURE:
<223> OTHER INFORMATION: Synthetic

<400> SEQUENCE: 39

Met Arg Gly Ser His His His His His His Ser Arg His Pro Asn Ser
1               5                   10                  15

Pro Leu Asp Glu Glu Asn Leu Thr Gln Glu Asn Gln Asp Arg Gly Thr
            20                  25                  30

His Val Asp Leu Gly Leu Ala Ser Ala Asn Val Asp Phe Ala Phe Ser
        35                  40                  45

Leu Tyr Lys Gln Leu Val Leu Lys Ala Pro Asp Lys Asn Val Ile Phe
    50                  55                  60

Ser Pro Leu Ser Ile Ser Thr Ala Leu Ala Phe Leu Ser Leu Gly Ala
65                  70                  75                  80
```

```
His Asn Thr Thr Leu Thr Glu Ile Leu Lys Gly Leu Lys Phe Asn Leu
                85                  90                  95

Thr Glu Thr Ser Glu Ala Glu Ile His Gln Ser Phe Gln His Leu Leu
            100                 105                 110

Arg Thr Leu Asn Gln Ser Ser Asp Glu Leu Gln Leu Ser Met Gly Asn
        115                 120                 125

Ala Met Phe Val Lys Glu Gln Leu Ser Leu Leu Asp Arg Phe Thr Glu
    130                 135                 140

Asp Ala Lys Arg Leu Tyr Gly Ser Glu Ala Phe Ala Thr Asp Phe Gln
145                 150                 155                 160

Asp Ser Ala Ala Ala Lys Lys Leu Ile Asn Asp Tyr Val Lys Asn Gly
                165                 170                 175

Thr Arg Gly Lys Ile Thr Asp Leu Ile Lys Asp Leu Asp Ser Gln Thr
            180                 185                 190

Met Met Val Leu Val Asn Tyr Ile Phe Phe Lys Ala Lys Trp Glu Met
        195                 200                 205

Pro Phe Asp Pro Gln Asp Thr His Gln Ser Arg Phe Tyr Leu Ser Lys
    210                 215                 220

Lys Lys Trp Val Met Val Pro Met Met Ser Leu His His Leu Thr Ile
225                 230                 235                 240

Pro Tyr Phe Arg Asp Glu Leu Ser Cys Thr Val Val Glu Leu Lys
                245                 250                 255

Tyr Thr Gly Asn Ala Ser Ala Leu Phe Ile Leu Pro Asp Gln Asp Lys
            260                 265                 270

Met Glu Glu Val Glu Ala Met Leu Leu Pro Glu Thr Leu Lys Arg Trp
        275                 280                 285

Arg Asp Ser Leu Glu Phe Arg Glu Ile Gly Glu Leu Tyr Leu Pro Lys
    290                 295                 300

Phe Ser Ile Ser Arg Asp Tyr Asn Leu Asn Asp Ile Leu Leu Gln Leu
305                 310                 315                 320

Gly Ile Glu Glu Ala Phe Thr Ser Lys Ala Asp Leu Ser Gly Ile Thr
                325                 330                 335

Gly Ala Arg Asn Leu Ala Val Ser Gln Val Val His Lys Ala Val Leu
            340                 345                 350

Asp Val Phe Glu Glu Gly Thr Glu Ala Ser Ala Ala Thr Ala Val Lys
        355                 360                 365

Gly Ser Leu Arg Ser Ala Leu Val Glu Thr Arg Thr Ile Val Arg Phe
    370                 375                 380

Asn Arg Pro Phe Leu Met Ile Ile Val Pro Thr Asp Thr Gln Asn Ile
385                 390                 395                 400

Phe Phe Met Ser Lys Val Thr Asn Pro Lys Gln Ala
                405                 410

<210> SEQ ID NO 40
<211> LENGTH: 412
<212> TYPE: PRT
<213> ORGANISM: Artificial Sequence
<220> FEATURE:
<223> OTHER INFORMATION: Synthetic

<400> SEQUENCE: 40

Met Arg Gly Ser His His His His His His Ser Arg His Pro Asn Ser
1               5                   10                  15

Pro Leu Asp Glu Glu Asn Leu Thr Gln Glu Asn Gln Asp Arg Gly Thr
            20                  25                  30
```

His Val Asp Leu Gly Leu Ala Ser Ala Asn Val Asp Phe Ala Phe Ser
            35                  40                  45

Leu Tyr Lys Gln Leu Val Leu Lys Ala Pro Asp Lys Asn Val Ile Phe
 50                  55                  60

Ser Pro Leu Ser Ile Ser Thr Ala Leu Ala Phe Leu Ser Leu Gly Ala
 65                  70                  75                  80

His Asn Thr Thr Leu Thr Glu Ile Leu Lys Gly Leu Lys Phe Asn Leu
                 85                  90                  95

Thr Glu Thr Ser Glu Ala Glu Ile His Gln Ser Phe Gln His Leu Leu
                100                 105                 110

Arg Thr Leu Asn Gln Ser Ser Asp Glu Leu Gln Leu Ser Met Gly Asn
            115                 120                 125

Ala Met Phe Val Lys Glu Gln Leu Ser Leu Leu Asp Arg Phe Thr Glu
130                 135                 140

Asp Ala Lys Arg Leu Tyr Gly Ser Glu Ala Phe Ala Thr Asp Phe Gln
145                 150                 155                 160

Asp Ser Ala Ala Ala Lys Lys Leu Ile Asn Asp Tyr Val Lys Asn Gly
                165                 170                 175

Thr Arg Gly Lys Ile Thr Asp Leu Ile Lys Asp Leu Asp Ser Gln Thr
                180                 185                 190

Met Met Val Leu Val Asn Tyr Ile Phe Phe Lys Ala Lys Trp Glu Met
            195                 200                 205

Pro Phe Asp Pro Gln Asp Thr His Gln Ser Arg Phe Tyr Leu Ser Lys
210                 215                 220

Lys Lys Trp Val Met Val Pro Met Met Ser Leu His His Leu Thr Ile
225                 230                 235                 240

Pro Tyr Phe Arg Asp Glu Glu Leu Ser Cys Thr Val Val Glu Leu Lys
                245                 250                 255

Tyr Thr Gly Asn Ala Ser Ala Leu Phe Ile Leu Pro Asp Gln Asp Lys
                260                 265                 270

Met Glu Glu Val Glu Ala Met Leu Leu Pro Glu Thr Leu Lys Arg Trp
            275                 280                 285

Arg Asp Ser Leu Glu Phe Arg Glu Ile Gly Glu Leu Tyr Leu Pro Lys
290                 295                 300

Phe Ser Ile Ser Arg Asp Tyr Asn Leu Asn Asp Ile Leu Leu Gln Leu
305                 310                 315                 320

Gly Ile Glu Glu Ala Phe Thr Ser Lys Ala Asp Leu Ser Gly Ile Thr
                325                 330                 335

Gly Ala Arg Asn Leu Ala Val Ser Gln Val Val His Lys Ala Val Leu
            340                 345                 350

Asp Val Phe Glu Glu Gly Thr Glu Ala Ser Ala Ala Thr Ala Val Lys
            355                 360                 365

Gly Ser Leu Arg Gly Ala Leu Val Glu Thr Arg Thr Ile Val Arg Phe
370                 375                 380

Asn Arg Pro Phe Leu Met Ile Ile Val Pro Thr Asp Thr Gln Asn Ile
385                 390                 395                 400

Phe Phe Met Ser Lys Val Thr Asn Pro Lys Gln Ala
                405                 410

<210> SEQ ID NO 41
<211> LENGTH: 412
<212> TYPE: PRT
<213> ORGANISM: Artificial Sequence
<220> FEATURE:
<223> OTHER INFORMATION: Synthetic

```
<400> SEQUENCE: 41

Met Arg Gly Ser His His His His His Ser Arg His Pro Asn Ser
1               5                   10                  15

Pro Leu Asp Glu Glu Asn Leu Thr Gln Glu Asn Gln Asp Arg Gly Thr
            20                  25                  30

His Val Asp Leu Gly Leu Ala Ser Ala Asn Val Asp Phe Ala Phe Ser
            35                  40                  45

Leu Tyr Lys Gln Leu Val Leu Lys Ala Pro Asp Lys Asn Val Ile Phe
    50                  55                  60

Ser Pro Leu Ser Ile Ser Thr Ala Leu Ala Phe Leu Ser Leu Gly Ala
65                  70                  75                  80

His Asn Thr Thr Leu Thr Glu Ile Leu Lys Gly Leu Lys Phe Asn Leu
                85                  90                  95

Thr Glu Thr Ser Glu Ala Glu Ile His Gln Ser Phe Gln His Leu Leu
            100                 105                 110

Arg Thr Leu Asn Gln Ser Ser Asp Glu Leu Gln Leu Ser Met Gly Asn
        115                 120                 125

Ala Met Phe Val Lys Glu Gln Leu Ser Leu Leu Asp Arg Phe Thr Glu
130                 135                 140

Asp Ala Lys Arg Leu Tyr Gly Ser Glu Ala Phe Ala Thr Asp Phe Gln
145                 150                 155                 160

Asp Ser Ala Ala Ala Lys Lys Leu Ile Asn Asp Tyr Val Lys Asn Gly
                165                 170                 175

Thr Arg Gly Lys Ile Thr Asp Leu Ile Lys Asp Leu Asp Ser Gln Thr
            180                 185                 190

Met Met Val Leu Val Asn Tyr Ile Phe Phe Lys Ala Lys Trp Glu Met
        195                 200                 205

Pro Phe Asp Pro Gln Asp Thr His Gln Ser Arg Phe Tyr Leu Ser Lys
    210                 215                 220

Lys Lys Trp Val Met Val Pro Met Met Ser Leu His His Leu Thr Ile
225                 230                 235                 240

Pro Tyr Phe Arg Asp Glu Glu Leu Ser Cys Thr Val Val Glu Leu Lys
                245                 250                 255

Tyr Thr Gly Asn Ala Ser Ala Leu Phe Ile Leu Pro Asp Gln Asp Lys
            260                 265                 270

Met Glu Glu Val Glu Ala Met Leu Leu Pro Glu Thr Leu Lys Arg Trp
        275                 280                 285

Arg Asp Ser Leu Glu Phe Arg Glu Ile Gly Glu Leu Tyr Leu Pro Lys
    290                 295                 300

Phe Ser Ile Ser Arg Asp Tyr Asn Leu Asn Asp Ile Leu Leu Gln Leu
305                 310                 315                 320

Gly Ile Glu Glu Ala Phe Thr Ser Lys Ala Asp Leu Ser Gly Ile Thr
                325                 330                 335

Gly Ala Arg Asn Leu Ala Val Ser Gln Val Val His Lys Ala Val Leu
            340                 345                 350

Asp Val Phe Glu Glu Gly Thr Glu Ala Ser Ala Ala Thr Ala Val Lys
        355                 360                 365

Ile Thr Leu Arg Gln Thr Asn Val Glu Thr Arg Thr Ile Val Arg Phe
    370                 375                 380

Asn Arg Pro Phe Leu Met Ile Ile Val Pro Thr Asp Thr Gln Asn Ile
385                 390                 395                 400

Phe Phe Met Ser Lys Val Thr Asn Pro Lys Gln Ala
                405                 410
```

-continued

```
<210> SEQ ID NO 42
<211> LENGTH: 412
<212> TYPE: PRT
<213> ORGANISM: Artificial Sequence
<220> FEATURE:
<223> OTHER INFORMATION: Synthetic

<400> SEQUENCE: 42

Met Arg Gly Ser His His His His His His Ser Arg His Pro Asn Ser
1               5                   10                  15

Pro Leu Asp Glu Glu Asn Leu Thr Gln Glu Asn Gln Asp Arg Gly Thr
            20                  25                  30

His Val Asp Leu Gly Leu Ala Ser Ala Asn Val Asp Phe Ala Phe Ser
        35                  40                  45

Leu Tyr Lys Gln Leu Val Leu Lys Ala Pro Asp Lys Asn Val Ile Phe
    50                  55                  60

Ser Pro Leu Ser Ile Ser Thr Ala Leu Ala Phe Leu Ser Leu Gly Ala
65                  70                  75                  80

His Asn Thr Thr Leu Thr Glu Ile Leu Lys Gly Leu Lys Phe Asn Leu
                85                  90                  95

Thr Glu Thr Ser Glu Ala Glu Ile His Gln Ser Phe Gln His Leu Leu
            100                 105                 110

Arg Thr Leu Asn Gln Ser Ser Asp Glu Leu Gln Leu Ser Met Gly Asn
        115                 120                 125

Ala Met Phe Val Lys Glu Gln Leu Ser Leu Leu Asp Arg Phe Thr Glu
    130                 135                 140

Asp Ala Lys Arg Leu Tyr Gly Ser Glu Ala Phe Ala Thr Asp Phe Gln
145                 150                 155                 160

Asp Ser Ala Ala Ala Lys Lys Leu Ile Asn Asp Tyr Val Lys Asn Gly
                165                 170                 175

Thr Arg Gly Lys Ile Thr Asp Leu Ile Lys Asp Leu Asp Ser Gln Thr
            180                 185                 190

Met Met Val Leu Val Asn Tyr Ile Phe Phe Lys Ala Lys Trp Glu Met
        195                 200                 205

Pro Phe Asp Pro Gln Asp Thr His Gln Ser Arg Phe Tyr Leu Ser Lys
    210                 215                 220

Lys Lys Trp Val Met Val Pro Met Met Ser Leu His His Leu Thr Ile
225                 230                 235                 240

Pro Tyr Phe Arg Asp Glu Glu Leu Ser Cys Thr Val Val Glu Leu Lys
                245                 250                 255

Tyr Thr Gly Asn Ala Ser Ala Leu Phe Ile Leu Pro Asp Gln Asp Lys
            260                 265                 270

Met Glu Glu Val Glu Ala Met Leu Leu Pro Glu Thr Leu Lys Arg Trp
        275                 280                 285

Arg Asp Ser Leu Glu Phe Arg Glu Ile Gly Glu Leu Tyr Leu Pro Lys
    290                 295                 300

Phe Ser Ile Ser Arg Asp Tyr Asn Leu Asn Asp Ile Leu Leu Gln Leu
305                 310                 315                 320

Gly Ile Glu Glu Ala Phe Thr Ser Lys Ala Asp Leu Ser Gly Ile Thr
                325                 330                 335

Gly Ala Arg Asn Leu Ala Val Ser Gln Val Val His Lys Ala Val Leu
            340                 345                 350

Asp Val Phe Glu Glu Gly Thr Glu Ala Ser Ala Ala Thr Ala Val Lys
        355                 360                 365
```

```
Ile Thr Gly Arg Gln Thr Asn Val Glu Thr Arg Thr Ile Val Arg Phe
    370                 375                 380

Asn Arg Pro Phe Leu Met Ile Ile Val Pro Thr Asp Thr Gln Asn Ile
385                 390                 395                 400

Phe Phe Met Ser Lys Val Thr Asn Pro Lys Gln Ala
                405                 410

<210> SEQ ID NO 43
<211> LENGTH: 412
<212> TYPE: PRT
<213> ORGANISM: Artificial Sequence
<220> FEATURE:
<223> OTHER INFORMATION: Synthetic

<400> SEQUENCE: 43

Met Arg Gly Ser His His His His His Ser Arg His Pro Asn Ser
1               5                   10                  15

Pro Leu Asp Glu Glu Asn Leu Thr Gln Glu Asn Gln Asp Arg Gly Thr
            20                  25                  30

His Val Asp Leu Gly Leu Ala Ser Ala Asn Val Asp Phe Ala Phe Ser
        35                  40                  45

Leu Tyr Lys Gln Leu Val Leu Lys Ala Pro Asp Lys Asn Val Ile Phe
50                  55                  60

Ser Pro Leu Ser Ile Ser Thr Ala Leu Ala Phe Leu Ser Leu Gly Ala
65                  70                  75                  80

His Asn Thr Thr Leu Thr Glu Ile Leu Lys Gly Leu Lys Phe Asn Leu
                85                  90                  95

Thr Glu Thr Ser Glu Ala Glu Ile His Gln Ser Phe Gln His Leu Leu
            100                 105                 110

Arg Thr Leu Asn Gln Ser Ser Asp Glu Leu Gln Leu Ser Met Gly Asn
        115                 120                 125

Ala Met Phe Val Lys Glu Gln Leu Ser Leu Leu Asp Arg Phe Thr Glu
130                 135                 140

Asp Ala Lys Arg Leu Tyr Gly Ser Glu Ala Phe Ala Thr Asp Phe Gln
145                 150                 155                 160

Asp Ser Ala Ala Ala Lys Lys Leu Ile Asn Asp Tyr Val Lys Asn Gly
                165                 170                 175

Thr Arg Gly Lys Ile Thr Asp Leu Ile Lys Asp Leu Asp Ser Gln Thr
            180                 185                 190

Met Met Val Leu Val Asn Tyr Ile Phe Phe Lys Ala Lys Trp Glu Met
        195                 200                 205

Pro Phe Asp Pro Gln Asp Thr His Gln Ser Arg Phe Tyr Leu Ser Lys
210                 215                 220

Lys Lys Trp Val Met Val Pro Met Met Ser Leu His His Leu Thr Ile
225                 230                 235                 240

Pro Tyr Phe Arg Asp Glu Glu Leu Ser Cys Thr Val Val Glu Leu Lys
                245                 250                 255

Tyr Thr Gly Asn Ala Ser Ala Leu Phe Ile Leu Pro Asp Gln Asp Lys
            260                 265                 270

Met Glu Glu Val Glu Ala Met Leu Leu Pro Thr Leu Lys Arg Trp
        275                 280                 285

Arg Asp Ser Leu Glu Phe Arg Glu Ile Gly Glu Leu Tyr Leu Pro Lys
290                 295                 300

Phe Ser Ile Ser Arg Asp Tyr Asn Leu Asn Asp Ile Leu Leu Gln Leu
305                 310                 315                 320
```

```
Gly Ile Glu Glu Ala Phe Thr Ser Lys Ala Asp Leu Ser Gly Ile Thr
                325                 330                 335

Gly Ala Arg Asn Leu Ala Val Ser Gln Val Val His Lys Ala Val Leu
            340                 345                 350

Asp Val Phe Glu Glu Gly Thr Glu Ala Ser Ala Ala Thr Ala Val Lys
        355                 360                 365

Ile Asn Gln Arg Ser Ser Leu Val Glu Thr Arg Thr Ile Val Arg Phe
370                 375                 380

Asn Arg Pro Phe Leu Met Ile Ile Val Pro Thr Asp Thr Gln Asn Ile
385                 390                 395                 400

Phe Phe Met Ser Lys Val Thr Asn Pro Lys Gln Ala
                405                 410

<210> SEQ ID NO 44
<211> LENGTH: 412
<212> TYPE: PRT
<213> ORGANISM: Artificial Sequence
<220> FEATURE:
<223> OTHER INFORMATION: Synthetic

<400> SEQUENCE: 44

Met Arg Gly Ser His His His His His Ser Arg His Pro Asn Ser
1               5                   10                  15

Pro Leu Asp Glu Glu Asn Leu Thr Gln Glu Asn Gln Asp Arg Gly Thr
            20                  25                  30

His Val Asp Leu Gly Leu Ala Ser Ala Asn Val Asp Phe Ala Phe Ser
        35                  40                  45

Leu Tyr Lys Gln Leu Val Leu Lys Ala Pro Asp Lys Asn Val Ile Phe
50                  55                  60

Ser Pro Leu Ser Ile Ser Thr Ala Leu Ala Phe Leu Ser Leu Gly Ala
65                  70                  75                  80

His Asn Thr Thr Leu Thr Glu Ile Leu Lys Gly Leu Lys Phe Asn Leu
                85                  90                  95

Thr Glu Thr Ser Glu Ala Glu Ile His Gln Ser Phe Gln His Leu Leu
            100                 105                 110

Arg Thr Leu Asn Gln Ser Ser Asp Glu Leu Gln Leu Ser Met Gly Asn
        115                 120                 125

Ala Met Phe Val Lys Glu Gln Leu Ser Leu Leu Asp Arg Phe Thr Glu
130                 135                 140

Asp Ala Lys Arg Leu Tyr Gly Ser Glu Ala Phe Ala Thr Asp Phe Gln
145                 150                 155                 160

Asp Ser Ala Ala Ala Lys Lys Leu Ile Asn Asp Tyr Val Lys Asn Gly
                165                 170                 175

Thr Arg Gly Lys Ile Thr Asp Leu Ile Lys Asp Leu Asp Ser Gln Thr
            180                 185                 190

Met Met Val Leu Val Asn Tyr Ile Phe Phe Lys Ala Lys Trp Glu Met
        195                 200                 205

Pro Phe Asp Pro Gln Asp Thr His Gln Ser Arg Phe Tyr Leu Ser Lys
210                 215                 220

Lys Lys Trp Val Met Val Pro Met Met Ser Leu His His Leu Thr Ile
225                 230                 235                 240

Pro Tyr Phe Arg Asp Glu Glu Leu Ser Cys Thr Val Val Glu Leu Lys
                245                 250                 255

Tyr Thr Gly Asn Ala Ser Ala Leu Phe Ile Leu Pro Asp Gln Asp Lys
            260                 265                 270
```

```
Met Glu Glu Val Glu Ala Met Leu Leu Pro Glu Thr Leu Lys Arg Trp
            275                 280                 285

Arg Asp Ser Leu Glu Phe Arg Glu Ile Gly Leu Tyr Leu Pro Lys
        290                 295                 300

Phe Ser Ile Ser Arg Asp Tyr Asn Leu Asn Asp Ile Leu Leu Gln Leu
305                 310                 315                 320

Gly Ile Glu Glu Ala Phe Thr Ser Lys Ala Asp Leu Ser Gly Ile Thr
                325                 330                 335

Gly Ala Arg Asn Leu Ala Val Ser Gln Val Val His Lys Ala Val Leu
            340                 345                 350

Asp Val Phe Glu Glu Gly Thr Glu Ala Ser Ala Ala Thr Ala Val Lys
        355                 360                 365

Ile Leu Gln Arg Ala Ile Leu Val Glu Thr Arg Thr Ile Val Arg Phe
370                 375                 380

Asn Arg Pro Phe Leu Met Ile Ile Val Pro Thr Asp Thr Gln Asn Ile
385                 390                 395                 400

Phe Phe Met Ser Lys Val Thr Asn Pro Lys Gln Ala
                405                 410

<210> SEQ ID NO 45
<211> LENGTH: 412
<212> TYPE: PRT
<213> ORGANISM: Artificial Sequence
<220> FEATURE:
<223> OTHER INFORMATION: Synthetic

<400> SEQUENCE: 45

Met Arg Gly Ser His His His His His His Ser Arg His Pro Asn Ser
1               5                   10                  15

Pro Leu Asp Glu Glu Asn Leu Thr Gln Glu Asn Gln Asp Arg Gly Thr
            20                  25                  30

His Val Asp Leu Gly Leu Ala Ser Ala Asn Val Asp Phe Ala Phe Ser
        35                  40                  45

Leu Tyr Lys Gln Leu Val Leu Lys Ala Pro Asp Lys Asn Val Ile Phe
50                  55                  60

Ser Pro Leu Ser Ile Ser Thr Ala Leu Ala Phe Leu Ser Leu Gly Ala
65                  70                  75                  80

His Asn Thr Thr Leu Thr Glu Ile Leu Lys Gly Leu Lys Phe Asn Leu
                85                  90                  95

Thr Glu Thr Ser Glu Ala Glu Ile His Gln Ser Phe Gln His Leu Leu
            100                 105                 110

Arg Thr Leu Asn Gln Ser Ser Asp Glu Leu Gln Leu Ser Met Gly Asn
        115                 120                 125

Ala Met Phe Val Lys Glu Gln Leu Ser Leu Leu Asp Arg Phe Thr Glu
130                 135                 140

Asp Ala Lys Arg Leu Tyr Gly Ser Glu Ala Phe Ala Thr Asp Phe Gln
145                 150                 155                 160

Asp Ser Ala Ala Ala Lys Lys Leu Ile Asn Asp Tyr Val Lys Asn Gly
                165                 170                 175

Thr Arg Gly Lys Ile Thr Asp Leu Ile Lys Asp Leu Asp Ser Gln Thr
            180                 185                 190

Met Met Val Leu Val Asn Tyr Ile Phe Phe Lys Ala Lys Trp Glu Met
        195                 200                 205

Pro Phe Asp Pro Gln Asp Thr His Gln Ser Arg Phe Tyr Leu Ser Lys
210                 215                 220
```

```
Lys Lys Trp Val Met Val Pro Met Met Ser Leu His His Leu Thr Ile
225                 230                 235                 240

Pro Tyr Phe Arg Asp Glu Glu Leu Ser Cys Thr Val Val Glu Leu Lys
            245                 250                 255

Tyr Thr Gly Asn Ala Ser Ala Leu Phe Ile Leu Pro Asp Gln Asp Lys
        260                 265                 270

Met Glu Glu Val Glu Ala Met Leu Leu Pro Glu Thr Leu Lys Arg Trp
    275                 280                 285

Arg Asp Ser Leu Glu Phe Arg Glu Ile Gly Glu Leu Tyr Leu Pro Lys
        290                 295                 300

Phe Ser Ile Ser Arg Asp Tyr Asn Leu Asn Asp Ile Leu Leu Gln Leu
305                 310                 315                 320

Gly Ile Glu Glu Ala Phe Thr Ser Lys Ala Asp Leu Ser Gly Ile Thr
                325                 330                 335

Gly Ala Arg Asn Leu Ala Val Ser Gln Val Val His Lys Ala Val Leu
            340                 345                 350

Asp Val Phe Glu Glu Gly Thr Glu Ala Ser Ala Ala Thr Ala Val Lys
        355                 360                 365

Gln Arg Leu Arg Asp Ala Leu Val Glu Thr Arg Thr Ile Val Arg Phe
    370                 375                 380

Asn Arg Pro Phe Leu Met Ile Ile Val Pro Thr Asp Thr Gln Asn Ile
385                 390                 395                 400

Phe Phe Met Ser Lys Val Thr Asn Pro Lys Gln Ala
                405                 410

<210> SEQ ID NO 46
<211> LENGTH: 412
<212> TYPE: PRT
<213> ORGANISM: Artificial Sequence
<220> FEATURE:
<223> OTHER INFORMATION: Synthetic

<400> SEQUENCE: 46

Met Arg Gly Ser His His His His His His Ser Arg His Pro Asn Ser
1               5                   10                  15

Pro Leu Asp Glu Glu Asn Leu Thr Gln Glu Asn Gln Asp Arg Gly Thr
            20                  25                  30

His Val Asp Leu Gly Leu Ala Ser Ala Asn Val Asp Phe Ala Phe Ser
        35                  40                  45

Leu Tyr Lys Gln Leu Val Leu Lys Ala Pro Asp Lys Asn Val Ile Phe
    50                  55                  60

Ser Pro Leu Ser Ile Ser Thr Ala Leu Ala Phe Leu Ser Leu Gly Ala
65                  70                  75                  80

His Asn Thr Thr Leu Thr Glu Ile Leu Lys Gly Leu Lys Phe Asn Leu
                85                  90                  95

Thr Glu Thr Ser Glu Ala Glu Ile His Gln Ser Phe Gln His Leu Leu
            100                 105                 110

Arg Thr Leu Asn Gln Ser Ser Asp Glu Leu Gln Leu Ser Met Gly Asn
        115                 120                 125

Ala Met Phe Val Lys Glu Gln Leu Ser Leu Leu Asp Arg Phe Thr Glu
    130                 135                 140

Asp Ala Lys Arg Leu Tyr Gly Ser Glu Ala Phe Ala Thr Asp Phe Gln
145                 150                 155                 160

Asp Ser Ala Ala Ala Lys Lys Leu Ile Asn Asp Tyr Val Lys Asn Gly
                165                 170                 175
```

```
Thr Arg Gly Lys Ile Thr Asp Leu Ile Lys Asp Leu Asp Ser Gln Thr
            180                 185                 190

Met Met Val Leu Val Asn Tyr Ile Phe Phe Lys Ala Lys Trp Glu Met
            195                 200                 205

Pro Phe Asp Pro Gln Asp Thr His Gln Ser Arg Phe Tyr Leu Ser Lys
            210                 215                 220

Lys Lys Trp Val Met Val Pro Met Met Ser Leu His Leu Thr Ile
225                 230                 235                 240

Pro Tyr Phe Arg Asp Glu Glu Leu Ser Cys Thr Val Val Glu Leu Lys
            245                 250                 255

Tyr Thr Gly Asn Ala Ser Ala Leu Phe Ile Leu Pro Asp Gln Asp Lys
            260                 265                 270

Met Glu Glu Val Glu Ala Met Leu Leu Pro Glu Thr Leu Lys Arg Trp
            275                 280                 285

Arg Asp Ser Leu Glu Phe Arg Glu Ile Gly Glu Leu Tyr Leu Pro Lys
            290                 295                 300

Phe Ser Ile Ser Arg Asp Tyr Asn Leu Asn Asp Ile Leu Leu Gln Leu
305                 310                 315                 320

Gly Ile Glu Glu Ala Phe Thr Ser Lys Ala Asp Leu Ser Gly Ile Thr
            325                 330                 335

Gly Ala Arg Asn Leu Ala Val Ser Gln Val Val His Lys Ala Val Leu
            340                 345                 350

Asp Val Phe Glu Glu Gly Thr Glu Ala Ser Ala Ala Thr Ala Val Lys
            355                 360                 365

Ile Pro Asp Arg His Met Leu Val Glu Thr Arg Thr Ile Val Arg Phe
            370                 375                 380

Asn Arg Pro Phe Leu Met Ile Ile Val Pro Thr Asp Thr Gln Asn Ile
385                 390                 395                 400

Phe Phe Met Ser Lys Val Thr Asn Pro Lys Gln Ala
                    405                 410

<210> SEQ ID NO 47
<211> LENGTH: 412
<212> TYPE: PRT
<213> ORGANISM: Artificial Sequence
<220> FEATURE:
<223> OTHER INFORMATION: Synthetic

<400> SEQUENCE: 47

Met Arg Gly Ser His His His His His His Ser Arg His Pro Asn Ser
1               5                   10                  15

Pro Leu Asp Glu Glu Asn Leu Thr Gln Glu Asn Gln Asp Arg Gly Thr
                20                  25                  30

His Val Asp Leu Gly Leu Ala Ser Ala Asn Val Asp Phe Ala Phe Ser
            35                  40                  45

Leu Tyr Lys Gln Leu Val Leu Lys Ala Pro Asp Lys Asn Val Ile Phe
        50                  55                  60

Ser Pro Leu Ser Ile Ser Thr Ala Leu Ala Phe Leu Ser Leu Gly Ala
65                  70                  75                  80

His Asn Thr Thr Leu Thr Glu Ile Leu Lys Gly Leu Lys Phe Asn Leu
                85                  90                  95

Thr Glu Thr Ser Glu Ala Glu Ile His Gln Ser Phe Gln His Leu Leu
            100                 105                 110

Arg Thr Leu Asn Gln Ser Ser Asp Glu Leu Gln Leu Ser Met Gly Asn
        115                 120                 125
```

Ala Met Phe Val Lys Glu Gln Leu Ser Leu Leu Asp Arg Phe Thr Glu
130                 135                 140

Asp Ala Lys Arg Leu Tyr Gly Ser Glu Ala Phe Ala Thr Asp Phe Gln
145                 150                 155                 160

Asp Ser Ala Ala Lys Lys Leu Ile Asn Asp Tyr Val Lys Asn Gly
165                 170                 175

Thr Arg Gly Lys Ile Thr Asp Leu Ile Lys Asp Leu Asp Ser Gln Thr
180                 185                 190

Met Met Val Leu Val Asn Tyr Ile Phe Phe Lys Ala Lys Trp Glu Met
195                 200                 205

Pro Phe Asp Pro Gln Asp Thr His Gln Ser Arg Phe Tyr Leu Ser Lys
210                 215                 220

Lys Lys Trp Val Met Val Pro Met Met Ser Leu His Leu Thr Ile
225                 230                 235                 240

Pro Tyr Phe Arg Asp Glu Glu Leu Ser Cys Thr Val Val Glu Leu Lys
245                 250                 255

Tyr Thr Gly Asn Ala Ser Ala Leu Phe Ile Leu Pro Asp Gln Asp Lys
260                 265                 270

Met Glu Glu Val Glu Ala Met Leu Leu Pro Glu Thr Leu Lys Arg Trp
275                 280                 285

Arg Asp Ser Leu Glu Phe Arg Glu Ile Gly Glu Leu Tyr Leu Pro Lys
290                 295                 300

Phe Ser Ile Ser Arg Asp Tyr Asn Leu Asn Asp Ile Leu Leu Gln Leu
305                 310                 315                 320

Gly Ile Glu Glu Ala Phe Thr Ser Lys Ala Asp Leu Ser Gly Ile Thr
325                 330                 335

Gly Ala Arg Asn Leu Ala Val Ser Gln Val Val His Lys Ala Val Leu
340                 345                 350

Asp Val Phe Glu Glu Gly Thr Glu Ala Ser Ala Ala Thr Ala Val Lys
355                 360                 365

Thr Val Asp Tyr Ala Ala Leu Val Glu Thr Arg Thr Ile Val Arg Phe
370                 375                 380

Asn Arg Pro Phe Leu Met Ile Ile Val Pro Thr Asp Thr Gln Asn Ile
385                 390                 395                 400

Phe Phe Met Ser Lys Val Thr Asn Pro Lys Gln Ala
            405                 410

<210> SEQ ID NO 48
<211> LENGTH: 406
<212> TYPE: PRT
<213> ORGANISM: Artificial Sequence
<220> FEATURE:
<223> OTHER INFORMATION: Synthetic

<400> SEQUENCE: 48

Met Arg Gly Ser His His His His His His Gly Ser Asp Asp Pro Gln
1               5                   10                  15

Gly Asp Ala Ala Gln Lys Thr Asp Thr Ser His His Asp Gln Asp His
                20                  25                  30

Pro Thr Phe Asn Lys Ile Thr Pro Asn Leu Ala Glu Phe Ala Phe Ser
            35                  40                  45

Leu Tyr Arg Gln Leu Ala His Gln Ser Asn Ser Thr Asn Ile Phe Phe
        50                  55                  60

Ser Pro Val Ser Ile Ala Thr Ala Phe Ala Met Leu Ser Leu Gly Thr
65                  70                  75                  80

```
Lys Ala Asp Thr His Asp Glu Ile Leu Glu Gly Leu Asn Phe Asn Leu
                85                  90                  95

Thr Glu Ile Pro Glu Ala Gln Ile His Glu Gly Phe Gln Glu Leu Leu
            100                 105                 110

Arg Thr Leu Asn Gln Pro Asp Ser Gln Leu Gln Leu Thr Thr Gly Asn
        115                 120                 125

Gly Leu Phe Leu Ser Glu Gly Leu Lys Leu Val Asp Lys Phe Leu Glu
    130                 135                 140

Asp Val Lys Lys Leu Tyr His Ser Glu Ala Phe Thr Val Asn Phe Gly
145                 150                 155                 160

Asp Thr Glu Glu Ala Lys Lys Gln Ile Asn Asp Tyr Val Glu Lys Gly
                165                 170                 175

Thr Gln Gly Lys Ile Val Asp Leu Val Lys Glu Leu Asp Arg Asp Thr
            180                 185                 190

Val Phe Ala Leu Val Asn Tyr Ile Phe Phe Lys Gly Lys Trp Glu Arg
        195                 200                 205

Pro Phe Glu Val Lys Asp Thr Glu Glu Glu Asp Phe His Val Asp Gln
    210                 215                 220

Ala Thr Thr Val Lys Val Pro Met Met Lys Arg Leu Gly Met Phe Asn
225                 230                 235                 240

Ile Gln His Cys Lys Lys Leu Ser Ser Trp Val Leu Leu Met Lys Tyr
                245                 250                 255

Leu Gly Asn Ala Thr Ala Ile Phe Phe Leu Pro Asp Glu Gly Lys Leu
            260                 265                 270

Gln His Leu Glu Asn Glu Leu Thr His Asp Ile Ile Thr Lys Phe Leu
        275                 280                 285

Glu Asn Glu Asp Arg Arg Ser Ala Ser Leu His Leu Pro Lys Leu Ser
    290                 295                 300

Ile Thr Gly Thr Tyr Asp Leu Lys Ser Val Leu Gly Gln Leu Gly Ile
305                 310                 315                 320

Thr Lys Val Phe Ser Asn Gly Ala Asp Leu Ser Gly Val Thr Glu Glu
                325                 330                 335

Ala Pro Leu Lys Leu Ser Lys Ala Val His Lys Ala Val Leu Thr Ile
            340                 345                 350

Asp Glu Lys Gly Thr Glu Ala Ala Gly Ala Met Phe Leu Glu Ala Ile
        355                 360                 365

Pro Met Ser Ile Pro Pro Glu Val Lys Phe Asn Lys Pro Phe Val Phe
    370                 375                 380

Leu Met Ile Glu Gln Asn Thr Lys Ser Pro Leu Phe Met Gly Lys Val
385                 390                 395                 400

Val Asn Pro Thr Gln Lys
                405

<210> SEQ ID NO 49
<211> LENGTH: 406
<212> TYPE: PRT
<213> ORGANISM: Artificial Sequence
<220> FEATURE:
<223> OTHER INFORMATION: Synthetic

<400> SEQUENCE: 49

Met Arg Gly Ser His His His His His His Gly Ser Asp Asp Pro Gln
1               5                   10                  15

Gly Asp Ala Ala Gln Lys Thr Asp Thr Ser His His Asp Gln Asp His
            20                  25                  30
```

Pro Thr Phe Asn Lys Ile Thr Pro Asn Leu Ala Glu Phe Ala Phe Ser
            35                  40                  45

Leu Tyr Arg Gln Leu Ala His Gln Ser Asn Ser Thr Asn Ile Phe Phe
 50                  55                  60

Ser Pro Val Ser Ile Ala Thr Ala Phe Ala Met Leu Ser Leu Gly Thr
 65                  70                  75                  80

Lys Ala Asp Thr His Asp Glu Ile Leu Glu Gly Leu Asn Phe Asn Leu
                85                  90                  95

Thr Glu Ile Pro Glu Ala Gln Ile His Glu Gly Phe Gln Glu Leu Leu
            100                 105                 110

Arg Thr Leu Asn Gln Pro Asp Ser Gln Leu Gln Leu Thr Thr Gly Asn
        115                 120                 125

Gly Leu Phe Leu Ser Glu Gly Leu Lys Leu Val Asp Lys Phe Leu Glu
130                 135                 140

Asp Val Lys Lys Leu Tyr His Ser Glu Ala Phe Thr Val Asn Phe Gly
145                 150                 155                 160

Asp Thr Glu Glu Ala Lys Lys Gln Ile Asn Asp Tyr Val Glu Lys Gly
                165                 170                 175

Thr Gln Gly Lys Ile Val Asp Leu Val Lys Glu Leu Asp Arg Asp Thr
            180                 185                 190

Val Phe Ala Leu Val Asn Tyr Ile Phe Phe Lys Gly Lys Trp Glu Arg
        195                 200                 205

Pro Phe Glu Val Lys Asp Thr Glu Glu Glu Asp Phe His Val Asp Gln
210                 215                 220

Ala Thr Thr Val Lys Val Pro Met Met Lys Arg Leu Gly Met Phe Asn
225                 230                 235                 240

Ile Gln His Cys Lys Lys Leu Ser Ser Trp Val Leu Leu Met Lys Tyr
                245                 250                 255

Leu Gly Asn Ala Thr Ala Ile Phe Phe Leu Pro Asp Glu Gly Lys Leu
            260                 265                 270

Gln His Leu Glu Asn Glu Leu Thr His Asp Ile Ile Thr Lys Phe Leu
        275                 280                 285

Glu Asn Glu Asp Arg Arg Ser Ala Ser Leu His Leu Pro Lys Leu Ser
290                 295                 300

Ile Thr Gly Thr Tyr Asp Leu Lys Ser Val Leu Gly Gln Leu Gly Ile
305                 310                 315                 320

Thr Lys Val Phe Ser Asn Gly Ala Asp Leu Ser Gly Val Thr Glu Glu
                325                 330                 335

Ala Pro Leu Lys Leu Ser Lys Ala Val His Lys Ala Val Leu Thr Ile
            340                 345                 350

Asp Glu Lys Gly Thr Glu Ala Ala Gly Ala Met Phe Leu Glu Gly Ser
        355                 360                 365

Leu Arg Ser Ile Pro Pro Glu Val Lys Phe Asn Lys Pro Phe Val Phe
370                 375                 380

Leu Met Ile Glu Gln Asn Thr Lys Ser Pro Leu Phe Met Gly Lys Val
385                 390                 395                 400

Val Asn Pro Thr Gln Lys
                405

<210> SEQ ID NO 50
<211> LENGTH: 406
<212> TYPE: PRT
<213> ORGANISM: Artificial Sequence
<220> FEATURE:
<223> OTHER INFORMATION: Synthetic

```
<400> SEQUENCE: 50

Met Arg Gly Ser His His His His His His Gly Ser Asp Asp Pro Gln
1               5                   10                  15

Gly Asp Ala Ala Gln Lys Thr Asp Thr Ser His His Asp Gln Asp His
            20                  25                  30

Pro Thr Phe Asn Lys Ile Thr Pro Asn Leu Ala Glu Phe Ala Phe Ser
        35                  40                  45

Leu Tyr Arg Gln Leu Ala His Gln Ser Asn Ser Thr Asn Ile Phe Phe
50                  55                  60

Ser Pro Val Ser Ile Ala Thr Ala Phe Ala Met Leu Ser Leu Gly Thr
65                  70                  75                  80

Lys Ala Asp Thr His Asp Glu Ile Leu Glu Gly Leu Asn Phe Asn Leu
                85                  90                  95

Thr Glu Ile Pro Glu Ala Gln Ile His Glu Gly Phe Gln Glu Leu Leu
            100                 105                 110

Arg Thr Leu Asn Gln Pro Asp Ser Gln Leu Gln Leu Thr Thr Gly Asn
        115                 120                 125

Gly Leu Phe Leu Ser Glu Gly Leu Lys Leu Val Asp Lys Phe Leu Glu
130                 135                 140

Asp Val Lys Lys Leu Tyr His Ser Glu Ala Phe Thr Val Asn Phe Gly
145                 150                 155                 160

Asp Thr Glu Glu Ala Lys Lys Gln Ile Asn Asp Tyr Val Glu Lys Gly
                165                 170                 175

Thr Gln Gly Lys Ile Val Asp Leu Val Lys Glu Leu Asp Arg Asp Thr
            180                 185                 190

Val Phe Ala Leu Val Asn Tyr Ile Phe Phe Lys Gly Lys Trp Glu Arg
        195                 200                 205

Pro Phe Glu Val Lys Asp Thr Glu Glu Asp Phe His Val Asp Gln
210                 215                 220

Ala Thr Thr Val Lys Val Pro Met Met Lys Arg Leu Gly Met Phe Asn
225                 230                 235                 240

Ile Gln His Cys Lys Lys Leu Ser Ser Trp Val Leu Leu Met Lys Tyr
                245                 250                 255

Leu Gly Asn Ala Thr Ala Ile Phe Phe Leu Pro Asp Glu Gly Lys Leu
            260                 265                 270

Gln His Leu Glu Asn Glu Leu Thr His Asp Ile Ile Thr Lys Phe Leu
        275                 280                 285

Glu Asn Glu Asp Arg Arg Ser Ala Ser Leu His Leu Pro Lys Leu Ser
290                 295                 300

Ile Thr Gly Thr Tyr Asp Leu Lys Ser Val Leu Gly Gln Leu Gly Ile
305                 310                 315                 320

Thr Lys Val Phe Ser Asn Gly Ala Asp Leu Ser Gly Val Thr Glu Glu
                325                 330                 335

Ala Pro Leu Lys Leu Ser Lys Ala Val His Lys Ala Val Leu Thr Ile
            340                 345                 350

Asp Glu Lys Gly Thr Glu Ala Ala Gly Ala Met Phe Leu Glu Gly Ser
        355                 360                 365

Leu Arg Gly Ile Pro Pro Glu Val Lys Phe Asn Lys Pro Phe Val Phe
370                 375                 380

Leu Met Ile Glu Gln Asn Thr Lys Ser Pro Leu Phe Met Gly Lys Val
385                 390                 395                 400

Val Asn Pro Thr Gln Lys
                405
```

-continued

```
<210> SEQ ID NO 51
<211> LENGTH: 406
<212> TYPE: PRT
<213> ORGANISM: Artificial Sequence
<220> FEATURE:
<223> OTHER INFORMATION: Synthetic

<400> SEQUENCE: 51
```

Met Arg Gly Ser His His His His His Gly Ser Asp Asp Pro Gln
1               5                   10                  15

Gly Asp Ala Ala Gln Lys Thr Asp Thr Ser His His Asp Gln Asp His
            20                  25                  30

Pro Thr Phe Asn Lys Ile Thr Pro Asn Leu Ala Glu Phe Ala Phe Ser
        35                  40                  45

Leu Tyr Arg Gln Leu Ala His Gln Ser Asn Ser Thr Asn Ile Phe Phe
50                  55                  60

Ser Pro Val Ser Ile Ala Thr Ala Phe Ala Met Leu Ser Leu Gly Thr
65                  70                  75                  80

Lys Ala Asp Thr His Asp Glu Ile Leu Glu Gly Leu Asn Phe Asn Leu
                85                  90                  95

Thr Glu Ile Pro Glu Ala Gln Ile His Glu Gly Phe Gln Glu Leu Leu
            100                 105                 110

Arg Thr Leu Asn Gln Pro Asp Ser Gln Leu Gln Leu Thr Thr Gly Asn
        115                 120                 125

Gly Leu Phe Leu Ser Glu Gly Leu Lys Leu Val Asp Lys Phe Leu Glu
130                 135                 140

Asp Val Lys Lys Leu Tyr His Ser Glu Ala Phe Thr Val Asn Phe Gly
145                 150                 155                 160

Asp Thr Glu Glu Ala Lys Lys Gln Ile Asn Asp Tyr Val Glu Lys Gly
                165                 170                 175

Thr Gln Gly Lys Ile Val Asp Leu Val Lys Glu Leu Asp Arg Asp Thr
            180                 185                 190

Val Phe Ala Leu Val Asn Tyr Ile Phe Phe Lys Gly Lys Trp Glu Arg
        195                 200                 205

Pro Phe Glu Val Lys Asp Thr Glu Glu Glu Asp Phe His Val Asp Gln
210                 215                 220

Ala Thr Thr Val Lys Val Pro Met Met Lys Arg Leu Gly Met Phe Asn
225                 230                 235                 240

Ile Gln His Cys Lys Lys Leu Ser Ser Trp Val Leu Leu Met Lys Tyr
                245                 250                 255

Leu Gly Asn Ala Thr Ala Ile Phe Phe Leu Pro Asp Glu Gly Lys Leu
            260                 265                 270

Gln His Leu Glu Asn Glu Leu Thr His Asp Ile Ile Thr Lys Phe Leu
        275                 280                 285

Glu Asn Glu Asp Arg Arg Ser Ala Ser Leu His Leu Pro Lys Leu Ser
290                 295                 300

Ile Thr Gly Thr Tyr Asp Leu Lys Ser Val Leu Gly Gln Leu Gly Ile
305                 310                 315                 320

Thr Lys Val Phe Ser Asn Gly Ala Asp Leu Ser Gly Val Thr Glu Glu
                325                 330                 335

Ala Pro Leu Lys Leu Ser Lys Ala Val His Lys Ala Val Leu Thr Ile
            340                 345                 350

Asp Glu Lys Gly Thr Glu Ala Ala Gly Ala Met Phe Leu Glu Ala Ile
        355                 360                 365

```
Pro Arg Gln Thr Asn Pro Glu Val Lys Phe Asn Lys Pro Phe Val Phe
    370                 375                 380

Leu Met Ile Glu Gln Asn Thr Lys Ser Pro Leu Phe Met Gly Lys Val
385                 390                 395                 400

Val Asn Pro Thr Gln Lys
                405

<210> SEQ ID NO 52
<211> LENGTH: 406
<212> TYPE: PRT
<213> ORGANISM: Artificial Sequence
<220> FEATURE:
<223> OTHER INFORMATION: Synthetic

<400> SEQUENCE: 52

Met Arg Gly Ser His His His His His His Gly Ser Asp Asp Pro Gln
1               5                   10                  15

Gly Asp Ala Ala Gln Lys Thr Asp Thr Ser His His Asp Gln Asp His
                20                  25                  30

Pro Thr Phe Asn Lys Ile Thr Pro Asn Leu Ala Glu Phe Ala Phe Ser
            35                  40                  45

Leu Tyr Arg Gln Leu Ala His Gln Ser Asn Ser Thr Asn Ile Phe Phe
50                  55                  60

Ser Pro Val Ser Ile Ala Thr Ala Phe Ala Met Leu Ser Leu Gly Thr
65                  70                  75                  80

Lys Ala Asp Thr His Asp Glu Ile Leu Glu Gly Leu Asn Phe Asn Leu
                85                  90                  95

Thr Glu Ile Pro Glu Ala Gln Ile His Glu Gly Phe Gln Glu Leu Leu
            100                 105                 110

Arg Thr Leu Asn Gln Pro Asp Ser Gln Leu Gln Leu Thr Thr Gly Asn
        115                 120                 125

Gly Leu Phe Leu Ser Glu Gly Leu Lys Leu Val Asp Lys Phe Leu Glu
130                 135                 140

Asp Val Lys Lys Leu Tyr His Ser Glu Ala Phe Thr Val Asn Phe Gly
145                 150                 155                 160

Asp Thr Glu Glu Ala Lys Lys Gln Ile Asn Asp Tyr Val Glu Lys Gly
                165                 170                 175

Thr Gln Gly Lys Ile Val Asp Leu Val Lys Glu Leu Asp Arg Asp Thr
            180                 185                 190

Val Phe Ala Leu Val Asn Tyr Ile Phe Phe Lys Gly Lys Trp Glu Arg
        195                 200                 205

Pro Phe Glu Val Lys Asp Thr Glu Glu Glu Asp Phe His Val Asp Gln
210                 215                 220

Ala Thr Thr Val Lys Val Pro Met Met Lys Arg Leu Gly Met Phe Asn
225                 230                 235                 240

Ile Gln His Cys Lys Lys Leu Ser Ser Trp Val Leu Leu Met Lys Tyr
                245                 250                 255

Leu Gly Asn Ala Thr Ala Ile Phe Phe Leu Pro Asp Glu Gly Lys Leu
            260                 265                 270

Gln His Leu Glu Asn Glu Leu Thr His Asp Ile Ile Thr Lys Phe Leu
        275                 280                 285

Glu Asn Glu Asp Arg Arg Ser Ala Ser Leu His Leu Pro Lys Leu Ser
290                 295                 300

Ile Thr Gly Thr Tyr Asp Leu Lys Ser Val Leu Gly Gln Leu Gly Ile
305                 310                 315                 320
```

```
Thr Lys Val Phe Ser Asn Gly Ala Asp Leu Ser Gly Val Thr Glu Glu
                325                 330                 335

Ala Pro Leu Lys Leu Ser Lys Ala Val His Lys Ala Val Leu Thr Ile
            340                 345                 350

Asp Glu Lys Gly Thr Glu Ala Ala Gly Ala Met Phe Leu Glu Ala Ile
        355                 360                 365

Gly Arg Gln Thr Asn Pro Val Lys Phe Asn Lys Pro Phe Val Phe
370                 375                 380

Leu Met Ile Glu Gln Asn Thr Lys Ser Pro Leu Phe Met Gly Lys Val
385                 390                 395                 400

Val Asn Pro Thr Gln Lys
                405

<210> SEQ ID NO 53
<211> LENGTH: 406
<212> TYPE: PRT
<213> ORGANISM: Artificial Sequence
<220> FEATURE:
<223> OTHER INFORMATION: Synthetic

<400> SEQUENCE: 53

Met Arg Gly Ser His His His His His His Gly Ser Asp Asp Pro Gln
1               5                   10                  15

Gly Asp Ala Ala Gln Lys Thr Asp Thr Ser His His Asp Gln Asp His
            20                  25                  30

Pro Thr Phe Asn Lys Ile Thr Pro Asn Leu Ala Glu Phe Ala Phe Ser
        35                  40                  45

Leu Tyr Arg Gln Leu Ala His Gln Ser Asn Ser Thr Asn Ile Phe Phe
    50                  55                  60

Ser Pro Val Ser Ile Ala Thr Ala Phe Ala Met Leu Ser Leu Gly Thr
65                  70                  75                  80

Lys Ala Asp Thr His Asp Glu Ile Leu Glu Gly Leu Asn Phe Asn Leu
                85                  90                  95

Thr Glu Ile Pro Glu Ala Gln Ile His Glu Gly Phe Gln Glu Leu Leu
            100                 105                 110

Arg Thr Leu Asn Gln Pro Asp Ser Gln Leu Gln Leu Thr Thr Gly Asn
        115                 120                 125

Gly Leu Phe Leu Ser Glu Gly Leu Lys Leu Val Asp Lys Phe Leu Glu
    130                 135                 140

Asp Val Lys Lys Leu Tyr His Ser Glu Ala Phe Thr Val Asn Phe Gly
145                 150                 155                 160

Asp Thr Glu Glu Ala Lys Lys Gln Ile Asn Asp Tyr Val Glu Lys Gly
                165                 170                 175

Thr Gln Gly Lys Ile Val Asp Leu Val Lys Glu Leu Asp Arg Asp Thr
            180                 185                 190

Val Phe Ala Leu Val Asn Tyr Ile Phe Phe Lys Gly Lys Trp Glu Arg
        195                 200                 205

Pro Phe Glu Val Lys Asp Thr Glu Glu Glu Asp Phe His Val Asp Gln
    210                 215                 220

Ala Thr Thr Val Lys Val Pro Met Met Lys Arg Leu Gly Met Phe Asn
225                 230                 235                 240

Ile Gln His Cys Lys Lys Leu Ser Ser Trp Val Leu Leu Met Lys Tyr
                245                 250                 255

Leu Gly Asn Ala Thr Ala Ile Phe Phe Leu Pro Asp Glu Gly Lys Leu
            260                 265                 270
```

Gln His Leu Glu Asn Glu Leu Thr His Asp Ile Ile Thr Lys Phe Leu
        275                 280                 285

Glu Asn Glu Asp Arg Arg Ser Ala Ser Leu His Leu Pro Lys Leu Ser
290                 295                 300

Ile Thr Gly Thr Tyr Asp Leu Lys Ser Val Leu Gly Gln Leu Gly Ile
305                 310                 315                 320

Thr Lys Val Phe Ser Asn Gly Ala Asp Leu Ser Gly Val Thr Glu Glu
                325                 330                 335

Ala Pro Leu Lys Leu Ser Lys Ala Val His Lys Ala Val Leu Thr Ile
            340                 345                 350

Asp Glu Lys Gly Thr Glu Ala Ala Gly Ala Met Phe Leu Glu Ala Asn
        355                 360                 365

Gln Arg Ser Ser Pro Pro Glu Val Lys Phe Asn Lys Pro Phe Val Phe
370                 375                 380

Leu Met Ile Glu Gln Asn Thr Lys Ser Pro Leu Phe Met Gly Lys Val
385                 390                 395                 400

Val Asn Pro Thr Gln Lys
                405

<210> SEQ ID NO 54
<211> LENGTH: 406
<212> TYPE: PRT
<213> ORGANISM: Artificial Sequence
<220> FEATURE:
<223> OTHER INFORMATION: Synthetic

<400> SEQUENCE: 54

Met Arg Gly Ser His His His His His His Gly Ser Asp Asp Pro Gln
1               5                   10                  15

Gly Asp Ala Ala Gln Lys Thr Asp Thr Ser His His Asp Gln Asp His
            20                  25                  30

Pro Thr Phe Asn Lys Ile Thr Pro Asn Leu Ala Glu Phe Ala Phe Ser
        35                  40                  45

Leu Tyr Arg Gln Leu Ala His Gln Ser Asn Ser Thr Asn Ile Phe Phe
    50                  55                  60

Ser Pro Val Ser Ile Ala Thr Ala Phe Ala Met Leu Ser Leu Gly Thr
65                  70                  75                  80

Lys Ala Asp Thr His Asp Glu Ile Leu Glu Gly Leu Asn Phe Asn Leu
                85                  90                  95

Thr Glu Ile Pro Glu Ala Gln Ile His Glu Gly Phe Gln Glu Leu Leu
            100                 105                 110

Arg Thr Leu Asn Gln Pro Asp Ser Gln Leu Gln Leu Thr Thr Gly Asn
        115                 120                 125

Gly Leu Phe Leu Ser Glu Gly Leu Lys Leu Val Asp Lys Phe Leu Glu
    130                 135                 140

Asp Val Lys Lys Leu Tyr His Ser Glu Ala Phe Thr Val Asn Phe Gly
145                 150                 155                 160

Asp Thr Glu Glu Ala Lys Lys Gln Ile Asn Asp Tyr Val Glu Lys Gly
                165                 170                 175

Thr Gln Gly Lys Ile Val Asp Leu Val Lys Glu Leu Asp Arg Asp Thr
            180                 185                 190

Val Phe Ala Leu Val Asn Tyr Ile Phe Phe Lys Gly Lys Trp Glu Arg
        195                 200                 205

Pro Phe Glu Val Lys Asp Thr Glu Glu Glu Asp Phe His Val Asp Gln
    210                 215                 220

```
Ala Thr Thr Val Lys Val Pro Met Met Lys Arg Leu Gly Met Phe Asn
225                 230                 235                 240

Ile Gln His Cys Lys Lys Leu Ser Ser Trp Val Leu Leu Met Lys Tyr
            245                 250                 255

Leu Gly Asn Ala Thr Ala Ile Phe Phe Leu Pro Asp Glu Gly Lys Leu
        260                 265                 270

Gln His Leu Glu Asn Glu Leu Thr His Asp Ile Ile Thr Lys Phe Leu
    275                 280                 285

Glu Asn Glu Asp Arg Arg Ser Ala Ser Leu His Leu Pro Lys Leu Ser
290                 295                 300

Ile Thr Gly Thr Tyr Asp Leu Lys Ser Val Leu Gly Gln Leu Gly Ile
305                 310                 315                 320

Thr Lys Val Phe Ser Asn Gly Ala Asp Leu Ser Gly Val Thr Glu Glu
                325                 330                 335

Ala Pro Leu Lys Leu Ser Lys Ala Val His Lys Ala Val Leu Thr Ile
                340                 345                 350

Asp Glu Lys Gly Thr Glu Ala Ala Gly Ala Met Phe Leu Glu Ala Leu
            355                 360                 365

Gln Arg Ala Ile Pro Pro Glu Val Lys Phe Asn Lys Pro Phe Val Phe
    370                 375                 380

Leu Met Ile Glu Gln Asn Thr Lys Ser Pro Leu Phe Met Gly Lys Val
385                 390                 395                 400

Val Asn Pro Thr Gln Lys
                405

<210> SEQ ID NO 55
<211> LENGTH: 406
<212> TYPE: PRT
<213> ORGANISM: Artificial Sequence
<220> FEATURE:
<223> OTHER INFORMATION: Synthetic

<400> SEQUENCE: 55

Met Arg Gly Ser His His His His His His Gly Ser Asp Asp Pro Gln
1               5                   10                  15

Gly Asp Ala Ala Gln Lys Thr Asp Thr Ser His His Asp Gln Asp His
            20                  25                  30

Pro Thr Phe Asn Lys Ile Thr Pro Asn Leu Ala Glu Phe Ala Phe Ser
        35                  40                  45

Leu Tyr Arg Gln Leu Ala His Gln Ser Asn Ser Thr Asn Ile Phe Phe
    50                  55                  60

Ser Pro Val Ser Ile Ala Thr Ala Phe Ala Met Leu Ser Leu Gly Thr
65                  70                  75                  80

Lys Ala Asp Thr His Asp Glu Ile Leu Glu Gly Leu Asn Phe Asn Leu
                85                  90                  95

Thr Glu Ile Pro Glu Ala Gln Ile His Glu Gly Phe Gln Glu Leu Leu
            100                 105                 110

Arg Thr Leu Asn Gln Pro Asp Ser Gln Leu Gln Leu Thr Thr Gly Asn
    115                 120                 125

Gly Leu Phe Leu Ser Glu Gly Leu Lys Leu Val Asp Lys Phe Leu Glu
130                 135                 140

Asp Val Lys Lys Leu Tyr His Ser Glu Ala Phe Thr Val Asn Phe Gly
145                 150                 155                 160

Asp Thr Glu Glu Ala Lys Lys Gln Ile Asn Asp Tyr Val Glu Lys Gly
                165                 170                 175
```

```
Thr Gln Gly Lys Ile Val Asp Leu Val Lys Glu Leu Asp Arg Asp Thr
                180                 185                 190
Val Phe Ala Leu Val Asn Tyr Ile Phe Phe Lys Gly Lys Trp Glu Arg
            195                 200                 205
Pro Phe Glu Val Lys Asp Thr Glu Glu Glu Asp Phe His Val Asp Gln
        210                 215                 220
Ala Thr Thr Val Lys Val Pro Met Met Lys Arg Leu Gly Met Phe Asn
225                 230                 235                 240
Ile Gln His Cys Lys Lys Leu Ser Ser Trp Val Leu Leu Met Lys Tyr
                245                 250                 255
Leu Gly Asn Ala Thr Ala Ile Phe Phe Leu Pro Asp Glu Gly Lys Leu
            260                 265                 270
Gln His Leu Glu Asn Glu Leu Thr His Asp Ile Ile Thr Lys Phe Leu
        275                 280                 285
Glu Asn Glu Asp Arg Arg Ser Ala Ser Leu His Leu Pro Lys Leu Ser
290                 295                 300
Ile Thr Gly Thr Tyr Asp Leu Lys Ser Val Leu Gly Gln Leu Gly Ile
305                 310                 315                 320
Thr Lys Val Phe Ser Asn Gly Ala Asp Leu Ser Gly Val Thr Glu Glu
                325                 330                 335
Ala Pro Leu Lys Leu Ser Lys Ala Val His Lys Ala Val Leu Thr Ile
            340                 345                 350
Asp Glu Lys Gly Thr Glu Ala Ala Gly Ala Met Phe Leu Glu Gln Arg
        355                 360                 365
Leu Arg Asp Ile Pro Pro Glu Val Lys Phe Asn Lys Pro Phe Val Phe
370                 375                 380
Leu Met Ile Glu Gln Asn Thr Lys Ser Pro Leu Phe Met Gly Lys Val
385                 390                 395                 400
Val Asn Pro Thr Gln Lys
                405

<210> SEQ ID NO 56
<211> LENGTH: 406
<212> TYPE: PRT
<213> ORGANISM: Artificial Sequence
<220> FEATURE:
<223> OTHER INFORMATION: Synthetic

<400> SEQUENCE: 56

Met Arg Gly Ser His His His His His His Gly Ser Asp Asp Pro Gln
1               5                   10                  15
Gly Asp Ala Ala Gln Lys Thr Asp Thr Ser His His Asp Gln Asp His
            20                  25                  30
Pro Thr Phe Asn Lys Ile Thr Pro Asn Leu Ala Glu Phe Ala Phe Ser
        35                  40                  45
Leu Tyr Arg Gln Leu Ala His Gln Ser Asn Ser Thr Asn Ile Phe Phe
    50                  55                  60
Ser Pro Val Ser Ile Ala Thr Ala Phe Ala Met Leu Ser Leu Gly Thr
65                  70                  75                  80
Lys Ala Asp Thr His Asp Glu Ile Leu Glu Gly Leu Asn Phe Asn Leu
                85                  90                  95
Thr Glu Ile Pro Glu Ala Gln Ile His Glu Gly Phe Gln Glu Leu Leu
            100                 105                 110
Arg Thr Leu Asn Gln Pro Asp Ser Gln Leu Gln Leu Thr Thr Gly Asn
        115                 120                 125
```

Gly Leu Phe Leu Ser Glu Gly Leu Lys Leu Val Asp Lys Phe Leu Glu
130                 135                 140

Asp Val Lys Lys Leu Tyr His Ser Glu Ala Phe Thr Val Asn Phe Gly
145                 150                 155                 160

Asp Thr Glu Glu Ala Lys Lys Gln Ile Asn Asp Tyr Val Glu Lys Gly
            165                 170                 175

Thr Gln Gly Lys Ile Val Asp Leu Val Lys Glu Leu Asp Arg Asp Thr
            180                 185                 190

Val Phe Ala Leu Val Asn Tyr Ile Phe Phe Lys Gly Lys Trp Glu Arg
            195                 200                 205

Pro Phe Glu Val Lys Asp Thr Glu Glu Glu Asp Phe His Val Asp Gln
210                 215                 220

Ala Thr Thr Val Lys Val Pro Met Met Lys Arg Leu Gly Met Phe Asn
225                 230                 235                 240

Ile Gln His Cys Lys Lys Leu Ser Ser Trp Val Leu Leu Met Lys Tyr
                245                 250                 255

Leu Gly Asn Ala Thr Ala Ile Phe Phe Leu Pro Asp Glu Gly Lys Leu
            260                 265                 270

Gln His Leu Glu Asn Glu Leu Thr His Asp Ile Ile Thr Lys Phe Leu
            275                 280                 285

Glu Asn Glu Asp Arg Arg Ser Ala Ser Leu His Leu Pro Lys Leu Ser
290                 295                 300

Ile Thr Gly Thr Tyr Asp Leu Lys Ser Val Leu Gly Gln Leu Gly Ile
305                 310                 315                 320

Thr Lys Val Phe Ser Asn Gly Ala Asp Leu Ser Gly Val Thr Glu Glu
                325                 330                 335

Ala Pro Leu Lys Leu Ser Lys Ala Val His Lys Ala Val Leu Thr Ile
            340                 345                 350

Asp Glu Lys Gly Thr Glu Ala Ala Gly Ala Met Phe Leu Glu Ala Pro
            355                 360                 365

Asp Arg His Met Pro Pro Glu Val Lys Phe Asn Lys Pro Phe Val Phe
            370                 375                 380

Leu Met Ile Glu Gln Asn Thr Lys Ser Pro Leu Phe Met Gly Lys Val
385                 390                 395                 400

Val Asn Pro Thr Gln Lys
                405

<210> SEQ ID NO 57
<211> LENGTH: 406
<212> TYPE: PRT
<213> ORGANISM: Artificial Sequence
<220> FEATURE:
<223> OTHER INFORMATION: Synthetic

<400> SEQUENCE: 57

Met Arg Gly Ser His His His His His His Gly Ser Asp Asp Pro Gln
1               5                   10                  15

Gly Asp Ala Ala Gln Lys Thr Asp Thr Ser His His Asp Gln Asp His
            20                  25                  30

Pro Thr Phe Asn Lys Ile Thr Pro Asn Leu Ala Glu Phe Ala Phe Ser
            35                  40                  45

Leu Tyr Arg Gln Leu Ala His Gln Ser Asn Ser Thr Asn Ile Phe Phe
        50                  55                  60

Ser Pro Val Ser Ile Ala Thr Ala Phe Ala Met Leu Ser Leu Gly Thr
65                  70                  75                  80

Lys Ala Asp Thr His Asp Glu Ile Leu Glu Gly Leu Asn Phe Asn Leu
                85                  90                  95

Thr Glu Ile Pro Glu Ala Gln Ile His Glu Gly Phe Gln Glu Leu Leu
            100                 105                 110

Arg Thr Leu Asn Gln Pro Asp Ser Gln Leu Gln Leu Thr Thr Gly Asn
            115                 120                 125

Gly Leu Phe Leu Ser Glu Gly Leu Lys Leu Val Asp Lys Phe Leu Glu
        130                 135                 140

Asp Val Lys Lys Leu Tyr His Ser Glu Ala Phe Thr Val Asn Phe Gly
145                 150                 155                 160

Asp Thr Glu Glu Ala Lys Lys Gln Ile Asn Asp Tyr Val Glu Lys Gly
                165                 170                 175

Thr Gln Gly Lys Ile Val Asp Leu Val Lys Glu Leu Asp Arg Asp Thr
            180                 185                 190

Val Phe Ala Leu Val Asn Tyr Ile Phe Phe Lys Gly Lys Trp Glu Arg
        195                 200                 205

Pro Phe Glu Val Lys Asp Thr Glu Glu Glu Asp Phe His Val Asp Gln
    210                 215                 220

Ala Thr Thr Val Lys Val Pro Met Met Lys Arg Leu Gly Met Phe Asn
225                 230                 235                 240

Ile Gln His Cys Lys Lys Leu Ser Ser Trp Val Leu Leu Met Lys Tyr
                245                 250                 255

Leu Gly Asn Ala Thr Ala Ile Phe Phe Leu Pro Asp Glu Gly Lys Leu
            260                 265                 270

Gln His Leu Glu Asn Glu Leu Thr His Asp Ile Ile Thr Lys Phe Leu
        275                 280                 285

Glu Asn Glu Asp Arg Arg Ser Ala Ser Leu His Leu Pro Lys Leu Ser
    290                 295                 300

Ile Thr Gly Thr Tyr Asp Leu Lys Ser Val Leu Gly Gln Leu Gly Ile
305                 310                 315                 320

Thr Lys Val Phe Ser Asn Gly Ala Asp Leu Ser Gly Val Thr Glu Glu
                325                 330                 335

Ala Pro Leu Lys Leu Ser Lys Ala Val His Lys Ala Val Leu Thr Ile
            340                 345                 350

Asp Glu Lys Gly Thr Glu Ala Ala Gly Ala Met Phe Leu Glu Thr Val
        355                 360                 365

Asp Tyr Ala Ile Pro Pro Glu Val Lys Phe Asn Lys Pro Phe Val Phe
    370                 375                 380

Leu Met Ile Glu Gln Asn Thr Lys Ser Pro Leu Phe Met Gly Lys Val
385                 390                 395                 400

Val Asn Pro Thr Gln Lys
                405

<210> SEQ ID NO 58
<211> LENGTH: 412
<212> TYPE: PRT
<213> ORGANISM: Artificial Sequence
<220> FEATURE:
<223> OTHER INFORMATION: Synthetic

<400> SEQUENCE: 58

Met Arg Gly Ser His His His His His His Ser Arg His Pro Asn Ser
1               5                   10                  15

Pro Leu Asp Glu Glu Asn Leu Thr Gln Glu Asn Gln Asp Arg Gly Thr
            20                  25                  30

His Val Asp Leu Gly Leu Ala Ser Ala Asn Val Asp Phe Ala Phe Ser
    35                  40                  45

Leu Tyr Lys Gln Leu Val Leu Lys Ala Pro Asp Lys Asn Val Ile Phe
 50                  55                  60

Ser Pro Leu Ser Ile Ser Thr Ala Leu Ala Phe Leu Ser Leu Gly Ala
 65                  70                  75                  80

His Asn Thr Thr Leu Thr Glu Ile Leu Lys Gly Leu Lys Phe Asn Leu
                 85                  90                  95

Thr Glu Thr Ser Glu Ala Glu Ile His Gln Ser Phe Gln His Leu Leu
                100                 105                 110

Arg Thr Leu Asn Gln Ser Ser Asp Glu Leu Gln Leu Ser Met Gly Asn
            115                 120                 125

Ala Met Phe Val Lys Glu Gln Leu Ser Leu Leu Asp Arg Phe Thr Glu
130                 135                 140

Asp Ala Lys Arg Leu Tyr Gly Ser Glu Ala Phe Ala Thr Asp Phe Gln
145                 150                 155                 160

Asp Ser Ala Ala Ala Lys Lys Leu Ile Asn Asp Tyr Val Lys Asn Gly
                165                 170                 175

Thr Arg Gly Lys Ile Thr Asp Leu Ile Lys Asp Leu Asp Ser Gln Thr
                180                 185                 190

Met Met Val Leu Val Asn Tyr Ile Phe Phe Lys Ala Lys Trp Glu Met
            195                 200                 205

Pro Phe Asp Pro Gln Asp Thr His Gln Ser Arg Phe Tyr Leu Ser Lys
210                 215                 220

Lys Lys Trp Val Met Val Pro Met Met Ser Leu His His Leu Thr Ile
225                 230                 235                 240

Pro Tyr Phe Arg Asp Glu Glu Leu Ser Cys Thr Val Val Glu Leu Lys
                245                 250                 255

Tyr Thr Gly Asn Ala Ser Ala Leu Phe Ile Leu Pro Asp Gln Asp Lys
                260                 265                 270

Met Glu Glu Val Glu Ala Met Leu Leu Pro Glu Thr Leu Lys Arg Trp
            275                 280                 285

Arg Asp Ser Leu Glu Phe Arg Glu Ile Gly Glu Leu Tyr Leu Pro Lys
290                 295                 300

Phe Ser Ile Ser Arg Asp Tyr Asn Leu Asn Asp Ile Leu Leu Gln Leu
305                 310                 315                 320

Gly Ile Glu Glu Ala Phe Thr Ser Lys Ala Asp Leu Ser Gly Ile Thr
                325                 330                 335

Gly Ala Arg Asn Leu Ala Val Ser Gln Val Val His Lys Ala Val Leu
            340                 345                 350

Asp Val Phe Glu Glu Gly Thr Glu Ala Ser Ala Ala Thr Ala Val Val
355                 360                 365

Gly Ser Leu Arg Ser Ala Leu Val Glu Thr Arg Thr Ile Val Arg Phe
370                 375                 380

Asn Arg Pro Phe Leu Met Ile Ile Val Pro Thr Asp Thr Gln Asn Ile
385                 390                 395                 400

Phe Phe Met Ser Lys Val Thr Asn Pro Lys Gln Ala
                405                 410

<210> SEQ ID NO 59
<211> LENGTH: 412
<212> TYPE: PRT
<213> ORGANISM: Artificial Sequence
<220> FEATURE:
<223> OTHER INFORMATION: Synthetic

```
<400> SEQUENCE: 59

Met Arg Gly Ser His His His His His Ser Arg His Pro Asn Ser
1               5                   10                  15

Pro Leu Asp Glu Glu Asn Leu Thr Gln Glu Asn Gln Asp Arg Gly Thr
            20                  25                  30

His Val Asp Leu Gly Leu Ala Ser Ala Asn Val Asp Phe Ala Phe Ser
        35                  40                  45

Leu Tyr Lys Gln Leu Val Leu Lys Ala Pro Asp Lys Asn Val Ile Phe
    50                  55                  60

Ser Pro Leu Ser Ile Ser Thr Ala Leu Ala Phe Leu Ser Leu Gly Ala
65                  70                  75                  80

His Asn Thr Thr Leu Thr Glu Ile Leu Lys Gly Leu Lys Phe Asn Leu
                85                  90                  95

Thr Glu Thr Ser Glu Ala Glu Ile His Gln Ser Phe Gln His Leu Leu
            100                 105                 110

Arg Thr Leu Asn Gln Ser Ser Asp Glu Leu Gln Leu Ser Met Gly Asn
        115                 120                 125

Ala Met Phe Val Lys Glu Gln Leu Ser Leu Leu Asp Arg Phe Thr Glu
130                 135                 140

Asp Ala Lys Arg Leu Tyr Gly Ser Glu Ala Phe Ala Thr Asp Phe Gln
145                 150                 155                 160

Asp Ser Ala Ala Ala Lys Lys Leu Ile Asn Asp Tyr Val Lys Asn Gly
                165                 170                 175

Thr Arg Gly Lys Ile Thr Asp Leu Ile Lys Asp Leu Asp Ser Gln Thr
            180                 185                 190

Met Met Val Leu Val Asn Tyr Ile Phe Phe Lys Ala Lys Trp Glu Met
        195                 200                 205

Pro Phe Asp Pro Gln Asp Thr His Gln Ser Arg Phe Tyr Leu Ser Lys
    210                 215                 220

Lys Lys Trp Val Met Val Pro Met Met Ser Leu His His Leu Thr Ile
225                 230                 235                 240

Pro Tyr Phe Arg Asp Glu Glu Leu Ser Cys Thr Val Val Glu Leu Lys
                245                 250                 255

Tyr Thr Gly Asn Ala Ser Ala Leu Phe Ile Leu Pro Asp Gln Asp Lys
            260                 265                 270

Met Glu Glu Val Glu Ala Met Leu Leu Pro Glu Thr Leu Lys Arg Trp
        275                 280                 285

Arg Asp Ser Leu Glu Phe Arg Glu Ile Gly Glu Leu Tyr Leu Pro Lys
    290                 295                 300

Phe Ser Ile Ser Arg Asp Tyr Asn Leu Asn Asp Ile Leu Leu Gln Leu
305                 310                 315                 320

Gly Ile Glu Glu Ala Phe Thr Ser Lys Ala Asp Leu Ser Gly Ile Thr
                325                 330                 335

Gly Ala Arg Asn Leu Ala Val Ser Gln Val Val His Lys Ala Val Leu
            340                 345                 350

Asp Val Phe Glu Glu Gly Thr Glu Ala Ser Ala Ala Thr Ala Val Lys
        355                 360                 365

Ile Thr Leu Arg Gln Thr Asn Asp Glu Thr Arg Thr Ile Val Arg Phe
    370                 375                 380

Asn Arg Pro Phe Leu Met Ile Ile Val Pro Thr Asp Thr Gln Asn Ile
385                 390                 395                 400

Phe Phe Met Ser Lys Val Thr Asn Pro Lys Gln Ala
                405                 410
```

```
<210> SEQ ID NO 60
<211> LENGTH: 27
<212> TYPE: DNA
<213> ORGANISM: Artificial Sequence
<220> FEATURE:
<223> OTHER INFORMATION: Synthetic

<400> SEQUENCE: 60
gcacaatggt acgcgtctcc actaatg                                            27

<210> SEQ ID NO 61
<211> LENGTH: 48
<212> TYPE: DNA
<213> ORGANISM: Artificial Sequence
<220> FEATURE:
<223> OTHER INFORMATION: Synthetic

<400> SEQUENCE: 61
taccgcggtc aaaatcaccc tccgttctcg agcagtggag acgcgtga                     48

<210> SEQ ID NO 62
<211> LENGTH: 48
<212> TYPE: DNA
<213> ORGANISM: Artificial Sequence
<220> FEATURE:
<223> OTHER INFORMATION: Synthetic

<400> SEQUENCE: 62
taccgcggtc aaaatcacca ggaggtctat cgatgtggag acgcgtga                     48

<210> SEQ ID NO 63
<211> LENGTH: 48
<212> TYPE: DNA
<213> ORGANISM: Artificial Sequence
<220> FEATURE:
<223> OTHER INFORMATION: Synthetic

<400> SEQUENCE: 63
taccgcggtc aaaatcaggg ggagatctga gttagtggag acgcgtga                     48

<210> SEQ ID NO 64
<211> LENGTH: 48
<212> TYPE: DNA
<213> ORGANISM: Artificial Sequence
<220> FEATURE:
<223> OTHER INFORMATION: Synthetic

<400> SEQUENCE: 64
taccgcggtc aaaatcaagc ttagaacaac attagtggag accgctga                     48

<210> SEQ ID NO 65
<211> LENGTH: 48
<212> TYPE: DNA
<213> ORGANISM: Artificial Sequence
<220> FEATURE:
<223> OTHER INFORMATION: Synthetic

<400> SEQUENCE: 65
taccgcggtc aaaatcatga caagatctaa cttagtggag acgcgtga                     48

<210> SEQ ID NO 66
<211> LENGTH: 48
<212> TYPE: DNA
<213> ORGANISM: Artificial Sequence
<220> FEATURE:
<223> OTHER INFORMATION: Synthetic
```

<400> SEQUENCE: 66
taccgcggtc aaaatcaccg agcgtgtctc gcccgtggag acgcgtga        48

<210> SEQ ID NO 67
<211> LENGTH: 16
<212> TYPE: DNA
<213> ORGANISM: Artificial Sequence
<220> FEATURE:
<223> OTHER INFORMATION: Synthetic

<400> SEQUENCE: 67
taccgcggtc aaaatc        16

<210> SEQ ID NO 68
<211> LENGTH: 14
<212> TYPE: DNA
<213> ORGANISM: Artificial Sequence
<220> FEATURE:
<223> OTHER INFORMATION: Synthetic

<400> SEQUENCE: 68
tcacgcgtgt ccac        14

<210> SEQ ID NO 69
<211> LENGTH: 29
<212> TYPE: DNA
<213> ORGANISM: Artificial Sequence
<220> FEATURE:
<223> OTHER INFORMATION: Synthetic

<400> SEQUENCE: 69
aggatgagga attcataatt ggtggccat        29

<210> SEQ ID NO 70
<211> LENGTH: 29
<212> TYPE: DNA
<213> ORGANISM: Artificial Sequence
<220> FEATURE:
<223> OTHER INFORMATION: Synthetic

<400> SEQUENCE: 70
cccaccgtct agaccatcat ttgtcccgc        29

<210> SEQ ID NO 71
<211> LENGTH: 26
<212> TYPE: DNA
<213> ORGANISM: Artificial Sequence
<220> FEATURE:
<223> OTHER INFORMATION: Synthetic

<400> SEQUENCE: 71
tatggatccg atgatcccca gggaga        26

<210> SEQ ID NO 72
<211> LENGTH: 26
<212> TYPE: DNA
<213> ORGANISM: Artificial Sequence
<220> FEATURE:
<223> OTHER INFORMATION: Synthetic

<400> SEQUENCE: 72
cgcgaagctt ttatttttgg gtggga        26

<210> SEQ ID NO 73
<211> LENGTH: 36
<212> TYPE: DNA
<213> ORGANISM: Artificial Sequence
<220> FEATURE:
<223> OTHER INFORMATION: Synthetic

<400> SEQUENCE: 73
actgaagctg ctggcgccga gctcttagag gccata         36

<210> SEQ ID NO 74
<211> LENGTH: 25
<212> TYPE: DNA
<213> ORGANISM: Artificial Sequence
<220> FEATURE:
<223> OTHER INFORMATION: Synthetic

<400> SEQUENCE: 74
gtctatcccc cctgaggtca agttc         25

<210> SEQ ID NO 75
<211> LENGTH: 49
<212> TYPE: DNA
<213> ORGANISM: Artificial Sequence
<220> FEATURE:
<223> OTHER INFORMATION: Synthetic

<400> SEQUENCE: 75
ccatgtttct agaggctctg cagcgtgcta tcccgcctga ggtcaagtt         49

<210> SEQ ID NO 76
<211> LENGTH: 49
<212> TYPE: DNA
<213> ORGANISM: Artificial Sequence
<220> FEATURE:
<223> OTHER INFORMATION: Synthetic

<400> SEQUENCE: 76
ccatgtttct agagaccgtt gactacgcta tcccgcctga ggtcaagtt         49

<210> SEQ ID NO 77
<211> LENGTH: 48
<212> TYPE: DNA
<213> ORGANISM: Artificial Sequence
<220> FEATURE:
<223> OTHER INFORMATION: Synthetic

<400> SEQUENCE: 77
taccgcggtc aaaatcctgc agcgtgctat cctggtggag acgcgtga         48

<210> SEQ ID NO 78
<211> LENGTH: 48
<212> TYPE: DNA
<213> ORGANISM: Artificial Sequence
<220> FEATURE:
<223> OTHER INFORMATION: Synthetic

<400> SEQUENCE: 78
taccgcggtc aaaaccgttg actacgctgc tctggtggag acgcgtga         48

<210> SEQ ID NO 79
<211> LENGTH: 21
<212> TYPE: DNA
<213> ORGANISM: Artificial Sequence
<220> FEATURE:
<223> OTHER INFORMATION: Synthetic

```
<400> SEQUENCE: 79
gctggcgcca tgtttctaga g                                      21

<210> SEQ ID NO 80
<211> LENGTH: 20
<212> TYPE: DNA
<213> ORGANISM: Artificial Sequence
<220> FEATURE:
<223> OTHER INFORMATION: Synthetic

<400> SEQUENCE: 80
ttgttgaact tgacctcagg                                        20

<210> SEQ ID NO 81
<211> LENGTH: 14
<212> TYPE: DNA
<213> ORGANISM: Artificial Sequence
<220> FEATURE:
<223> OTHER INFORMATION: Synthetic

<400> SEQUENCE: 81
gtaccgcggt caaa                                              14

<210> SEQ ID NO 82
<211> LENGTH: 14
<212> TYPE: DNA
<213> ORGANISM: Artificial Sequence
<220> FEATURE:
<223> OTHER INFORMATION: Synthetic

<400> SEQUENCE: 82
tcacgcgtgt ccac                                              14

<210> SEQ ID NO 83
<211> LENGTH: 20
<212> TYPE: DNA
<213> ORGANISM: Artificial Sequence
<220> FEATURE:
<223> OTHER INFORMATION: Synthetic

<400> SEQUENCE: 83
tgagctagtc tagataggtg                                        20

<210> SEQ ID NO 84
<211> LENGTH: 17
<212> TYPE: DNA
<213> ORGANISM: Artificial Sequence
<220> FEATURE:
<223> OTHER INFORMATION: Synthetic

<400> SEQUENCE: 84
tgcagcgact gctatga                                           17

<210> SEQ ID NO 85
<211> LENGTH: 20
<212> TYPE: PRT
<213> ORGANISM: Homo sapiens

<400> SEQUENCE: 85

Gly Thr Glu Ala Ala Gly Ala Met Phe Leu Glu Ala Ile Pro Met Ser
1               5                   10                  15

Ile Pro Pro Glu
            20
```

<210> SEQ ID NO 86
<211> LENGTH: 20
<212> TYPE: PRT
<213> ORGANISM: Homo sapiens

<400> SEQUENCE: 86

Gly Thr Glu Ala Thr Gly Ala Pro His Leu Glu Glu Lys Ala Trp Ser
1               5                   10                  15

Lys Tyr Gln Thr
            20

<210> SEQ ID NO 87
<211> LENGTH: 20
<212> TYPE: PRT
<213> ORGANISM: Homo sapiens

<400> SEQUENCE: 87

Gly Val Glu Ala Ala Ala Ala Thr Ser Ile Ala Met Ser Arg Met Ser
1               5                   10                  15

Leu Ser Ser Phe
            20

<210> SEQ ID NO 88
<211> LENGTH: 20
<212> TYPE: PRT
<213> ORGANISM: Homo sapiens

<400> SEQUENCE: 88

Gly Thr Glu Ala Ser Ala Ala Thr Ala Val Lys Ile Thr Leu Leu Ser
1               5                   10                  15

Ala Leu Val Glu
            20

<210> SEQ ID NO 89
<211> LENGTH: 20
<212> TYPE: PRT
<213> ORGANISM: Homo sapiens

<400> SEQUENCE: 89

Gly Ser Glu Ala Ala Ala Ser Thr Ala Val Val Ile Ala Gly Arg Ser
1               5                   10                  15

Leu Asn Pro Asn
            20

<210> SEQ ID NO 90
<211> LENGTH: 20
<212> TYPE: PRT
<213> ORGANISM: Homo sapiens

<400> SEQUENCE: 90

Gly Thr Glu Ala Ala Ala Gly Ser Gly Ser Glu Ile Asp Ile Arg Ile
1               5                   10                  15

Arg Val Pro Ser
            20

<210> SEQ ID NO 91
<211> LENGTH: 20
<212> TYPE: PRT
<213> ORGANISM: Homo sapiens

```
<400> SEQUENCE: 91

Gly Asn Pro Phe Asp Gln Asp Ile Tyr Gly Arg Glu Glu Leu Arg Ser
1               5                   10                  15

Pro Lys Leu Phe
            20

<210> SEQ ID NO 92
<211> LENGTH: 20
<212> TYPE: PRT
<213> ORGANISM: Homo sapiens

<400> SEQUENCE: 92

Gly Thr Lys Ala Ser Ala Ala Thr Ala Ile Leu Ile Ala Arg Ser
1               5                   10                  15

Ser Pro Pro Trp
            20

<210> SEQ ID NO 93
<211> LENGTH: 20
<212> TYPE: PRT
<213> ORGANISM: Homo sapiens

<400> SEQUENCE: 93

Gly Thr Gln Ala Thr Thr Val Thr Thr Val Gly Phe Met Pro Leu Ser
1               5                   10                  15

Thr Gln Val Arg
            20

<210> SEQ ID NO 94
<211> LENGTH: 20
<212> TYPE: PRT
<213> ORGANISM: Homo sapiens

<400> SEQUENCE: 94

Gly Val Glu Ala Ala Ala Ala Ser Ala Ile Ser Val Ala Arg Thr Leu
1               5                   10                  15

Leu Val Phe Glu
            20

<210> SEQ ID NO 95
<211> LENGTH: 20
<212> TYPE: PRT
<213> ORGANISM: Homo sapiens

<400> SEQUENCE: 95

Gly Thr Glu Ala Ala Ala Ala Thr Ala Gly Ile Ala Thr Phe Cys Met
1               5                   10                  15

Leu Met Pro Glu
            20

<210> SEQ ID NO 96
<211> LENGTH: 20
<212> TYPE: PRT
<213> ORGANISM: Homo sapiens

<400> SEQUENCE: 96

Gly Thr Arg Ala Ala Ala Ala Thr Gly Thr Ile Phe Thr Phe Arg Ser
1               5                   10                  15

Ala Arg Leu Asn
            20
```

<210> SEQ ID NO 97
<211> LENGTH: 20
<212> TYPE: PRT
<213> ORGANISM: Homo sapiens

<400> SEQUENCE: 97

Gly Thr Glu Ala Ala Ala Ala Thr Thr Phe Ala Ile Lys Phe Phe Ser
1               5                   10                  15

Ala Gln Thr Asn
            20

<210> SEQ ID NO 98
<211> LENGTH: 20
<212> TYPE: PRT
<213> ORGANISM: Homo sapiens

<400> SEQUENCE: 98

Gly Gly Asp Ser Ile Glu Val Pro Gly Ala Arg Ile Leu Gln His Lys
1               5                   10                  15

Asp Glu Leu Asn
            20

<210> SEQ ID NO 99
<211> LENGTH: 20
<212> TYPE: PRT
<213> ORGANISM: Homo sapiens

<400> SEQUENCE: 99

Gly Ser Glu Ala Ala Ala Val Ser Gly Met Ile Ala Ile Ser Arg Met
1               5                   10                  15

Ala Val Leu Tyr
            20

<210> SEQ ID NO 100
<211> LENGTH: 20
<212> TYPE: PRT
<213> ORGANISM: Homo sapiens

<400> SEQUENCE: 100

Gly Thr Val Ala Ser Ser Ser Thr Ala Val Ile Val Ser Ala Arg Met
1               5                   10                  15

Ala Pro Glu Glu
            20

<210> SEQ ID NO 101
<211> LENGTH: 20
<212> TYPE: PRT
<213> ORGANISM: Homo sapiens

<400> SEQUENCE: 101

Gly Thr Glu Ala Ala Ala Gly Thr Gly Gly Val Met Thr Gly Arg Thr
1               5                   10                  15

Gly His Gly Gly
            20

<210> SEQ ID NO 102
<211> LENGTH: 20
<212> TYPE: PRT
<213> ORGANISM: Homo sapiens

```
<400> SEQUENCE: 102

Gly Ala Gly Thr Thr Pro Ser Pro Gly Leu Gln Pro Ala His Leu Thr
1               5                   10                  15

Phe Pro Leu Asp
            20

<210> SEQ ID NO 103
<211> LENGTH: 20
<212> TYPE: PRT
<213> ORGANISM: Homo sapiens

<400> SEQUENCE: 103

Gly Thr Glu Ala Ala Ala Thr Ala Ala Ile Met Met Met Arg Cys
1               5                   10                  15

Ala Arg Phe Val
            20

<210> SEQ ID NO 104
<211> LENGTH: 20
<212> TYPE: PRT
<213> ORGANISM: Homo sapiens

<400> SEQUENCE: 104

Gly Thr Glu Ala Ala Ala Ala Thr Ala Val Val Arg Asn Ser Arg Cys
1               5                   10                  15

Ser Arg Met Glu
            20

<210> SEQ ID NO 105
<211> LENGTH: 20
<212> TYPE: PRT
<213> ORGANISM: Homo sapiens

<400> SEQUENCE: 105

Gly Thr Glu Ala Ala Ala Ala Ser Ser Cys Phe Val Val Ala Glu Cys
1               5                   10                  15

Cys Met Glu Ser
            20

<210> SEQ ID NO 106
<211> LENGTH: 20
<212> TYPE: PRT
<213> ORGANISM: Homo sapiens

<400> SEQUENCE: 106

Gly Ala Glu Ala Ala Ala Ala Thr Ala Val Val Gly Phe Gly Ser Ser
1               5                   10                  15

Pro Ala Ser Thr
            20

<210> SEQ ID NO 107
<211> LENGTH: 20
<212> TYPE: PRT
<213> ORGANISM: Homo sapiens

<400> SEQUENCE: 107

Gly Val Glu Ala Ala Ala Ala Thr Ala Val Val Val Val Glu Leu Ser
1               5                   10                  15

Ser Pro Ser Thr
            20
```

```
<210> SEQ ID NO 108
<211> LENGTH: 20
<212> TYPE: PRT
<213> ORGANISM: Homo sapiens

<400> SEQUENCE: 108

Gly Thr Glu Ala Ala Val Pro Glu Val Glu Leu Ser Asp Gln Pro
1               5                   10                  15

Glu Asn Thr Phe
            20

<210> SEQ ID NO 109
<211> LENGTH: 20
<212> TYPE: PRT
<213> ORGANISM: Homo sapiens

<400> SEQUENCE: 109

Gly Thr Glu Ala Thr Ala Ala Thr Gly Ser Asn Ile Val Glu Lys Gln
1               5                   10                  15

Leu Pro Gln Ser
            20

<210> SEQ ID NO 110
<211> LENGTH: 20
<212> TYPE: PRT
<213> ORGANISM: Homo sapiens

<400> SEQUENCE: 110

Gly Ser Glu Ala Ala Thr Ser Thr Gly Ile His Ile Pro Val Ile Met
1               5                   10                  15

Ser Leu Ala Gln
            20

<210> SEQ ID NO 111
<211> LENGTH: 25
<212> TYPE: DNA
<213> ORGANISM: Artificial Sequence
<220> FEATURE:
<223> OTHER INFORMATION: Synthetic sequence

<400> SEQUENCE: 111
gtgattttga ccgcggtggc agcag                                    25

<210> SEQ ID NO 112
<211> LENGTH: 27
<212> TYPE: DNA
<213> ORGANISM: Artificial Sequence
<220> FEATURE:
<223> OTHER INFORMATION: Synthetic sequence

<400> SEQUENCE: 112
gcacaatggt acgcgtctcc actaatg                                  27

<210> SEQ ID NO 113
<211> LENGTH: 70
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (26)..(27)
<223> OTHER INFORMATION: n is a, c, g, or t
```

```
<220> FEATURE:
<221> NAME/KEY: misc_feature
<222> LOCATION: (28)..(28)
<223> OTHER INFORMATION: s is g or c
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (31)..(31)
<223> OTHER INFORMATION: s is g or c
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (34)..(34)
<223> OTHER INFORMATION: s is g or c
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (37)..(37)
<223> OTHER INFORMATION: s is g or c
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (40)..(40)
<223> OTHER INFORMATION: s is g or c

<400> SEQUENCE: 113
tgagctagtc tagataggtg gcggtnnsnn snnsnnsnns gggtcgacgt cggtcatagc      60
agtcgctgca                                                            70

<210> SEQ ID NO 114
<211> LENGTH: 20
<212> TYPE: DNA
<213> ORGANISM: Artificial Sequence
<220> FEATURE:
<223> OTHER INFORMATION: Synthetic sequence

<400> SEQUENCE: 114
acaatgagct gcgtgtggct                                                 20

<210> SEQ ID NO 115
<211> LENGTH: 21
<212> TYPE: DNA
<213> ORGANISM: Artificial Sequence
<220> FEATURE:
<223> OTHER INFORMATION: Synthetic sequence

<400> SEQUENCE: 115
tctccttaat gtcacgcacg a                                               21

<210> SEQ ID NO 116
<211> LENGTH: 13
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (6)..(10)
<223> OTHER INFORMATION: Xaa can be any naturally occurring amino acid
```

```
<400> SEQUENCE: 116

Gly Ala Leu Gly Gly Xaa Xaa Xaa Xaa Xaa Gly Ser Thr
1               5                   10

<210> SEQ ID NO 117
<211> LENGTH: 5
<212> TYPE: PRT
<213> ORGANISM: Artificial Sequence
<220> FEATURE:
<223> OTHER INFORMATION: Synthetic sequence

<400> SEQUENCE: 117

Gly Gly Gly Gly Gly
1               5

<210> SEQ ID NO 118
<211> LENGTH: 5
<212> TYPE: PRT
<213> ORGANISM: Artificial Sequence
<220> FEATURE:
<223> OTHER INFORMATION: Synthetic sequence

<400> SEQUENCE: 118

Val Gly Ser Leu Arg
1               5

<210> SEQ ID NO 119
<211> LENGTH: 5
<212> TYPE: PRT
<213> ORGANISM: Artificial Sequence
<220> FEATURE:
<223> OTHER INFORMATION: Synthetic sequence

<400> SEQUENCE: 119

Arg Gln Thr Asn Asp
1               5

<210> SEQ ID NO 120
<211> LENGTH: 5
<212> TYPE: PRT
<213> ORGANISM: Artificial Sequence
<220> FEATURE:
<223> OTHER INFORMATION: Synthetic sequence

<400> SEQUENCE: 120

Asn Gln Arg Ser Ser
1               5

<210> SEQ ID NO 121
<211> LENGTH: 5
<212> TYPE: PRT
<213> ORGANISM: Artificial Sequence
<220> FEATURE:
<223> OTHER INFORMATION: Synthetic sequence

<400> SEQUENCE: 121

Leu Gln Arg Ala Ile
1               5

<210> SEQ ID NO 122
<211> LENGTH: 5
<212> TYPE: PRT
<213> ORGANISM: Artificial Sequence
<220> FEATURE:
<223> OTHER INFORMATION: Synthetic sequence
```

```
<400> SEQUENCE: 122

Gln Arg Leu Arg Asp
1               5

<210> SEQ ID NO 123
<211> LENGTH: 5
<212> TYPE: PRT
<213> ORGANISM: Artificial Sequence
<220> FEATURE:
<223> OTHER INFORMATION: Synthetic sequence

<400> SEQUENCE: 123

Pro Asp Arg His Met
1               5

<210> SEQ ID NO 124
<211> LENGTH: 5
<212> TYPE: PRT
<213> ORGANISM: Artificial Sequence
<220> FEATURE:
<223> OTHER INFORMATION: Synthetic sequence

<400> SEQUENCE: 124

Leu Ser Gly Gly Arg
1               5

<210> SEQ ID NO 125
<211> LENGTH: 5
<212> TYPE: PRT
<213> ORGANISM: Artificial Sequence
<220> FEATURE:
<223> OTHER INFORMATION: Synthetic sequence

<400> SEQUENCE: 125

Leu Ser Arg Asp Asn
1               5

<210> SEQ ID NO 126
<211> LENGTH: 5
<212> TYPE: PRT
<213> ORGANISM: Artificial Sequence
<220> FEATURE:
<223> OTHER INFORMATION: Synthetic sequence

<400> SEQUENCE: 126

Arg Gly Lys Thr Asn
1               5

<210> SEQ ID NO 127
<211> LENGTH: 5
<212> TYPE: PRT
<213> ORGANISM: Artificial Sequence
<220> FEATURE:
<223> OTHER INFORMATION: Synthetic sequence

<400> SEQUENCE: 127

Asn Asn Lys Leu Arg
1               5

<210> SEQ ID NO 128
<211> LENGTH: 5
<212> TYPE: PRT
<213> ORGANISM: Artificial Sequence
<220> FEATURE:
<223> OTHER INFORMATION: Synthetic sequence
```

```
<400> SEQUENCE: 128

Arg Val Thr Ser Thr
1               5

<210> SEQ ID NO 129
<211> LENGTH: 5
<212> TYPE: PRT
<213> ORGANISM: Artificial Sequence
<220> FEATURE:
<223> OTHER INFORMATION: Synthetic sequence

<400> SEQUENCE: 129

Val Val Met Lys Asp
1               5

<210> SEQ ID NO 130
<211> LENGTH: 5
<212> TYPE: PRT
<213> ORGANISM: Artificial Sequence
<220> FEATURE:
<223> OTHER INFORMATION: Synthetic sequence

<400> SEQUENCE: 130

Thr Val Asp Tyr Ala
1               5

<210> SEQ ID NO 131
<211> LENGTH: 5
<212> TYPE: PRT
<213> ORGANISM: Artificial Sequence
<220> FEATURE:
<223> OTHER INFORMATION: Synthetic sequence

<400> SEQUENCE: 131

Ala Tyr Gly Tyr Lys
1               5

<210> SEQ ID NO 132
<211> LENGTH: 5
<212> TYPE: PRT
<213> ORGANISM: Artificial Sequence
<220> FEATURE:
<223> OTHER INFORMATION: Synthetic sequence

<400> SEQUENCE: 132

Val Gly Leu Tyr Asp
1               5

<210> SEQ ID NO 133
<211> LENGTH: 5
<212> TYPE: PRT
<213> ORGANISM: Artificial Sequence
<220> FEATURE:
<223> OTHER INFORMATION: Synthetic sequence

<400> SEQUENCE: 133

Tyr Gln Ser Leu Asn
1               5

<210> SEQ ID NO 134
<211> LENGTH: 5
<212> TYPE: PRT
<213> ORGANISM: Artificial Sequence
<220> FEATURE:
<223> OTHER INFORMATION: Synthetic sequence
```

```
<400> SEQUENCE: 134

Thr Ser Tyr Leu Asn
1               5

<210> SEQ ID NO 135
<211> LENGTH: 4
<212> TYPE: PRT
<213> ORGANISM: Artificial Sequence
<220> FEATURE:
<223> OTHER INFORMATION: Synthetic sequence

<400> SEQUENCE: 135

Ala Ala Pro Phe
1

<210> SEQ ID NO 136
<211> LENGTH: 4
<212> TYPE: PRT
<213> ORGANISM: Artificial Sequence
<220> FEATURE:
<223> OTHER INFORMATION: Synthetic sequence

<400> SEQUENCE: 136

Ala Ala Pro Val
1

<210> SEQ ID NO 137
<211> LENGTH: 5
<212> TYPE: PRT
<213> ORGANISM: Artificial Sequence
<220> FEATURE:
<223> OTHER INFORMATION: Synthetic sequence

<400> SEQUENCE: 137

Thr Phe Arg Ser Ala
1               5

<210> SEQ ID NO 138
<211> LENGTH: 5
<212> TYPE: PRT
<213> ORGANISM: Artificial Sequence
<220> FEATURE:
<223> OTHER INFORMATION: Synthetic sequence

<400> SEQUENCE: 138

Thr Leu Leu Ser Ala
1               5

<210> SEQ ID NO 139
<211> LENGTH: 6
<212> TYPE: PRT
<213> ORGANISM: Artificial Sequence
<220> FEATURE:
<223> OTHER INFORMATION: Synthetic sequence

<400> SEQUENCE: 139

Gly Arg Gln Thr Asn Asp
1               5

<210> SEQ ID NO 140
<211> LENGTH: 5
<212> TYPE: PRT
<213> ORGANISM: Artificial Sequence
<220> FEATURE:
<223> OTHER INFORMATION: Synthetic sequence
```

```
<400> SEQUENCE: 140

Ile Pro Met Ser Ile
1               5

<210> SEQ ID NO 141
<211> LENGTH: 6
<212> TYPE: PRT
<213> ORGANISM: Artificial Sequence
<220> FEATURE:
<223> OTHER INFORMATION: Synthetic sequence

<400> SEQUENCE: 141

Val Gly Ser Leu Arg Gly
1               5

<210> SEQ ID NO 142
<211> LENGTH: 5
<212> TYPE: PRT
<213> ORGANISM: Artificial Sequence
<220> FEATURE:
<223> OTHER INFORMATION: Synthetic sequence

<400> SEQUENCE: 142

Met Gln Val Lys His
1               5

<210> SEQ ID NO 143
<211> LENGTH: 5
<212> TYPE: PRT
<213> ORGANISM: Artificial Sequence
<220> FEATURE:
<223> OTHER INFORMATION: Synthetic sequence

<400> SEQUENCE: 143

Thr Thr Asp Leu Arg
1               5

<210> SEQ ID NO 144
<211> LENGTH: 5
<212> TYPE: PRT
<213> ORGANISM: Artificial Sequence
<220> FEATURE:
<223> OTHER INFORMATION: Synthetic sequence

<400> SEQUENCE: 144

Ser Thr Lys Gly Ile
1               5

<210> SEQ ID NO 145
<211> LENGTH: 5
<212> TYPE: PRT
<213> ORGANISM: Artificial Sequence
<220> FEATURE:
<223> OTHER INFORMATION: Synthetic sequence

<400> SEQUENCE: 145

Lys Leu Lys Glu Thr
1               5

<210> SEQ ID NO 146
<211> LENGTH: 5
<212> TYPE: PRT
<213> ORGANISM: Artificial Sequence
<220> FEATURE:
<223> OTHER INFORMATION: Synthetic sequence
```

```
<400> SEQUENCE: 146

Arg Val Asp Thr Gly
1               5

<210> SEQ ID NO 147
<211> LENGTH: 5
<212> TYPE: PRT
<213> ORGANISM: Artificial Sequence
<220> FEATURE:
<223> OTHER INFORMATION: Synthetic sequence

<400> SEQUENCE: 147

Gly His Arg Ile Asn
1               5

<210> SEQ ID NO 148
<211> LENGTH: 5
<212> TYPE: PRT
<213> ORGANISM: Artificial Sequence
<220> FEATURE:
<223> OTHER INFORMATION: Synthetic sequence

<400> SEQUENCE: 148

Ser Asp Lys Val Tyr
1               5

<210> SEQ ID NO 149
<211> LENGTH: 5
<212> TYPE: PRT
<213> ORGANISM: Artificial Sequence
<220> FEATURE:
<223> OTHER INFORMATION: Synthetic sequence

<400> SEQUENCE: 149

His Glu Thr Leu Lys
1               5

<210> SEQ ID NO 150
<211> LENGTH: 5
<212> TYPE: PRT
<213> ORGANISM: Artificial Sequence
<220> FEATURE:
<223> OTHER INFORMATION: Synthetic sequence

<400> SEQUENCE: 150

Met Gln Ala Thr Lys
1               5

<210> SEQ ID NO 151
<211> LENGTH: 5
<212> TYPE: PRT
<213> ORGANISM: Artificial Sequence
<220> FEATURE:
<223> OTHER INFORMATION: Synthetic sequence

<400> SEQUENCE: 151

Glu Ala Pro Ala Lys
1               5

<210> SEQ ID NO 152
<211> LENGTH: 5
<212> TYPE: PRT
<213> ORGANISM: Artificial Sequence
<220> FEATURE:
<223> OTHER INFORMATION: Synthetic sequence
```

```
<400> SEQUENCE: 152

Pro Val His Leu Tyr
1               5

<210> SEQ ID NO 153
<211> LENGTH: 5
<212> TYPE: PRT
<213> ORGANISM: Artificial Sequence
<220> FEATURE:
<223> OTHER INFORMATION: Synthetic sequence

<400> SEQUENCE: 153

Gln Pro Asn Gly Tyr
1               5

<210> SEQ ID NO 154
<211> LENGTH: 5
<212> TYPE: PRT
<213> ORGANISM: Artificial Sequence
<220> FEATURE:
<223> OTHER INFORMATION: Synthetic sequence

<400> SEQUENCE: 154

Ala Tyr Gly Leu Ala
1               5

<210> SEQ ID NO 155
<211> LENGTH: 5
<212> TYPE: PRT
<213> ORGANISM: Artificial Sequence
<220> FEATURE:
<223> OTHER INFORMATION: Synthetic sequence

<400> SEQUENCE: 155

Tyr Gln Asn Ser Ser
1               5

<210> SEQ ID NO 156
<211> LENGTH: 5
<212> TYPE: PRT
<213> ORGANISM: Artificial Sequence
<220> FEATURE:
<223> OTHER INFORMATION: Synthetic sequence

<400> SEQUENCE: 156

Ser Ala Val Arg Pro
1               5

<210> SEQ ID NO 157
<211> LENGTH: 5
<212> TYPE: PRT
<213> ORGANISM: Artificial Sequence
<220> FEATURE:
<223> OTHER INFORMATION: Synthetic sequence

<400> SEQUENCE: 157

Leu Arg Ser Arg Ala
1               5

<210> SEQ ID NO 158
<211> LENGTH: 5
<212> TYPE: PRT
<213> ORGANISM: Artificial Sequence
<220> FEATURE:
<223> OTHER INFORMATION: Synthetic sequence
```

```
<400> SEQUENCE: 158

Arg Arg Ser Ile Asp
1               5

<210> SEQ ID NO 159
<211> LENGTH: 5
<212> TYPE: PRT
<213> ORGANISM: Artificial Sequence
<220> FEATURE:
<223> OTHER INFORMATION: Synthetic sequence

<400> SEQUENCE: 159

Arg Gly Arg Ser Glu
1               5

<210> SEQ ID NO 160
<211> LENGTH: 5
<212> TYPE: PRT
<213> ORGANISM: Artificial Sequence
<220> FEATURE:
<223> OTHER INFORMATION: Synthetic sequence

<400> SEQUENCE: 160

Lys Leu Arg Thr Thr
1               5

<210> SEQ ID NO 161
<211> LENGTH: 5
<212> TYPE: PRT
<213> ORGANISM: Artificial Sequence
<220> FEATURE:
<223> OTHER INFORMATION: Synthetic sequence

<400> SEQUENCE: 161

Met Thr Arg Ser Asn
1               5

<210> SEQ ID NO 162
<211> LENGTH: 5
<212> TYPE: PRT
<213> ORGANISM: Artificial Sequence
<220> FEATURE:
<223> OTHER INFORMATION: Synthetic sequence

<400> SEQUENCE: 162

Glu Arg Val Ser Pro
1               5

<210> SEQ ID NO 163
<211> LENGTH: 4
<212> TYPE: PRT
<213> ORGANISM: Artificial Sequence
<220> FEATURE:
<223> OTHER INFORMATION: Synthetic sequence

<400> SEQUENCE: 163

Leu Leu Ser Ala
1

<210> SEQ ID NO 164
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag
```

```
<400> SEQUENCE: 164

His His His His His His
1               5

<210> SEQ ID NO 165
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Gly Gly Gly Ser
1

<210> SEQ ID NO 166
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Val Lys Ile Thr Leu Leu Ser Ala Leu Val Glu Thr
1               5                   10

<210> SEQ ID NO 167
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Val Lys Ile Thr Leu Arg Ser Arg Ala Val Glu Thr
1               5                   10

<210> SEQ ID NO 168
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Val Lys Ile Thr Arg Arg Ser Ile Asp Val Glu Thr
1               5                   10

<210> SEQ ID NO 169
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Val Lys Ile Arg Gly Arg Ser Glu Leu Val Glu Thr
1               5                   10
```

```
<210> SEQ ID NO 170
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Val Lys Ile Lys Leu Arg Thr Thr Leu Val Glu Thr
1               5                   10

<210> SEQ ID NO 171
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Val Lys Ile Met Thr Arg Ser Asn Ala Val Glu Thr
1               5                   10

<210> SEQ ID NO 172
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Val Lys Ile Thr Glu Arg Val Ser Pro Val Glu Thr
1               5                   10

<210> SEQ ID NO 173
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
gtcaaaatca ccctcctttc tgcattagtg gaggtc                              36

<210> SEQ ID NO 174
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Thr Ile Phe Thr Phe Arg Ser Ala Arg Leu Asn Ser
1               5                   10

<210> SEQ ID NO 175
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 175

Val Lys Ile Thr Phe Arg Ser Ala Leu Val Glu Thr
1               5                   10

<210> SEQ ID NO 176
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
gtcaaaatca cctttagatc tgcattagtg gaggtc                              36

<210> SEQ ID NO 177
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Leu Glu Ala Ile Pro Met Ser Ile Pro Pro Glu
1               5                   10

<210> SEQ ID NO 178
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Leu Glu Ala Leu Gln Arg Ala Ile Pro Pro Glu
1               5                   10

<210> SEQ ID NO 179
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Leu Glu Thr Val Asp Tyr Ala Ile Pro Pro Glu
1               5                   10

<210> SEQ ID NO 180
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Val Lys Ile Thr Leu Leu Ser Ala Leu Val Glu
1               5                   10

<210> SEQ ID NO 181
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Val Lys Ile Leu Gln Arg Ala Ile Leu Val Glu
1               5                   10

<210> SEQ ID NO 182
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Val Lys Thr Val Asp Tyr Ala Ala Leu Val Glu
1               5                   10

<210> SEQ ID NO 183
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Val Lys Ile Thr Leu Leu Ser Ala Leu Val Val
1               5                   10

<210> SEQ ID NO 184
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Val Lys Gly Ser Leu Arg Ser Ala Leu Val Val
1               5                   10

<210> SEQ ID NO 185
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Val Lys Gly Ser Leu Arg Gly Ala Leu Val Val
1               5                   10

<210> SEQ ID NO 186
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Val Val Gly Ser Leu Arg Ser Ala Leu Val Glu
1               5                   10

```
<210> SEQ ID NO 187
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Val Lys Ile Thr Leu Arg Gln Thr Asn Val Val
1               5                   10

<210> SEQ ID NO 188
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Val Lys Ile Thr Gly Arg Gln Thr Asn Val Val
1               5                   10

<210> SEQ ID NO 189
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Val Lys Ile Thr Leu Arg Gln Thr Asn Asp Val
1               5                   10

<210> SEQ ID NO 190
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Val Lys Ile Asn Gln Arg Ser Ser Leu Val Val
1               5                   10

<210> SEQ ID NO 191
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Val Lys Ile Leu Gln Arg Ala Ile Leu Val Val
1               5                   10

<210> SEQ ID NO 192
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 192

Val Lys Gln Arg Leu Arg Asp Ala Leu Val Val
1               5                   10

<210> SEQ ID NO 193
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Val Lys Ile Pro Asp Arg His Met Leu Val Val
1               5                   10

<210> SEQ ID NO 194
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Val Lys Thr Val Asp Tyr Ala Ala Leu Val Val
1               5                   10

<210> SEQ ID NO 195
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Leu Glu Gly Ser Leu Arg Ser Ile Pro Pro Glu
1               5                   10

<210> SEQ ID NO 196
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Leu Glu Gly Ser Leu Arg Gly Ile Pro Pro Glu
1               5                   10

<210> SEQ ID NO 197
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Leu Val Gly Ser Leu Arg Ser Ile Pro Pro Glu
1               5                   10
```

```
<210> SEQ ID NO 198
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Leu Glu Ala Ile Pro Arg Gln Thr Asn Pro Glu
1               5                   10

<210> SEQ ID NO 199
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Leu Glu Ala Ile Gly Arg Gln Thr Asn Pro Glu
1               5                   10

<210> SEQ ID NO 200
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Leu Glu Ala Asn Gln Arg Ser Ser Pro Pro Glu
1               5                   10

<210> SEQ ID NO 201
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Leu Glu Gln Arg Leu Arg Asp Ile Pro Pro Glu
1               5                   10

<210> SEQ ID NO 202
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Leu Glu Ala Pro Asp Arg His Met Pro Pro Glu
1               5                   10

<210> SEQ ID NO 203
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
-continued

<220> FEATURE:
<221> NAME/KEY: MOD_RES
<222> LOCATION: (6)..(6)
<223> OTHER INFORMATION: Dap(Dnp)

<400> SEQUENCE: 203

Thr Phe Arg Ser Ala Xaa
1               5
```

USE OF SERINE PROTEASE INHIBITORS IN THE TREATMENT OF SKIN DISEASES

CROSS-REFERENCE TO RELATED APPLICATIONS

This application is a continuation of U.S. patent application Ser. No. 14/447,317, filed Jul. 30, 2014, which is a continuation of U.S. patent application Ser. No. 12/863,651, filed Jan. 11, 2009, which is a national stage application under 35 U.S.C. § 371 of PCT Application No. PCT/IB2009/000089, filed Jan. 21, 2009, which claims priority to and the benefit of U.S. provisional patent applications Ser. No. 61/022,386, filed Jan. 21, 2008 and Ser. No. 61/006,576, filed Jan. 22, 2008, each of which is incorporated herein by reference in its entirety.

The instant application contains a Sequence Listing which has been filed electronically in ASCII format and is hereby incorporated by reference in its entirety. Said ASCII copy, created on May 15, 2020, is named 121089-0102_SL.txt and is 184,930 bytes in size.

FIELD OF THE INVENTION

This invention relates to therapeutic compounds which are inhibitors of serine proteases, to pharmaceutical compositions thereof and to their use in the treatment of the human or animal body. More specifically, the present invention relates to a method for the treatment, diagnosis or prognosis of skin diseases comprising the administration to a subject in need thereof of a therapeutically effective amount of a Serine protease inhibitor.

BACKGROUND OF THE INVENTION

Proteases or proteolytic enzymes are essential in organisms, from bacteria and viruses to mammals Proteases digest and degrade proteins by hydrolyzing peptide bonds. Serine proteases (EC. 3.4.21) have common features in the active site, primarily an active serine residue. There are two main types of serine proteases; the chymotrypsin/trypsin/elastase-like and subtilisin-like, which have an identical spatial arrangement of catalytic His, Asp, and Ser but in quite different protein scaffolds. However, over twenty families (S1-S27) of serine proteases have been identified that are grouped into 6 clans on the basis of structural similarity and other functional evidence, SA, SB, SC, SE, SF & SG. The family of chymotrypsin/trypsin/elastase-like serine proteases have been subdivided into two classes. The "large" class (ca 230 residues) includes mostly mammalian enzymes such as trypsin, chymotrypsin, elastase, kallikrein, and thrombin. The "small" class (ca 190 residues) includes the bacterial enzymes.

The catalytic His, Asp and Ser are flanked by substrate amino acid side chain residue binding pockets termed S1', S2', S3' etc on the C-terminal or 'prime' side of the substrate and S1, S2, S3 etc on the N-terminal side. This nomenclature is as described in Structure and Mechanism in Protein Science: A Guide to Enzyme Catalysis and Protein Folding, Alan Fersht, 1999 (W.H. Freeman and Company) pages 40-43 and Brik et al, Org. Biomol. Chem., 2003, 1, 5-14. The chymotrypsin/trypsin/elastase-like serine proteases can also be further subdivided by the residues present in the 51 pocket as described in Introduction to Protein Structure, Carl Branden and John Tooze, 1991 (Garland Publishing Inc) pages 231-241. The subdivisions are chymotrypsin-like (Gly-226, Ser-189 and Gly-216 in S1 pocket), trypsin-like (Gly-226, Asp-189 and Gly-216 in S1) and elastase-like (Val-226 and Thr-216 in S1) where the residues numbering is taken from the standard chymotrypsin numbering. The trypsin-like serine proteases prefer substrates which place either Lys or Arg in the S1 pocket.

The serine proteases have a common catalytic mechanism characterized by a particularly reactive Ser residue at position 195 using the chymotrypsin numbering system. Examples of serine proteases include trypsin, tryptase, chymotrypsin, elastase, thrombin, plasmin, kallikrein, Complement Cl, acrosomal protease, lysosomal protease, cocoonase, α-lytic protease, protease A, protease B, serine carboxypeptidase 7E, subtilisin, urokinase (uPA), Factor Vila, Factor IXa, and Factor Xa. The serine proteases have been investigated extensively for many years and are a major focus of research as a drug target due to their role in regulating a wide variety of physiological processes.

Processes involving serine proteases include coagulation, fibrinolysis, fertilization, development, malignancy, neuromuscular patterning and inflammation. It is well known that these compounds inhibit a variety of circulating proteases as well as proteases that are activated or released in tissue. It is also known that serine protease inhibitors inhibit critical cellular processes, such as adhesion, migration, free radical production and apoptosis. In addition, animal experiments indicate that intravenously administered serine protease inhibitors, variants or cells expressing serine protease inhibitors, provide protection against tissue damage.

The serine proteases Kallikreins (KLK) are shown to play an essential role in the normal physiology of skin. KLK5 and 7 were originally isolated and cloned from the stratum corneum (Hansson et al., 1994; Brattsand and Egelrud, 1999) and were shown to be involved in skin desquamation through processing of extracellular adhesive proteins of the corneodesmosomes, i.e. corneodesmosin (CDSN), desmoglein 1 (DSG1), and desmocollin 1 (DSC1) (Caubet et al., 2004; Descargues et al., 2005). KLK5 was shown to cleave all three components, while KLK7 was able to digest only CDSN and DSC1 (Caubet et al., 2004). Further IHC studies supported the proposed role of KLK7 in desquamation (Sondell et al., 1995). In-vitro studies demonstrated an potential activation mechanism of KLK7 through a proteolytic cascade, involving KLK5, and 14 (Brattsand et al., 2005). Also, varying levels of KLKs 1, 6, 8, 10, 11, and 13 have been reported in SC (Komatsu et al., 2005; Borgono et al., 2006) and KLK1, 5, 6, and 14 are believed to be involved in skin desquamation through DSG1 processing (Borgono et al., 2006). KLK14 is believed to play a major role in skin remodeling as it contributes to approximately half of the total trypsin-like proteolytic activity in the SC layer (Stefansson et al., 2006). KLK8 is suggested to play an overlapping function in skin desquamation processing DSG1 and CDSN (Kishibe et al., 2006). An additional antimicrobial function KLKs in skin through the regulation of cathelicidin peptides was shown in vitro and in vivo (Yamasaki et al., 2006).

Imbalances in the proteolytic activity of KLKs, through gene over-expression or dysregulation of activity is reported in a large number of skin disorders, including chronic itchy dermatitis, peeling skin syndrome, psoriasis, atopic dermatitis, and Netherton syndrome (Komatsu et al., 2005b; Descargues et al., 2005; Hachem et al., 2006; Komatsu et al., 2006; Hansson et al., 2002; Ekholm and Egelrud, 1999). The expression of multiple KLKs is significantly upregulated in psoriasis, atopic dermatitis, peeling skin syndrome type-B, and chronic lesions of atopic dermatitis (Komatsu et al., 2005b; Komatsu et al., 2006; Hansson et al., 2002). Patients with Netherton syndrome, an autosomal recessive skin disorder, have shown frame shifts and non-sense mutations in the SPINK5 gene encoding for LEKTI (Chavanas et al., 2000; Komatsu et al., 2002; Chavanas et al., 2000; Sprecher et al., 2001), LEKTI being a serine protease inhibitor with activity against several KLKs, including KLK5, 6, 7, 13, and 14 (Borgono et al., 2006; Egelrud et al., 2005; Deraison et al., 2007). Such genetic defects lead to loss of inhibitory domains (Chavanas et al., 2000; Sprecher et al., 2001).

Also of interest is the potential involvement of kallikreins in the skin inflammation aspect of desquamation type disorders through activation of protease activated receptors (PARs). PARs 1-4 are G protein-coupled receptors, activated by various proteases including kallikreins. PAR2 is of special interest, as it is activated by trypsin cleavage and is co-localized with tissue kallikreins in skin tissue. In skin lesions from atopic dermatitis and Netherton syndrome patients, PAR2 receptors were found overexpressed and co-localized with human tissue kallikreins (Descargues et al., 2006). This lead to the hypothesis that such a KLK-PAR pathway is involved in the pathogenesis of these diseases and that KLKs induce inflammation in these skin disorders via PAR2 activation.

Recent in vitro and in vivo work by Oikonomopoulou et al. (2006) has demonstrated that PAR activity may be targeted by active KLK5, 6, and 14. KLK5 and KLK6 were shown to activate PAR2, whereas KLK14 was reported to inactivate PAR1 and activate PAR2 and PAR4. Other reports showed activation of either PAR1 or PAR2 by KLK1, 2, 4, 5, 6 and 14 in different cell ltypes (Mize et al., 2008; Stefansson et al., 2008; Vandell et al., 2008)

PAR2 receptors are attractive research targets for dermatologists and cosmeticians due to implication in skin inflammation, cell proliferation, tumor suppression, skin pigmentation, and skin moisture. As activators of PAR2 receptors, kallikreins are of increasing interest to researchers investigating the above-mentioned skin processes. Natural non-denatured soybean-derived trypsin inhibitors are used as ingredients of cosmetic products targeting skin pigmentation, UV exposure, and skin moisture. Soybean-derived soy seeds and soymilk contain soybean trypsin inhibitor (STI) and Bowman-Birk inhibitor (BBI), respectively (Paine et al., 2001). The desired effects of these products are attributed to trypsin inhibition leading to blockade of PAR2 activation. KLK5 and KLK7 have been shown to be overexpressed under UVB irradiation concomitantly to a decrease of LEKTI expression, suggesting a contribution of these skin kallikreins in stratum corneum desquamation under UVB stress (Nin M et al., 2008).

It has been suggested that STI reduces UV light-induced skin cancer, as topical application of STI halts tumor progression in mice exposed to UVB for long periods (Huang et al., 2004). It is suggested that products containing natural soybean extracts block PAR2 activation by kallikrein inhibition. STI has been proven to inhibit trypsin-like KLK5 and 14 with high efficiency (Brattsand et al., 2005). Reduced KLK5 and 7 expression in the upper SC of dry skin and elevated KLK activity following UV radiation have been reported (Voegeli et al., 2007).

Serine protease inhibitors have also been predicted to have potential beneficial uses in the treatment of disease a wide variety of clinical areas such as oncology, neurology, hematology, pulmonary medicine, immunology, inflammation and infectious disease. Serine protease inhibitors may also be beneficial in the treatment of thrombotic diseases, asthma, emphysema, cirrhosis, arthritis, carcinoma, melanoma, restenosis, atheroma, trauma, shock and reperfusion injury. A useful review is found in Expert Opin. Ther. Patents (2002), 12(8). Serine protease inhibitors are disclosed in US published patent applications US 2003/0100089 and 2004/0180371 and in U.S. Pat. Nos. 6,784,182, 6,656,911, 6,656,910, 6,608,175, 6,534,495 and 6,472,393.

Skin diseases such as contact hypersensitivity, atopic dermatitis, rare genetic skin diseases (e.g. Netherton syndrome) and psoriasis are characterized by hyperproliferative and inflammatory skin reactions. A large population suffers from these diseases. For example, atopic dermatitis, a hereditary chronic disease of the skin, affects approximately 8 million adults and children in the United States. It is believed that a combination of multiple factors including genetic, environmental, and immunological factors may cause skin diseases. Although most skin diseases are not fatal, they significantly affect quality of life of those who suffer from the diseases.

Commonly used steroid-containing ointment or anti-histamine agents for treating skin diseases frequently cause considerable side effects. For example, steroids of external or oral application make the skin layer thin, cause osteoporosis, and inhibit growth in children upon long-term use. It was also observed that the termination of steroid application is often followed by lesion recurrence.

Therefore is a need to develop improved non-steroid agents for therapeutic, prophylactic or diagnostic approaches for the treatment of skin diseases. The present invention provides an improved and reliable method for the treatment, diagnosis or prophylaxis of skin diseases comprising the administration to a subject in need thereof of a therapeutically effective amount of a Serine protease inhibitor.

These and other objects as will be apparent from the foregoing have been achieved by the present invention.

SUMMARY OF THE INVENTION

The present invention concerns a method of treating or preventing as skin disease comprising administering to a mammal a pharmaceutical composition comprising a recombinant Serine protease inhibitor.

Also disclosed is the use of a Serine protease inhibitor in the preparation of a medicament for the treatment of a skin disease.

Another object of the invention is a kit for treating or preventing as skin disease comprising a pharmaceutical composition of a recombinant Serine protease inhibitor.

Other objects and advantages will become apparent to those skilled in the art from a review of the ensuing detailed description, which proceeds with reference to the following illustrative drawings, and the attendant claims.

BRIEF OF THE FIGURES

FIG. 1 represents the DNA and protein sequences of hK2 protease inhibitor MD 820

FIG. 2 represents the DNA and protein sequences of hK2 protease inhibitor MD 62

FIG. 3 represents the DNA and protein sequences of hK2 protease inhibitor MD 83

FIG. 4 represents the DNA and protein sequences of hK2 protease inhibitor MD 67

FIG. 5 represents the DNA and protein sequences of hK2 protease inhibitor MD 61

FIG. 6 represents the DNA and protein sequences of hK2 protease inhibitor MD 518

FIG. 7 represents the DNA and protein sequences of hK2 protease inhibitor MDCI

FIG. 8 represents the DNA and protein sequences of ACT-wildtype.

FIG. 9 represents the DNA and protein sequences of hK14 protease inhibitor ACT-G1.

FIG. 10 represents the DNA and protein sequences of hK14 protease inhibitor ACT-G1G FIG. 11 represents the DNA and protein sequences of hK14 protease inhibitor ACT-C11.

FIG. 12 represents the DNA and protein sequences of hK14 protease inhibitor ACT-C11G.

FIG. 13 represents the DNA and protein sequences of hK14 protease inhibitor ACT-E5.

FIG. 14 represents the DNA and protein sequences of hK14 protease inhibitor ACT-E8.

FIG. 15 represents the DNA and protein sequences of hK14 protease inhibitor ACT-F11.

FIG. 16 represents the DNA and protein sequences of hK14 protease inhibitor ACT-F3.

FIG. 17 represents the DNA and protein sequences of hK14 protease inhibitor ACT-G9.

FIG. 18 represents the DNA and protein sequences of AAT-wildtype.

FIG. 19 represents the DNA and protein sequences of hK14 protease inhibitor AAT-G1.

FIG. 20 represents the DNA and protein sequences of hK14 protease inhibitor AAT-G1G FIG. 21 represents the DNA and protein sequences of hK14 protease inhibitor AAT-C11.

FIG. 22 represents the DNA and protein sequences of hK14 protease inhibitor AAT-C11G.

FIG. 23 represents the DNA and protein sequences of hK14 protease inhibitor AAT-E5.

FIG. 24 represents the DNA and protein sequences of hK14 protease inhibitor AAT-E8.

FIG. 25 represents the DNA and protein sequences of hK14 protease inhibitor AAT-F11.

FIG. 26 represents the DNA and protein sequences of hK14 protease inhibitor AAT-F3.

FIG. 27 represents the DNA and protein sequences of hK14 protease inhibitor AAT-G9.

FIG. 28 represents the DNA and protein sequences of hK14 protease inhibitor AAT-G1V.

FIG. 29 represents the DNA and protein sequences of hK14 protease inhibitor AAT-C11D.

Figure 31:
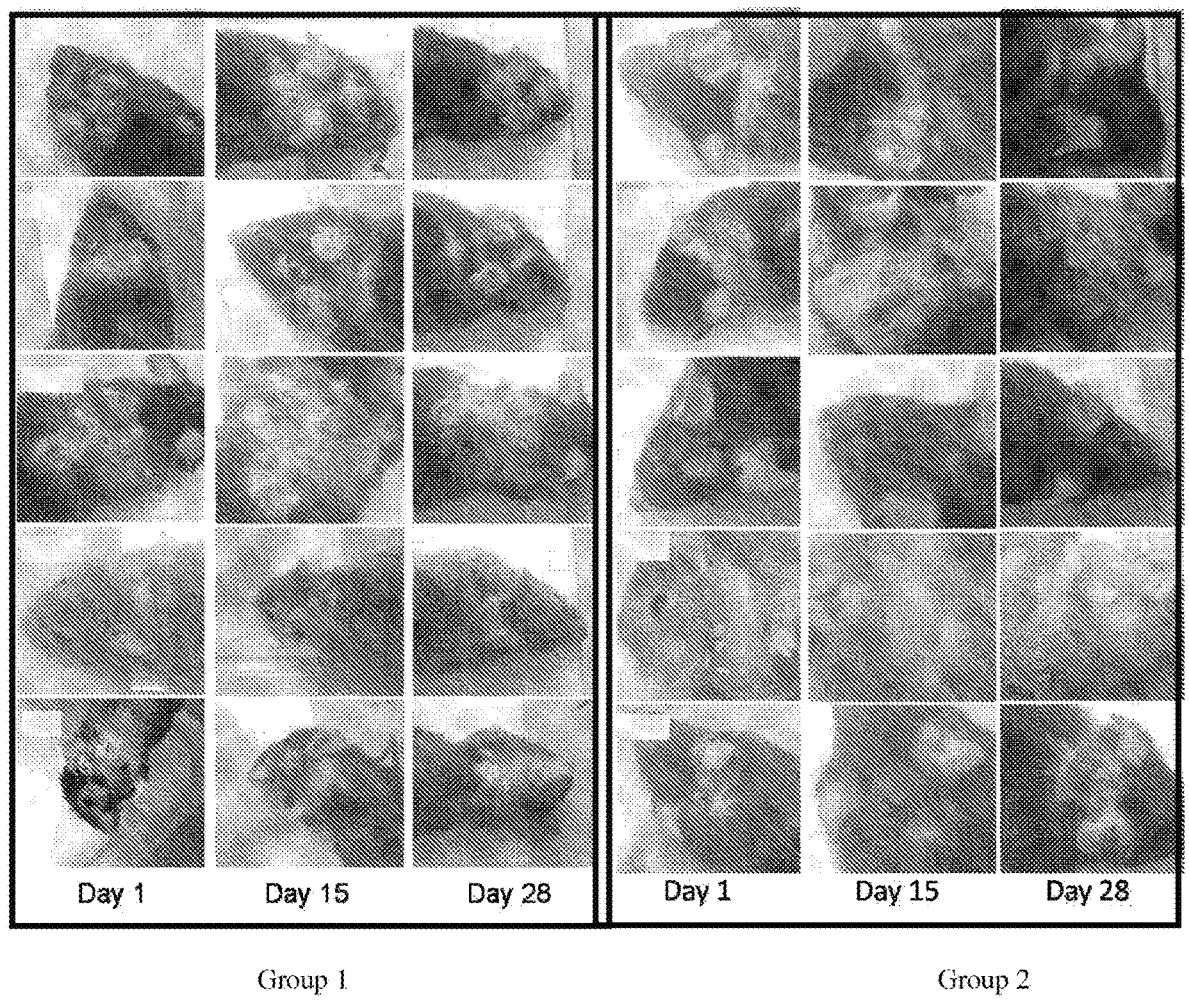

FIG. 31 shows the skin lesion size development on Netherton Syndrom mouse model. Monitoring of lesion sizes and lesion grade after 1, 15 and 28 days of topical application of 2% NATROSOL® (hydroxyethylcellulose (HEC)) (group 1, control) or MDPK67b in 2% NATROSOL® (hydroxyethylcellulose (HEC)) (group 2).

DETAILED DESCRIPTION OF THE INVENTION

The present invention relates to the use of a Serine protease inhibitor in the preparation of a medicament for the treatment of a skin disease. Biologically active fragments of a Serine protease inhibitor are also useful in the preparation of said medicament.

Some of the serine proteases of the chymotrypsin superfamily, including t-PA, plasmin, u-PA and the proteases of the blood coagulation cascade are large molecules that contain, in addition to the serine protease catalytic domain, other structural domains responsible in part for regulation of their activity (Barrett, 1986; Gerard et al, 1986; Blasi et al., 1986). Among important serine proteases are trypsin-like enzymes, such as trypsin, tryptase, thrombin, kallikrein, and factor Xa. The serine protease targets are associated with processes such as blood clotting; complement mediated lysis, the immune response, glomerulonephritis, pain sensing, inflammation, pancreatitis, cancer, regulating fertilization, bacterial infection and viral maturation. By inhibiting serine proteases which have high specificity for a particular target, one can inhibit in vivo numerous biological processes, which may have dramatic effects on a host.

Serine proteinase inhibitors (serpins) comprise a diverse group of proteins that form a superfamily already including more than 100 members, from such diverse organisms as viruses, plants and humans Serpins have evolved over 500 million years and diverged phylogenetically into proteins with inhibitory function and non-inhibitory function (Hunt and Dayhoff, 1980). Non-inhibitory serpins such as ovalbumin lack protease inhibitory activity (Remold-O'Donnell, 1993). The primary function of serpin family members appears to be neutralizing overexpressed serine proteinase activity (Potempa et al., 1994). Serpins play a role in extracellular matrix remodeling, modulation of inflammatory response and cell migration (Potempa et al., 1994).

Serine protease inhibitors are divided into the following families: the bovine pancreatic trypsin inhibitor (Kunitz) family, also known as basic protease inhibitor (Ketcham et al., 1978); the Kazal family; the *Streptomyces* subtilisin inhibitor family; the serpin family; the soybean trypsin inhibitor (Kunitz) family; the potato inhibitor family; and the Bowman-Birk family (Laskowski et al., 1980; Read et al., 1986; Laskowski et al., 1987). Serine protease inhibitors belonging to the serpin family include the plasminogen activator inhibitors PAI-1, PAI-2 and PAI-3, Cl esterase inhibitor, alpha-2-antiplasmin, contrapsin, alpha-1-antitrypsin, antithrombin III, protease nexin I, alpha-1-antichymotrypsin, protein C inhibitor, heparin cofactor II and growth hormone regulated protein (Carrell et al., 1987; Sommer et al., 1987; Suzuki et al., 1987; Stump et al., 1986).

Many of the serine protease inhibitors have a broad specificity and are able to inhibit both the chymotrypsin superfamily of proteases, including the blood coagulation serine proteases, and the *Streptomyces* subtilisin superfamily of serine proteases (Laskowski et al., 1980). The inhibition of serine proteases by serpins has been reviewed in Travis et al. (1983); Carrell et al. (1985); and Sprengers et al. (1987). Crystallographic data are available for a number of intact inhibitors including members of the BPTI, Kazal, SSI, soybean trypsin and potato inhibitor families, and for a cleaved form of the serpin alpha-1-antitrypsin (Read et al., 1986). Despite the fact that these serine protease inhibitors are proteins of diverse size and sequence, the intact inhibitors studied to date all have in common a characteristic loop, termed the reactive site loop, extending from the surface of the molecule that contains the recognition sequence for the active site of the cognate serine protease (Levin et al., 1983). The structural similarity of the loops in the different serine protease inhibitors is remarkable (Papamokos et al., 1982). The specificity of each inhibitor is thought to be determined primarily by the identity of the amino acid that is immediately amino-terminal to the site of potential cleavage of the inhibitor by the serine protease. This amino acid, known as the Pi site residue, is thought to form an acyl bond with the serine in the active site of the serine protease (Laskowski et al., 1980). Whether or not a serpin possesses inhibitory function depends strongly on the consensus sequence located in the hinge region of the reactive site loop near the carboxy-terminus of the coding region. Outside of the reactive site loop, the serine protease inhibitors of different families are generally unrelated structurally, although the Kazal family and *Streptomyces* subtilisin family of inhibitors display some structural and sequence similarity.

As used herein, the following definitions are supplied in order to facilitate the understanding of the present invention.

"A" or "an" means "at least one" or "one or more."

The term "comprise" is generally used in the sense of include, that is to say permitting the presence of one or more features or components.

As used herein, the terms "protein", "polypeptide", "polypeptidic", "peptide" and "peptidic" or "peptidic chain" are used interchangeably herein to designate a series of amino acid residues connected to the other by peptide bonds between the alpha-amino and carboxy groups of adjacent residues.

Preferably, the Serine protease inhibitor is a recombinant Serine protease inhibitor and is selected from the group comprising the SEQ ID NOS:2, 4, 6, 8, 10, 12 and 14 or a biologically active fragment thereof having a Serine protease inhibitor activity.

Preferably also the recombinant Serine protease inhibitor is selected from the group comprising the SEQ ID NOS:39 to 59 or a biologically active fragment thereof having a Serine protease inhibitor activity.

"Amino acid residue" means any amino acid residue known to those skilled in the art. This encompasses naturally occurring amino acids (including for instance, using the three-letter code, Ala, Arg, Asn, Asp, Cys, Gln, Glu, Gly, His, Be, Leu, Lys, Met, Phe, Pro, Ser, Thr, Trp, Tyr, Val), as well as rare and/or synthetic amino acids and derivatives thereof (including for instance Aad, Abu, Acp, Ahe, Aib, Apm, Dbu, Des, Dpm, Hyl, McLys, McVal, Nva, and the like).

Said amino acid residue or derivative thereof can be any isomer, especially any chiral isomer, e.g. the L- or D-isoform.

By amino acid derivative, we hereby mean any amino acid derivative as known in the art. For instance, amino acid derivatives include residues derivable from natural amino acids bearing additional side chains, e.g. alkyl side chains, and/or heteroatom substitutions.

"Biologically active fragments" refer to sequences sharing at least 40% amino acids in length with the respective sequence of the substrate active site. These sequences can be used as long as they exhibit the same properties as the native sequence from which they derive. Preferably these sequences share more than 70%, preferably more than 80%, in particular more than 90% amino acids in length with the respective sequence the substrate active site.

The present invention also includes variants of a Serine protease inhibitor sequence. The term "variants" refer to polypeptides having amino acid sequences that differ to some extent from a native sequence polypeptide that is amino acid sequences that vary from the native sequence by conservative amino acid substitutions, whereby one or more amino acids are substituted by another with same characteristics and conformational roles. The amino acid sequence variants possess substitutions, deletions, and/or insertions at certain positions within the amino acid sequence of the native amino acid sequence. Conservative amino acid substitutions are herein defined as exchanges within one of the following five groups:

I. Small aliphatic, nonpolar or slightly polar residues: Ala, Ser, Thr, Pro, Gly
II. Polar, positively charged residues: His, Arg, Lys
III. Polar, negatively charged residues: and their amides: Asp, Asn, Glu, Gln
IV. Large, aromatic residues: Phe, Tyr, Trp
V. Large, aliphatic, nonpolar residues: Met, Leu, He, Val, Cys.

"Administering", as it applies in the present invention, refers to contact of a pharmaceutical, therapeutic, diagnostic agent or composition, to the subject, preferably a human.

The term "kallikrein" relates to glandular or tissue kallikreins. Glandular or tissue kallikreins are a sub-family of serine proteases, with a high degree of substrate specificity and diverse expression in various tissues and biological fluids. The term "kallikrein" appeared in the literature for the first time in the 1930s, when large amounts of protease enzymes were found in pancreas isolates (pancreas is "Kallikreas" in Greek) (Kraut et al. 1930, Werle 1934). Nowadays kallikrein enzymes are divided into two groups, plasma and tissue kallikreins, which differ significantly in their molecular weight, substrate specificity, immunological characteristics, gene structure, and type of the kinin released.

Kallikreins comprise a family of 15 homologous single chain, secreted serine endopeptidases of ~25-30 kDa, with orthologues present in species from at least six mammalian orders. These kallikreins are hK2, hK3, hK2, hK5, hK6, hK7, hK8, hK9 hK10, hK11, hK12, hK13, hK14 and hK15. Preferably, kallikreins to be inhibited are selected from the group comprising hK2, hK5, hK7, and hK14.

"Disease", as used herein, refers to a pathological condition of a part, organ, or system of an organism resulting from various causes, such as infection, genetic defect, or environmental stress, and characterized by an identifiable group of signs or symptoms.

The epidermis has been shown to express several serine proteases including kallikrein, urokinase, plasmin, tyrptase-like and neutrophile elastase enzymes. These serine proteases are involved in multiple activities in the skin including epidermal cell proliferation, cell differentiation, skin and lipid barrier homeostasis and tissue remodelling. Most importantly, proteolysis of stratum corneum (SC) corneodesmosomes by serine proteases together with other enzymes is a crucial event prior to shedding of the outermost skin layer, called desquamation. Furthermore, increased protease activity, including kallikrein, plasmin and urokinase enzymes are implicated in inflammatory reactions of the skin. A list with inflammatory skin diseases is shown in TABLE XX.

Increased protease activity was also observed as stress response to various stimuli including environmental factors as ultraviolet radiation exposure and temperature changes or as reaction to different surfactants.

Several kallikreins, notably hK5, hK7 and hK14 have been implicated in the proteolytic cascade in skin desquamation. This proteolytic process is controlled through a complex inhibition and activation process and its deregulation can cause serious skin disorders. Rare genetic diseases (Netherton Syndrome, peeling skin syndrome) as well as more common skin diseases like atopic dermatitis or psoriasis are characterized by increased desquamation of the skin caused at least in part by an increased kallikrein activity.

The present invention also relates to the use of a Serine protease in the preparation of a cosmetic or cosmeceutical agent for the treatment or improvement of an undesirable skin condition. Biologically active fragments of a Serine protease inhibitor are also useful in the preparation of said cosmetic or cosmeceutical agent.

"An undesirable skin condition" refers, in the present invention, to a problem affecting the skin or the appearance of the skin which might not always be considered as a disease.

As used herein "Cosmetics" are compositions used to enhance or protect the appearance of the human skin. Cosmetics include skin-care creams, lotions, powders, perfumes, lipsticks, fingernail and toenail polishes, eye and facial makeup, permanent waves, hair colors, hair sprays and gels, deodorants, baby products, bath oils, bubble baths, bath salts, butters and many other types of products.

"Cosmeceuticals" are cosmetic products that are thought to have drug-like benefits. Examples of products typically labeled as cosmeceuticals include anti-aging creams and moisturizers. Cosmeceuticals may contain purported active ingredients such as vitamins, phytochemicals, enzymes, antioxidants, and essential oils.

As used herein, "Skin disease" relates to conditions affecting the skin. Usually, the skin disease is selected from Table XX. Preferably, the invention is suitable for treatment of skin diseases, such as atopic dermatitis, contact dermatitis (allergy), contact dermatitis (irritant), eczema, psoriasis, acne, epidermal hyperkeratosis, acanthosis, epidermal inflammation, dermal inflammation or pruritus, rosacea, netherton syndrome, peeling skin syndrome type A and B, hereditary ichtyosis, hidradenitis suppurativa and erythroderma (generalized exfoliative dermatitis). Most preferably, the skin disease is selected from the group comprising Netherton syndrome, Atopic dermatitis, Psoriasis and Peeling Skin Syndrome.

Netherton syndrome (NS) is a rare autosomal recessive genodermatosis caused by mutations in SPINK5 (LEKTI) one of the major inhibitor of the skin kallikrein cascade. Increased kallikrein activities have been shown to be causative for its clinical symptoms.
NS, a multisystem ichthyosiform syndrome, is characterized by ichthyosis, erythroderma, hair shaft defects and atopic features. Multiple infections due to the seriously impaired barrier function of the skin are very common.
NS is very rare, but little data on frequency is available, probably in part due to the difficulty to identify NS. Currently, less than 10 cases per million are diagnosed.
Treatment options are very limited and non-curative. They concentrate mainly on management of the various cutaneous infections and reduction of itching and pain (e.g. corticosteroid).
Excessive kallikrein activity (hK5, hK7, hK14) was proven causative for symptoms of the skin disorder. Decreased activity of the natural kallikrein inhibitor (LEKTI) could be replaced by alternative kallikrein inhibitors.

Surprisingly, Applicants have shown, e.g. in example 4, that the application of Serine protease inhibitors including MD67 (SEQ ID NO:8) mouse model (orthotopic hK5 overexpressing) considerably decreased the severity of the symptoms, which were observed in the untreated skin disease (e.g. NS) models. The symptoms are characterized by severe peeling of the skin, due to premature desmosomal protein degradation resulting in splitting of corneodesmosomes and stratum corneum detachment. This causes a severe loss of skin barrier functions leading to severe dehydratation, erythema and intense scratching.

Atopic dermatitis (AD) is a pruritic disease of not well defined origin that usually starts in early infancy and is typified by itching, eczematous lesions and dry, thick skin. AD is associated with other atopic diseases (eg, asthma, allergic reactions in about 30% of patients) and cutaneous infections are common.

The pathophysiology of AD is poorly understood. There appears to be a genetic component. An immune defect involving an abnormality of TH2 cells is suggested and a dysregulation of protease activity was found to be involved in the disease. This dysregulation is believed to cause a defective barrier function in the stratum corneum leading to the entry of antigens, which results in the production of various inflammatory cytokines. The prevalence rate in US is 10-12% in children and 0.9% in adults. In other developed countries the prevalence rate is as high as 18% and is rising, especially in developed countries. The disease is chronic, but the majority of patients improve from childhood to adult age.
No curative treatment is available yet. Depending on the severity of the symptoms topical steroids, antihistamines and immunomodulators or antibiotics, antiviral and antifungal agents are usually prescribed.

Psoriasis is a chronic disease, it is noncontagious and commonly appears as inflamed, edematous skin lesions, but also occurs on the oral mucosa. Joints (arthritis) also are affected in 10% of patients. Flares are related to various systemic and environmental factors including stress events or infections. There is a genetic predisposition for psoriasis and there is mounting evidence for signs of an autoimmune disorder. Increased protease (e.g. kallikrein) activity is involved in the typical excessive desquamation of the skin. In the US 2 to 3% of the population are affected and over 200,000 new cases occur annually. Approximately 1.5 million people with psoriatic arthritis seek medical care each year and 400 hundred people die annually from psoriasis-related causes. Incidence of psoriasis in other countries is similar but dependent on the climate and genetic heritage of the population. It is less common in the tropics and in dark-skinned persons.

Currently, there is no curative treatment. Depending on severity of symptoms topical corticosteroids, coal tar, keratolytic agents or retinoids are prescribed.

"Mammal" for purposes of treatment refers to any animal classified as a mammal, including humans, domestic and farm animals, and zoo, sports, or pet animals, such as dogs, horses, cats, cows, monkeys etc. Preferably, the mammal is human.

"Treatment" refers to both therapeutic treatment and prophylactic or preventative measures. Those in need of treatment include those already with the disorder as well as those in which the disorder is to be prevented. Hence, the mammal to be treated herein may have been diagnosed as having the disorder or may be predisposed or susceptible to the disorder.

The term "subject" refers to patients of human or other mammal and includes any individual it is desired to examine or treat using the methods according to the present invention. However, it will be understood that "patient" does not automatically imply that symptoms or diseases are present.

The phrase "pharmaceutically acceptable" refers to molecular entities and compositions that are physiologically tolerable and do not typically produce an allergic or similar untoward reaction, such as gastric upset, dizziness and the like, when administered to a human.

As used herein, the term "protease" refers to a class of enzymes which recognizes a molecule and cleaves an activation sequence in the molecule. The protease can be an endopeptidase which cleaves internal peptide bonds. Alternatively, the protease can be an exopeptidase which hydrolyzes the peptide bonds from the N-terminal end or the C-terminal end of the polypeptide or protein molecule. The protease folds into a conformation to form a catalytic site which receives and cleaves the activation sequence.

"Inhibitors" refer to a polypeptide, or a chemical compound, that specifically inhibit the function of a kallikrein or serine protease by, preferably, binding to said kallikrein or serine protease.

"Reactive Serpin Loop" or "Reactive Site Loop" or RSL refers to an exposed flexible reactive-site loop found in serpin and which is implicated in the interaction with the putative target protease. From the residue on the amino acid side of the scissile bond, and moving away from the bond, residues are conventionally called P1, P2, P3, etc. Residues that follow the scissile bond are called P1', P2', P3', etc. Usually, the RSL is composed of 6 to 12 amino acid residues.

"Serine protease inhibitors" or serpin according to the invention can be selected from the group comprising the α-1antichymotrypsin (ACT), protein C inhibitor (PCI), α-1antiproteinase (AAT), human α-1antitrypsin-related protein precursor (ATR), α-2-plasmin inhibitor (AAP), human anti-thrombin-III precursor (ATIII), protease inhibitor 10 (PI10), human collagen-binding protein 2 precursor (CBP2), protease inhibitor 7 (PI7), protease inhibitor leuserpin 2 (HLS2), human plasma protease C1 inhibitor (C1 INH), monocyte/neutrophil elastase inhibitor (M/NEI), plasminogen activator inhibitor-3 (PAI3), protease inhibitor 4 (PI4), protease inhibitor 5 (PI5), protease inhibitor 12 (PI12), human plasminogen activator inhibitor-1 precursor endothelial (PAI-1), human plasminogen activator inhibitor-2 placental (PAI2), human pigment epithelium-derived factor precursor (PEDF), protease inhibitor 6 (PI6), protease inhibitor 8 (PI8), protease inhibitor 9 (PI9), human squamous cell carcinoma antigen 1 (SCCA-1), human squamous cell carcinoma antigen 2 (SCCA-2), T4-binding globulin (TBG), Megsin, and protease inhibitor 14 (PI14), fragments thereof, molecular chimeras thereof, combinations thereof and/or variants thereof.

Since most of these serpins have different names, Applicant includes below a table I summarizing their specifications:

TABLE I

| Serpin | Accession Number | RSL sequence |
|---|---|---|
| PI or AAT, A1AT_HUMAN ALPHA-1-ANTITRYPSIN PRECURSOR (ALPHA-1 PROTEASE INHIBITOR) (ALPHA-1-ANTIPROTEINASE) | sp\|P01009\| | GTEAAGAMFLEAIPMSIPPE SEQ ID NO: 85 |
| PIL or ATR, A1AU_HUMAN ALPHA-1-ANTITRYPSIN-RELATED PROTEIN PRECURSOR | sp\|P20848\| | GTEATGAPHLEEKAWSKYQT SEQ ID NO: 86 |
| PLI OR AAP, A2AP_HUMAN ALPHA-2-ANTIPLASMIN PRECURSOR (ALPHA-2-PLASMIN INHIBITOR) (ALPHA-2-PI) (ALPHA-2-AP) | sp\|P08697\| | GVEAAAATSIAMSRMSLSSF SEQ ID NO: 87 |
| AACT, AACT_HUMAN ALPHA-1-ANTICHYMOTRYPSIN PRECURSOR (ACT) | sp\|P01011\| | GTEASAATAVKITLLSALVE SEQ ID NO: 88 |
| AT3, ANT3_HUMAN ANTITHROMBIN-III PRECURSOR (ATIII) | sp\|P01008\| | GSEAAASTAVVIAGRSLNPN SEQ ID NO: 89 |
| PI10, BOMA_HUMAN BOMAPIN (PROTEASE INHIBITOR 10) | sp\|P48595\| | GTEAAAGSGSEIDIRIRVPS SEQ ID NO: 90 |
| CBP2, CBP2_HUMAN COLLAGEN-BINDING PROTEIN 2 PRECURSOR (COLLIGIN 2) | sp\|P50454\| | GNPFDQDIYGREELRSPKLF SEQ ID NO: 91 |
| PI7 or PN1, GDN_HUMAN GLIA DERIVED NEXIN PRECURSOR (GDN) (PROTEASE NEXIN I) (PN-1) (PROTEASE INHIBITOR 7) | sp\|P07093\| | GTKASAATTAILIARSSPPW SEQ ID NO: 92 |
| HCF2, HEP2_HUMAN HEPARIN COFACTOR II PRECURSOR (HC-II) (PROTEASE INHIBITOR LEUSERPIN 2) (HLS2) | sp\|P05546\| | GTQATTVTTVGFMPLSTQVR SEQ ID NO: 93 |
| C1NH or C1IN, IC1_HUMAN PLASMA PROTEASE C1 INHIBITOR PRECURSOR (C1 INH) | sp\|P05155\| | GVEAAAASAISVARTLLVFE SEQ ID NO: 94 |
| ELANH2 or PI2, ILEU_HUMAN LEUKOCYTE ELASTASE INHIBITOR (LEI) (MONOCYTE/NEUTROPHIL ELASTASE INHIBITOR) (M/NEI) (EI) | sp\|P30740\| | GTEAAAATAGIATFCMLMPE SEQ ID NO: 95 |
| PCI or PLANH3 or PROCI, IPSP_HUMAN PLASMA SERINE PROTEASE INHIBITOR PRECURSOR (PCI) (PROTEIN C INHIBITOR) (PLASMINOGEN ACTIVATOR INHIBITOR-3) (PAI3) | sp\|P05154\| | GTRAAAATGTIFTFRSARLN SEQ ID NO: 96 |
| PI4 or KST, KAIN_HUMAN KALLISTATIN PRECURSOR (KALLIKREIN INHIBITOR) (PROTEASE INHIBITOR 4) | sp\|P29622\| | GTEAAAATTFAIKFFSAQTN SEQ ID NO: 97 |
| PI5, MASP_HUMAN MASPIN PRECURSOR (PROTEASE INHIBITORS) | sp\|P36952\| | GGDSIEVPGARILQHKDELN SEQ ID NO: 98 |
| PI12, NEUS_HUMAN NEUROSERPIN PRECURSOR (PROTEASE INHIBITOR 12) | sp\|Q99574\| | GSEAAAVSGMIAISRMAVLY SEQ ID NO: 99 |
| PAI1 or PLANH1, sp\|P05121\|PAI1_HUMAN PLASMINOGEN ACTIVATOR INHIBITOR-1 PRECURSOR, ENDOTHELIAL (PAI-1) | sp\|P05121\| | GTVASSSTAVIVSARMAPEE SEQ ID NO: 100 |

TABLE I-continued

| Serpin | Accession Number | RSL sequence |
|---|---|---|
| PAI2 or PLANH2, PAI2_HUMAN PLASMINOGEN ACTIVATOR INHIBITOR-2, PLACENTAL (PAI-2) (MONOCYTE ARG-SERPIN) (UROKINASE INHIBITOR) | sp\|P05120\| | GTEAAAGTGGVMTGRTGHGG SEQ ID NO: 101 |
| PEDF, PEDF_HUMAN PIGMENT EPITHELIUM-DERIVED FACTOR PRECURSOR (PEDF) (EPC-1) | sp\|P36955\| | GAGTTPSPGLQPAHLTFPLD SEQ ID NO: 102 |
| PI6 or PTI, PTI6_HUMAN PLACENTAL THROMBIN INHIBITOR (CYTOPLASMIC ANTIPROTEINASE) (CAP) (PROTEASE INHIBITOR 6) | sp\|P35237\| | GTEAAAATAAIMMMRCARFV SEQ ID NO: 103 |
| PI8, PTI8_HUMAN CYTOPLASMIC ANTIPROTEINASE 2 (CAP2) (CAP-2) (PROTEASE INHIBITOR 8) | sp\|P50452\| | GTEAAAATAVVRNSRCSRME SEQ ID NO: 104 |
| PI9, PTI9_HUMAN CYTOPLASMIC ANTIPROTEINASE 3 (CAP3) (CAP-3) (PROTEASE INHIBITOR 9) | sp\|P50453\| | GTEAAAASSCFVVAECCMES SEQ ID NO: 105 |
| SCCA1, SCC1_HUMAN SQUAMOUS CELL CARCINOMA ANTIGEN 1 (SCCA-1) (PROTEIN T4-A) | sp\|P29508\| | GAEAAAATAVVGFGSSPAST SEQ ID NO: 106 |
| SCCA2, SCC2_HUMAN SQUAMOUS CELL CARCINOMA ANTIGEN 2 (SCCA-2) (LEUPIN) | sp\|P48594\| | GVEAAAATAVVVVELSSPST SEQ ID NO: 107 |
| TBG, THBG_HUMAN THYROXINE-BINDING GLOBULIN PRECURSOR (T4-BINDING GLOBULIN) | sp\|P05543\| | GTEAAAVPEVELSDQPENTF SEQ ID NO: 108 |
| MEGSIN | gi\|4505149\|ref\| NP_003775.1\| | GTEATAATGSNIVEKQLPQS SEQ ID NO: 109 |
| PI14, pancpin, TSA2004 | gi\|3724282\|dbj\| BAA33766.11\| | GSEAATSTGIHIPVIMSLAQ SEQ ID NO: 110 |

Advantageously, the serine protease inhibitor of the invention may be a serine protease trypsin-like enzyme and preferably a Kallikrein inhibitor. Kallikrein inhibitors of the invention are selected amongst hK2, hK3, hK4, hK5, hK6, hK7, hK8, hK9 hK10, hK11, hK12, hK13, hK14 or hK15 inhibitors. Preferably kallikreins inhibitors are selected among hK2, hK5, hK7, and hK14 inhibitors.

In case the kallikrein inhibitor is an inhibitor directed against hK2, said inhibitor can be selected among those disclosed in International Patent Application PCT/IB2004/001040, which content is incorporated herein by reference in its entirety. Preferably, the kallikrein inhibitor of the invention may be selected from the group comprising MD820, MD62, MD61, MD67 and MDCI. Most preferably this inhibitor is MD67. This application discloses a recombinant inhibitor protein of a protease comprising an inhibiting polypeptidic sequence and at least one polypeptidic sequence of a substrate-enzyme interaction site specific for a protease as well as a method for producing the recombinant inhibitor protein of a protease. Preferably the recombinant Serine protease inhibitor is selected from the group comprising the SEQ ID NOS:2, 4, 6, 8, 10, 12 and 14 or a biologically active fragment thereof having a Serine protease inhibitor activity.

As an example of serine protease inhibitor according to the invention, Applicants have surprisingly found 7 new recombinant inhibitor proteins specific for the protease hK2 as resumed below in table II, these inhibitors are:

TABLE II

| Recombinant inhibitors | Other name | SEQ ID NO: (protein) |
|---|---|---|
| rACT$_{8.20}$ | MD820 | 2 |
| rACT$_{6.2}$ | MD62 | 4 |

TABLE II-continued

| Recombinant inhibitors | Other name | SEQ ID NO: (protein) |
|---|---|---|
| rACT$_{8.3}$ | MD83 | 6 |
| rACT$_{6.7}$ | MD67 | 8 |
| rACT$_{6.1}$ | MD61 | 10 |
| ACT$_{5.18}$ | MD518 | 12 |
| ACT$_{PCI}$ | MDCI | 14 |

These inhibitor proteins have been obtained by modifying the RSL of α1-antichymotrypsin (rACT), which is known to inhibit a large panel of human enzymes such as chymotrypsin, mast cell chymase, cathepsin G, prostatic kallikreins hK2 and PSA (hK3), in order to change the specificity of this serpin. Peptide sequences, selected as substrates for the enzyme hK2 by phage display technology as explained in International Patent Application PCT/IB2004/001040, have been used to replace the scissile bond and neighbour amino acid residues of the RSL. Usually, recombinant inhibitors were produced in bacteria and purified by affinity chromatography.

Additionally, Applicants have also found that replacing residues P3-P3' located in RSL structure of rACT$_{WT}$ by substrate pentapeptide coding for the RSL of Protein C inhibitor (PCI) lead to the production of a recombinant inhibitor (MDCI) which is able to inhibit kallikreins hK2 and hK3.

In case the kallikrein inhibitor is an inhibitor directed against hK14, then said inhibitor can be selected among those disclosed in the International Patent Application PCT/IB2005/000504, which content is incorporated herein by reference in its entirety. Preferably, said recombinant inhibitor may be selected from the group comprising AAT$_{G1}$, AAT$_{G1G}$, AAT$_{C11}$, AAT$_{C11G}$, AAT$_{E5}$, AAT$_{E8}$, AAT$_{F11}$, $AAT_{F3}$, $AAT_{G9}$, $ACT_{G1}$, $AcT_{G1G}$, $ACT_{C11}$, $ACT_{C11G}$, $ACT_{E5}$, $ACT_{E8}$, $ACT_{F11}$, $ACT_{F3}$, $ACT_{G9}$, $ACT_{G1V}$, $ACT_{WT}$ and $ACT_{C11D}$. Preferably, said inhibitor protein of an hK14 protease is $AAT_{G1}$ $AAT_{G1G}$, $AAT_{C11}$, $AAT_{C11G}$, $AAT_{E5}$, $AAT_{E8}$, $AAT_{F3}$, $AAT_{G9}$, $ACT_{G1G}$, $ACT_{C11}$, $ACT_{C11G}$, $ACT_{E5}$, $ACT_{E8}$, $AGT_{F11}$, $ACT_{F3}$, $ACT_{G9}$, $ACT_{G1V}$, or $ACT_{C11D}$.

This application discloses a recombinant inhibitor protein of an hK14 protease having an inhibiting polypeptidic sequence and at least a polypeptidic sequence of a substrate-enzyme interaction site specific for said hK14 protease. Preferably, said recombinant inhibitor protein of an hK14 protease has, under physiological conditions,
  i) a stochiometry of inhibition (SI) equal or below to 11.7 after at least 4 hours of incubation,
  ii) an association rate (Ka) of at least 7,500 $M^{-1}$ $s^{-1}$,
  iii) an inhibitory activity of 100% after at least 30 minutes of incubation.

In addition, the inhibiting polypeptidic sequence of the protease inhibitor may also be selected from a cysteine protease since there are now a number of well-documented instances of inhibition of cysteine proteases by serpins (Gettins P. G. W., 2002 "Serpin structure, mechanism, and function" in *Chem. Rev,* 102, 4751-4803). These examples include inhibition of cathepsins K, L and S by the serpin squamous cell carcinoma antigen1, inhibition of prohormone thiol proteinase by the α-1antichymotrypsin, and inhibition of members of the caspase family, including caspase 1 (interleukine 1β converting enzyme), caspase 3, and caspase 8 by the viral serpin crmA and caspases 1, 4 and 8 by the human serpin PI9.

Usually, the serine protease inhibitor is a recombinant inhibitor protein. Thus, when recombinant techniques are employed to prepare a Serine protease inhibitor, nucleic acid molecules or fragments thereof encoding the polypeptides are preferably used.

Therefore the present invention also relates to a purified and isolated DNA sequence encoding the Serine protease inhibitor as described above.

"A purified and isolated DNA sequence" refers to the state in which the nucleic acid molecule encoding the recombinant inhibitor protein of a protease of the invention, or nucleic acid encoding such recombinant inhibitor protein of a protease will be, in accordance with the present invention. Nucleic acid will be free or substantially free of material with which it is naturally associated such as other polypeptides or nucleic acids with which it is found in its natural environment, or the environment in which it is prepared (e. g. cell culture) when such preparation is by recombinant DNA technology practiced in vitro or in vivo.

DNA which can be used herein is any polydeoxynuclotide sequence, including, e.g. double-stranded DNA, single-stranded DNA, double-stranded DNA wherein one or both strands are composed of two or more fragments, double-stranded DNA wherein one or both strands have an uninterrupted phosphodiester backbone, DNA containing one or more single-stranded portion(s) and one or more double-stranded portion(s), double-stranded DNA wherein the DNA strands are fully complementary, double-stranded DNA wherein the DNA strands are only partially complementary, circular DNA, covalently-closed DNA, linear DNA, covalently crosslinked DNA, cDNA, chemically-synthesized DNA, semi-synthetic DNA, biosynthetic DNA, naturally-isolated DNA, enzyme-digested DNA, sheared DNA, labeled DNA, such as radiolabeled DNA and fluorochrome-labeled DNA, DNA containing one or more non-naturally occurring species of nucleic acid.

DNA sequences that encode the Serine protease inhibitor, or a biologically active fragment thereof having a Serine protease inhibitor activity, can be synthesized by standard chemical techniques, for example, the phosphotriester method or via automated synthesis methods and PCR methods.

The purified and isolated DNA sequence encoding the Serine protease inhibitor according to the invention may also be produced by enzymatic techniques. Thus, restriction enzymes, which cleave nucleic acid molecules at predefined recognition sequences can be used to isolate nucleic acid sequences from larger nucleic acid molecules containing the nucleic acid sequence, such as DNA (or RNA) that codes for the recombinant inhibitor protein or for a fragment thereof.

Encompassed by the present invention is also a nucleic acid in the form of a polyribonucleotide (RNA), including, e.g., single-stranded RNA, double-stranded RNA, double-stranded RNA wherein one or both strands are composed of two or more fragments, double-stranded RNA wherein one or both strands have an uninterrupted phosphodiester backbone, RNA containing one or more single-stranded portion(s) and one or more double-stranded portion(s), double-stranded RNA wherein the RNA strands are fully complementary, double-stranded RNA wherein the RNA strands are only partially complementary, covalently crosslinked RNA, enzyme-digested RNA, sheared RNA, mRNA, chemically-synthesized RNA, semi-synthetic RNA, biosynthetic RNA, naturally-isolated RNA, labeled RNA, such as radiolabeled RNA and fluorochrome-labeled RNA, RNA containing one or more non-naturally-occurring species of nucleic acid.

The purified and isolated DNA sequence encoding a Serine protease inhibitor is preferably selected from the group comprising SEQ ID NO:1, SEQ ID NO:3, SEQ ID NO:5, SEQ ID NO:7, SEQ ID NO:9, SEQ ID NO:11, SEQ ID NO:13, SEQ ID NO:16 to SEQ ID NO:37.

The present invention also includes variants of the aforementioned sequences, that is nucleotide sequences that vary from the reference sequence by conservative nucleotide substitutions, whereby one or more nucleotides are substituted by another with same characteristics.

Also encompassed in the present invention is the use of a purified and isolated DNA sequence encoding a Serine protease inhibitor in the preparation of a medicament for the treatment of a skin disease.

Alternatively, the Kallikrein inhibitors or the serine protease inhibitors of the invention comprise a detectable label or bind to a detectable label to form a detectable complex.

"Detectable labels" are detectable molecules or detection moiety for diagnostic purposes, such as enzymes or peptides having a particular binding property, e.g. streptavidin or horseradish peroxidase. Detection moiety further includes chemical moieties such as biotin which may be detected via binding to a specific cognate detectable moiety, e. g. labelled avidin.

Preferably, detectable labels include fluorescent labels and labels used conventionally in the art for MRI-CT imagine. A number of fluorescent materials are known and can be utilized as labels. These include, for example, fluorescein, rhodamine, auramine, Texas Red, AMCA blue and Lucifer Yellow.

The Kallikrein inhibitors or the serine protease inhibitors of the invention may carry a radioactive label as the detection moiety, such as the isotopes 3H, 14C, 32P, 35S, 36Cl, 51Cr, 57Co, 58Co, 59Fe, 90Y, 121I, 124I, 125I, 131I, 111In, 211At, 198Au, 67Cu, 225Ac, 213bu, 99Tc and 186Re. When radioactive labels are used, known currently available counting procedures may be utilized to identify and quantitate the specific binding members.

In the instance where the label is an enzyme, detection may be accomplished by any of the presently utilized colorimetric, spectrophotometric, fluorospectrophotometric, amperometric or gasometric techniques known in the art.

The radioactive labels are useful in in vitro diagnostics techniques, ex vivo and in in vivo radioimaging techniques. In a further aspect, the radioactive labels are useful in radioimmuno-guided surgery techniques, wherein they can identify and indicate the presence and/or location of cancer cells, precancerous cells, tumor cells, and hyperproliferative cells, prior to, during or following surgery to remove such cells.

In the instance of in vivo imaging, the labels of the present invention may be conjugated to an imaging agent rather than a radioisotope(s), including but not limited to a magnetic resonance image enhancing agent. Examples of chelating groups include EDTA, porphyrins, polyamines crown ethers and polyoximes.

Examples of paramagnetic ions include gadolinium, iron, manganese, rhenium, europium, lanthanium, holmium and erbium.

The present invention is also directed to a pharmaceutical composition comprising the serine protease inhibitor as described herein as an active agent, optionally in combination with one or more pharmaceutically acceptable carriers.

Preferably the composition, as a pharmaceutical composition, according to the invention is to be administered to a patient in need of treatment via any suitable route, usually by injection into the bloodstream or CSF, or directly into the site of the disease, or close to this site. The precise dose will depend upon a number of factors, including whether the composition is for diagnosis, prognosis, prophylaxis of or for treatment, the size and location of, for example, desquamation, the precise nature of the composition, and the nature of the detectable or functional label attached to the Kallikrein inhibitor or the serine protease inhibitor.

The present pharmaceutical composition comprises as an active substance a pharmaceutically effective amount of the composition as described, optionally in combination with pharmaceutically acceptable carriers, diluents and adjuvants.

"A pharmaceutically effective amount" refers to a chemical material or compound which, when administered to a human or animal organism induces a detectable pharmacological and/or physiologic effect.

The pharmaceutically effective amount of a dosage unit of the polypeptide usually is in the range of 0.001 ng to 100 μg per kg of body weight of the patient to be treated.

The pharmaceutical composition may contain one or more pharmaceutically acceptable carriers, diluents and adjuvants.

Acceptable carriers, diluents and adjuvants which facilitates processing of the active compounds into preparation which can be used pharmaceutically are non-toxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl orbenzyl alcohol; alkyl parabens such as methyl or propyl paraben; catechol; resorcinol; cyclohexanol; 3-pentanol; and m-cresol; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, hydroxyethylcellulose (NATROSOL® (hydroxyethylcellulose (HEC)) or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN® (polysorbate or polyoxyethylene sorbitol ester), PLURONIC® (polyoxyalkylene ether) or polyethylene glycol (PEG).

The form of administration of the pharmaceutical composition may be systemic or topical. For example, administration of such a composition may be various parenteral routes such as subcutaneous, intravenous, intradermal, intramuscular, intraperitoneal, intranasal, transdermal, buccal routes or via an implanted device, and may also be delivered by peristaltic means.

The pharmaceutical composition, as described herein, may also be incorporated or impregnated into a bioabsorbable matrix, with the matrix being administered in the form of a suspension of matrix, a gel or a solid support. In addition the matrix may be comprised of a biopolymer such as NATROSOL® (hydroxyethylcellulose (HEC)).

Sustained-release preparations may be prepared. Suitable examples of sustained-release preparations include semi permeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and [gamma] ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished for example by filtration through sterile filtration membranes.

It is understood that the suitable dosage of the present composition will be dependent upon the age, sex, health, and weight of the recipient, kind of concurrent treatment, if any and the nature of the effect desired.

The appropriate dosage form will depend on the disease, the inhibitor, and the mode of administration; possibilities include tablets, capsules, lozenges, dental pastes, suppositories, inhalants, solutions, ointments and parenteral depots.

Since amino acid modifications of the amino acids (of the inhibitor for example) are also encompassed in the present invention, this may be useful for cross-linking the inhibitor to a water-insoluble matrix or the other macromolecular carriers, or to improve the solubility, adsorption, and permeability across the blood brain barrier. Such modifications are well known in the art and may alternatively eliminate or attenuate any possible undesirable side effect of the peptide and the like.

Another subject matter of the present invention is to provide a kit for the diagnosis, prognosis, prophylaxis or treatment of skin disease in a mammal, said kit comprising a recombinant serine protease, optionally with reagents and/or instructions for use.

The kit of the present invention may further comprise a separate pharmaceutical dosage form comprising other pharmaceutical compositions and combinations thereof.

Generally, the Kit comprises a container and a label or package insert on or associated with the container. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The label or package insert indicates that the composition is used for treating the condition of choice, such as cancer.

Alternatively, or additionally, the Kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The present invention also discloses the use of the composition of the invention, as a pharmacological tool in the development and standardization of in vitro and in vivo test systems for the diagnosis, prognosis, prophylaxis or treatment of skin diseases in mammals.

Also encompassed by the present invention is a detection assay for the diagnosis, prognosis, prophylaxis or treatment of skin diseases in a tissue sample comprising contacting the tissue sample with the composition of the invention, determining and measuring the amount of detected label and correlating this amount to the presence or absence of a disease in said tissue sample.

Yet another object of the present invention is to provide a method for killing a skin cell expressing kallikrein molecules, comprising contacting the cell with the composition of the invention so as to kill the cell, destroying or avoiding the survival of cells expressing kallikrein molecules.

It is also an object of the present invention to provide a method for inhibiting skin cell expressing serine protease and in particular kallikrein molecules, comprising contacting said skin cell with the composition of the invention.

Yet another object of the present invention is to provide a cosmetic composition comprising a Serine protease inhibitor, or a biologically active fragment thereof having a Serine protease inhibitor activity as described herein as well as the use of this composition for the improvement of an undesirable skin condition.

Preferably, the Serine protease inhibitor is a recombinant inhibitor protein of the invention.

Usually, the Serine protease is selected from the group comprising kallikrein, plasmin, chymotrypsin (Chtr), urokinase (uPA), tryptase and neutrophile elastase (HNE) enzymes and/or a combination thereof.

Preferably, the kallikrein is selected from the group comprising hK2, hK5, hK7, and hK14 and/or a combination thereof.

The invention also provides the use of a Serine protease inhibitor, or a biologically active fragment thereof having a Serine protease inhibitor activity, in the preparation of cosmetic composition for the improvement of an undesirable skin condition.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

The foregoing description will be more fully understood with reference to the following Examples. Such Examples, are, however, exemplary of methods of practicing the present invention and are not intended to limit the scope of the invention.

EXAMPLES

Example 1

Development of Recombinant ACT Inhibitors Specific to Human hK2 Using Phage Display Selected Substrates.

The content of Application PCT/IB2004/001040 (Université de Lausanne) is incorporated herein by reference in its entirety Material hK2 and hK3 (PSA) were purified from human semen as previously described (Frenette G, Gervais Y, Tremblay R R, Dube J Y. 1998 "Contamination of purified prostate-specific antigen preparations by kallikrein hK2" *J Urol* 159, 1375-8), anti-hK2 and anti-PSA monoclonal antibodies were a gift from Professor RR Tremblay, Laval University, Canada. Human chymotrypsin (Chtr), urokinase plasminogen activator (uPA), human kallikrein hK1, human plasma kallikrein (PK), human neutrophil elastase (HNE) and commercial ACT (human plasma α-1-antichymotrypsin) were purchased from Calbiochem. Z-Phe-Arg-AMC, Suc-Ala-Ala-Pro-Phe-AMC (AAPF SEQ ID NO: 135), Z-Gly-Gly-Arg-AMC, MeOSuc-Ala-Ala-Pro-Val-AMC (AAPV SEQ ID NO: 136) were purchased from Calbiochem. CFP-TFRSA-YFP (TFRSA SEQ ID NO: 137) fluorescent substrate was developed as previously described (Mahajan N P et al. 1999 "Novel mutant green fluorescent protein protease substrates reveal the activation of specific caspases during apoptosis" *Chem Biol* 6, 401-9). The cDNA for human al-antichymotrypsin (ACT) was a generous gift from Dr. Harvey Rubin (University of Pennsylvania).

Site-Directed Mutagenesis

Following the subcloning of ACT cDNA into pQE-9 expression vector (Qiagen, Germany) and the introduction of an $His_6$ tag (SEQ ID NO: 164) at the N-terminal of $rACT_{WT}$, two restriction sites Sac II and MluI, were incorporated 18 bp upstream and 18 bp downstream of P1 codon in RSL domain respectively. These sites were created by silent mutation using oligonucleotides 5'-GTGAT-TTTGACCGCGGTGGCAGCAG-3' (SEQ ID NO:111) for Sac II and 5'-GCACAATGGTACGCGTC TCCACTAATG-3' (SEQ ID NO:112) for Mlu I site and following the quickchange mutagenesis protocol supplied by Stratagene.

Construction of the Substrate Phage Display Library

Substrate phage libraries were generated using a modified pH0508b phagemid (Lowman et al. 1991 "Selecting high-affinity binding proteins by monovalent phage display" *Biochemistry* 12, 10832-8). The construction consists of a $His_6$ (SEQ ID NO: 164) tag at either end of a Gly-Gly-Gly-Ser-repeat-rich region (GGGS SEQ ID NO: 165) that precedes the carboxyl-terminal domain (codons 249-406) of the M13 gene III. The random pentamers were generated by PCR extension of the template oligonucleotides with appropriate restriction sites positioned on both side of the degenerate codons: 5'TGAGCTAGTCTAGATAGGTGGCGG TNNSNNSNNSNNSNNSGGGTCGACGTCGGTCATAG CAGTCGCTGCA-3' (SEQ ID NO:113) (where N is any nucleotide and S is either G or C) using 5' biotinylated primers corresponding to the flanking regions: 5'TGAGCTAGTCTAGATAGGTG-3' (SEQ ID NO:83) and 5'-TGCAGCGACTGCTATGA-3' (SEQ ID NO:84).

PCR templates are digested and purified as described previously (Smith G. P, Scott J. K. 1993 "Libraries of peptides and proteins displayed on filamentous phage" *Methods Enzymol.* 217, 228-57), inserted into XbaI/SalI digested pH0508b vector, and electroporated into XL1-Blue (F⁻). The extent of the library was estimated from the transformation efficiency determined by plating a small portion of the transformed cells onto Luria-Bertani plates containing ampicillin and tetracycline (100 and 15 µg·mL⁻¹, respectively). The rest of the transformed cells were used to prepare a phage library by incubating overnight by adding an M13K07 helper phage at a concentration giving a multiplicity of infection of 100 plaque forming units (p.f.u.) per mL. Phages were collected from the supernatant and purified by poly(ethylene glycol) precipitation. Of these, 200 clones were selected arbitrarily for sequencing to verify the randomization of the library.

Phage-Displayed Pentapeptide Library Screening

This new pentapeptide library was subjected to eight rounds of screening with hK2. One hundred microliters of Ni²⁺-nitrilotriacetic acid coupled to sepharose beads (Ni²⁺-nitrilotriacetic acid resin) was washed with 10 mL NaCl/P$_i$ containing 1 mg·mL⁻¹ BSA. Phage particles (10¹¹) were added to the equilibrated Ni²⁺-nitrilotriacetic acid resin and allowed to bind with gentle agitation for 3 h at 4° C. The resin was subsequently washed (NaCl/P$_i$/BSA 1 mg·mL⁻¹, 5 mM imidazole, 0.1% TWEEN® 20 (polysorbate 20 or polyoxyethylene sorbitol ester) to remove unbound phages and then equilibrated in NaCl/Pi. The substrate phage was exposed to 27 nM (final concentration) of hK2 for 45 min at 37° C. A control selection without protease was also performed. The cleaved phages released into the supernatant were amplified using XL1-Blue *Escherichia coli* and then used for subsequent rounds of selection. After eight rounds of panning, about 15 individual clones were picked from the fifth, sixth and eighth round of selection and plasmid DNA were isolated and sequenced in the region encoding for the substrate.

Construction and Expression of Recombinant Wild Type ACT and its Variants.

Six variants, which correspond to a change in the reactive site loop in positions between P3 and P3' (see Table III below), were generated by PCR extension of the template oligonucleotides:

rACT$_{8.20}$,
(SEQ ID NO: 61)
5'-TACCGCGGTCAAAATCACCCTCCGTTCTCGAGCAGTGGA
GACGCGT GA-3';

rACT$_{6.3}$,
((SEQ ID NO: 62)
5'-TACCGCGGTCAAAATCACCAGGAGGTCTATCGATGT
GGAGACGCGTGA-3';

rACT$_{8.3}$,
(SEQ ID NO: 63)
5'-TACCGCGGTCAAAATCAGGGGGAGATCTGAGTTAGTG
GAGACGCGTGA-3';

rACT$_{6.7}$,
((SEQ ID NO: 64)
5'-TACCGCGGTCAAAATCAAGCTTAGAACAACATTAG
TGGAGACCGCTGA-3';

rACT$_{6.1}$,
(SEQ ID NO: 65)
5'-TACCGCGGTCAAAATCATGACAAGATCTAACTTAGT
GGAGACGCGTGA-3';

rACT$_{5.18}$,
(SEQ ID NO: 66)
5'-TACCGCGGTCAAAATCACCGAGCGTGTCTCGCCCGTG
GAGACGCGTGA-3'

(where underlined sequences encode new cleavage sites in the reactive site loop), using primers corresponding to the flanking regions: 5'-TACCGCGGTCAAAATC-3' (SEQ ID NO:67) and 5'-TCACGCGTGTCCAC-3' (SEQ ID NO:68). PCR products were digested with Sac II and Mlu I restriction enzymes and then subcloned into digested rACT$_{WT}$ construct. Recombinant serpins were produced in TG1 *E. coli* strain. Cells were grown at 37° C. in 2×TY media (16 g tryptone, 10 g yeast extract, 5 g NaCl per L) containing 100 µg/ml ampicillin to A$_{600}$=0.5. Isopropylthio-β-galactoside (IPTG) was then added to a final concentration of 0.5 mM allowing the expression of recombinant serpins for 16 h at 16° C. The cells from 100 ml of culture were harvested by centrifugation, resuspended in cold PBS and then passed through a french press to recover the total soluble cytoplasmic proteins. Cell debris were removed by centrifugation and Ni²⁺-nitilotriacetic affinity agarose beads were added to supernatant for 90 min at 4° C. to bind recombinant serpins. The resin was subsequently washed with 50 mM Tris pH 8.0, 500 mM NaCl, 25 mM Imidazole and the bound proteins were eluted for 10 min with 50 mM Tris pH 8.0, 500 mM NaCl and 150 mM Imidazole. Once purification was completed, rACT were dialysed against 50 mM Tris pH 8.0, 500 mM NaCl, 0.05% Triton X-100 for 16 h at 4° C. The protein concentration was determined for each purification by Bradford assay and normalized by densitometry of Coomassie Blue-stained SDS-PAGE gels (Laemmli U K. 1970 "Cleavage of structural proteins during the assembly of the head of bacteriophage T4" *Nature* 227, 680-5).

TABLE III

Alignment of RSL (Reactive Serpin Loop) of recombinant serpin a1-antichymotrypsin (ACT) and its variants (SEQ ID NOS. 166-172, respectively).

| Serpin | Selected[a] Substrate Peptide | P6 | P5 | P4 | P3 | P2 | P1 | P'1 | P'2 | P'3 | P'4 | P'5 | P'6 |
|---|---|---|---|---|---|---|---|---|---|---|---|---|---|
| rACT$_{WT}$ | | V | K | I | T | L | L* | S | A | L | V | E | T |
| rACT$_{8.20}$ | LR↓SRA SEQ ID NO: 157 | V | K | I | T | <u>L</u> | <u>R</u>* | S | <u>R</u> | <u>A</u> | V | E | T |

TABLE III-continued

Alignment of RSL (Reactive Serpin Loop) of recombinant serpin α1-antichymotrypsin (ACT) and its variants (SEQ ID NOS. 166-172, respectively).

| Serpin | Selected[a] Substrate Peptide | P6 | P5 | P4 | P3 | P2 | P1 | P'1 | P'2 | P'3 | P'4 | P'5 | P'6 |
|---|---|---|---|---|---|---|---|---|---|---|---|---|---|
| rACT$_{6.2}$ | RR↓SID SEQ ID NO: 158 | V | K | I | T | R | R\* | S | I | D | V | E | T |
| rACT$_{8.3}$ | RGR↓SE SEQ ID NO: 159 | V | K | I | R | G | R\* | S | E | L | V | E | T |
| rACT$_{6.7}$ | KLR↓TT SEQ ID NO: 160 | V | K | I | K | L | R\* | T | T | L | V | E | T |
| rACT$_{6.1}$ | MTR↓SN SEQ ID NO: 161 | V | K | I | M | T | R\* | S | N | A | V | E | T |
| ACT$_{5.18}$ | ER↓VSP SEQ ID NO: 162 | V | K | I | T | E | R\* | V | S | P | V | E | T |

[a]Substrate peptides selected by kallikrein hK2 using a phage-displayed random pentapeptide library.
Plain type residues are common to rACT$_{WT}$, bold and underlined residues correspond to substrate peptides relocated in RSL of ACT variants. The scissile bond by hK2 in substrate peptides is designated by ↓ and putative cleavage site in serpins is marked by asterisks between the P1-P1' residues.

Inhibition Assays and Stoichiometry of Inhibition (SI)

The stoichiometry of inhibition (SI) values were determined for the inhibition of rACT WT and its variants with hK2 and different other enzymes. An initial test was made with a molar excess of rACT (100 fold) over hK2, PSA, hK1, chymotrypsin (Chtr), plasma kallikrein (PK), urokinase (uPA) and human neutrophile elastase (HNE) enzymes. The reaction was carried out for 30 min at 25° C. (90 min at 37° C. for PSA) in reaction buffer (50 mM Tris pH 7.5, 150 mM NaCl, 0,05% Triton X-100, 0,01% BSA) and residual enzyme activity was measured by adding fluorescent substrates (Z-Phe-Arg-AMC for hK1, hK2 and PK, Suc-Ala-Ala-Pro-Phe-AMC for Chtr (AAPF SEQ ID NO: 135), Z-Gly-Gly-Arg-AMC for uPA, MeOSuc Ala-Ala-Pro-Val-AMC for HNE (AAPV SEQ ID NO: 136), and CFP-TFRSA-YFP (TFRSA SEQ ID NO: 137) for PSA). Activity of enzyme in presence of inhibitors was compared to uninhibited reaction. For reactions where an inhibition was observed, SI was determined by incubating different concentrations of recombinant serpins. Using linear regression analysis of fractional activity velocity of inhibited enzyme reaction/velocity of uninhibited enzyme reaction) versus the molar ratio of the inhibitor to enzyme ($[I_o]/[E_o]$), the stoichiometry of inhibition, corresponding to the abscissa intercept, was obtained.

Kinetics

The association rate constants for interactions of hK2, chymotrypsin, PK and HNE with different rACTs were determined under pseudo-first order conditions using the progress curve 80% (Morrison J F, Walsh C T. 1988 "The behavior and significance of slow-binding enzyme inhibitors" Adv. Enzymol. Relat. Areas Mol. Biol 61, 201-301). Under these conditions, a fixed amount of enzyme (2 nM) was mixed with different concentrations of inhibitor (0-800 nM) and an excess of substrate (10 µM). Each reaction was made in reaction buffer (50 mM Tris pH 7.5, 150 mM NaCl, 0.05% Triton X-100, 0.01% BSA) at 25° C. for 45 min and the rate of product formation was measured using a FL$_x$800 fluorescence 96-well microplate reader (Biotek, USA). In this model, inhibition is considered to be irreversible over the course of reaction and the progress of enzyme activity is expressed by product formation (P), beginning at a rate ($v_z$) and is inhibited over time (t) at a first-order rate ($k_{obs}$), rate constant that is dependent only on inhibitor concentration.

$$P = (v_z/k_{obs}) \times [1 - e^{(-k_{obs}t)}] \qquad \text{eq 1}$$

For each inhibitor, a $k_{obs}$ was calculated, for four different concentrations of inhibitors, by non linear regression of the data using equation 1. By plotting the $k_{obs}$ versus inhibitor concentration [I], a second-order rate constant, k', equal to the slope of the curve ($k' = \Delta k_{obs}/\Delta[I]$), was determined. Due to the competition between inhibitor and the substrate, equation 2 below is used to correct the second order rate constant k' by taking in account the substrate concentration [S] and the $K_m$ of the enzyme for its substrate, giving the $k_a$.

$$k_a = (1 + [S]/K_m) \times k' \qquad \text{eq 2}$$

The $K_m$ of hK2 for Z-FR-AMC, chymotrypsin for Suc-AAPF-AMC (AAPF SEQ ID NO:135), PK for Z-FR-AMC and HNE for MeOSuc-AAPV-AMC (AAPV SEQ ID NO:136) were 67 µM, 145 µM, 170 µM and 130 µM respectively.

Western Blot Analysis of Complex Formation and Inhibitor Degradation.

Kallikrein hK2 was incubated 3 hours at 37° C. with different recombinant ACTs at a $[I]_o$:$[E]_o$ ratio of 100:1 in 50 mM Tris, 200 mM NaCl, 0,05% Triton X-100. Protein samples were heated at 95° C. for 5 min, separated by SDS-PAGE (12% acrylamid 19:1 T:C ratio) and then electroblotted onto Hybond-ECL (Amersham Pharmacia) nitrocellulose. The free-hK2 and hK2-ACT complexes were detected using a mouse anti-hK2 monoclonal antibody and an alkaline phosphatase-conjugated goat anti-mouse secondary antibody. Western blot was visualized using the ECL detection kit (Amersham Pharmacia Biotech). hK2 was also incubated with ACT$_{8.3}$ or ACT$_{6.7}$ 30 min at 25° C. (kinetic conditions) at a $[I]_o$: $[E]_o$ ratio of 10:1 in 50 mM Tris, 200 mM NaCl, 0,05% Triton X-100. Proteins were detected by western blot, using an anti-His6 monoclonal antibody ("His$_6$" disclosed as SEQ ID NO: 164) followed by detection with the secondary antibody and protocol described above.

Production of Soluble Recombinant Wild Type and Variant ACTs

Wild type serpin α1-antichymotrypsin was used to develop specific inhibitors of the kallikrein hK2. Residues P3-P3' located in RSL structure of rACT$_{WT}$ were replaced by substrate pentapeptides, previously selected by phage display technology as described above. Six variants of rACT shown in table IV, have been designed and constructed. The scissile bond in substrate peptides was aligned according to Leu-358-Ser-359 into RSL of the serpin. rACT$_{WT}$ and its variants were expressed in *E. coli* TG1 as fusion proteins containing an His tag in N-terminal position. Each of them was produced at low temperature allowing protein accumulation mainly in active soluble form. Purified under native conditions, the level of production varied between 1.0 to 2.5 mg/L. The purity of purified serpins, such as for example Variant 6.1 and wild type ACT, as estimated by SDS-PAGE analysis is more than 98%.

rACT Variants are Mainly Specific to Kallikrein hK2

A panel of enzymes including human neutrophil elastase, chymotrypsin-like (Chtr, PSA or hK3) and trypsin-like (hK2, hK1, PK, uPA) proteinases have been screened to determine inhibitory specificity of rACT variants (Table IV).

TABLE IV

Inhibitory profile of rACT$_{WT}$ and its variants.

| Protease | ACT$_{8.20}$ (LR↓SRA)$^a$ SEQ ID NO: 157 MD 820 | ACT$_{6.2}$ (RR↓SID)$^a$ SEQ ID NO: 158 MD 62 | ACT$_{8.3}$ (RGR↓SE)$^a$ SEQ ID NO: 159 MD 83 | ACT$_{6.7}$ (KLR↓TT)$^a$ SEQ ID NO: 160 MD 67 | ACT$_{6.1}$ (MTR↓SN)$^a$ SEQ ID NO: 161 MD 61 | ACT$_{5.18}$ (ER↓VSP)$^a$ SEQ ID NO: 162 MD518 | ACT$_{WT}$ (LL↓SA)$^a$ SEQ ID NO: 163 |
|---|---|---|---|---|---|---|---|
| | | | | INHIBITION %$^B$ | | | |
| hK2 | 95 | 100 | 100 | 100 | 100 | 73 | 0 |
| Chtr | 66 | 0 | 0 | 0 | 0 | 0 | 100 |
| PK | 54 | 100 | 0 | 36 | 100 | 0 | 0 |
| HNE | 30 | 0 | 0 | 0 | 60 | 0 | 15 |
| PSA (hK3) | 45 | 0 | 0 | 0 | 0 | 0 | 80 |
| hK1 | 0 | 0 | 0 | 0 | 0 | 0 | 0 |
| Urokinase | 0 | 0 | 0 | 0 | 0 | 0 | 0 |

$^a$Amino acid sequence cleaved in RSL (Reactive Serpin Loop) of recombinant ACTs corresponding to selected substrate peptide by hK2.
$^B$Protease and serpins were incubated for 30 min at 25° C. (90 min at 37° for PSA) at a [I]$_o$/[E]$_o$ ratio of 100:1. Percent inhibition correspond to 100 × (1 − (velocity in presence of inhibitor/velocity of uninhibited control)).

Incubating with an excess of inhibitors ([I]$_o$/[E]$_o$ of 100:1) for 30 minutes, hK2 is completely inhibited by rACT$_{6.2}$, rACT$_{8.3}$, rACT$_{6.7}$ and rACT$_{6.1}$, whereas rACT$_{8.20}$ and rACT$_{5.18}$ inhibited 95% and 73% of enzyme activity, respectively. Under this condition, wild type rACT showed no inhibition activity toward hK2. Among these variants, two (rACT$_{8.3}$ and rACT$_{5.18}$) are specific to hK2, inhibiting no other tested enzyme. Two other variants, rACT$_{6.7}$ and rACT$_{6.2}$, inhibited as well PK at 36% and 100% respectively. As wild-type ACT, variant rACT$_{8.20}$ inhibited the two chymotrypsin-like proteases Chtr and PSA but additionally also PK and HNE. None of the recombinant serpins showed inhibitory activity against the kallikrein hK1 and uPA.

Stoichiometries of Inhibitory of Variant ACTs for hK2 are Improved Drastically in Comparison to Wild Type ACT The determination of the stoichiometry of inhibitory was accomplished under physiological conditions of pH and ionic strength for all enzymes to ensure the most valuable comparison. Recombinant wild type ACT gave a SI value of 2 (table V) with chymotrypsin which is identical to the value obtained with commercial ACT under similar conditions (data not shown).

TABLE V

Comparison of stoichiometry of inhibition values and second-order rate constants (k$_a$) for the reaction of rACT$_{WT}$ and its variants with hK2 and others proteinases.

| Protease | ACT$_{8.20}$ (LR↓SRA)$^c$ MD820 SEQ ID NO: 157 | | ACT$_{6.2}$ (RR↓SID) MD62$^c$ SEQ ID NO: 158 | | ACT$_{8.3}$ (RGR↓SE) MD83$^c$ SEQ ID NO: 159 | | ACT$_{6.7}$ (KLR↓TT) MD67$^c$ SEQ ID NO: 160 | | ACT$_{6.1}$ (MTR↓SN) MD61$^c$ SEQ ID NO: 161 | | ACT$_{5.18}$ (ER↓VSP) MD518$^c$ SEQ ID NO: 162 | | ACT$_{WT}$ (LL↓SA)$^c$ SEQ ID NO: 163 | |
|---|---|---|---|---|---|---|---|---|---|---|---|---|---|---|
| | SI | (k$_a$)$^b$ M$^{-1}$s$^{-1}$ | SI | k$_a$$^b$ M$^{-1}$s$^{-1}$ | SI | k$_a$$^b$ M$^{-1}$s$^{-1}$ | SI | k$_a$$^b$ M$^{-1}$s$^{-1}$ | SI | k$_a$$^b$ M$^{-1}$s$^{-1}$ | SI | k$_a$$^b$ M$^{-1}$s$^{-1}$ | SI | k$_a$$^b$ M$^{-1}$s$^{-1}$ |
| hK2 | 105 | 1779 | 25 | 6261 | 34 | 2439 | 9 | 8991 | 19 | 3442 | 139 | 595 | — | — |
| Chtr | 134 | 905 | — | — | — | — | — | — | — | — | — | — | 2 | 61295 |

TABLE V-continued

Comparison of stoichiometry of inhibition values and second-order rate constants ($k_a$) for the reaction of rACT$_{WT}$ and its variants with hK2 and others proteinases.

| | ACT$_{8.20}$ (LR↓SRA)[c] MD820 SEQ ID NO: 157 | | ACT$_{6.2}$ (RR↓SID) MD62[c] SEQ ID NO: 158 | | ACT$_{8.3}$ (RGR↓SE) MD83[c] SEQ ID NO: 159 | | ACT$_{6.7}$ (KLR↓TT) MD67[c] SEQ ID NO: 160 | | ACT$_{6.1}$ (MTR↓SN) MD61[c] SEQ ID NO: 161 | | ACT$_{5.18}$ (ER↓VSP) MD518[c] SEQ ID NO: 162 | | ACT$_{WT}$ (LL↓SA)[c] SEQ ID NO: 163 | |
|---|---|---|---|---|---|---|---|---|---|---|---|---|---|---|
| Protease | SI | $(k_a)^b$ $M^{-1}s^{-1}$ | SI | $k_a^b$ $M^{-1}s^{-1}$ | SI | $k_a^b$ $M^{-1}s^{-1}$ | SI | $k_a^b$ $M^{-1}s^{-1}$ | SI | $k_a^b$ $M^{-1}s^{-1}$ | SI | $k_a^b$ $M^{-1}s^{-1}$ | SI | $k_a^b$ $M^{-1}s^{-1}$ |
| PK | 150 | 424 | 18 | 6217 | — | — | 277 | 201 | 16 | 8024 | — | — | — | — |
| HNE | 334 | 158 | — | — | — | — | — | — | 159 | 1192 | — | — | — | — |

[a]SI values reported were determined using linear regression analysis to extrapolate the I/E ratio.
[b]Second order rate constants for serpin-proteinase reactions were measured under pseudo-first- or second order conditions as described in "Experimental Procedure".
[c]Amino acid sequence of P3-P3' residues in RSL (Reactive Serpin Loop) of recombinant ACT corresponding to selected substrate peptide by hK2
—, No detectable inhibitory activity.

In order to determine the SI values of all the recombinant variants, Applicants have incubated hK2 (5 nM) with different concentrations (6.25-500 nM) of rACT$_{8.20}$, rACT$_{6.2}$, rACT$_{8.3}$, rACT$_{6.7}$, rACT$_{6.1}$, rACT$_{5.18}$, rACT$_{WT}$, at 25° C. for 30 min in reaction buffer. Residual activities (velocity) for hK2, were assayed by adding the fluorescent substrate (10 μM) Z-FR-AMC. Fractional velocity corresponds to the ratio of the velocity of inhibited enzyme ($v_i$) to the velocity of the uninhibited control ($v_o$). The SI was determined using linear regression analysis to extrapolate the I/E ratio (i.e. the x intercept).

All newly constructed variants of ACT showed lower SI values with hK2 than wild type ACT. From these variants rACT$_{6.7}$, rACT$_{6.1}$ and rACT$_{6.2}$ had the lowest stoichiometry of inhibition values for hK2 (9, 19 and 25 respectively). Whereas rACT$_{6.2}$ and rACT$_{6.1}$ had also the lowest SI values (18 and 16) for PK, the SI for rACT6.7 was much higher (277). The two recombinant ACTs specific for hK2, rACT$_{8.3}$ and rACT$_{5.18}$ had a higher SI ratio of 34 and 139, respectively. The SI value of rACT$_{8.20}$ inhibitor was superior to 100 for all tested proteases including hK2.

Variant ACTs Form Stable Complexes with hK2 without Degradation of Inhibitors hK2 was incubated 3 h at 37° C. with rACT$_{8.20}$, rACT$_{6.2}$, rACT$_{8.3}$, rACT$_{6.7}$, rACT$_{6.1}$, rACT$_{5.18}$ and wild type rACT, at a I:E ratio of 100:1. Western Blot analysis of the reaction products of rACTs with hK2 (rACT$_{8.20}$), rACT$_{6.2}$, rACT$_{8.3}$, rACT$_{6.7}$, rACT$_{6.1}$, rACT$_{5.18}$ and wild type rACT has been done under reducing conditions using a mouse anti-hK2 antibody to determine the fate of inhibitors after the interaction with the enzyme. When hK2 is incubated with ACT variants, free hK2 (E) disappeared completely to form a covalent complex (EI). This covalent complex demonstrated a high stability as it did not break down over a 16 h incubation period (data not shown). Wild type ACT inhibited more slowly hK2, which was mainly uncomplexed after 3 hours of incubation. Elevated SI values measured with hK2 were not due to non-complex forming degradation of ACT variant inhibitors.

Further on ACT$_{8.3}$ or ACT$_{6.7}$ were incubated with hK2 under kinetic conditions (30 min at 25° C.) at a I:E ratio of 10:1. The complex formation was analysed by western blot under reducing conditions using a mouse monoclonal anti-his tag. All inhibitor proteins were either complexed with hK2 or present as uncleaved form, indicating that the possible substrate pathway for the serpin-enzyme interaction is marginal.

Variant ACTs Showed Highest Association Constants with hK2

The rate of inhibitory reaction with variant ACTs was determined for each protease showing reactivity with these inhibitors. To that end, interaction of hK2 and recombinant serpins was measured under pseudo-first order conditions using progress curve method. hK2 (2 nM) and substrate Z-FR-AMC (10 μM) were added to varying amounts (20n-800 nM) of inhibitors rACT$_{8.20}$, rACT$_{5.18}$ and inhibitors rACT$_{6.2}$, rACT$_{8.3}$, rACT$_{6.7}$, rACT$_{6.1}$ (data not shown). Representative progress curves were subjected to non linear regression analysis using eq 1 and the rate ($k_{obs}$) was plotted against the serpin concentrations. After determination of kobs, association constants (ka) were calculated using $K_m$ of the proteases for their corresponding substrates (table VI). The ka value of wild type ACT with chymotrypsin was identical as to published data (Cooley et al. 2001 "The serpin MNEI inhibits elastase-like and chymotrypsin-like serine proteases through efficient reactions at two active sites" *Biochemistry* 40, 15762-70). The recombinant rACT$_{6.7}$ showed a highest ka (8991 $M^{-1}$ $s^{-1}$) with hK2 whereas that obtained with PK was 45 fold inferior. In contrast, recombinant rACT$_{6.2}$ gave equivalent ka with hK2 and PK demonstrating a lack of discrimination between the two proteases. ka values of hK2 specific recombinant inhibitors rACT$_{8.3}$ and rACT$_{5.18}$ were lower, 2439 and 595 $M^{-1}$ $s^{-1}$ respectively, whereas non specific ACT$_{8.20}$ exhibited a ka of 1779 $M^{-1}$ $s^{-1}$, for hK2, superior compared to Chtr, PK and HNE. One of the recombinant serpins, rACT$_{6.1}$, was reacting at higher velocity with PK than with hK2.

Residues P3-P3' located in RSL structure of rACT$_{WT}$ were replaced by substrate pentapeptide coding for the RSL of Protein C Inhibitor (PCI) (Table VI) as described in example 1.

TABLE VI

Alignment of RSL (Reactive Serpin Loop) of recombinant serpins ACT (SEQ ID NOS. 166 and 173), PCI (SEQ ID NO: 174) and $ACT_{PCI}$ (SEQ ID NOS: 175 and 176).

| Serpin | | P6 | P5 | P4 | P3 | P2 | P1 | P'1 | P'2 | P'3 | P'4 | P'5 | P'6 |
|---|---|---|---|---|---|---|---|---|---|---|---|---|---|
| $rACT_{WT}$ | Amino acid sequence | V | K | I | T | L | L | S | A | L | V | E | T |
| | DNA sequence (codon) | GTC | AAA | ATC | ACC | CTC | CTT | TCT | GCA | TTA | GTG | GAG | GTC |
| $rPCI_{WT}$ | Amino acid sequence | T | I | F | T | F | R | S | A | R | L | N | S |
| $rACT_{PCI}$ (MD CI) | Amino acid sequence | V | K | I | T | F | R | S | A | L | V | E | T |
| | DNA (codon) | GTC | AAA | ATC | ACC | TTT | AGA | TCT | GCA | TTA | GTG | GAG | GTC |

Plain type residues are common to $rACT_{WT}$, bold and underlined residues correspond to substrate peptides relocated in RSL of ACT variants. The scissile bond in substrate peptides is designated by ↓ and putative cleavage site in serpins is marked by asterisks between the P1-P1' residues.

Briefly, to produce the recombinant protein $ACT_{PCI}$ (MDCI), TG1 cells were transformed with the corresponding constructions followed by growth in appropriate culture media. Cells were then induced to an optimal density to express recombinant inhibitors for 16 h at 16° C. Recombinant inhibitor $ACT_{PCI}$ was extracted from cytoplasm bacteria and separated by affinity chromatography using Ni-NTA column as described for the previous example.

Analysis of Recombinant ACT Expression by SDS-PAGE.

The purity of the different inhibitors developed in example 1 and 2 was tested by SDS-PAGE analysis under reducing conditions.

Evaluation of the Inhibitors.

These inhibitors were further analysed to assess their specificity and affinity to inhibit the human kallikreins hK2 and hK3 and plasma kallikrein, trypsin, urokinase, elastase, thrombin, hK14 and human kallikrein 8 (Table VII). These two enzymes possess different enzymatic specificities (hK2: trypsin-like, hK3: chymotrypsin-like) but are naturally inhibited by ACT. While ACT is considered to be the natural hK3 inhibitor in blood circulation, its inhibition of hK2 is weaker.

Analysis of the inhibitory reaction between rACTs and the human kallikreins were analysed by Western Blot (data not shown). For each variants of ACT, 1 μg of inhibitor was incubated with 100 ng of either hK2 or hK3 during 1 hour at 37° C. under physiological conditions.

The amino acid changes within the reactive loop using substrate sequences selected for hK2 specificity transformed ACT into an inhibitor highly specific for hK2 (MD820, MD61, MD62) without inhibiting hK3. These results confirm those previously shown in Table IV. Only MDCI, based on the reactive loop of the inhibitor of the Protein C (PCI) is able to inhibit both kallikreins tested (hK2 and hK3).

MD61 and MD62 are inhibitors with very high affinity for hK2 inhibiting all hK2 protein in less than 3 minutes (under the same conditions) compared to wild type or commercial α1-antichymotrypsin, which requires more than 12 hours of incubation to inhibit the same amount of hK2 (data not shown).

TABLE VII

Inhibitory profile of $MD_{CI}$.

| PROTEASE | INHIBITION %[B] | SI | $k_a$ $M^{-1}$ $s^{-1}$ |
|---|---|---|---|
| Chymotrypsin | 98 | 1 | 86216 |
| Plasma Kallikrein | 100 | 4.6 | 25900 |
| Trypsin | 100 | 1 | 1126025 |
| Urokinase | 0 | — | — |
| Elastase | 0 | — | — |
| Thrombin | 0 | — | — |
| hK14 | 100 | 3.2 | 287000 |
| Human Kallikrein 8 | ~25 | ~180 | |

Example 2

Development of substrate active sites specific to human hK14.

The content of Application N+ PCT/IB2006/000574 (Université de Lausanne) is incorporated herein by reference in its entirety.

Materials

The following materials were obtained from commercial sources: elastase, trypsin, chymotrypsin, and plasma kallikrein (Calbiochem), human laminin 10 & 11 (Chemicon), human collagen IV (Life Technologies), T4 DNA ligase (Invitrogen), T4 polynucleotide kinase (Qbiogene), $Ni^{2+}$-nitrilotriacetic acid agarose beads (Qiagen), restrictions enzymes (Roche, Amersham Pharmacia, Promega), anti-His antibody (Sigma). Oligonucleotide synthesis was carried out by Invitrogen and DNA sequencing by Synergene Biotech GmbH. Human kallikrein 2 and prostate specific antigen were purified from human seminal plasma as previously described (Frenette et al., 1997; Frenette et al., 1998). Matrilin-4 is a gift from R. Wagener (Cologne, Germany). Cloning of KLK14 into *P. pastoris* Expression Vector pPICZαA First-strand cDNA synthesis was performed by reverse transcriptase using the SUPERSCRIPT® (reverse transcriptase) preamplification system (Gibco BRL, Gaithersburg, Md.) with 2 μg of total human cerebellum RNA (Clontech, Palo Alto, Calif.) as a template. The final reaction volume was 20 μL. To confirm the efficiency of RT-PCR, 1 μL of cDNA was subsequently amplified by PCR with primers specific for actin, a housekeeping gene (ActinS: 5' ACAATGAGCTGCGTGTGGCT (SEQ ID NO:114), ActinAS: 5' TCTCCTTAATGTCACGCACGA (SEQ ID NO:115)). Actin PCR products with an expected length of 372 base pairs (bp) were visualized on a 2% agarose gel stained with ethidium bromide. PCR amplification of KLK14 cDNA encoding the 227 amino acids of the mature hK14 protein (corresponding to amino acids 25-251 of Genbank accession no. AAK48524) was carried out in a 50 µL reaction mixture containing 1 pt of cerebellum cDNA as a template, 100 ng primers (FPL6: 5' AGG ATG AGG AAT TCA TAA TTG GTG GCC AT (SEQ ID NO:69) and RPL6: 5' CCC ACC GTC TAG ACC ATC ATT TGT CCC GC (SEQ ID NO:70)), 10 mM Tris-HCl (pH 8.3), 50 mM KCl, 1.5 mM $MgCl_2$, 200 µM deoxynucleoside triphosphates (dNTPs) and 0.75 µL (2.6 U) of Expand Long Template PCR polymerase mix (Roche Diagnostics, Mannheim, Germany), using an Eppendorf master cycler. The PCR conditions were 94° C. for 2 min, followed by 94° C. for 10 s, 52° C. for 30 s, 68° C. for 1 min for 40 cycles, and a final extension at 68° C. for 7 min. Following PCR, amplified KLK14 was visualized with ethidium bromide on 2% agarose gels, extracted, digested with EcoRI/XbaI and ligated into expression vector pPICZαA of the EASYSELECT™ Pichia pastoris expression system (Invitrogen, Carlsbad, Calif.) at corresponding restriction enzyme sites using standard techniques (Sambrook et al., 1989). The KLK14 sequence within the construct was confirmed with an automated DNA sequencer using vector-specific primers in both directions.

Protein Production

PmeI-linearized pPICZαA-KLK14, as well as empty pPICZαA (negative control), were transformed into chemically competent P. pastoris yeast strain X-33 after which they integrated into the yeast genome by homologous recombination. Transformed X-33 cells were then plated on YPDS (1% yeast extract, 2% peptone, 2% dextrose, 1 M sorbitol, 2% agar) plates containing Zeocin™, a selective reagent. A stable yeast transformant was selected as per the manufacturer's recommendations, inoculated in buffered minimal glycerol-complex (BMGY) medium [1% yeast extract, 2% peptone, 100 mM potassium phosphate (pH 6.0), 1.34% yeast nitrogen base, 40 mg/litre biotin, and 1% glycerol] overnight at 30° C. on a plate agitator at 250 rpm, diluted to $OD_{600}$=1.0 in BMMY (same as BMGY except that 1% glycerol is replaced with 0.5% methanol) and incubated under the same conditions as above for 6 days with a daily supplement of 1% methanol. The supernatant was collected by centrifugation at 4000×g for 20 min.

Protein Purification

Recombinant hK14 was purified from yeast culture supernatant by cation exchange using a 5 mL HiTrap™ carboxymethyl (CM) Sepharose Fast Flow column on the AKTAFPLC chromatography system (Amersham Biosciences, Piscataway, N.J.). First, the supernatant was filtered with a 0.22 µm disposable filter and concentrated 50-fold by ultrafiltration with an AMICON™ (protein concentrating and desalting, regenerated cellulose, ultrafiltration centrifugal filter) YM10 membrane (Millipore Corporation, Bedford, Mass.). The filtered, concentrated supernatant was then introduced into the injector of the AKTAFPLC system and loaded onto the CM sepharose column, previously equilibrated with 5 mL of 10 mM MES buffer (pH 5.3) at a flow rate of 0.8 ml/min. The column was washed with the aforementioned equilibration buffer and the adsorbed hK14 was eluted with a 150 mL continuous linear KCl gradient from 0 to 1 M in 10 mM MES (pH 5.3) at a flow rate of 3 ml/min. Elution fractions of 5 ml were collected and analyzed. Fractions containing hK14 were pooled and further concentrated 10 times using Biomax-10 Ultrafree®-15 Centrifugal Filter Device (Millipore Corporation, Bedford, Mass.). The protein concentration of the purified hK14 was determined by the bicinchoninic acid method (Smith et al., 1985), which uses bovine serum albumin as calibrator (Pierce Chemical Co., Rockford, Ill.). The purity of the recombinant hK14 protein was analyzed by SDS-PAGE (Laemmli, 1970) followed by Coomassie blue staining and/or Western blot analysis using a previously produced polyclonal rabbit antibody raised against hK14 (Borgono et al., 2003) and its identity was confirmed by tandem mass spectrometry, as described in detail for recombinant hK10 (Luo et al., 2001).

Phage-Displayed Pentapeptide Library Screening.

A monovalent type phagemid supplied by Dr Lowman (Genentech company, San Fransisco, Calif.) was previously modified in order to generate a substrate phage library containing six His residues (SEQ ID NO: 164) N terminal to the random pentapeptide fused to the g3p (Cloutier et al, 2002). The six His residues (SEQ ID NO: 164) allow the phage fixation to the Ni-NTA column.

Preparation of the duplex that is inserted into the phagemid was performed by PCR reaction of a degenerated oligonucleotide, in which the 5 random amino acids are coded by NSS (N=A, T, G, C and S=G, C). The resulting library was composed of $1.8 \times 10^8$ transformants, which is largely enough to get all random sequences represented.

This phage display substrate library was subjected to six rounds of screening with hK14. Briefly, substrate phages ($10^{11}$) were incubated with sixty microliters of $Ni^{2+}$-nitrilotriacetic acid resin in PBS 1× containing BSA at 1 mg/mL, washed four times (PBS 1×, BSA 1 mg/mL, 5 mM imidazole, 0.1% TWEEN® 20 (polysorbate 20 or polyoxyethylene sorbitol ester)) to remove unbound phages and then exposed to 65 nM (final concentration) of hK14 for 45 minutes at 37° C. in 50 mM Tris, 100 mM NaCl, 0.05% Triton, pH 7.5. The released phages were subsequently amplified using XL1-Blue Escherichia coli and then used after purification for subsequent rounds of selection. 32 individual clones from the last round of selection were sequenced for determination of their corresponding amino acid sequences.

Expression of CFP-YFP Fluorescent Substrate

Recombinant fluorescent substrates, using cyan fluorescent protein as donor and yellow fluorescent protein as acceptor, were constructed as described recently (Felber et al., 2004). CFP-XXXXX-YFP-6×His ("6×His" disclosed as SEQ ID NO: 164) recombinant proteins were constructed with varying pentapeptides (in bold) between CFP and YFP proteins using synthetic genes possessing the appropriate restriction sites (BssHII; SalI). The constructs contain the following amino acid sequences between CFP and YFP proteins: Gly-Ala-Leu-Gly-Gly-XXXXX-Gly-Ser-Thr (GALGGXXXXXGST (SEQ ID NO:116)). To produce recombinant proteins, TG1 cells were transformed with the corresponding constructs and purified by affinity chromatography using $Ni^{2+}$-NTA agarose beads. The purity and quantity of the purified CFP-YFP recombinant substrates were evaluated by SDS gel electrophoresis according to Laemmli followed by Coomassie Blue staining and Western blot analysis using a specific anti-His primary antibody (1/3000 dilution), a mouse anti-Fab secondary antibody (1/50000 dilution) and the ECL system (Amersham) for detection. All clones were sequenced prior to evaluation.

Direct Determination of the Kcat/Km and Specificity Studies Using CFP-YFP Fluorescent Substrates Substrate specificity of CFP-substrate-YFP proteins was tested towards different proteases and Kcat/Km values calculated as previously described (Felber et al., 2004). Briefly, fluorescence of CFP-$X_5$-YFP proteins was measured in black 96-well plates using a microplate fluorescence reader (Bio-Tek Instruments, Inc.) with excitation at 440 nm (±15) and emissions at 485 nm (±10) and 528 nm (±10). Each recombinant substrate, at a concentration of 150 nM, was incubated with hK14, chymotrypsin, trypsin, PSA, hK2, plasma kallikrein or elastase at a final concentration of 8 nM, 0.1 nM, 0.3 nM, 2 µM, 10 nM, 10 nM and 0.5 nM respectively. The reaction was performed for 60 min at 37° C. in reaction buffer (50 mM Tris pH 7.5, 100 mM NaCl, 0.05% Triton-X100). The enzyme concentration for initial-rate determinations was chosen at a level intended to hydrolyze specifically the substrate linker and not a GGGGG (SEQ ID NO:117) substrate, which was used as negative control. The appearance of fluorescence, corresponding to product formation, was measured spectrometrically with excitation at 440 nm (±15) and emission at 485 nm (±10). The slope was converted into units of nmol of product generated per sec, based on a calibration curve obtained from the complete hydrolysis of each peptide, evaluated on SDS-PAGE. The kinetic parameter $k_{cat}/K_m$ was determined under pseudo-first order conditions using a substrate concentration far below the estimated Km (Felber et al., 2004).

The cleavage products were separated by SDS-polyacrylamide gel electrophoresis, transferred to an Immobilon polyvinylidene difluoride membrane (Bio-Rad), and subjected to automated Edman degradation with an Applied Biosystems (model ABI493A) sequenator to determine the cleavage site.

Selection of Phage Substrate for hK14

The substrate phage library was panned against hK14 to select substrates cleaved by its hydrolytic activity. Cleaved phages were amplified in E. coli TG1 cells and then subjected to five more rounds of enzyme digestion and screening. The amount of released phages increased with each round, indicating the presence of a higher number of hK14-susceptible phages after each round of selection. The amino acid sequences of 32 phage peptides from the last round of selection were determined by sequencing. The sequences corresponding to the substrate regions are listed in Table 1. From all selected and cleaved peptides, 69% possess a basic residue in P1 position, as expected for a putative trypsin-like activity of hK14, whereas 31% of peptides have a tyrosine residue specific for a chymotrypsin-like enzyme in P1.

Kinetic Characterization of Substrate Hydrolysis by hK14

To verify that the sequences from the phage display analysis were indeed substrates for hK14, and to identify the cleavage site, all selected peptides were constructed in fluorescent substrate form. Applicants substrate system is based on the transfer of energy from CFP to YFP which are linked by the substrate. Cleavage of the linker by a protease separates the two fluorophores and results in a loss of the energy transfer. Thus, hydrolysis of the substrate can be evaluated by the measurement of increasing fluorescence intensity of the donor at 485 nm, corresponding to the wavelength of CFP emission (Mitra et al., 1996; Felber et al., 2004).

All substrates were hydrolyzed by hK14 with variable level of efficacy and Kcat/Km values ranged from 2 000 to 481 000 $M^{-1}$ $s^{-1}$. The specificity of cleavage was demonstrated with CFP-GGGGG-YFP (SEQ ID NO:117) which is not hydrolyzed by hK14 (not shown).

Results clearly indicate that the preferred P1 amino acid for hK14 susceptibility is Arg (Table 1) since the best hK14 substrates with Kcat/Km greater than 200,000 $M^{-1}$ $s^{-1}$ possess an Arg in P1 position. Interestingly, from the four peptides cleaved most efficiently by hK14, two contained a Gln at the P2 position. In contrast, a broad variety of amino acids were found in P1' position, demonstrating no significant preference at this position. However, two substrates possess an aspartic acid in P1' position and are cleaved relatively efficiently.

On the other hand, all substrates with a Lys at the P1 position were cleaved at low rate with a Kcat/Km equal to or below 34 000 $M^{-1}$ $s^{-1}$. Similarly, the cleavage rate for substrates with a P1 tyrosine was very low except for one substrate, peptide G9, which had a Kcat/Km of 134 000 $M^{-1}$ $s^{-1}$. With the exception of P1' position, where glycine residue is found in about 50% of P1 Lysine or Tyrosine substrates, no amino acid was recovered more frequently at the other positions. Nevertheless, it has to be stated that the majority of glycine residues found in position P1' were originating from the phage linker region flanking the selected pentapeptide substrates, where Lys or Tyr residues are found in position 5 of the selected peptide.

Specificity of Preferred Selected Substrates

Since many of the selected substrates contained motifs potentially susceptible to cleavage by other proteases, Applicants measured the degree to which hK2, plasma kallikrein, PSA, chymotrypsin, trypsin and elastase could cleave these hK14 substrates (Table VIII). Each substrate was tested at enzyme concentration leading to specific cleavage in the substrate linker and not hydrolyzing the GGGGG (SEQ ID NO:117) control substrate.

Not surprisingly, most of trypsin-like substrates are cleaved by trypsin with a variable efficacy which was not strictly in correlation with hK14 preferences. For instance, the two pentapeptides VGSLR (SEQ ID NO:118) and RQTND (SEQ ID NO:119) were the best substrates for hK14 but were not very efficiently cleaved by trypsin in comparison to other peptides like LSGGR (SEQ ID NO:124) exhibiting a Kcat/Km of almost 5,000,0000 M-1·s-1. In contrast, peptides possessing a Gln in P2 position were excellent substrates for hK14 as well as for trypsin. Only two hK14 substrates with low trypsin-like hK14 activity, RVTST (SEQ ID NO:128) and VVMKD (SEQ ID NO:129), but four out of five substrates with chymotrypsin like hK14 activity were not cleaved by trypsin.

All chymotrypsin-like substrates were cleaved by chymotrypsin more efficiently than with hK14, except for the substrate TVDYA (SEQ ID NO:130) which gave almost the same kcat/Km with hK14, chymotrypsin and elastase. Elastase also proteolyzed the two selected peptides TSYLN (SEQ ID NO:134) and YQSLN (SEQ ID NO:133), which is also cleaved weakly by PSA. Preferred substrates displayed a high selectivity for hK14 in comparison to other human kallikreins such as hK1, hK2, PSA and PK. Only hK2 proteolyzed most of the trypsin-like substrates with Kcat/Km values always at least 5 fold lower than for hK14. For example, NQRSS (SEQ ID NO:120) peptide is 27 and 78 fold more selective for hK14 than for hK2 and PK, respectively and F3 peptide demonstrates high hK14 specificity and no cleavage with another kallikrein could be detected.

TABLE VIII

Specificity of phage selected hK14 substrates toward different human proteases.

| Peptide | Sequence | hK14 | Trypsin | Chymo-Trypsin | Elastase | Plasma kallikrein | hK1 | hK2 | PSA |
|---------|----------|------|---------|---------------|----------|-------------------|-----|-----|-----|
| | | \multicolumn{8}{c}{Trypsin-like substrate} |
| | | \multicolumn{8}{c}{Kcat/Km (M-1.s-1)} |
| G1 | VGSLR SEQ ID NO: 118 | 481'000 | 270'000 | 145'000 | — | — | — | 21'000 | — |
| C11 | RQTND SEQ ID NO: 119 | 415'000 | 260'000 | 251'000 | — | — | — | 23'000 | — |
| E5 | NQRSS SEQ ID NO: 120 | 388'000 | 2'070'000 | — | — | 5'000 | — | 14'000 | — |
| E8 | LQRAI SEQ ID NO: 121 | 367'000 | 2'270'000 | — | 209'000 | 5'000 | — | 25'000 | — |
| F11 | QRLRD SEQ ID NO: 122 | 307'000 | 1'420'000 | 168'000 | — | — | L.C. | 32'000 | — |
| F3 | PDRHM SEQ ID NO: 123 | 243'000 | 319'000 | 192'000 | — | — | — | — | — |
| E2 | LSGGR SEQ ID NO: 124 | 207'000 | 4'676'000 | 83'000 | — | — | — | 14'000 | — |
| E7 | LSRDN SEQ ID NO: 125 | 127'000 | 246'000 | 155'000 | — | — | — | 16'000 | — |
| D9 | RGKTN SEQ ID NO: 126 | 80'000 | 2'111'000 | 94'000 | — | — | — | 21'000 | — |
| E9 | NNKLR SEQ ID NO: 127 | 74'000 | 384'000 | 77'000 | — | — | — | 12'000 | — |
| E12 | RVTST SEQ ID NO: 128 | 26'000 | — | 100'000 | 200'000 | — | — | — | — |
| E10 | VVMKD SEQ ID NO: 129 | 15'000 | — | — | 65'000 | — | — | — | — |
| | | \multicolumn{8}{c}{Chymotrypsin-like substrate} |
| | | \multicolumn{8}{c}{kcat/Km (M-1.s-1)} |
| G9 | TVDYA SEQ ID NO: 130 | 134'000 | — | 145'000 | 181'000 | — | — | — | — |
| E1 | AYGYK SEQ ID NO: 131 | 24'000 | 129'000 | 618'000 | — | — | — | — | — |
| F6 | VGLYD SEQ ID NO: 132 | 18'000 | — | 409'000 | — | — | — | — | — |
| F10 | YQSLN SEQ ID NO: 133 | 12'000 | — | 134'000 | 49'000 | — | — | — | L.C. |

TABLE VIII-continued

Specificity of phage selected hK14 substrates toward different human proteases.

| Peptide | Sequence | hK14 | Trypsin | Chymo-Trypsin | Elastase | Plasma kallikrein | hK1 | hK2 | PSA |
|---|---|---|---|---|---|---|---|---|---|
| D7 | TSYLN SEQ ID NO: 134 | 9'000 | — | 266'000 | 90'000 | — | — | — | — |

L.C.: low cleavage, kcat/Km not determined; — no detectable cleavage

Example 2

Materials

The following materials were obtained from commercial sources: elastase, trypsin, chymotrypsin, thrombin and plasma kallikrein (Calbiochem), T4 DNA ligase (Invitrogen), T4 polynucleotide kinase (Qbiogene), $Ni^{2+}$-nitrilotriacetic acid agarose beads (Qiagen), restrictions enzymes (Roche, Amersham Pharmacia, Promega), anti-His antibody and an alkaline phosphatase-conjugated goat anti-mouse secondary antibody (Sigma). Fluorescent substrates Z-Phe-Arg-AMC, Suc-Ala-Ala-Pro-Phe-AMC (AAPF SEQ ID NO:135), Z-Gly-Gly-Arg-AMC and MeOSuc-Ala-Ala-Pro-Val-AMC (AAPV SEQ ID NO:136) were purchased from Calbiochem, Boc-Val-Pro-Arg-AMC from Bachem, Abz-Thr-Phe-Arg-Ser-Ala-Dap(Dnp)-NH2 (SEQ ID NO: 203) from Neosystem. Oligonucleotide synthesis was carried out by Invitrogen and DNA sequencing by Synergene Biotech GmbH. Human kallikrein 2, 5, 13 and 14 were produced in a yeast system (Yousef et al., 03c; Kapadia et al., 03; Borgono et al., 03). Human kallikrein 6 was produced in a 293 human embryonic kidney cell system and human kallikrein 8 with a baculovirus vector and HighFive insect cells (Little et al., 97; Kishi et al., 03). HK6 and hK8 were activated with Lys-C(Shimizu et al., 98).

Construction of Expression Vectors for Recombinant Wild-Type AAT, ACT and their Variants.

Human AAT cDNA (Invitrogen, UK) was amplified by PCR using the oligonucleotides 5'-TATGGATCCGATGATCCCCAGGGAGA-3' (SEQ ID NO:71) and 5'-CGCGAAGCTTTTATTTTTGGGTGGGA-3' (SEQ ID NO:72). The BamHI-HindIII fragment of the amplified AAT gene was cloned into the vector pQE9 (Qiagen, Germany) resulting in plasmid pAAT, which contains an open reading frame of the mature AAT with an N-terminal $His_6$-tag (SEQ ID NO: 164). Silent mutations producing KasI and Bsu36I restriction sites were introduced in pAAT 24 bp upstream and 11 bp downstream of the P1 codon of the RSL domain, respectively. The restriction sites were created using the oligonucleotides 5'-ACTGAAGCTGCTGGCGCCGAGCTCTTAGAGGCCATA-3' (SEQ ID NO:73) for the KasI and 5'-GTCTATCCCCCCTGAGGTCAAGTTC-3' (SEQ ID NO:74) for the Bsu36I site following the QuikChange mutagenesis protocol supplied by Stratagene. Construction of the plasmid expressing wild-type ACT was described previously (Cloutier et al., 2004). rAAT and rACT variants were produced by replacement of the RSL region with corresponding DNA fragments amplified from appropriate template oligonucleotides:

$rAAT_{E8}$,
(SEQ ID NO: 75)
5'-CCATGTTTCTAGAGGCTCTGCAGCGTGCTATCCCGCCTGAGGTCAAG TT-3';

$rAAT_{G9}$,
(SEQ ID NO: 76)
5'-CCATGTTTCTAGAGACCGTTGACTACGCTATCCCGCCTGAGGTCAAG TT-3', $rACT_{E8}$,
(SEQ ID NO: 77)
5'-TACCGCGGTCAAAATCCTGCAGCGTGCTATCCTGGTGGAGACGCGTG A-3'
and $rACT_{G9}$,
(SEQ ID NO: 78)
5'-TACCGCGGTCAAAACCGTTGACTACGCTGCTCTGGTGGAGACGCGTG A-3'.

Templates were amplified using primers corresponding to their respective flanking regions, 5'-GCTGGCGCCATGTTTCTAGAG-3' (SEQ ID NO:79; AAT variants1) and 5'-TTGTTGAACTTGACCTCAGG-3'(SEQ ID NO:80; AAT variants 2) for AAT variants and 5'-GTACCGCGGTCAAA-3'(SEQ ID NO:81; ACT variants 1) and 5'-TCACGCGTGTCCAC-3'(SEQ ID NO:82; ACT variants 2) for ACT variants. Resulting PCR fragments were cloned as KasI/Bsu36I fragments into pAAT and as MluI/SacII fragments into $rACT_{WT}$ constructs and confirmed by DNA sequencing. Changes in the reactive site loop between positions P4 and P2' are shown in Table IX.

Expression and Purification of Recombinant Serpins

Recombinant serpins were produced in *Escherichia coli* strain TG1. Cells were grown at 37° C. in 2× TY media (16 g tryptone, 10 g yeast extract, 5 g NaCl per L) containing 100 μg/ml ampicillin to $O.D._{600}$=0.5-0.7. Isopropyl thio-β-D-galactoside (IPTG) was added to a final concentration of 0.5 mM for production of rACT proteins and 0.1 mM for rAAT proteins and recombinant serpins were expressed for 16 h at 18° C. Cells were harvested by centrifugation and resuspended in 0.1 volume of cold PBS 2×. After 45 min of incubation with lysozyme (0.5 mg/ml) on ice, total soluble cytoplasmic proteins were extracted by four cycles of freeze/thaw and total DNA was degraded with DNase I. Cell debris was removed by centrifugation (25 min., 17'500 g) and $Ni^{2+}$-nitrilotriacetic affinity agarose beads were added to the supernatant for 90 min at 4° C. to bind recombinant serpins. The resin was washed three times with 50 mM Tris, pH 7.5, 150 mM NaCl, 20 mM imidazole and bound proteins were eluted with 50 mM Tris, pH 7.5, 150 mM NaCl, 150 mM imidazole. Eluted proteins were dialyzed against 50 mM Tris, pH 7.5, 150 mM NaCl, 0.01% Triton X-100 for 16 h at 4° C. and protein purity was assessed by Coomassie Blue-stained SDS-PAGE. Protein concentrations were determined by the bicinchoninic acid method (Smith et al., 1985), using bovine serum albumin as standard (Pierce Chemical Co., Rockford, Ill.). $AAT_{E8}$, $ACT_{E8}$ and $AAT_{G9}$, $ACT_{G9}$ were titrated with trypsin and chymotrypsin, respectively.

Stoichiometry of Inhibition (SI)

SI values of rAAT, rACT, and their variants were determined with hK14 incubating the protease with varying concentrations of inhibitor. After an incubation of 4 hours at 37° C. in reaction buffer (50 mM Tris, pH 7.5, 150 mM NaCl, 0.05% Triton X-100, 0.01% BSA), the residual activity was detected by the addition of fluorescent substrate (Boc-Val-Pro-Arg-AMC). Fluorescence was measured with excitation at 340 nm (±15) and emission at 485 nm (±10) in black 96 well plates using a microplate fluorescence reader $FL_x800$ (Bio-Tek Instruments, Inc.). The SI value corresponds to the abscissa intercept of the linear regression analysis of fractional velocity (velocity of inhibited enzyme reaction (vi)/velocity of uninhibited enzyme reaction ($v_0$)) vs. the molar ratio of the inhibitor to enzyme ($[I_0]/[E_0]$).

Kinetic Analysis

The association rate constants for interactions of hK14, with different inhibitors were determined under pseudo-first order conditions using the progress curve method (Morrison and Walsh, 1988). Under these conditions, a fixed amount of enzyme (2 nM) was mixed with different concentrations of inhibitor (0-80 nM) and an excess of substrate (20 µM). Reactions were performed in reaction buffer (50 mM Tris pH 7.5, 150 mM NaCl, 0.05% Triton X-100, 0.01% BSA) at 37° C. for 45 min and the rate of product formation was measured using a $FL_x800$ fluorescence 96-well microplate reader (Biotek, USA). Inhibition is considered to be irreversible over the course of reaction and the progression of enzyme activity is expressed as product formation (P), beginning at a rate ($v_z$) and is inhibited over time (t) at a first-order rate ($k_{obs}$), where the rate constant is only dependent on the inhibitor concentration.

$$P=(v_z/k_{obs})\times[1-e^{(-k_{obs}t)}] \quad \text{eq 1}$$

For each inhibitor, a $k_{obs}$ was calculated for four different concentrations of inhibitor, by non linear regression of the data using equation 1. By plotting the $k_{obs}$ versus inhibitor concentration [I], a second-order rate constant, k', equal to the slope of the curve ($k'=\Delta k_{obs}/\Delta[I]$), was determined. Due to the competition between the inhibitor and the substrate, equation 2 below is used to correct the second order rate constant k' by taking into account the substrate concentration [S] and the $K_m$ of the enzyme for its substrate, giving the $k_a$.

$$k_a=(1+[S]/K_m)\times k' \quad \text{eq 2}$$

The $K_m$ of hK14 for MeOSuc-VPR-AMC was 8 µM. However, it will be understood that, depending on the purity grade and specific activity of the hK14 protease, the $K_m$ may vary.

SDS-PAGE Analysis of Enzyme-Inhibitor Complexes

A constant amount of the different inhibitors (ranging from 1 to 2 ug) was incubated for 4 h in reaction buffer (50 mM Tris pH 7.5, 150 mM NaCl, 0.05% Triton X-100) with different amounts of hK14 corresponding to 0.5, 1 and 2 times the SI value. Samples were heated at 90° C. for 10 minutes, resolved on a 10% SDS gel under reducing conditions and visualized by Coomassie Blue staining.

Inhibitory Specificity of Recombinant rAAT and rACT Variants (Table IX)

2 nM of trypsin, chymotrypsin, plasma kallikrein, human neutrophil elastase and thrombin and 10 nM of hK2, hK3, hK5, hK6, hK8, hK13 and hK14 were incubated for 30 minutes at 37° C. with 100 nM and 500 nM of recombinant inhibitors, respectively. Residual activities were detected by the addition of fluorescent substrates (Z-Phe-Arg-AMC for trypsin and plasma kallikrein, Suc-Ala-Ala-Pro-Phe-AMC (SEQ ID NO: 135) for chymotrypsin, Z-Gly-Gly-Arg-AMC for thrombin and MeOSuc-Ala-Ala-Pro-Val-AMC (SEQ ID NO: 136) for human neutrophil elastase and Abz-Thr-Phe-Arg-Ser-Ala-Dap(Dnp)-NH2 (SEQ ID NO: 203) for human kallikreins).

Stability of the Complex

HK14 (2 nM) was incubated with different amounts of inhibitors, corresponding to 0, 1 and 2 times the SI. After incubations for 4, 8 and 24 h at 37° C. in reaction buffer (50 mM Tris, pH 7.5, 150 mM NaCl, 0.05% Triton X-100, 0.01% BSA), the residual activity was detected by addition of 20 µM of the fluorescent substrates Boc-Val-Pro-Arg-AMC. The slope (velocity) of each inhibitory reaction was divided by the slope of the corresponding reaction without inhibitor.

Design and Production of Soluble Recombinant Serpins

To develop specific inhibitors for hK14, Applicants substituted five residues surrounding the scissile bond of rAATwt and rACTwt by two substrate pentapeptides, previously selected with hK 14 using phage-display technology (Felber et al., 05). Profiling of hK14 enzymatic activity demonstrated that hK14 has a dual trypsin and chymotrypsin-like activity. Applicants therefore decided to develop inhibitors with two substrate peptides, E8 and G9, specific for trypsin and chymotrypsin-like activity, respectively. The scissile bond of these substrates was aligned according to the P1-P'1 of the rAATwt and rACTwt. The RSL regions of the serpin variants are shown in Table IX (SEQ ID NOS. 177-182, respectively).

TABLE IX

| Serpin | Selected[a] Substrate Peptide | P6 | P5 | P4 | P3 | P2 | P1 | P1' | P2' | P3' | P4' | P5' |
|---|---|---|---|---|---|---|---|---|---|---|---|---|
| AAT$_{WT}$ | | L | E | A | I | P | M* | S | I | P | P | E |
| AAT$_{E8}$ | LQR↓AI SEQ ID NO: 121 | L | E | A | L | Q | R* | A | I | P | P | E |
| AAT$_{G9}$ | TVDY↓A SEQ ID NO: 130 | L | E | T | V | D | Y* | A | I | P | P | E |
| ACT$_{WT}$ | | V | K | I | T | L | L* | S | A | L | V | E |
| ACT$_{E8}$ | LQR↓AI SEQ ID NO: 121 | V | K | I | L | Q | R* | A | I | L | V | E |
| ACT$_{G9}$ | TVDY↓A SEQ ID NO: 130 | V | K | T | V | D | Y* | A | A | L | V | E |

Comparison of amino acid sequence of the scissile bond region of the reactive serpin loop (RSL) of wild type AAT, ACT and their variants.
[a]Substrate peptides selected by kallikrein hK14 using a phage-displayed random pentapeptide library (Felber et al., 2004).
Plain type residues are common to wild type serpin, bold residues correspond to substrate peptides relocated in RSL of AAT and ACT variants. The scissile bond cleaved by hK14 in substrate peptides is designated by ↓ and putative cleavage sites in serpins are marked by asterisks between the P1-P1' residues.

The recombinant serpins were produced as soluble, active form and were purified under native conditions from cytoplasmic proteins in a one-step procedure over a nickel affinity column. Analysis on SDS-PAGE under reducing conditions revealed a single band for each inhibitor, rAAT and rACT variants, migrating at apparent sizes of 45 to 50 kDa, corresponding with their molecular weight, except for the protein $AAT_{E8}$, which is migrating slightly faster (data not shown). All inhibitors were estimated to be more than 95% pure by densitometric analysis, with a range of production yield of 1 to 5 mg/L.

Stoichiometry of Inhibition, Association Constants and Complex Stability

Determination of stoichiometry of inhibition (SI) was performed under physiological conditions of pH and ionic strength. The SI indicates the number of inhibitor molecule required to inhibit one molecule of hK14. Applicants observed that titration curves were linear, even for SI values >>1, indicating that the reaction is completely finished. The calculated SI values of the serpin variants range from ~1 to 1.5, except for $rAAT_{E8}$ which resulted in a SI of 7.4 (Table X).

Whereas wild type ACT did not react with hK14 under the tested conditions, $AAT_{WT}$ was found to be a good inhibitor for hK14 with a SI of 1. Substitution of ACT RSL region with hK14 substrate peptides not only allowed generating reactivity toward the enzyme but creating inhibitors with high affinity. On the other hand, using $AAT_{WT}$ as scaffold, modification of the RSL was less favorable since all inhibitors are less efficient than wild type version (Table X).

TABLE X

| Inhibitor | Selected[a] Substrate Peptide | SI | $k_a$ M$^{-1}$ s$^{-1}$ |
|---|---|---|---|
| $AAT_{WT}$ | IPM*SI<br>SEQ ID NO: 140 | 1.0 | 263 000 |
| $AAT_{E8}$ | LQR↓AI<br>SEQ ID NO: 121 | 7.4 | n.a. |
| $AAT_{G9}$ | TVDY↓A<br>SEQ ID NO: 130 | 1.2 | 217 000 |
| $ACT_{WT}$ | TLL*SA<br>SEQ ID NO: 138 | — | — |
| $ACT_{E8}$ | LQR↓AI<br>SEQ ID NO: 121 | 1.2 | 575 000 |
| $ACT_{G9}$ | TVDY↓A<br>SEQ ID NO: 130 | 1.5 | 74 000 |

Stoichiometry Inhibition (SI) and second-order rate constants ($k_a$) values for the reaction of rAATwt, rACTwt and their variants with hK14.
[a]Substrate peptide selected by phage display technology with hK14 (Felber et al., 2005) and used to modify the rAATwt and rACTwt.
—, No detectable inhibitory activity.

Calculated SI values were consistent with the ratio between cleaved and complexed forms of the serpins after reaction with hK14 as demonstrated by SDS-PAGE analysis (data not shown). Each variant was incubated with different concentrations of hK14 corresponding to a ratio of inhibitor to protease below, equal and above the SI value. The analysis of SDS-PAGE showed the formation of covalent complexes (C) for each serpin variant hK14 pair, with apparent molecular masses consistent with expected values. When hK14 concentration was 0.5 time the SI value, degraded forms of the complex was observed which is certainly generated by the uncomplexed and free hK14.

Besides the formation of an inhibitor complex, reaction with hK14 also produced a fraction of hydrolyzed inhibitor, with a molecular size consistent with the serpin being cleaved at or near the reactive site of the RSL. The amount of this fraction was largely lowered when the SI value is close to 1 (AAT-G9, ACT-E8 and ACT-G9). In contrast, the only variant with a SI values >>1 ($rAAT_{E8}$) exhibited a substrate behavior with hK14, resulting mainly in accumulation of the cleaved form of the inhibitor rather than formation of the irreversible complex. As expected, the presence of intact inhibitor was observed when the ratio $[I]_o/[E]_o$ was above the SI with a weak band of complex.

Surprisingly, most of complexes were found to be SDS stable (data not shown) even if a relatively slow breakdown of the complex was observed with $AAT_{G9}$ resulting in the reappearance of hK14 activity after 8 hours of incubation.

Kinetic analysis of the inhibition of human hK14 by recombinant serpins were performed under pseudo-first-order conditions using an excess of inhibitor at various molar ratios of hK14. The time-dependent inactivation of the enzyme through reaction with serpin was monitored continuously, following the decrease in the rate of substrate turnover. Progress curves for reactions with different serpin concentrations were fitted to equation 1 to calculate values describing the rate constant (kobs). The association rate constants ($k_a$) were determined from the slope of kobs values versus the concentration of the hK14 inhibitors. Independently of the inhibitor scaffold (AAT or ACT), the recombinant serpins modified with the substrate E8 showed superior $k_a$ values than the equivalent G9 inhibitor.

Serpins modified with the chymotrypsin-like substrate, $rAAT_{G9}$ and $rACT_{G9}$, demonstrated only a moderate affinity for hK14, with association constants of respectively 217,000 and 74,000 M$^{-1}$ s$^{-1}$ while $rACT_{E8}$ possessed association constants of 575,000 M$^{-1}$ s$^{-1}$.

Inhibitory Specificity of Recombinant rAAT and rACT Variants

In order to define the inhibitory specificity of hK14 inhibitors, Applicants investigated the reaction of purified variants with a broad panel of proteinases. First at all, proteinases with broad specificities were examined, including trypsin, chymotrypsin, plasma kallikrein, human neutrophil elastase and thrombin. Additionally, Applicants assessed the specificity of hK14 inhibitors towards enzymes belonging to the same protease family, i.e. hK2, hK3, hK5, hK6, hK8 and hK13 (Table XI). Following 30 minutes of incubation of hK14 with an excess of inhibitors ($[I]_o/[E]_o$ of 50:1), no residual activity was detected with all modified serpins and rAATwt.

Under these conditions, only rACTwt showed weak inhibitory activity against hK14, with only 17% of inhibition. Serpins modified with the E8 substrate showed a moderate specificity since several other enzymes were inhibited by these inhibitors. A very high specificity was observed with $AAT_{G9}$ and $ACT_{G9}$ and none of the tested enzymes was inhibited, except for chymotrypsin and to a lower extent for hK5.

TABLE XI

| Protease | AATwt | $AAT_{E8}$ | $AAT_{G9}$ | ACTwt | $ACT_{E8}$ | $ACT_{G9}$ |
|---|---|---|---|---|---|---|
| hK14 | 100 | 100 | 100 | 17 | 100 | 100 |
| Trypsin | 100 | 100 | 0 | 0 | 100 | 0 |
| Chtr | 100 | 19 | 100 | 100 | 14 | 100 |
| PK | 17 | 100 | 0 | 46 | 36 | 0 |
| HNE | 100 | 0 | 0 | 16 | 0 | 0 |

TABLE XI-continued

| Protease | AATwt | AAT$_{E8}$ | AAT$_{G9}$ | ACTwt | ACT$_{E8}$ | ACT$_{G9}$ |
|---|---|---|---|---|---|---|
| Thrombin | 4 | 0 | 0 | 18 | 0 | 0 |
| hK2 | 0 | 19 | 0 | 0 | 100 | 0 |
| hK3 | 0 | 0 | 0 | 100 | 0 | 0 |
| hK4 | na | na | na | Na | 100 | 0 |
| hK5 | 28 | 100 | 30 | 7 | 100 | 0 |
| hK6 | 33 | 100 | 0 | 24 | 72 | 0 |
| hK8 | 0 | 36 | 0 | 0 | 34 | 0 |
| hK13 | 0 | 30 | 0 | 0 | 0 | 0 |

Inhibitory specificity of hK14 inhibitors. Percentage inhibition conrresponding to 100 × [1 − (velocity in presence of inhibitor/velocity of uninhibited control)]. Reaction of 30 min. incubation with an excess of inhibitors ([I]$_o$/[E]$_o$ of 50:1).

Example 3

Production and Purification of Active hK14

Human Kallikrein 14 was produced and purified as previously described.

Selection of substrate peptides for hk14 using phage display technology

The substrate phage library was panned against hK14 to select substrates hydrolyzed by its hydrolytic activity. Cleaved phages were amplified in *E. coli* TG1 cells and then subjected to five more rounds of enzyme digestion and screening. The amount of released phages increased with each round, thus verifying a higher number of hK14-susceptible phages after each round of selection. The amino acid sequences of 32 phage peptides from the last round of selection were determined by sequencing and the obtained sequences corresponding to the substrate regions were listed in Table 8. From all selected and cleaved peptides, 69% possess at least one basic residue in P1 position as expected with the putative trypsin-like activity of hK14 whereas 31% of peptides have a tyrosine residue specific to chymotrypsin-like enzyme in P1.

Kinetic Characterization of Substrate Hydrolysis by hK14

To verify that the sequences from the phage display analysis were indeed substrates for hK14 and to identify the cleavage site, all selected peptides were constructed in fluorescent substrate form. All substrates were hydrolyzed by hK14 with variable level of efficacy and kcat/Km ranged from 2,000 to 481,000 M$^{-1}$ s$^{-1}$. The specificity of cleavage was demonstrated by CFP-GGGGG-YFP (SEQ ID NO:117) which is not hydrolyzed by hK14.

Results clearly indicate that the preferred P1 amino acid for hK14 susceptibility is Arg (Table XIII) since all of the best hK14 substrates with kcat/Km superior to 200 000 M$^{-1}$ s$^{-1}$ possess an Arg in P1 position. Interestingly, from the four peptides cleaved most efficiently by hK14, two contained Glu at the P2 position. In contrast, a broad variety of amino acids occurred in P'1 position demonstrating no significant preference at this position. However, two substrates possess an aspartic acid in P'1 position and are cleaved relatively efficiently.

On the other hand, all substrates with a Lys at the P1 position were cleaved at very low rate with a Kcat/Km below 34 000 M$^{-1}$ s$^{-1}$. Similarly, the cleavage rate for the substrate with a P1 Tyrosine was very low excepted one substrate, peptide G9, which has a Kcat/Km of 134 000 M$^{-1}$ s$^{-1}$. With the exception of P'1 position, where glycine residue is recovered in almost 50% of P1 Lysine or Tyrosine substrates, none amino acid in particular was recovered more frequently at the other positions.

Since many of the selected substrates contained some motifs susceptible to be cleaved by other proteases, Applicants measured the degree to which hK2, plasma kallikrein, PSA, chymotrypsin, trypsin and elastase could cleave these hK14 substrates (Table XII). Each substrate was tested at enzyme concentration giving a specific cleavage in the substrate linker.

Not surprisingly, most of trypsin-like substrates are cleaved by trypsin with a variable efficacy which was not strictly in correlation with hK14 preferences. For instance, the two pentapeptides VGSLR (SEQ ID NO:118) and RQTND (SEQ ID NO:119) were best substrates for hK14 but were not very efficiently cleaved by trypsin in comparison to other peptides like LSGGR (SEQ ID NO:124) peptide giving a Kcat/Km of almost 5,000,0000 M$^{-1}$·s$^{-1}$ with trypsin. In contrast, peptides possessing a Gln in P2 position were best substrates as well as for hK14 than for trypsin. Only two hK14 substrates, RVTST (SEQ ID NO:128) and VVMKD (SEQ ID NO:129), in exception to chymotrypsin-like substrates were not cleaved by trypsin.

Chymotrypsin-like substrates were cleaved by chymotrypsin more efficiently than with hK14 excepted TVDYA (SEQ ID NO:130) substrate which gave almost the same Kcat/Km with hK14, chymotrypsin and elastase. This last enzyme also proteolyzed the two selected peptides YQSLN (SEQ ID NO:133), which is also cleaved weakly by PSA, and TSYLN (SEQ ID NO:134). Selected substrates displayed a high selectivity for hK14 in comparison to other human kallikreins such as hK1, hK2, PSA and PK. Only hK2 proteolyzed most of the trypsin-like substrates with Kcat/Km values always at least 5 fold less than for hK14. For example, NQRSS (SEQ ID NO:120) peptide is 27 and 78 fold more selective for hK14 than for hK2 and PK, respectively.

TABLE XII

Specificity of preferred selected substrates Comparison of specificity constant (kcat/Km) values of CFP-X5-YFP substrates based on selected substrates for hK14. (P1 positions of scissile bonds are in bold).

| Clone | Sequence | $k_{cat}/K_m$ (M$^{-1}$.s$^{-1}$) |
|---|---|---|
| G1 | VGSLR SEQ ID NO: 118 | 481'000 |
| C11 | RQTND SEQ ID NO: 119 | 415'000 |
| E5 | NQRSS SEQ ID NO: 120 | 388'000 |
| E8 | LQRAI SEQ ID NO: 121 | 367'000 |
| F11 | QRLRD SEQ ID NO: 122 | 307'000 |
| F3 | PDRHM SEQ ID NO: 123 | 243'000 |
| E2 | LSGGR SEQ ID NO: 124 | 207'000 |
| G9 | TVDYA SEQ ID NO: 130 | 134'000 |
| E7 | LSRDN SEQ ID NO: 125 | 127'000 |
| D9 | RGKTN SEQ ID NO: 126 | 80'000 |
| E9 | NNKLR SEQ ID NO: 127 | 74'000 |

TABLE XII-continued

Specificity of preferred selected substrates Comparison of specificity constant (kcat/Km) values of CFP-X5-YFP substrates based on selected substrates for hK14. (P1 positions of scissile bonds are in bold).

| Clone | Sequence | $k_{cat}/K_m$ (M$^{-1}$·s$^{-1}$) |
|---|---|---|
| E6 | MQVKH<br>SEQ ID NO: 142 | 34'000 |
| E4 | TTDLR<br>SEQ ID NO: 143 | 27'000 |
| E12 | RVTST<br>SEQ ID NO: 128 | 26'000 |
| E1 | AYGYK<br>SEQ ID NO: 131 | 24'000 |
| G3 | STKGI<br>SEQ ID NO: 144 | 20'000 |
| F5 | KLKET<br>SEQ ID NO: 145 | 19'000 |
| F6 | VGLYD<br>SEQ ID NO: 132 | 18'000 |
| E10 | VVMKD<br>SEQ ID NO: 129 | 15'000 |
| D11 | RVDTG<br>SEQ ID NO: 146 | 15'000 |
| F7 | GHRIN<br>SEQ ID NO: 147 | 12'000 |
| F10 | YQSLN<br>SEQ ID NO: 133 | 12'000 |
| C5 | SDKVY<br>SEQ ID NO: 148 | 9'000 |
| G11 | HETLK<br>SEQ ID NO: 149 | 9'000 |
| D7 | TSYLN<br>SEQ ID NO: 134 | 9'000 |
| F4 | MQATK<br>SEQ ID NO: 150 | 8'000 |
| G7 | EAPAK<br>SEQ ID NO: 151 | 8'000 |
| F12 | PVHLY<br>SEQ ID NO: 152 | 7'000 |
| F1 | QPNGY<br>SEQ ID NO: 153 | 6'000 |
| G5 | AYGLA<br>SEQ ID NO: 154 | 6'000 |
| C9 | YQNSS<br>SEQ ID NO: 155 | 6'000 |
| E11 | SAVRP<br>SEQ ID NO: 156 | 5'000 |

TABLE XIII

Specificity of phage selected hK14 substrates toward different human proteases.

| Peptide | Sequence | hK14 | Trypsin | Chymo-Trypsin | Elastase | Plasma kallikrein | hK1 | hK2 | PSA |
|---|---|---|---|---|---|---|---|---|---|
| | | | | Trypsin-like substrate | | | | | |
| | | | | $k_{cat}/K_m$ (M$^{-1}$·s$^{-1}$) | | | | | |
| G1 | VGSLR<br>SEQ ID NO: 118 | 481'000 | 270'000 | 145'000 | — | — | — | 21'000 | — |
| C11 | RQTND<br>SEQ ID NO: 119 | 415'000 | 260'000 | 251'000 | — | — | — | 23'000 | — |
| E5 | NQRSS<br>SEQ ID NO: 120 | 388'000 | 2'070'000 | — | — | 5'000 | — | 14'000 | — |
| E8 | LQRAI<br>SEQ ID NO: 121 | 367'000 | 2'270'000 | — | 209'000 | 5'000 | — | 25'000 | — |
| F11 | QRLRD<br>SEQ ID NO: 122 | 307'000 | 1'420'000 | 168'000 | — | — | L.C. | 32'000 | — |
| F3 | PDRHM<br>SEQ ID NO: 123 | 243'000 | 319'000 | 192'000 | — | — | — | — | — |

TABLE XIII-continued

Specificity of phage selected hK14 substrates toward different human proteases.

| Peptide | Sequence | hK14 | Trypsin | Chymo-Trypsin | Elastase | Plasma kallikrein | hK1 | hK2 | PSA |
|---|---|---|---|---|---|---|---|---|---|
| E2 | LSGGR SEQ ID NO: 124 | 207'000 | 4'676'000 | 83'000 | — | — | — | 14'000 | — |
| E7 | LSRDN SEQ ID NO: 125 | 127'000 | 246'000 | 155'000 | — | — | — | 16'000 | — |
| D9 | RGKTN SEQ ID NO: 126 | 80'000 | 2'111'000 | 94'000 | — | — | — | 21'000 | — |
| E9 | NNKLR SEQ ID NO: 127 | 74'000 | 384'000 | 77'000 | — | — | — | 12'000 | — |
| E12 | RVTST SEQ ID NO: 128 | 26'000 | — | 100'000 | 200'000 | — | — | — | — |
| E10 | VVMKD SEQ ID NO: 129 | 15'000 | — | — | 65'000 | — | — | — | — |
| Chymotrypsin-like substrate | | | | | | | | | |
| | | | | $k_{cat}/K_m$ (M$^{-1} \cdot$s$^{-1}$) | | | | | |
| G9 | TVDYA SEQ ID NO: 130 | 134'000 | — | 145'000 | 181'000 | — | — | — | — |
| E1 | AYGYK SEQ ID NO: 131 | 24'000 | 129'000 | 618'000 | — | — | — | — | — |
| F6 | VGLYD SEQ ID NO: 132 | 18'000 | — | 409'000 | — | — | — | — | — |
| F10 | YQSLN SEQ ID NO: 133 | 12'000 | — | 134'000 | 49'000 | — | — | — | L.C. |
| D7 | TSYLN SEQ ID NO: 134 | 9'000 | — | 266'000 | 90'000 | — | — | — | — |

L.C.: low cleavage, kcat/Km not determined; — no detectable cleavage

This study identified two classes of pentapeptide substrates for hK14: trypsin-like and chymotrypsin-like substrates. However, Applicants showed that hK14 has trypsin-rather than chymotrypsin-like cleavage specificity despite the selection of several aromatic residue-containing substrates. The substrates with the highest Kcat/Km have an arginine in P1 position indicating a preference for this amino acid (Table XIV). Lysine, on the other hand, seems to be less suitable than tyrosine in P1 position. If the two amino acids were present in the same peptide, hK14 cleaved after the tyrosine residue. In addition, one of the chymotrypsin-like substrates, TVDYA (SEQ ID NO:130), gave a significantly higher kinetic value, 134,000 M$^{-1} \cdot$s$^{-1}$, than all the lysine-P1 substrates, with Kcat/km values not higher than 34,000 M$^{-1} \cdot$s$^{-1}$. No selectivity of hK14 was observed for the P1' position, where different types of amino acids such as small and uncharged, hydrophobic, positively charged or negatively charged residues have been recovered in the best substrates Analysis of other surrounding positions demonstrated that hK14 can be accommodated by a large variety of amino acids. This observation does not mean that hK14 has a large spectrum of activities like trypsin or chymotrypsin but demonstrates an ability to cleave different sequences depending to the context.

The chymotrypsin-like activity of hK14, even if it is inferior to its trypsin-like activity, is interesting. To Applicants knowledge, except for the Phe-Phe link cleaved by hK1 in kallistatin and some derived peptides, this is the first human kallikrein described with a dual activity. The conformation of the specificity pocket in hK14 should therefore accommodate both aromatic and basic amino acid side chains at the substrate P1 position to explain the dual chymotrypsin and trypsin-like activity of hK14.

Development of hK14 Specific Inhibitors

Modifications of the RSL of α1-antichymotrypsin (ACT) and α1-antitrypsin (AT or AAT) have been performed to change the specificity of this inhibitor. Selected substrates (G1, C11, E5, E8, F3, F11, G9) were then transplanted into the reactive site loop of serpins to generate new variants, able to inhibit the human kallikrein hK14. More than one inhibitor variants have been constructed using sequences from peptides G1 and C11.

TABLE XIV

Alignment of RSL (reactive serpin loop) region of recombinant serpin α1-antichymotrypsin (ACT) and its variants (SEQ ID NOS: 183-194, respectively).

| Serpin | Selected[a] Substrate Peptide | P6 | P5 | P4 | P3 | P2 | P1 | P'1 | P'2 | P'3 | P'4 | P'5 |
|---|---|---|---|---|---|---|---|---|---|---|---|---|
| ACT$_{WT}$ | | V | K | I | T | L | L* | S | A | L | V | V |
| ACT$_{G1}$ | vGSLR SEQ ID NO: 118 | V | K | G | S | L | R* | S | A | L | V | V |
| ACT$_{G1g}$ | vGSLRG SEQ ID NO: 141 | V | K | G | S | L | R* | G | A | L | V | V |
| ACT$_{G1v}$ | VGSLR SEQ ID NO: 118 | V | V | G | S | L | R* | S | A | L | V | E |
| ACT$_{C11}$ | RQTNd SEQ ID NO: 119 | V | K | I | T | L | R* | Q | T | N | V | V |
| ACT$_{C11g}$ | gRQTNd SEQ ID NO: 139 | V | K | I | T | G | R* | Q | T | N | V | V |
| ACT$_{C11D}$ | gRQTND SEQ ID NO: 139 | V | K | I | T | L | R* | Q | T | N | D | V |
| ACT$_{E5}$ | NQRSS SEQ ID NO: 120 | V | K | I | N | Q | R* | S | S | L | V | V |
| ACT$_{E8}$ | LQRAI SEQ ID NO: 121 | V | K | I | L | Q | R* | A | I | L | V | V |
| ACT$_{F11}$ | QRLRD SEQ ID NO: 122 | V | K | Q | R | L | R* | D | A | L | V | V |
| ACT$_{F3}$ | PDRHM SEQ ID NO: 123 | V | K | I | P | D | R* | H | M | L | V | V |
| ACT$_{G9}$ | TVDYA SEQ ID NO: 130 | V | K | T | V | D | Y* | A | A | L | V | V |

[a]Substrate peptides selected by kallikrein hK14 using a phage-displayed random pentapeptide library. Plain type residues are common to rACT$_{WT}$, underlined residues correspond to substrate peptides relocated in RSL of ACT variants. The scissile bond by hK14 in substrate peptides is designated by bold and putative cleavage site in serpins is marked by asterisks between the P1-P1' residues.

TABLE XV

Alignment of RSL (reactive serpin loop) of recombinant serpin alpha-1-antitrypsin (AAT) and its variants (SEQ ID NOS: 177, 195-200, 178, 201, 202, and 179, respectively).

| Serpin | Selected[a] Substrate Peptide | P6 | P5 | P4 | P3 | P2 | P1 | P'1 | P'2 | P'3 | P'4 | P'5 |
|---|---|---|---|---|---|---|---|---|---|---|---|---|
| AAT$_{WT}$ | | L | E | A | I | P | M* | S | I | P | P | E |
| AAT$_{G1}$ | vGSLR SEQ ID NO: 118 | L | E | G | S | L | R* | S | I | P | P | E |
| AAT$_{G1g}$ | vGSLRG SEQ ID NO: 141 | L | E | G | S | L | R* | G | I | P | P | E |
| AAT$_{G1v}$ | VGSLR SEQ ID NO: 118 | L | V | G | S | L | R* | S | I | P | P | E |
| AAT$_{C11}$ | RQTND SEQ ID NO: 119 | L | E | A | I | P | R* | Q | T | N | P | E |
| AAT$_{C11g}$ | gRQTND SEQ ID NO: 139 | L | E | A | I | G | R* | Q | T | N | P | E |
| AAT$_{E5}$ | NQRSS SEQ ID NO: 120 | L | E | A | N | Q | R* | S | S | P | P | E |
| AAT$_{E8}$ | LQRAI SEQ ID NO: 121 | L | E | A | L | Q | R* | A | I | P | P | E |

TABLE XV-continued

Alignment of RSL (reactive serpin loop) of recombinant serpin alpha-1-antitrypsin (AAT) and its variants
(SEQ ID NOS: 177, 195-200, 178, 201, 202, and 179, respectively).

| Serpin | Selected[a] Substrate Peptide | P6 | P5 | P4 | P3 | P2 | P1 | P'1 | P'2 | P'3 | P'4 | P'5 |
|---|---|---|---|---|---|---|---|---|---|---|---|---|
| $AAT_{F11}$ | QRLRD SEQ ID NO: 122 | L | E | Q | R | L | R* | D | I | P | P | E |
| $AAT_{F3}$ | PDRHM SEQ ID NO: 123 | L | E | A | P | D | R* | H | M | P | P | E |
| $AAT_{G9}$ | TVDYA SEQ ID NO: 130 | L | E | T | V | D | Y* | A | I | P | P | E |

[a]Substrate peptides selected by kallikrein hK14 using a phage-displayed random pentapeptide library. Plain type residues are common to $rAAT_{WT}$, underlined residues correspond to substrate peptides relocated in RSL of AT variants. The scissile bond by hK14 in substrate peptides is designated by bold and putative cleavage site in serpins is marked by asterisks between the P1-P1' residues.

The determination of the stoichiometry of inhibitory (SI) and the rate of inhibitory reaction (ka) were performed under physiological conditions of pH and ionic strength to ensure a more relevant comparison. Almost all the newly constructed variants of ACT showed lower SI values with hK14 than wild type ACT. From these variants $rACT_{C11}$, $rACT_{C11D}$, $rACT_{G9}$ and $rACT_{E8}$ had the lowest stoichiometry of inhibition values for hK14 (4.8, 2.8, 1.5 and 1.2 respectively) and the highest association constants (65000, 74000, 75000 and 575000 $M^{-1}$ $s^{-1}$ respectively). Contrary to ACT, the serpin AATwt is a good inhibitor for hK14 with an association constant of 263 000 $M^{-1}$ $s^{-1}$. All the AAT variants had a lower association constant than AATwt, but several of them still react at high velocity with hK14, as $AAT_{G1}$, $AAT_{G9}$, $AAT_{E8}$, $AAT_{G1g}$ and $AAT_{C11}$ exhibiting a ka of 168 000, 217 000, 242 000, 257 000 and 63 000 $M^{-1}$ $s^{-1}$ respectively. Only two AT variants did not inhibit hK14.

TABLE XVI

Comparison of Stoichiometry Inhibition values and second-order rate constants ($k_a$) for the reaction of ACT variants with hK14.

| Clone | Selected[a] Substrate Peptide | SI | $k_a$ $M^{-1}$ $s^{-1}$ |
|---|---|---|---|
| $ACT_{WT}$ | — | — | — |
| $ACT_{G1}$ | vGSLR↓ SEQ ID NO: 118 | 13.3 | 3 200* |
| $ACT_{G1g}$ | vGSLR↓G SEQ ID NO: 141 | — | — |
| $ACT_{G1v}$ | VGSLR↓ SEQ ID NO: 118 | 11.7 | 22 000* |
| $ACT_{C11}$ | R↓QTNd SEQ ID NO: 119 | 4.8 | 65 000* |
| $ACT_{C11g}$ | gR↓QTNd SEQ ID NO: 139 | 13.8 | 7 600* |
| $ACT_{C11D}$ | gR↓QTND SEQ ID NO: 139 | 2.8 | 74 000* |
| $ACT_{E5}$ | NQR↓SS SEQ ID NO: 120 | — | — |
| $ACT_{E8}$ | LQR↓AI SEQ ID NO: 121 | 1.2 | 575 000 |
| $ACT_{F11}$ | QRLR↓D SEQ ID NO: 122 | — | — |
| $ACT_{F3}$ | PDR↓HM SEQ ID NO: 123 | — | — |
| $ACT_{G9}$ | TVDY↓A SEQ ID NO: 130 | 1.5 | 74 000 |

*Calculation based on reaction conditions in which $[I_0]/[E_0] < 5*SI$

TABLE XVII

Comparison of Stoichiometry Inhibition values and second-order rate constants ($k_a$) for the reaction of AT variants with hK14.

| Clone | Selected[a] Substrate Peptide | SI | $k_a$ M$^{-1}$ s$^{-1}$ |
|---|---|---|---|
| AAT$_{WT}$ | | 1.0 | 263 000 |
| AAT$_{G1}$ | vGSLR↓<br>SEQ ID NO: 118 | 3.6 | 168 00* |
| AAT$_{G1g}$ | vGSLR↓G<br>SEQ ID NO: 141 | 2.3 | 257 000* |
| AAT$_{G1v}$ | VGSLR↓<br>SEQ ID NO: 118 | - | - |
| AAT$_{C11}$ | R↓QTNd<br>SEQ ID NO: 119 | 2.8 | 63 000* |
| AAT$_{C11g}$ | gR↓QTNd<br>SEQ ID NO: 139 | 9 | 42 000* |
| AAT$_{E5}$ | NQR↓SS<br>SEQ ID NO: 120 | 10 | 28 000* |
| AAT$_{E8}$ | LQR↓AI<br>SEQ ID NO: 121 | 7.4 | 242 000* |
| AAT$_{F11}$ | QRLR↓D<br>SEQ ID NO: 122 | — | — |
| AAT$_{F3}$ | PDR↓HM<br>SEQ ID NO: 123 | 11.7 | 13 000* |
| AAT$_{G9}$ | TVDY↓A<br>SEQ ID NO: 130 | 1.2 | 217 000 |

*Calculation based on reaction conditions in which [I$_0$]/[E$_0$] < 5*SI

A panel of enzymes including trypsin, human neutrophil elastase, chymotrypsin, plasma kallikrein (PK), urokinase (uPA), and thrombin were screened to determine inhibitory specificity of ACT and AAT variants with a SI for hK14 lower than 10 (Table XVIII). When incubated for 30 min with an excess of inhibitor ([I]o/[E]o) of 50:1), hK14 is completely inhibited (100%). Under this condition, wild type ACT showed only 17% inhibition activity toward hK14 contrary to AATwt (100% of inhibition). Among the ACT variants, two (rACT$_{C11}$ and rACT$_{C11D}$) show specificity to hK14, inhibiting no other tested enzymes apart from trypsin and chymotrypsin. For AAT variants, these new inhibitors clearly exhibited a higher specificity toward hK14 than AATwt. AAT$_{G9}$ demonstrated to be highly specific to hK14, showing no reactivity with any trypsin-like proteases.

TABLE XVIII

Inhibitory profile of ACT$_{WT}$, AAT$_{WT}$ and its variants.

| Protease | ACT$_{C11}$ | ACT$_{C11D}$ | ACT$_{E8}$ | ACT$_{WT}$ | AAT$_{G1}$ | AAT$_{G1g}$ | AAT$_{C11}$ | AAT$_{E8}$ | AAT$_{G9}$ | AAT$_{WT}$ |
|---|---|---|---|---|---|---|---|---|---|---|
| | | | | | % Inhibition | | | | | |
| HK14 | 100 | 100 | 100 | 17 | 100 | 100 | 100 | 100 | 100 | 100 |
| Trypsin | 100 | 100 | 100 | 0 | 100 | 100 | 100 | 100 | 0 | 100 |
| Chtr | 84 | 83 | 14 | 100 | 27 | 17 | 18 | 19 | 100 | 100 |
| PK | 0 | 0 | 36 | 46 | 100 | 100 | 8 | 100 | 0 | 17 |
| HNE | 0 | 0 | 0 | 26 | 0 | 0 | 0 | 0 | 0 | 100 |
| Urokinase | 0 | 0 | 0 | 0 | 17 | 0 | 0 | 0 | 0 | 0 |
| Trombin | 0 | 0 | 0 | 18 | 51 | 0 | 100 | 0 | 0 | 4 |

[a]Serpins and proteases were incubated for 30 min at 37° C. at a [I]$_o$/[E]$_o$ ratio of 50:1. Percent inhibition correspond to 100 × (1 − (velocity in presence of inhibitor/velocity of uninhibited control)).

Additional hK14 inhibiting ACT variants were screened against a larger panel of tissue kallikreins related to hK14. Partial inhibition was observed against different subsets of tested kallikreins.

TABLE XIX

| Protease | $ACT_{G1}$ | $ACT_{G1g}$ | $ACT_{C11g}$ % Inhibition$^a$ | $ACT_{E5}$ | $ACT_{F11}$ |
|---|---|---|---|---|---|
| hK2 | 15 | 0 | 25 | 0 | 25 |
| hK4 | 0 | 0 | 0 | 75 | 45 |
| hK5 | 50 | 10 | 5 | 10 | 15 |
| hK6 | 20 | 0 | 0 | 0 | 0 |
| hK8 | 0 | 0 | 0 | 10 | 0 |

$^a$Protease and serpins were incubated for 30 min at 37° C. (90 min at 37° for PSA) at a $[I]_o/[E]_o$ ratio of 50:1. Percent inhibition correspond to 100 × (1 − (velocity in presence of inhibitor/velocity of uninhibited control)).

The permutation of RSL cleavage site for hK14 phage display selected substrates has changed wild type serpins (ACT and AAT) into highly sensitive inhibitors for hK14, especially $AAT_{G9}$ showing a unique reactivity. To Applicants knowledge, this is the first report describing the development of a specific inhibitor for hK14. The fact that some recombinant inhibitors also inhibited other enzymes than hK14 is not surprising because of the homology of substrate between trypsin-like proteases. Moreover, the velocity of reaction should be determined for recombinant inhibitors toward other enzymes.

TABLE XX

Acanthosis Nigricans,
Acne Conglobata,
Acne Fulminans,
Acne Keloidalis Nuchae,
Acne Vulgaris,
Acneiform Eruptions,
Acquired Digital Fibrokeratoma,
Acquired Progressive Lymphangioma
Acrochordon,
Acrodermatitis Chronica Atrophicans,
Acrodermatitis Enteropathica,
Acrodynia,
Acrokeratoelastoidosis,
Acrokeratosis Neoplastica,
Acrokeratosis Verruciformis of Hopf,
Acromegaly,
Acropustulosis of Infancy,
Actinic Keratosis,
Actinic Prurigo,
Actinic Purpura,
Actinomycosis,
Acute Febrile Neutrophilic Dermatosis,
Acute Hemorrhagic Edema of Infancy,
Addison Disease,
Adiposis Dolorosa,
Advancement Flaps,
Ainhum,
Albinism,
Albright Syndrome,
Alezzandrini Syndrome,
Alopecia Areata,
Alopecia Mucinosa,
Amyloidosis, Lichen,
Amyloidosis, Macular,
Amyloidosis, Nodular Localized Cutaneous,
Amyloidosis, Primary Systemic,
Anagen Effluvium,
Anatomy in Cutaneous Surgery,
Androgenetic Alopecia,
Anetoderma,
Angina Bullosa Hemorrhagica,
Angioedema, Acquired,
Angioedema, Hereditary,
Angioendotheliomatosis,
Angioimmunoblastic Lymphadenopathy With Dysproteinemia,
Angiokeratoma Circumscriptum,
Bacterial Mouth Infections,
Balanitis Circumscripta Plasmacellularis,
Balanitis Xerotica Obliterans,
Balanoposthitis,
Basal Cell Carcinoma,
Basic Excisional Surgery,
Becker Melanosis,
Bedbug Bites,
Behcet Disease,
Berloque Dermatitis,
Birt-Hogg-Dube Syndrome,
Black Heel (Calcaneal Petechiae),
Black Widow Spider Bite,
Bloom Syndrome (Congenital Telangiectatic Erythema),
Blue Nevi,
Blue Rubber Bleb Nevus Syndrome,
Botanical Dermatology,
Botulinum Toxin,
Boutonneuse Fever,
Bowen Disease,
Bowenoid Papulosis,
Branchial Cleft Cyst,
Bromhidrosis,
Brown Recluse Spider Bite,
Bruton Agammaglobulinemia,
Bullous Disease of Diabetes,
Bullous Disease of Dialysis,
Bullous Pemphigoid,
Burns, Chemical,
Burns, Electrical,
Buruli Ulcer,
Calcinosis Cutis,
Calciphylaxis,
Cancers of the Oral Mucosa,
Candidiasis, Chronic Mucocutaneous,
Candidiasis, Cutaneous,
Candidiasis, Mucosal,
Capillary Malformation,
Carney Syndrome,
Carotenemia,
Catscratch Disease,
Cellulitis,
Chancroid,
Chediak-Higashi Syndrome,
Cheek Reconstruction,
Cheilitis Glandularis,
Cheilitis Granulomatosa (Miescher-Melkersson-Rosenthal Syndrome),
Confluent and Reticulated Papillomatosis,
Congenital Hypertrichosis Lanuginosa,
Congenital Nevi,
Congenital Onychodystrophy of the Index Fingers,
Congenital Patterned Leukodermas,
Connective Tissue Nevus,
Contact Dermatitis, (Allergic),
Contact Dermatitis, (Irritant),
Contact Stomatitis,
Corns,
Cosmeceuticals,
Cosmetics,
Cowden Disease (Multiple Hamartoma Syndrome),
Cowpox Infection, Human,
CREST Syndrome,
Cronkhite-Canada Syndrome,
Crouzon Syndrome,
Cryotherapy,
Cutaneous CD30 + (Ki-1) Anaplastic Large-Cell Lymphoma,
Cutaneous Cholesterol Emboli,
Cutaneous Columnar Cysts,
Cutaneous Cryptococcus,
Cutaneous Ectopic Brain,
Cutaneous Horn,
Cutaneous Kikuchi Disease,
Cutaneous Larva Migrans,
Cutaneous Laser Resurfacing: Carbon Dioxide,
Cutaneous Laser Resurfacing: Erbium: YAG,
Cutaneous Manifestations Following Exposures to Marine Life,
Cutaneous Manifestations of Cholesterol Embolism,
Cutaneous Manifestations of Hepatitis C,
Cutaneous Manifestations of HIV Disease,
Cutaneous Manifestations of Smoking,
Cutaneous Melanoacanthoma,
Cutaneous T-Cell Lymphoma,
Cutaneous Tuberculosis,
Cutis Laxa (Elastolysis),
Cutis Marmorata Telangiectatica Congenita,
Cutis Verticis Gyrata, TABLE XX-continued Angiokeratoma Corporis Diffusum (Fabry Syndrome),
Angiokeratoma of the Scrotum,
Angiolymphoid Hyperplasia with Eosinophilia,
Angioma Serpiginosum,
Animal Bites,
Aphthous Stomatitis,
Aplasia Cutis Congenita,
Apocrine Hidrocystoma,
*Arcanobacterium Haemolyticum*,
Argyria,
Arsenical Keratosis,
Aspergillosis,
Asteatotic Eczema,
Asymmetric Periflexural Exanthem of Childhood,
Ataxia-Telangiectasia,
Atopic Dermatitis,
Atrophia Maculosa Varioliformis Cutis,
Atrophoderma of Pasini and Pierini,
Atypical Fibroxanthoma,
Atypical Mole (Dysplastic Nevus),
Atypical Mycobacterial Diseases,
Avitaminosis A,
Axillary Granular Parakeratosis,
Bacillary Angiomatosis,
Digital Mucous Cyst,
Digital Photography,
Dilated Pore of Winer,
Disseminate and Recurrent Infundibular Folliculitis,
Down Syndrome,
Drug Eruptions,
Drug-Induced Bullous Disorders,
Drug-Induced Gingival Hyperplasia,
Drug-Induced Photosensitivity,
Drug-Induced Pigmentation,
Drug-Induced Pseudolymphoma Syndrome,
Dupuytren Contracture,
Dyshidrotic Eczema,
Dyskeratosis Congenita,
Dysmorphophobia,
Ear Reconstruction,
Eccrine Carcinoma,
Eccrine Spiradenoma,
Ecthyma,
Ecthyma Gangrenosum,
Ectodermal Dysplasia,
Ehlers-Danlos Syndrome,
Elastofibroma,
Elastosis Perforans Serpiginosum,
Elejalde Syndrome,
Endemic Syphilis,
Enteroviral Infections,
Eosinophilia-Myalgia Syndrome,
Eosinophilic Fasciitis,
Eosinophilic Pustular Folliculitis,
Eosinophilic Ulcer,
Ephelides (Freckles),
Epidermal Inclusion Cyst,
Epidermal Nevus Syndrome,
Epidermodysplasia Verruciformis,
Epidermolysis Bullosa,
Epidermolysis Bullosa Acquisita,
Epidermolytic Hyperkeratosis (Bullous Congenital Ichthyosiform Erythroderma),
Epulis Fissuratum,
Eruptive Vellus Hair Cysts,
Erysipelas,
Erysipeloid,
Erythema Ab Igne,
Erythema Annulare Centrifugum,
Erythema Dyschromicum
Chemical Peels,
Chemotherapy-Induced Oral Mucositis,
Cherry Hemangioma,
Chickenpox,
CHILD Syndrome,
Childhood HIV Disease,
Chondrodermatitis Nodularis Helicis,
Chromhidrosis,
Chromoblastomycosis
Chronic Granulomatous Disease
Churg-Strauss Syndrome, (Allerqic Granulomatosis),
Cicatricial Pemphigoid,
Clavus,
Closure of Complicated Wounds,
Clubbing of the Nails,
Cobb Syndrome,
Coccidioidomycosis,
Cockayne Syndrome,
Cold Panniculitis,
Colloid Milium,
Common Variable Immunodeficiency,
Complement Receptor Deficiency,
Complications of Dermatologic Laser Surgery,
Florid Cutaneous Papillomatosis
Focal Dermal Hypoplasia Syndrome,
Fogo Selvagem,
Follicular Infundibulum Tumor,
Folliculitis,
Folliculoma,
Forehead and Temple Reconstruction,
Fox-Fordyce Disease,
Friction Blisters,
Frostbite,
Gardner Syndrome
Generalized Essential Telangiectasia
Geographic Tongue
Gianotti-Crosti Syndrome (Papular Acrodermatitis of Childhood)
Giant Condylomata Acuminata of Buschke and Lowenstein
Glomus Tumor
Glucagonoma Syndrome
Glycogen Storage Diseases Types I-VII
Gonococcemia
Graft Versus Host Disease
Graham-Little-Piccardi-Lasseur Syndrome
Gram-Negative Folliculitis
Gram-Negative Toe Web Infection
Granuloma Annulare
Granuloma Faciale
Granuloma Gluteale Infantum
Granuloma Inguinale (Donovanosis)
Granulosis Rubra Nasi
Griscelli Syndrome
Haberland Syndrome
Hair Transplantation
Hair Transplantation: Follicular Unit Transplant Method
Hairy Tongue
Halo Nevus
Halogenoderma
Hand-Foot-and-Mouth Disease
Handheld Computers in Dermatology
Hartnup Disease
Hemochromatosis
Cylindroma,
Dabska Tumor
de Lange Syndrome,
Degos Disease,
Delusions of Parasitosis,
Dengue,
Denture Stomatitis,
Dermabrasion,
Dermal Fillers,
Dermatitis Artefacta,
Dermatitis Herpetiformis,
Dermatofibroma,
Dermatofibrosarcoma Protuberans,
Dermatofibrosis Lenticularis (Buschke-Ollendorf Syndrome),
Dermatologic Aspects of Bioterrorism Agents,
Dermatologic Aspects of Bioterrorism Agents, Anthrax,
Dermatologic Manifestations of Cardiac Disease,
Dermatologic Manifestations of Gastrointestinal Disease,
Dermatologic Manifestations of Hematologic Disease,
Dermatologic Manifestations of Neurologic Disease,
Dermatologic Manifestations of Pulmonary Disease,
Dermatologic Manifestations of Renal Disease,
Dermatology Internet Sites,
Dermatomyositis,
Dermatopathia Pigmentosa Reticularis,
Dermatosis Papulosa Nigra,
Dermoid Cyst,
Dermoscopy,
Desmoid Tumor, DiGeorge Syndrome,
Intertrigo
Jellyfish Stings
Jessner Lymphocytic Infiltration of the Skin
Job Syndrome
Juvenile Xanthogranuloma (Nevoxanthoendothelioma)
Kaposi Sarcoma
Kaposi Variceliform Eruption
Kawasaki Disease
Keloid and Hypertrophic Scar
Keratoacanthoma
Keratosis Follicularis (Darier Disease)
Keratosis Palmaris et Plantaris
Keratosis Pilaris
Kimura Disease
Kindler Syndrome
Klippel-Trenaunay-Weber Syndrome
Knuckle Pads
Kyrie Disease
Langerhans Cell Histiocytosis
Laser Revision of Scars
Laser Treatment of Acquired and Congenital Vascular Lesions
Laser Treatment of Benign Pigmented Lesions
Laser Treatment of Leg Veins
Laser-Assisted Hair Removal
Laugier-Hunziker Syndrome
Lawrence-Seip Syndrome
Leiomyoma
Leishmaniasis
Lentigo
LEOPARD Syndrome
Leprosy
Leukemia Cutis
Leukoplakia, Oral TABLE XX-continued Perstans,
Erythema Elevatum Diutinum,
Erythema Gyratum Repens,
Erythema Induratum (Nodular Vasculitis),
Erythema Infectiosum (Fifth Disease),
Erythema Multiforme,
Erythema Nodosum,
Erythema Toxicum Neonatorum
Erythrasma,
Erythroderma (Generalized Exfoliative Dermatitis),
Erythrokeratodermia Variabilis,
Erythroplasia of Queyrat (Bowen Disease of the Glans Penis),
Erythropoietic Porphyria,
Erythropoietic Protoporphyria,
Essentials of Tissue Movement,
Eumycetoma (Fungal Mycetoma),
Extracorporeal Photopheresis,
Extramammary Paget Disease,
Familial Benign Pemphigus (Hailey-Hailey Disease),
Favre-Racouchot Syndrome (Nodular Elastosis with Cysts and Comedones),
Favus,
Fibrodysplasia Ossificans,
Fibrous Papule of the Face,
Filariasis,
Fire Ant Bites,
Fissured Tongue,
Materials for Wound Closure
Measles, Rubeola
Melanotic Neuroectodermal Tumor of Infancy
Melasma
Meningococcemia
Menkes Kinky Hair Disease
Merkel Cell Carcinoma
Metastatic Carcinoma of the Skin
Metastatic Neoplasms to the Oral Cavity
Microcystic Adnexal Carcinoma
Milia
Miliaria
Milker's Nodules
Mixed Connective Tissue Disease
Mohs Micrographic Surgery
Moisturizers
Molluscum Contagiosum
Mondor Disease
Mongolian Spot
Monilethrix
Monkeypox
Morphea
Mucocele and Ranula
Mucopolysaccharidoses Types I-VII
Mucous Cyst
Muehrcke Lines of the Fingernails
Muir-Torre Syndrome
Multicentric Reticulohistiocytosis
Multinucleate Cell Angiohistiocytoma
Multiple Endocrine Neoplasia Type 1
Mycetoma
*Mycobacterium Avium-*Intracellulare Infection
*Mycobacterium Marinum* Infection of the Skin
Naegeli-Franceschetti-Jadassohn Syndrome
Nail Cosmetics
Nail Surgery
Nail-Patella Syndrome
Henoch-Schönlein Purpura (Anaphylactoid Purpura)
Hermansky-Pudlak Syndrome
Herpes Simplex
Herpes Zoster
Hidradenitis Suppurativa
Hirsutism
Homocystinuria
Human Bites
Human Herpesvirus 6
Hutchinson-Gilford Progeria
Hydroa Vacciniforme
Hypereosinophilic Syndrome
Hyperhidrosis
Hyperkeratosis Lenticularis Perstans (Flegel Disease)
Hyperkeratosis of the Nipple and Areola
Hypersensitivity Vasculitis (Leukocytoclastic Vasculitis)
Hypnosis: Applications in Dermatology and Dermatologic Surgery
Hypomelanosis of Ito
Ichthyosis Fetalis
Ichthyosis Vulgaris, Hereditary and Acquired
Ichthyosis, Lamellar
Ichthyosis, X-Linked
Id Reaction (Autoeczematization)
Idiopathic Guttate Hypomelanosis
Impetigo
Incontinentia Pigmenti
Infantile Digital Fibromatosis
Infantile Hemangioma
Insect Bites
Insect Repellents
Interactive Teledermatology
Oral Examination
Oral Fibromas and Fibromatoses
Oral Florid Papillomatosis
Oral Frictional Hyperkeratosis
Oral Granular Cell Tumors
Oral Hemangiomas
Oral Lichen Planus
Oral Lymphangiomas
Oral Malignant Melanoma
Oral Manifestations of Autoimmune Blistering Diseases
Oral Manifestations of Drug Reactions
Oral Manifestations of Systemic Diseases
Oral Melanoacanthoma
Oral Neurofibroma
Oral Nevi
Oral Pyogenic Granuloma
Oral Submucous Fibrosis
Orf
Osler-Weber-Rendu Syndrome
Osteoma Cutis
Outpatient Surgical Suite
Pachydermoperiostosis
Pachyonychia Congenita
Paget Disease, Mammary
Papular Urticaria
Papulonecrotic Tuberculids
Paraneoplastic Diseases
Parapsoriasis
Paronychia
Pearly Penile Papules
Pedicle/Interpolation Flaps
Pellagra
Pemphigoid Gestationis
Pemphigus Erythematosus
Pemphigus Foliaceus
Pemphigus Herpetiformis
Pemphigus Vulgaris
Pemphigus, Drug-Induced
Lice
Lichen Myxedematosus
Lichen Nitidus
Lichen Planus
Lichen Sclerosus et Atrophicus
Lichen Simplex Chronicus
Lichen Spinulosus
Lichen Striatus
Linear IgA Dermatosis
Lip Reconstruction
Lipodystrophy, HIV
Lipodystrophy, Localized
Lipodystrophy, Progressive
Lipoid Proteinosis
Lipomas
Liposarcoma
Livedoid Vasculopathy
Lobomycosis
Local Anesthesia and Regional Nerve Block Anesthesia
Loose Anagen Syndrome
Lupus Erythematosus, Acute
Lupus Erythematosus, Bullous
Lupus Erythematosus, Discoid
Lupus Erythematosus, Drug-Induced
Lupus Erythematosus, Subacute Cutaneous
Lupus Miliaris Disseminatus Faciei
Lyme Disease
Lymphangiectasia
Lymphangioma
Lymphocytoma Cutis
Lymphogranuloma Venereum
Lymphomatoid Papulosis
Maffucci Syndrome
Majocchi Granuloma
Malakoplakia
Malignant Melanoma
Mastocytosis
Postinflammatory Hyperpigmentation
Preauricular Sinuses
Premalignant Fibroepithelial Tumor (Pinkus Tumor)
Preoperative Evaluation and Management
Pretibial Myxedema
Proliferating Pilar Tumor
Protein-Energy Malnutrition
Proteus Syndrome
Protothecosis, Cutaneous
Prurigo Nodularis
Pruritic Urticarial Papules and Plaques of Pregnancy
Pruritus and Systemic Disease
Pseudo-Kaposi Sarcoma (Acroangiodermatitis)
Pseudoatrophoderma Colli
Pseudocyst of the Auricle
Pseudofolliculitis of the Beard
Pseudolymphoma, Cutaneous
Pseudomonas Folliculitis
Pseudopelade, Brocq
Pseudoporphyria
Pseudoxanthoma Elasticum
Psoriasis, Guttate
Psoriasis, Nails
Psoriasis, Plaque
Psoriasis, Pustular
Psoriatic Arthritis
Pulp Polyp
Punch Biopsy and Scalpel Biopsy
Pyoderma Gangrenosum
Pyoderma Vegetans
Pyogenic Granuloma (Lobular Capillary Hemangioma)
Reactive Arthritis TABLE XX-continued

| | | |
|---|---|---|
| Nasal Reconstruction | Pemphigus, IgA | Reactive Perforating |
| Nasopalatine Duct Cyst | Pemphigus, Paraneoplastic | Collagenosis |
| Necrobiosis Lipoidica | Penile Squamous Cell | Refsum Disease |
| Necrolytic Acral Erythema | Carcinoma | Relapsing Polychondritis |
| Necrotizing Fasciitis | Perforating Folliculitis | Reticulate Pigmented Anomaly |
| Necrotizing Sialometaplasia | Perifolliculitis Capitis Abscedens | Rhinoscleroma |
| Neonatal Lupus Erythematosus | Et Suffodiens | Riehl Melanosis |
| Nephrogenic Fibrosing | Perioral Dermatitis | Rocky Mountain Spotted Fever |
| Dermopathy | Peripheral Giant Cell Granuloma | Rosacea |
| Neurilemoma | Pernio | Roseola Infantum |
| Neurofibromatosis | Peyronie Disease | Rotation Flaps |
| Neurotic Excoriations | Phenylketonuria | Rothmund-Thomson Syndrome |
| Neutrophilic Eccrine Hidradenitis | Photodynamic Therapy for the | Rubella |
| Nevi of Ota and Ito | Dermatologist | Rubinstein-Taybi Syndrome |
| Nevi, Melanocytic | Phytophotodermatitis | Rud Syndrome |
| Nevoid Basal Cell Carcinoma | Piebaldism | Sarcoidosis |
| Syndrome | Piedra | Scabies |
| Nevus Anemicus | Piezogenic Pedal Papules | Scalp Reconstruction |
| Nevus Araneus (Spider Nevus) | Pigmented Purpuric Dermatitis | Scar Revision |
| Nevus Comedonicus | Pilar Cyst | Scarlet Fever |
| Nevus Sebaceus | Pilomatrixoma | Schnitzler Syndrome |
| Nicotine Stomatitis | Pitted Keratolysis | Scleredema |
| Niemann-Pick Disease | Pityriasis Alba | Sclerema Neonatorum |
| Nijmegen Breakage Syndrome | Pityriasis Lichenoides | Scrub Typhus |
| Nocardiosis | Pityriasis Rosea | Scurvy |
| Nonablative Resurfacing | Pityriasis Rotunda | Seabather's Eruption |
| Noncandidal Fungal Infections of | Pityriasis Rubra Pilaris | Sebaceous Adenoma |
| the Mouth | Pityrosporum Folliculitis | Sebaceous Carcinoma |
| Nonlaser Hair Removal | Plantar Fibromatosis | Sebaceous Hyperplasia |
| Techniques | POEMS Syndrome | Seborrheic Dermatitis |
| Nummular Dermatitis | Poikiloderma of Civatte | Seborrheic Keratosis |
| Ochronosis | Polymorphous Light Eruption | Severe Combined |
| Onchocerciasis (River | Porokeratosis | Immunodeficiency |
| Blindness) | Poroma | Sign of Leser-Trelat |
| Onycholysis | Porphyria Cutanea Tarda | Sjogren Syndrome |
| Onychomycosis | Urticaria, Cholinergic | Sjogren-Larsson Syndrome |
| Oral Brush Biopsy With | Urticaria, Chronic | Skin and Hair Cleansers |
| Computer-Assisted Analysis | Urticaria, Contact Syndrome | Skin Grafting |
| Oral Cutaneous Fistulas | Urticaria, Dermographism | Skin Lightening and |
| Smokeless Tobacco Lesions | Urticaria, Pressure | Depigmenting Agents |
| Smoker's Melanosis | Urticaria, Solar | Smallpox |
| South American Blastomycosis | Urticarial Vasculitis | Transposition Flaps |
| Speckled Lentiginous Nevus | Varicose Vein Treatment with | Traumatic Ulcers |
| Spitz Nevus | Endovenous Laser Therapy | Trichilemmoma |
| Sporotrichosis | Varicose Veins and Spider Veins | Trichoepithelioma |
| Squamous Cell Carcinoma | Varicose Veins Treated with | Trichofolliculoma |
| Staphylococcal Scalded Skin | Ambulatory Phlebectomy | Trichomycosis Axillaris |
| Syndrome | Varicose Veins Treated with | Trichomycosis Pubis |
| Stasis Dermatitis | Radiofrequency Ablation | Trichorrhexis Invaginata |
| Steatocystoma Multiplex | Therapy | (Netherton Syndrome or |
| Stevens-Johnson Syndrome and | Variegate Porphyria | Bamboo Hair) |
| Toxic Epidermal Necrolysis | Venous Insufficiency | Trichorrhexis Nodosa |
| Stewart-Treves Syndrome | Venous Lakes | Trichostasis Spinulosa |
| Store-and-Forward | Verruciform Xanthoma | Trichotillomania |
| Teledermatology | Verrucous Carcinoma | Tuberous Sclerosis |
| Striae Distensae | Vesicular Palmoplantar Eczema | Tufted Angioma |
| Strongyloidiasis | Vibrio Vulnificus Infection | Tufted Hair Folliculitis |
| Stucco Keratosis | Viral Hemorrhagic Fevers | Tumescent Liposuction |
| Subacute Nodular Migratory | Viral Infections of the Mouth | Tungiasis |
| Panniculitis (Vilanova Disease) | Vitiligo | Ulerythema |
| Subcorneal Pustular Dermatosis | Vogt-Koyanagi-Harada | Unilateral Nevoid Telangiectasia |
| Subcutaneous Fat Necrosis of | Syndrome | Urticaria, Acute |
| the Newborn | Vohwinkel Syndrome | Transient Neonatal Pustular |
| Sunscreens and Photoprotection | Waardenburg Syndrome | Melanosis |
| Supernumerary Digit | Warts, Genital | Tinea Corporis |
| Supernumerary Nipple | Warts, Nongenital | |
| Surgical Complications | Warty Dyskeratoma | |
| Surgical Dressings | Wegener Granulomatosis | |
| Suturing Techniques | Wells Syndrome (Eosinophilic | |
| Syphilis | Cellulitis) | |
| Syringoma | Werner Syndrome | |
| Systemic Sclerosis | Winchester Syndrome | |
| Targetoid Hemosiderotic | Wiskott-Aldrich Syndrome | |
| Hemangioma | Xanthomas | |
| Tattoo Lasers | Xeroderma Pigmentosum | |
| Tattoo Reactions | Yaws | |
| Teledermatology | Tinea Cruris | |
| Telogen Effluvium | Tinea Faciei | |
| Temporal (Giant Cell) Arteritis | Tinea Nigra | |
| The Role of Antibiotics in | Tinea Pedis | |

| | |
|---|---|
| Cutaneous Surgery | Tinea Versicolor |
| The Role of Sentinel Node Biopsy in Skin Cancer | Tooth Discoloration |
| | Toxic Shock Syndrome |
| Thermal Burns | Traction Alopecia |
| Thrombophlebitis | Transient Acantholytic Dermatosis |
| Tinea Barbae | |
| Tinea Capitis | |

TABLE XX-continued

Example 4

A potential therapeutic effect of MDPK67b (rACT$_{6.7}$) on skin diseases has been tested on a Netherton syndrome mouse model as a topical application.

Trial Design

The molecule has been formulated at 2 mg/ml in NATROSOL® (hydroxyethylcellulose (HEC)) 2% (w/v). The formulation has been chosen following in vitro diffusion criteria retaining MDPK67b inhibition property over trypsin (surrogate in vitro substrate). MDPK67b 2 mg/ml, prepared as a solution, is formulated in 2% NATROSOL® (hydroxyethylcellulose (HEC)) (w/v), PBS1× pH7.4 at 4° C. under slow agitation to prevent molecule shearing. The preparation is carefully homogenized under stirring at 4° C. to ensure proper inhibitor repartition within the hydrogel. NATROSOL® (hydroxyethylcellulose (HEC)) has to be added as a powder to MDPK67b solution to avoid clumps and to allow a homogenous formulation without shearing.

To maintain sterility the solutions are autoclaved or filtered through a 0.22 u filter.

MDPK67b 2 mg/ml/Hydroxyethylcellulose formulation contains 4 mg MDPK67b, 2 ml PBS1× pH7.4 and 0.04 g NATROSOL® (hydroxyethylcellulose (HEC)). The formulation is then stored at 4° C. or lyophilized overnight and stored at −20° C. Protease inhibition properties of MDPK67b are tested in vitro upon formulation before in vivo use.

Figure 30:
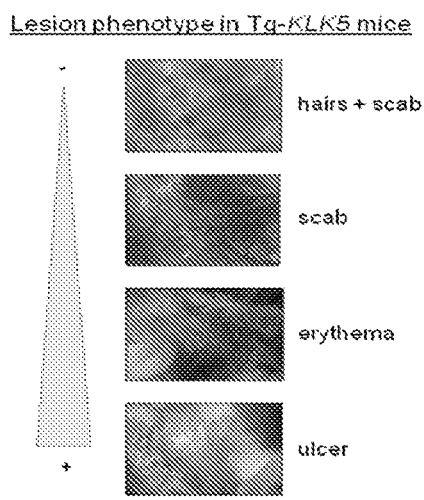
FIG. 30 shows the grading system for skin lesions on transgeninc hKLK5 mouse Netherton Model.

MDPK67b potential therapeutic effect has been assessed on a group of 12 transgenic KLK5 mice with different lesion grade severity, starting from a low severity grade (grade 1) to a more severe grade (grade 4) (FIG. 30). Group 1 has been treated once per day with 0.3 ml of vehicle, 2% NATROSOL® (hydroxyethylcellulose (HEC)) and group 2 once per day with 0.3 ml of MDPK67b formulated at 2 mg/ml in 2% NATROSOL® (hydroxyethylcellulose (HEC)) over 28 days. This time period corresponds to two epiderma renewals in the mouse model.

Mice have been monitored for changes in lesion grade and lesion size phenotypes. Lesion size has been measured every 3 days and lesion grade was monitored daily Results (FIG. 31)

Comparison of the development of skin lesions on KLK5 transgenic mice of MDPK67b treated versus non-treated mice showed a decrease of lesion sizes within the MDPK67b group (group 2) compared to vehicle group (group 1). Whereas lesion sizes increased in a majority of the vehicle control group, the majority of the MDPK67b treated group showed a decrease in lesion size. A clear size increase was observed in 3 test animals of group1 and 1 within group 2. A slight lesion size increase was observed 1 animal of group 2. No change was reported in 1 animal of group 1. A decrease in lesion size was observed in 1 test animals of group1 and 3 within group 2. The protective effect seems larger in mice with low grade symptoms.

TABLE XXI

| Lesion size evolution | Group 1 (control) | Group 2 (MDPK67b) |
|---|---|---|
| evolution | 3 | 1 |
| slight evolution | 0 | 1 |
| stable | 1 | 0 |
| decrease | 1 | 3 |

Lesion grade development was also positively affected by topical application of MDPK67b. One MDPK67b treated test animal showed a complete reversion of the phenotype. A partial reversion was seen on a second MDPK67b treated animal. The protective effect seems larger in mice with low grade symptoms.

REFERENCE LIST

Barrett. In: Proteinase Inhibitors. Ed. Barrett, A. J. et al, Elsevier, Amsterdam, pages 3-22 (1986)
Blasi. In: Human Genes and Diseases. Ed. Blasi, F., John Wiley & Sons, Ltd., pages 377-414 (1986)
Borgono et al. Cancer Res. 63, 9032-9041 (2003)
Borgono et al. J. Biol. Chem 282(6):3640-52 (2007)
Brattsand and Egelrud. J. Biol. Chem. 274, 30033-40 (1999)
Brattsand et al. J Invest Dermatol. 124, 198-203 (2005)
Carrell et al. Trends Biochem Sci. 10:20-24 (1985)
Carrell et al. Cold Spring Harbor Symp Quant Biol. 52:527-35 (1987)
Caubet et al. J. Invest Dermatol. 122, 1235-1244 (2004)
Chavanas et al. Nat. Genet. 25, 141-142 (2000)
Cloutier et al. Eur J Biochem 271, 607-613 (2004)
Cloutier et al. Eur J Biochem. 269, 2747-2754 (2002)
Cooley et al. Biochemistry 40, 15762-70 (2001)
Deraison et al. Mol Biol Cell. 18(9):3607-19 (2007).
Descargues et al. J Invest Dermatol. 126(7):1622-32 (2006)
Descargues et al. Nat Genet. 37(1):56-65 (2005)
Egelrud et al. Br. J. Dermatol. 153, 1200-1203(2005)
Ekholm and Egelrud. Arch Dermatol Res. 291, 195-200. (1999)
Felber et al. Biol Chem. 386(3):291-8 (2005)
Felber et al. Biotechniques 36, 878-885 (2004)
Felber et al. FEBS J. 273(11):2505-14 (2006)
Frenette et al. Biochim Biophys Acta 1334, 109-115 (1997)
Frenette et al. J Urol 159, 1375-8 (1998)
Gerard et al. Mol Biol Med. 2:449-457 (1986)
Hachem et al. J. Invest Dermatol. 126, 1609-1621 (2006)
Hansson et al. J. Biol. Chem. 269, 19420-19426 (1994)
Hansson et al. J. Invest Dermatol. 118, 444-449. (2002)
Huang et al. Oncol Res. 14, 387-397. (2004).
Hunt and Dayhoff. Biochem Biophys Res Commun. 95(2):864-71 (1980)
Kapadia. Clin Chem 49, 77-86 (2003)
Ketcham et al. In: Atlas of Protein Sequence and Structure. Ed. Dayhoff, pages 131-143 (1978)
Kishi et al. Clin Chem 49, 87-96 (2003)
Kishibe et al. J. Biol. Chem. 282(8):5834-41 (2007)

Komatsu et al. Br. J. Dermatol. 153, 274-281 (2005)
Komatsu et al. J. Invest Dermatol. 118, 436-443. (2002)
Komatsu et al. J. Invest Dermatol. 125, 1182-1189. (2005)
Komatsu et al. J. Invest Dermatol. 126, 2338-2342. (2006)
Kraut et al. Z Physiol Chem 192: 1-21 (1930)
Laemmli Nature 227, 680-5 (1970)
Laskowski et al. Annu Rev Biochem. 49:593-626 (1980)
Laskowski et al. Cold Spring Harbor Symp Quant Biol. 545-553 (1987)
Levin et al. Proc Natl Acad Sci USA. 80:6804-6808 (1983)
Little et al. J Biol Chem 272, 25135-25142 (1997)
Lowman et al. Biochemistry 12, 10832-8 (1991)
Luo et al. Clin. Chem. 47, 237-246 (2001)
Mahajan et al. Chem Biol 6, 401-9
Mitra et al. Gene 173, 13-17 (1996)
Mize et al. Mol Cancer Res. 6(6):1043-51. 2008
Morrison and Walsh. Adv Enzymol Relat Areas Mol Biol 61, 201-301 (1988)
Nin et al. J Dermatol Sci. 2008 (2008).
Oikonomopoulou et al. J. Biol. Chem. 281, 32095-32112. (2006).
Paine et al. J. Invest. Dermatol. 116, 587-595. (2001).
Papamokos et al. J Mol Biol. 158(3):515-37 (1982)
Potempa et al. J Biol Chem. 269(23):15957-60 (1994)
Read, R. J. et al, In: Proteinase Inhibitors. Ed. Barrett, Elsevier, Amsterdam, pages 301-336 (1986)
Remold-O'Donnell. FEBS Lett. 315(2):105-8 (1993)
Shimizu et al. J Biol Chem 273, 11189-11196 (1998)
Smith and Scott. Methods Enzymol. 217, 228-57 (1993)
Sommer et al. Biochemistry. 26(20):6407-10 (1987)
Sondell et al. J. Invest Dermatol. 104, 819-823. (1995)
Sprecher et al. J. Invest Dermatol. 117, 179-187(2001)
Sprengers et al. Blood. 69(2):381-7 (1987)
Stefansson et al. Biol. Chem. 387, 761-768 (2006)
Stefansson et al. J Invest Dermatol. 128(1):18-25 (2008)
Stump et al. J Biol Chem. 261(27):12759-66 (1986)
Suzuki et al. J Biol Chem. 262(2):611-6 (1987)
Travis et al. Annu Rev Biochem. 52:655-709 (1983)
Vandell et al. J Neurochem. 107(3):855-70 (2008)
Voegeli et al. Int. J. Cosm. Sci. 29, 191-200. (2007).
Werle. Biochem Z. 269:415-34.
Yamasaki et al. LFASEB J. 20, 2068-2080. (2006)
Yousef et al. Cancer Res 63, 3958-3965 (2003)

What is claimed is:

1. A method of treating a skin disease or undesirable skin condition selected from the group consisting of Netherton syndrome, atopic dermatitis, psoriasis, rosacea, pruritus, and peeling skin syndrome, comprising administering to a patient in need thereof an effective amount of a pharmaceutical composition comprising a serine protease inhibitor comprising a reactive site loop (RSL) of the amino acid sequence of SEQ ID NO:160, wherein the patient is suffering from one or more of Netherton syndrome, atopic dermatitis, psoriasis, rosacea, pruritus, and peeling skin syndrome.

2. The method of claim 1, wherein the serine protease inhibitor has the amino acid sequence of SEQ ID NO:8 or a fragment thereof comprising a RSL of the amino acid sequence of SEQ ID NO:160.

3. The method of claim 1, wherein the serine protease inhibitor has the amino acid sequence of SEQ ID NO:8 or a fragment thereof sharing more than 80% in length thereof, wherein the fragment comprises a RSL of the amino acid sequence of SEQ ID NO:160.

4. The method of claim 1, wherein the serine protease inhibitor has the amino acid sequence of SEQ ID NO:8 or a fragment thereof sharing more than 90% in length thereof, wherein the fragment comprises a RSL of the amino acid sequence of SEQ ID NO:160.

5. The method of claim 1, wherein the amino acid sequence of the serine protease inhibitor comprises residues 13-412 of SEQ ID NO:8.

6. The method of claim 1, wherein the amino acid sequence of the serine protease inhibitor comprises the amino acid sequence of SEQ ID NO:8.

7. The method of claim 1, wherein the amino acid sequence of the serine protease inhibitor consists of SEQ ID NO:8.

8. The method of claim 1, wherein the serine protease inhibitor is administered systemically.

9. The method of claim 1, wherein the serine protease inhibitor is administered topically.

10. A method of treating Netherton syndrome, comprising administering to a patient in need thereof an effective amount of a pharmaceutical composition comprising a serine protease inhibitor comprising a reactive site loop (RSL) of the amino acid sequence of SEQ ID NO:160, wherein the patient is suffering from Netherton syndrome.

11. The method of claim 10, wherein the serine protease inhibitor has the amino acid sequence of SEQ ID NO:8 or a fragment thereof comprising a RSL of the amino acid sequence of SEQ ID NO:160.

12. The method of claim 10, wherein the serine protease inhibitor has the amino acid sequence of SEQ ID NO:8 or a fragment thereof sharing more than 80% in length thereof, wherein the fragment comprises a RSL of the amino acid sequence of SEQ ID NO:160.

13. The method of claim 10, wherein the serine protease inhibitor has the amino acid sequence of SEQ ID NO:8 or a fragment thereof sharing more than 90% in length thereof, wherein the fragment comprises a RSL of the amino acid sequence of SEQ ID NO:160.

14. The method of claim 10, wherein the amino acid sequence of the serine protease inhibitor comprises residues 13-412 of SEQ ID NO:8.

15. The method of claim 10, wherein the amino acid sequence of the serine protease inhibitor comprises the amino acid sequence of SEQ ID NO:8.

16. The method of claim 10, wherein the amino acid sequence of the serine protease inhibitor consists of SEQ ID NO:8.

17. The method of claim 10, wherein the serine protease inhibitor is administered topically.

18. The method of claim 10, wherein the serine protease inhibitor is administered systemically.

* * * * *